(12) United States Patent
Milton et al.

(10) Patent No.: US 11,884,950 B2
(45) Date of Patent: *Jan. 30, 2024

(54) METHODS AND REAGENTS FOR SYNTHESISING POLYNUCLEOTIDE MOLECULES

(71) Applicant: Oxford Nanopore Technologies PLC, Oxford (GB)

(72) Inventors: John Milton, Oxford (GB); Sobia Nayyar, Oxford (GB); Jan Riedl, Oxford (GB); Ryosuke Ogaki, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 260 days.

This patent is subject to a terminal disclaimer.

(21) Appl. No.: 17/143,318

(22) Filed: Jan. 7, 2021

(65) Prior Publication Data

US 2021/0324436 A1 Oct. 21, 2021

Related U.S. Application Data

(63) Continuation of application No. 16/479,141, filed as application No. PCT/GB2018/050165 on Jan. 19, 2018, now Pat. No. 10,927,394.

(30) Foreign Application Priority Data

Jan. 19, 2017 (GB) .................................. 1700937

(51) Int. Cl.
| | | |
|---|---|---|
| *C12P 19/34* | (2006.01) | |
| *B01J 19/00* | (2006.01) | |
| *C12N 9/12* | (2006.01) | |
| *C12N 15/10* | (2006.01) | |

(52) U.S. Cl.
CPC ........... *C12P 19/34* (2013.01); *B01J 19/0046* (2013.01); *C12N 9/1247* (2013.01); *C12N 9/1252* (2013.01); *C12N 15/1093* (2013.01); *C12Y 207/07006* (2013.01); *C12Y 207/07007* (2013.01); *B01J 2219/00596* (2013.01); *B01J 2219/00608* (2013.01); *B01J 2219/00722* (2013.01)

(58) Field of Classification Search
None
See application file for complete search history.

(56) References Cited

U.S. PATENT DOCUMENTS

| | | | |
|---|---|---|---|
| 5,681,947 | A | 10/1997 | Bergstrom et al. |
| 8,653,832 | B2 | 2/2014 | Hadwen et al. |
| 8,808,989 | B1 | 8/2014 | Efcavitch et al. |
| 8,828,336 | B2 | 9/2014 | Hadwen et al. |
| 10,927,394 | B2 | 2/2021 | Milton et al. |
| 2006/0115850 | A1 | 6/2006 | Schatz |
| 2008/0044862 | A1 | 2/2008 | Schatz et al. |
| 2013/0085073 | A1 | 4/2013 | Meuleman et al. |
| 2014/0197028 | A1 | 7/2014 | Jacobs et al. |
| 2014/0202863 | A1 | 7/2014 | Hadwen |
| 2014/0363852 | A1 | 12/2014 | Efcavitch et al. |
| 2016/0046973 | A1 | 2/2016 | Efcavitch et al. |
| 2016/0046974 | A1 | 2/2016 | Efcavitch et al. |
| 2016/0108382 | A1 | 4/2016 | Efcavitch et al. |
| 2016/0168611 | A1 | 6/2016 | Efcavitch et al. |
| 2021/0198710 | A1 | 7/2021 | Milton et al. |
| 2021/0388432 | A1 | 12/2021 | Milton et al. |
| 2022/0177938 | A1 | 6/2022 | Milton et al. |
| 2022/0213537 | A1 | 7/2022 | Milton et al. |
| 2022/0396818 | A1 | 12/2022 | Milton et al. |

FOREIGN PATENT DOCUMENTS

| | | |
|---|---|---|
| AU | 2015248673 A1 | 11/2016 |
| CA | 2485218 A1 | 12/2003 |
| EP | 1181395 B1 | 4/2006 |
| EP | 1314783 B1 | 11/2008 |
| GB | 2559117 A | 8/2018 |
| WO | WO 2001/088173 A2 | 11/2001 |
| WO | WO 2003/100058 A2 | 12/2003 |
| WO | WO 2010/025310 A2 | 3/2010 |
| WO | WO 2011/150168 A1 | 12/2011 |
| WO | WO 2012/078312 A2 | 6/2012 |
| WO | WO 2014/064444 A1 | 5/2014 |
| WO | WO 2015/055981 A2 | 4/2015 |
| WO | WO 2015/110813 A1 | 7/2015 |
| WO | WO 2015/159023 A1 | 10/2015 |
| WO | WO 2015/176070 A1 | 11/2015 |
| WO | WO 2016/034807 A1 | 3/2016 |
| WO | WO 2016/128731 A1 | 8/2016 |
| WO | WO 2016/139477 A1 | 9/2016 |
| WO | WO 2017/009663 A1 | 1/2017 |
| WO | WO 2018/134616 A1 | 7/2018 |

(Continued)

OTHER PUBLICATIONS

Search Report for Application No. GB 1913041.8, dated Feb. 21, 2020.
International Search Report and Written Opinion for Application No. PCT/GB2020/052172, dated Dec. 15, 2020.
International Search Report and Written Opinion for Application No. PCT/GB2018/050165, dated Mar. 20, 2018.
International Preliminary Report on Patentability for Application No. PCT/GB2018/050165, dated Aug. 1, 2019.
International Search Report and Written Opinion for Application No. PCT/GB2019/051423, dated Sep. 20, 2019.

(Continued)

*Primary Examiner* — Kaijiang Zhang
(74) *Attorney, Agent, or Firm* — Wolf, Greenfield & Sacks, P.C.

(57) ABSTRACT

The invention relates to new methods for synthesising polynucleotide molecules according to a predefined nucleotide sequence. The invention also relates to methods for the assembly of synthetic polynucleotides following synthesis, as well as systems and kits for performing the synthesis and/or assembly methods.

20 Claims, 64 Drawing Sheets

Specification includes a Sequence Listing.

(56) References Cited

FOREIGN PATENT DOCUMENTS

| WO | WO 2019/140353 A1 | 7/2019 |
| WO | WO 2019/150134 A1 | 8/2019 |
| WO | WO 2019/224544 A1 | 11/2019 |

OTHER PUBLICATIONS

International Preliminary Report on Patentability for Application No. PCT/GB2019/051423, dated Dec. 3, 2020.
International Search Report and Written Opinion for Application No. PCT/GB2019/052035, dated Oct. 11, 2019.
International Preliminary Report on Patentability for Application No. PCT/GB2019/052035, dated Jan. 28, 2021.
International Search Report and Written Opinion for Application No. PCT/GB2019/052036, dated Oct. 14, 2019.
International Preliminary Report on Patentability for Application No. PCT/GB2019/052036, dated Jan. 28, 2021.
International Search Report and Written Opinion for Application No. PCT/GB2019/052037, dated Oct. 15, 2019.
International Preliminary Report on Patentability for Application No. PCT/GB2019/052037, dated Jan. 28, 2021.
Berger et al., Universal bases for hybridization, replication and chain termination. Nucleic Acids Res. Aug. 1, 2000;28(15):2911-4.
Chou et al., Recent Advances in Applications of Droplet Microfluidics. Micromachines Sep. 2, 2015;6(9):1249-71. https://doi.org/10.3390/mi6091249.
David et al., Chemistry of Glycosylases and Endonucleases Involved in Base-Excision Repair. Chem Rev. May 7, 1998;98(3):1221-1262.
Deangelis et al., Solid-phase reversible immobilization for the isolation of PCR products. Nucleic Acids Res. Nov. 25, 1995; 23(22): 4742-4743. doi: 10.1093/nar/23.22.4742.
Gañán-Calvo et al., Focusing capillary jets close to the continuum limit. Nature Physics. Sep. 2, 2007;3:737-42. https://doi.org/10.1038/nphys710.
Kosuri et al., Large-scale de novo DNA synthesis: technologies and applications. Nat Methods. May 2014;11(5):499-507. doi: 10.1038/nmeth.2918.
Minhaz Ud-Dean, A theoretical model for template-free synthesis of long DNA sequence. Syst Synth Biol. Dec. 2008;2(3-4):67-73. doi: 10.1007/s11693-009-9023-x. Epub Apr. 3, 2009.
Motea et al., Terminal deoxynucleotidyl transferase: the story of a misguided DNA polymerase. Biochim Biophys Acta. May 2010;1804(5):1151-66. doi: 10.1016/j.bbapap.2009.06.030. Epub Jul. 29, 2009.
Ponferrada-Marín et al., ROS1 5-methylcytosine DNA glycosylase is a slow-turnover catalyst that initiates DNA demethylation in a distributive fashion. Nucleic Acids Res. Jul. 2009;37(13):4264-74. doi: 10.1093/nar/gkp390. Epub May 13, 2009.
Quan et al., Parallel on-chip gene synthesis and application to optimization of protein expression. Nat Biotechnol. May 2011;29(5):449-52. doi: 10.1038/nbt.1847. Epub Apr. 24, 2011.
Ramadan et al., De novo DNA synthesis by human DNA polymerase lambda, DNA polymerase mu and terminal deoxyribonucleotidyl transferase. J Mol Biol. May 28, 2004;339(2):395-404.
Roy et al., Synthesis of DNA/RNA and their analogs via phosphoramidite and H-phosphonate chemistries. Molecules. Nov. 18, 2013;18(11):14268-84. doi: 10.3390/molecules181114268.
Schweitzer et al., Hydrophobic, Non-Hydrogen-Bonding Bases and Base Pairs in DNA. J Am Chem Soc. Feb. 22, 1995;117(7):1863-1872. doi: 10.1021/ja00112a001.
Tannous et al., Role of RNase H1 in DNA repair: removal of single ribonucleotide misincorporated into DNA in collaboration with RNase H2. Scientific Reports. 2015;5(9969). doi: 10.1038/screp09969. 11 pages.
Tian et al., Template-free, polymerase-free DNA polymerization. Chem Commun (Camb). Jun. 7, 2005;(21):2669-71. doi: 10.1039/b501132a. Epub Apr. 14, 2005.
Trevino et al., DNA microarrays: a powerful genomic tool for biomedical and clinical research. Mol Med. Sep.-Oct. 2007; 13(9-10): 527-541. EPub Jun. 11, 2007. doi: 10.2119/2006-00107.Trevino.
Woodman et al., Archaeal Hel308 domain V couples DNA binding to ATP hydrolysis and positions DNA for unwinding over the helicase ratchet. J Mol Biol. Dec. 14, 2007;374(5):1139-44. Epub Oct. 10, 2007.
Wu, Molecular Engineering of Novel Nucleotide Analogues for DNA Sequencing by Synthesis. PhD Thesis. Columbia University. 2008. 231 pages.
International Preliminary Report on Patentability for Application No. PCT/GB2020/052172, dated Mar. 24, 2022.

Version 3 Method

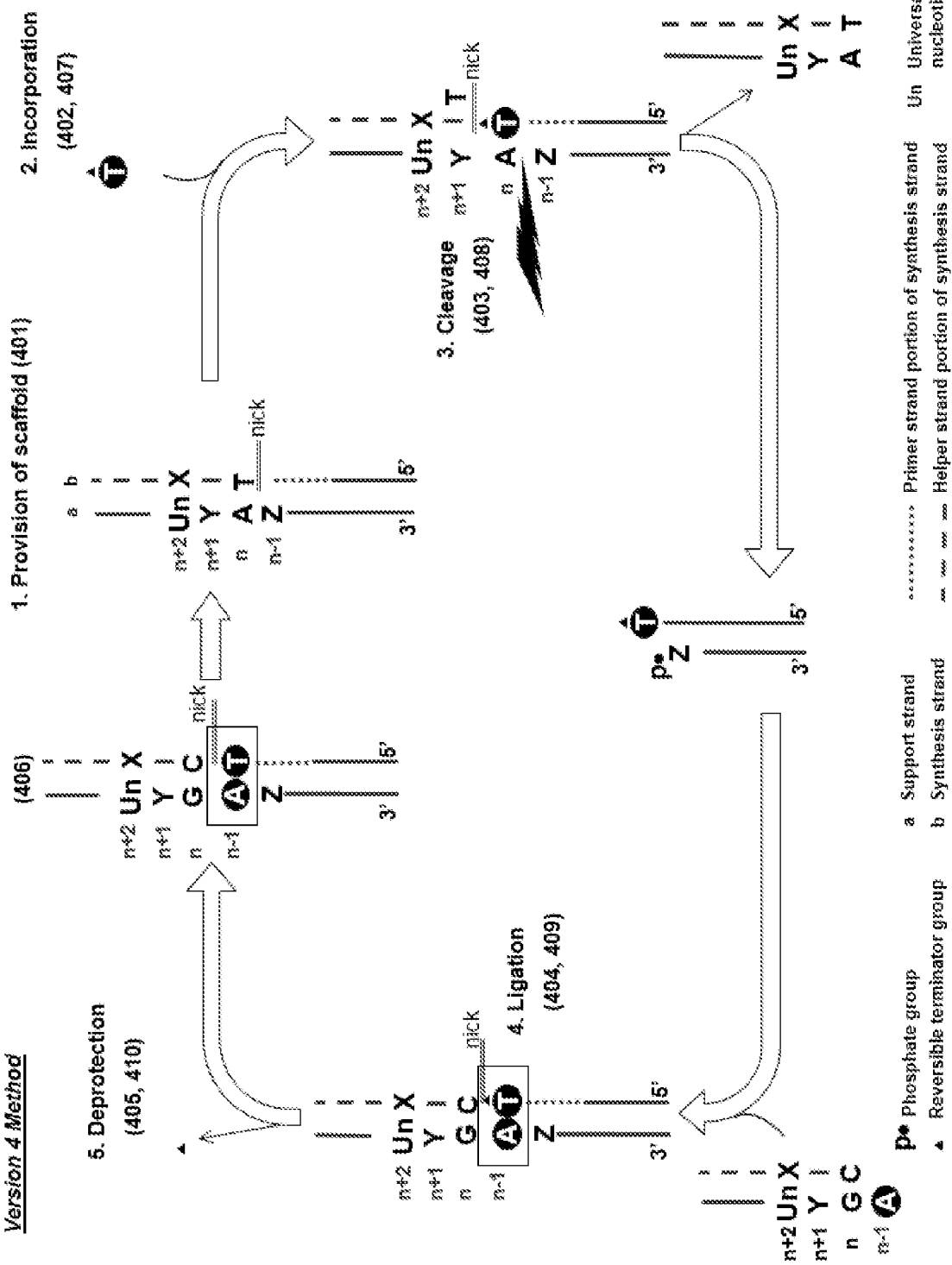

Version 5 Method a   Support strand  ·········· Primer strand portion of synthesis strand
b   Synthesis strand  — — — — Helper strand portion of synthesis strand
Un  Universal
    nucleotide Figure 4 j
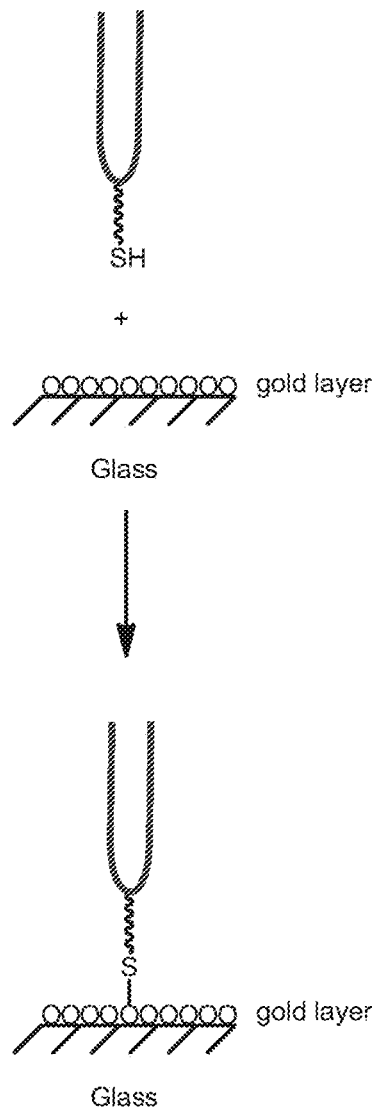
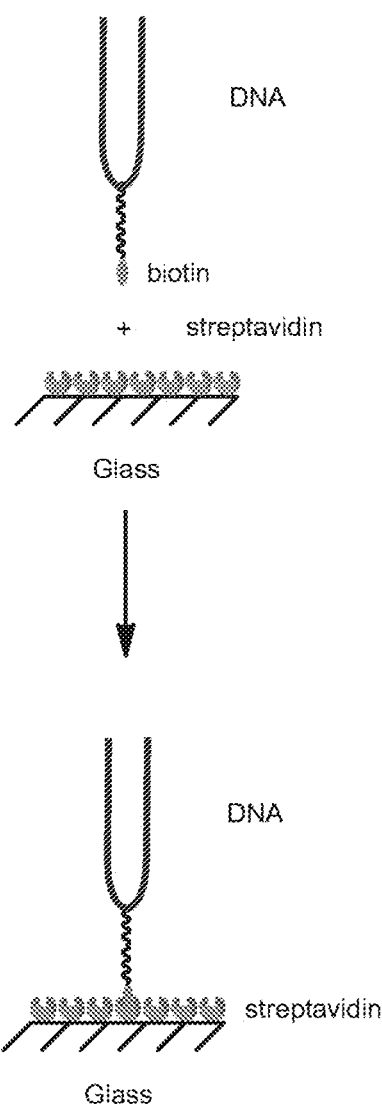

Figure 5a
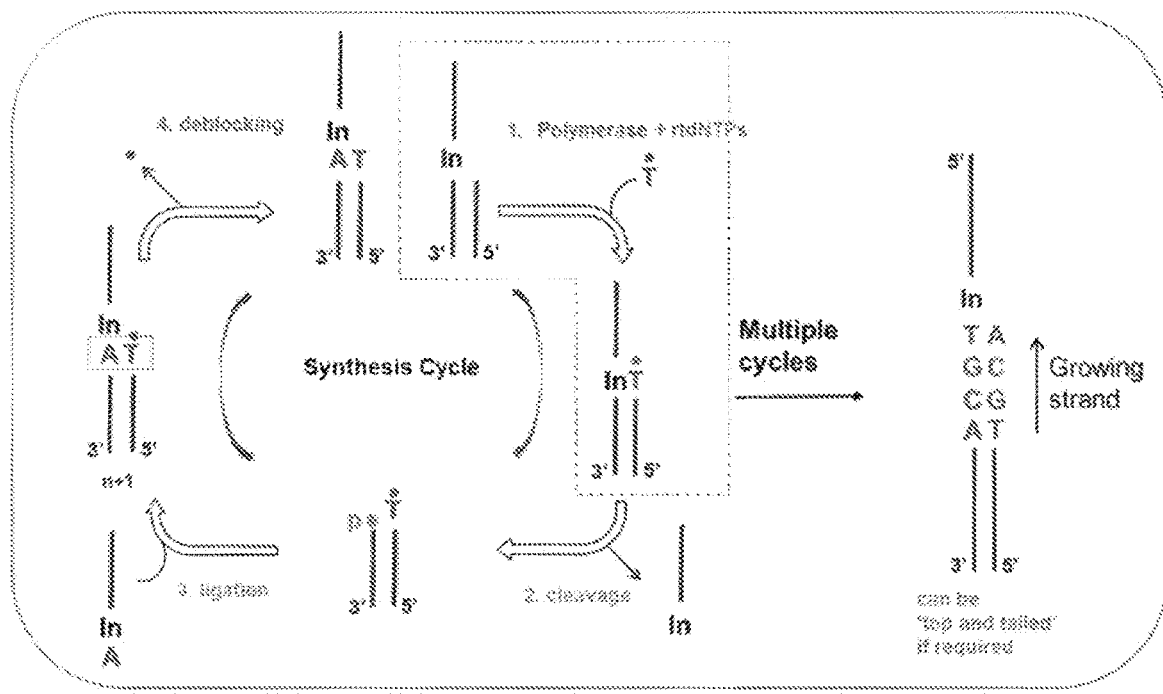
Figure 5b
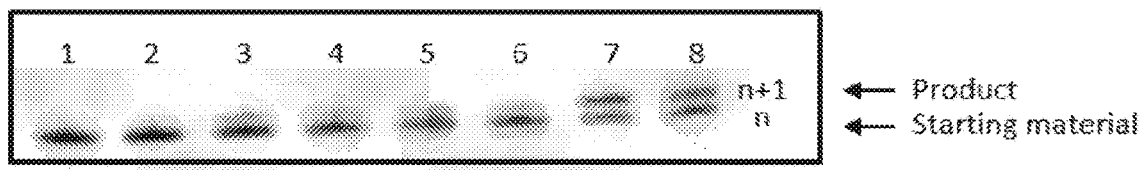
Figure 5c
| Lane no. | Incorporation at 50°C | DNA polymerase | conversion |
|---|---|---|---|
| 1 | 3'-O-allyl-dTTPs | Bst | <1% |
| 2 | 3'-O-azidomethyl-dTTPs | Bst | <1% |
| 3 | 3'-O-allyl-dTTPs | Deep Vent (exo-) | 5% |
| 4 | 3'-O-azidomethyl-dTTPs | Deep Vent (exo-) | 5% |
| 5 | 3'-O-allyl-dTTPs by | Therminator I | 8% |
| 6 | 3'-O-azidomethyl-dTTPs | Therminator I | 8% |
| 7 | 3'-O-allyl-dTTPs | Therminator IX | 55% |
| 8 | 3'-O-azidomethyl-dTTPs | Therminator IX | 48% |

Figure 5d

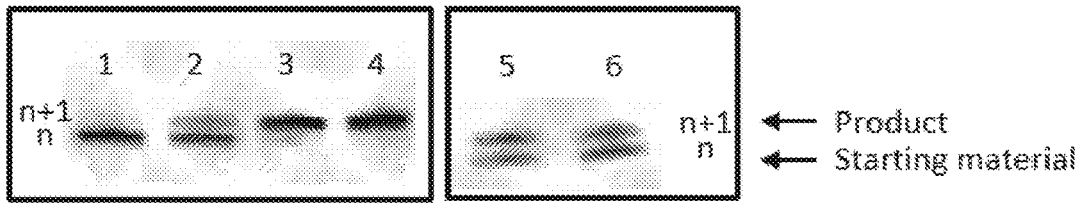

Figure 5e

| Lane No. | Incorporation | Enzyme | Temp. | Conversion |
|---|---|---|---|---|
| 1 | 3'-O-allyl-dTTPs | Therminator IX | 37 °C | <5% |
| 2 | 3'-O-azidomethyl-dTTPs | Therminator IX | 37 °C | 15% |
| 3 | 3'-O-allyl-dTTPs | Therminator IX | 50 °C | 55% |
| 4 | 3'-O-azidomethyl-dTTPs | Therminator IX | 50 °C | 48% |
| 5 | 3'-O-allyl-dTTPs | Therminator IX | 65 °C | >90% |
| 6 | 3'-O-azidomethyl-dTTPs | Therminator IX | 65 °C | >90% |

Figure 5f

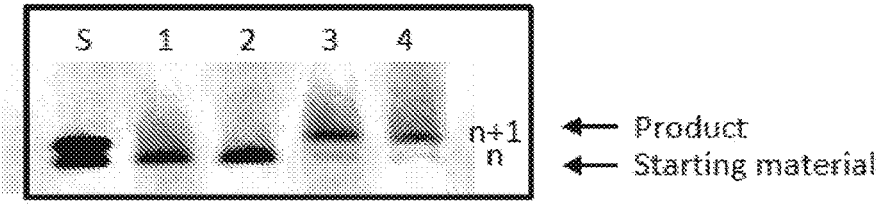

Figure 5g

| Lane No. | incorporation | Enzyme | Temp | 2mM $Mn^{2+}$ | conversion |
|---|---|---|---|---|---|
| 1 | 3'-O-allyl-dTTPs | Therminator IX | 65 °C | No | <1% |
| 2 | 3'-O-azidomethyl-dTTPs | Therminator IX | 65 °C | No | <1% |
| 3 | 3'-O-allyl-dTTPs | Therminator IX | 65 °C | Yes | >90% |
| 4 | 3'-O-azidomethyl-dTTPs | Therminator IX | 65 °C | Yes | >90% |

Figure 5h

| SEQ ID NO: | Oligonucleotide name | Sequence | Modification |
|---|---|---|---|
| 1 | Primer | 5'-GCGACAGGTGACTGCAGC-3' | TAMRA at 5'-end (attached to terminal guanine) |
| 2 | Template | 5'-CACATCACGTCGTAGTCXGCTGCAGTCACCTGTCGC-3' | X = 2'-deoxyinosine |

Figure 6c

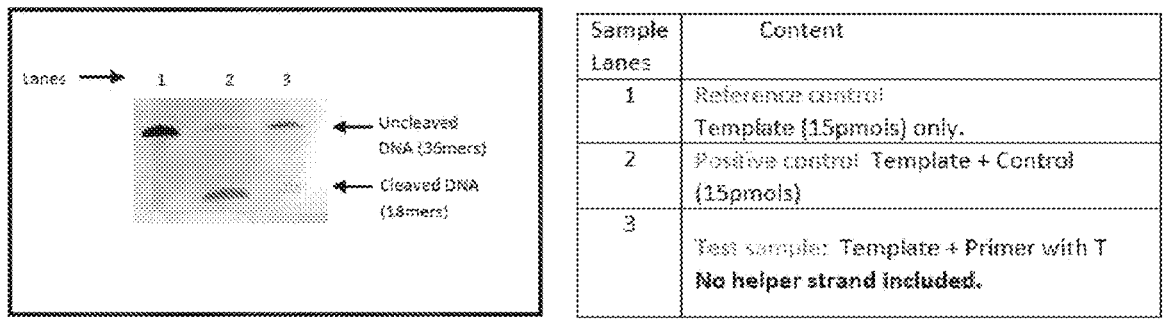

| Sample Lanes | Content |
|---|---|
| 1 | Reference control Template (15pmols) only. |
| 2 | Positive control Template + Control (15pmols) |
| 3 | Test sample: Template + Primer with T No helper strand included. |

Figure 6d

| Gel | Cleavage reaction combination | % Conversion of cleaved DNA without a helper strand |
|---|---|---|
| A | hAAG/ Chemical base | < 10 |
| B | hAAG/Endo VIII | < 7 |

Figure 6e

| SEQ ID NO: | Oligonucleotide name | Sequence | Modification |
|---|---|---|---|
| 3 | Template | 5'-CACATCACGTCGTAGTCXGCTGCAGTCACCTGTCGC-3' | TAMRA at 5'-end X = 2' deoxyinosine |
| 4 | Primer with T | 5'-GCGACAGGTGACTGCAGCT-3' | None |
| 5 | Control | 5'-GCGACAGGTGACTGCAGCTGACTACGACGTGATGTG-3' | None |

Figure 7a

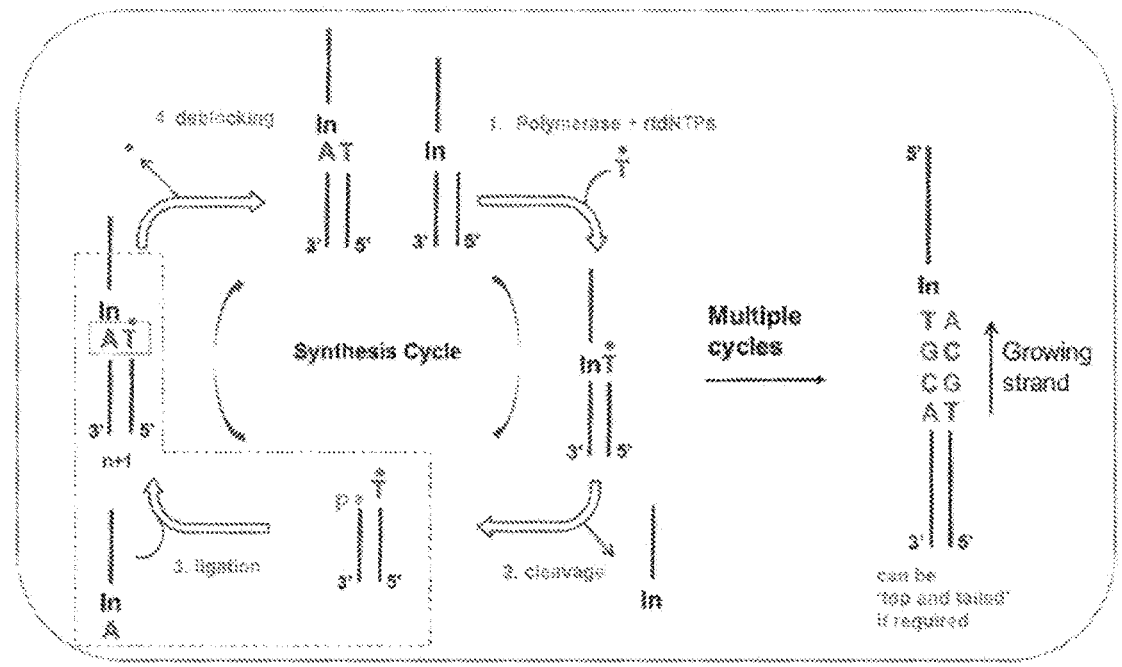

Figure 7b

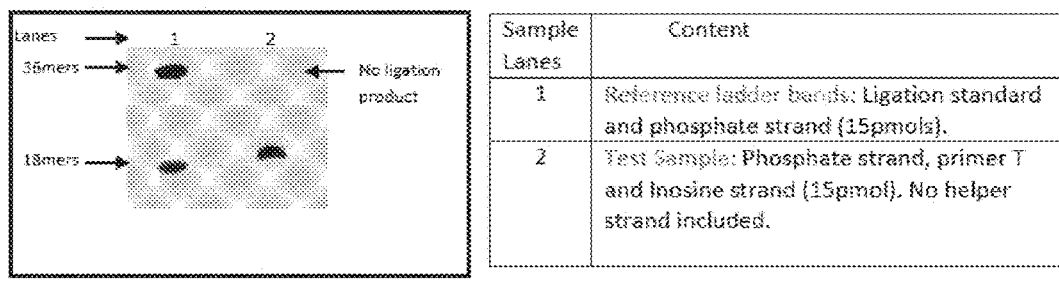

| Sample Lanes | Content |
|---|---|
| 1 | Reference ladder bands: Ligation standard and phosphate strand (15pmols). |
| 2 | Test Sample: Phosphate strand, primer T and Inosine strand (15pmol). No helper strand included. |

Figure 7c

| SEQ ID NO: | Oligonucleotide name | Sequence | Modification |
|---|---|---|---|
| 6 | Ligation standard | 5'-CACATCACGTCGTAGTXAGCTGCAGTCACCTGTCGC-3' | X = 2'-deoxyinosine |
| 7 | Phosphate strand | 5'-GCTGCAGTCACCTGTCGC-3' | TAMRA at 3'-end (attached to terminal cytosine), phosphate at 5' end |
| 8 | Primer with T | 5'-GCGACAGGTGACTGCAGCT-3' | None |
| 9 | Inosine strand | 5'-CACATCACGTCGTAGTXA-3' | X = 2'-deoxyinosine |

| SEQ ID NO: | Oligonucleotide name | Sequence | Modification |
|---|---|---|---|
| 10 | Primer | 5'-GCGACAGGTGACTGCAGC-3' | TAMRA at 5'-end (attached to terminal guanine) |
| 11 | Template | 5'-CACATCACGTCGTAGTCXGCTGCAGTCACCTGTCGC-3' | X = 2'-deoxyinosine |
| 12 | Helper strand | 5'-CGACTACGACGTGATGTG-3' | None |

| Sample Lanes | Content |
|---|---|
| 1 | Reference control<br>Template (15pmols) only. |
| 2 | Positive control<br>Template + Control (15pmols) |
| 3 | Test sample I:<br>Template + Primer with T<br>No helper strand included (15pmols) |
| 4 | Test Sample II :<br>Template + Primer with T + Helper strand (15pmols) |

Figure 9c

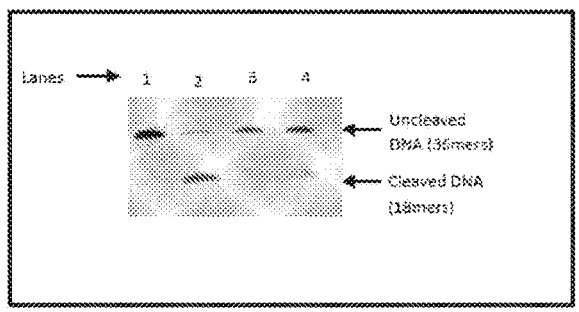

| Sample Lanes | Content |
|---|---|
| 1 | Reference control Template (15pmols) only. |
| 2 | Positive control Template + Control (15pmols) |
| 3 | Test sample I: Template + Primer with T No helper strand included. (15pmols) |
| 4 | Test Sample II: Template + Primer with T + Helper strand (15pmols). |

Figure 9d

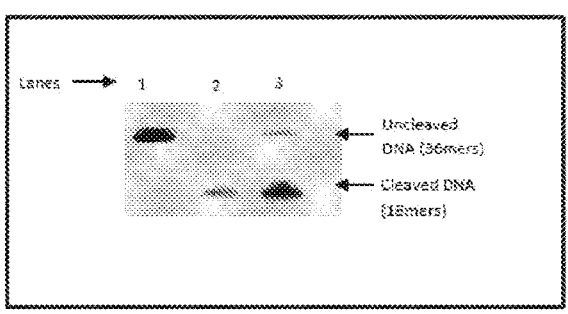

| Sample Lanes | Content |
|---|---|
| 1 | Reference control Template (15pmols) only. |
| 2 | Positive control Template + Control (15pmols) |
| 3 | Test Sample I: Template + Primer with T + Helper strand (15pmols). |

Figure 9e

| Gel | Cleavage reaction combination | % Conversion of cleaved DNA with a helper strand |
|---|---|---|
| A | hAAG/ Chemical base | 50 |
| B | hAAG/Endo VIII | < 10 |
| C | hAAG/Alternative chemical base | 90* |

Figure 9f

| SEQ ID NO: | Oligonucleotide name | Sequence | Modification |
|---|---|---|---|
| 13 | Template | 5'-CACATCACGTCGTAGTCXGCT GCAGTCACCTGTCGC-3' | TAMRA at 5'-end (attached to terminal cytosine), X = deoxyinosine |
| 14 | Primer with T | 5'-GCGACAGGTGACTGCAGCT-3' | None |
| 15 | Control | 5'-GCGACAGGTGACTGCAGCTGA CTACGACGTGATGTG-3' | None |
| 16 | Helper Strand | 5'-TGACTACGACGTGATGTG-3' | None |

Figure 10b

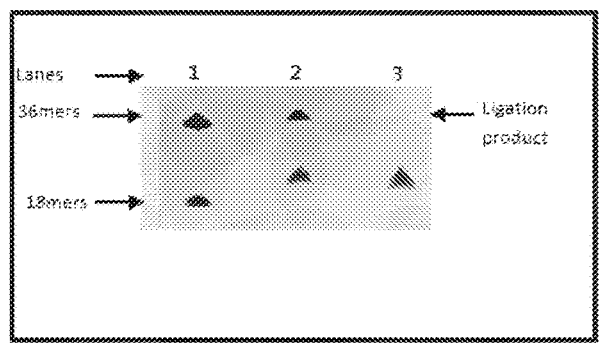

| Sample Lanes | Content |
|---|---|
| 1 | Reference ladder bands: Ligation standard and phosphate strand (15pmols). |
| 2 | Test Sample I: Phosphate strand, primer T and Inosine strand + With helper strand (15pmol) |
| 3 | Test Sample II: Phosphate strand, primer T and Inosine strand + without helper strand (15pmol) ( Sample after 1hr incubation |

Figure 10c

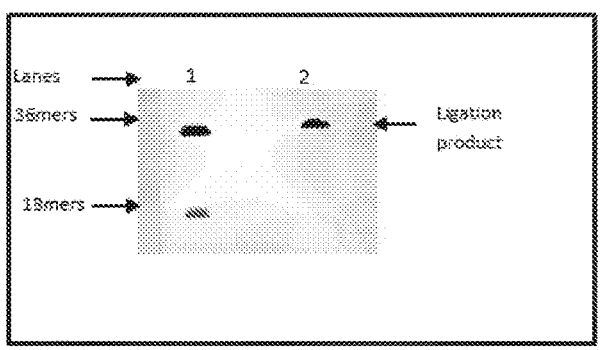

| Sample Lanes | Content |
|---|---|
| 1 | Reference ladder bands: Ligation standard and phosphate strand (15pmols). |
| 2 | Test Sample I: Phosphate strand, primer T and Inosine strand + With helper strand (15pmol) |

Figure 10d

| SEQ ID NO: | Oligonucleotide name | Sequence | Modification |
|---|---|---|---|
| 17 | Ligation standard | 5'-CACATCACGTCGTAGTXAGCTGCAGTCACCTGTCGC-3' | X = 2'-deoxyinosine |
| 18 | Phosphate strand | 5'-GCTGCAGTCACCTGTCGC-3' | TAMRA at 3'-end, (attached to terminal cytosine), phosphate at 5' end |
| 19 | Primer with T | 5'-GCGACAGGTGACTGCAGCT-3' | None |
| 20 | Inosine strand | 5'-CACATCACGTCGTAGTXA-3' | X = 2'-deoxyinosine |
| 21 | Helper strand | 5'-CACTACGACGTGATGTG-3' | None |

Figure 11g
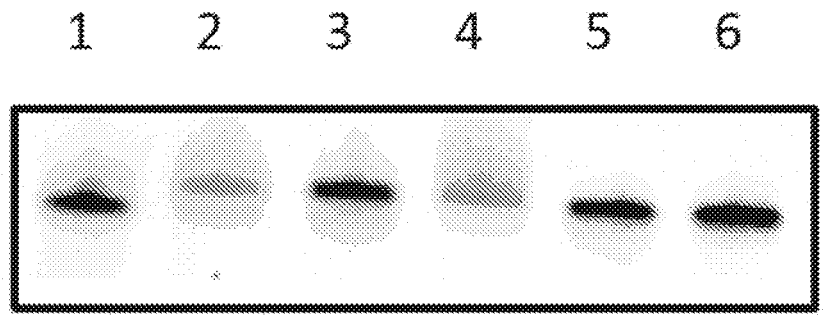
Figure 11h
|  | 0 min | 1 min | 2 min | 5 min | 10 min | 20 min |
|---|---|---|---|---|---|---|
| 27°C without $Mn^{2+}$ | 0 | 5 | 10 | 20 | 35 | 40 |
| 37°C without $Mn^{2+}$ | 0 | 30 | 58 | 90 | 90 | 90 |
| 47°C without $Mn^{2+}$ | 0 | 30 | 65 | 90 | 90 | 90 |
| 27°C with $Mn^{2+}$ | 0 | 70 | 85 | 92 | 95 | 95 |
| 37°C with $Mn^{2+}$ | 0 | 85 | 90 | >96 | >96 | >96 |
| 47°C with $Mn^{2+}$ | 0 | 85 | 90 | >96 | >96 | >96 |
Figure 11i
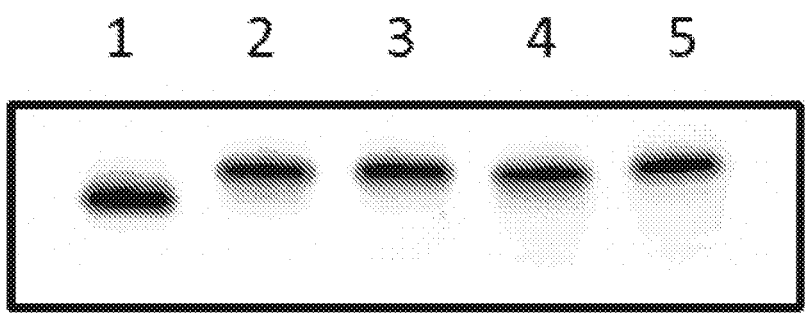

Figure 11j

| SEQ ID NO: | Oligonucleotide name | Sequence | Modification |
|---|---|---|---|
| 22 | Primer | 5'-GCGACAGGTGACTGCAGC-3' | TAMRA at 5'-end (attached to terminal guanine) |
| 23 | Template-A | 5'-CACATCACGTCGTAGTCXAGCTGCAGTCACCTGTCGC-3' | X = 2'-deoxyinosine |
| 24 | Template-G | 5'-CACATCACGTCGTAGTCXGGCTGCAGTCACCTGTCGC-3' | X = 2'-deoxyinosine |
| 25 | Template-T | 5'-CACATCACGTCGTAGTCXAGCTGCAGTCACCTGTCGC-3' | X = 2'-deoxyinosine |
| 26 | Template-C | 5'-CACATCACGTCGTAGTCXAGCTGCAGTCACCTGTCGC-3' | X = 2'-deoxyinosine |
| 27 | Helper strand-T | 5'-TCGACTACGACGTGATGTG-3' | None |
| 28 | Helper strand-C | 5'-CCGACTACGACGTGATGTG-3' | None |
| 29 | Helper strand-A | 5'-ACGACTACGACGTGATGTG-3' | None |
| 30 | Helper strand-G | 5'-GCGACTACGACGTGATGTG-3' | None |

| Sample Lanes | Content |
|---|---|
| 1 | Reference control: Template (15pmols) only. |
| 2 | Positive control: Template + Control (15pmols) |
| 3 | Test sample I: Template + Primer with T (15pmols) No helper strand included. |
| 4 | Test sample II: Template + Primer with T Helper strand included (15pmols). |

Figure 12c

| Cleavage reaction combination | % Conversion of cleaved DNA |
|---|---|
| Full length positive control | 80 |
| Presence of helper strand | >99 |
| Absence of helper strand | >99 |

Figure 12d

| SEQ ID NO: | Oligonucleotide name | Sequence | Modification |
|---|---|---|---|
| 31 | Template | 5'-CACATCACGTCGTAGTCXAGCTGCAGTCACCTGTCGC-3' | TAMRA at 5'-end (attached to terminal cytosine), X = deoxyinosine |
| 32 | Primer with T | 5'-GCGACAGGTGACTGCAGCT-3' | None |
| 33 | Control | 5'-GCGACAGGTGACTGCAGCTGACTACGACGTGATGTG-3' | None |
| 34 | Helper strand | 5'-TCGACTACGACGTGATGTG-3' | None |

| SEQ ID NO: | Oligonucleotide name | Sequence | Modification |
|---|---|---|---|
| 35 | Phosphate strand | 5'-GCTGCAGTCACCTGTCGC-3' | TAMRA at 3'-end (attached to terminal cytosine), phosphate at 5' end |
| 36 | Primer with T | 5'-GCGACAGGTGACTGCAGCT-3' | None |
| 37 | Inosine strand | 5'-CACATCACGTCGTAGTXGA-3' | X = 2'-deoxyinosine |
| 38 | Helper strand | 5'-CCACTACGACGTGATGTG-3' | None |

Figure 14h

| Incorporation | Deprotection by 50 mM TCEP | Deprotection by 300 mM TCEP |
|---|---|---|
| 3'-O-azidomethyl-dTTP | 50% | 95% |
| 3'-O-azidomethyl-dCTP | 20% | 95% |
| 3'-O-azidomethyl-dATP | Not tested | 95% |
| 3'-O-azidomethyl-dGTP | Not tested | 95% |

Figure 14i

| SEQ ID NO: | Oligonucleotide name | Sequence | Modification |
|---|---|---|---|
| 39 | Primer | 5'-GCGACAGGTGACTGCAGC-3' | TAMRA at 5'-end (attached to terminal cytosine) |
| 40 | Template-A | 5'-CACATCACGTCGTAGTCAGCTGCAGTCACCTGTCGC-3' | None |
| 41 | Template-G | 5'-CACATCACGTCGTAGTCGGCTGCAGTCACCTGTCGC-3' | None |
| 42 | Template-T | 5'-CACATCACGTCGTAGTCTGCTGCAGTCACCTGTCGC-3' | None |
| 43 | Template-C | 5'-CACATCACGTCGTAGTCCGCTGCAGTCACCTGTCGC-3' | None |

| SEQ ID NO: | Oligonucleotide name | Sequence | Modification |
|---|---|---|---|
| 44 | Dual hairpin model for incorporation | 5'-TCGACTACGACGTGACTTTTAGTCACGTCGTAGTCXAGCTGCAGTCACCTGCTGCTTYTTGCAGCAGGTGACTGCAGC-3' | X = 2'-deoxyinosine<br><br>Y = Tamra-dT |

Figure 16b

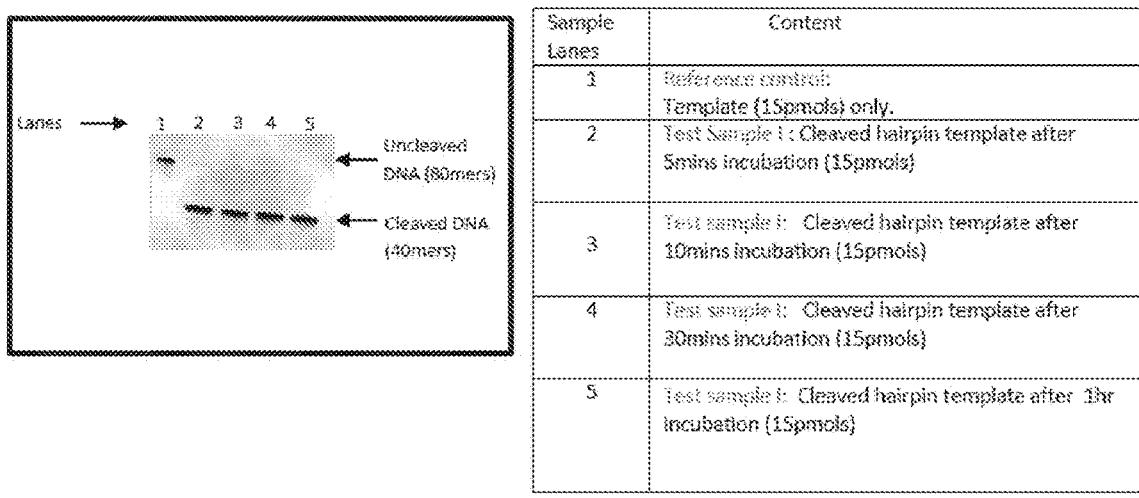

| Sample Lanes | Content |
|---|---|
| 1 | Reference control: Template (15pmols) only. |
| 2 | Test Sample 1: Cleaved hairpin template after 5mins incubation (15pmols) |
| 3 | Test sample 1: Cleaved hairpin template after 10mins incubation (15pmols) |
| 4 | Test sample 1: Cleaved hairpin template after 30mins incubation (15pmols) |
| 5 | Test sample 1: Cleaved hairpin template after 1hr incubation (15pmols) |

Figure 16c

| SEQ ID NO: | Oligonucleotide name | Sequence | Modification |
|---|---|---|---|
| 45 | Dual hairpin model for incorporation | 5'- TCGACTACGACGTGACTTTTAGTCAC GTCGTAGTCXAGCTGCAGTCACCTGCTG CTTYTTGCAGCAGGTGACTGCAGCT-3' | X = 2'-deoxyinosine<br><br>Y = Tamra-dT |

Figure 17b

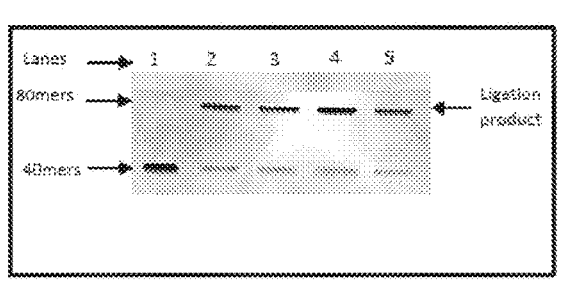

| Sample Lanes | Content |
|---|---|
| 1 | Reference control: Phosphate Template (15pmols) only. |
| 2 | Test Sample 1: Ligated hairpin product after 1min incubation (15pmols) |
| 3 | Test sample 1: Ligated hairpin product after 2min incubation (15pmols) |
| 4 | Test sample 1: Ligated hairpin product after 3mins incubation (15pmols) |
| 5 | Test sample 1: Ligated hairpin product after 4mins incubation (15pmols) |

Figure 17c

| SEQ ID NO: | Oligonucleotide name | Sequence | Modification |
|---|---|---|---|
| 46 | Phosphate hairpin | 5'-GCTGCAGTCACCTGCTGCTTYTTGCAGCAGGTGACTGCAGCT-3' | Y = Tamra-dT phosphate |
| 47 | Inosine Hairpin | 5'- CCGACTACGACGTGACTTTTAGTCACGTCGTAGTCXGA-3' | X = 2-deoxyinosine |

Figure 18c

| SEQ ID NO: | Oligonucleotide name | Sequence | Modification |
|---|---|---|---|
| 48 | Double hairpin model | 5'- TCGACTACGACGTGACTTTTAGTCAC GTCGTAGTCXAGCTGCAGTCACCTGCTGC TTYTTGCAGCAGGTGACTGCAGC-3' | X = 2'-deoxyinosine  Y = Tamra-dT |
| 49 | Strand for ligation | 5'- CCGACTACGACGTGACTTTTAGTCAC GTCGTAGTCXGA-3' | X = 2'-deoxyinosine |

| SEQ ID NO: | Oligonucleotide name | Sequence | Modification |
|---|---|---|---|
| 50 | Single hairpin model for incorporation | 5'- AGTCACGTCGTAGTCXAGCTGCAGTC ACCTGCTGCTTYTTGCAGCAGGTGACTGCAG C-3' | X = 2'-deoxyinosine<br><br>Y = Tamra-dT |
| 51 | Helper strand | 5'- TCGACTACGACGTGACT-3' | |
| 52 | Strand for ligation | 5'- AGTCACGTCGTAGTCXGA | X = 2'-deoxyinosine |
| 53 | Helper strand for ligation | 5'- CCGACTACGACGTGACT-3' | |

| SEQ ID NO: | Oligonucleotide name | Sequence | Modification |
|---|---|---|---|
| 54 | Double hairpin model | 5'- CGACTACGACGTGACTTTTAGTCAC GTCGTAGTCXAGCTGCAGTCACCTGCTGC TTYTTGCAGCAGGTGACTGCAGCT-3' | X = 2'-deoxyinosine<br><br>Y = Tamra-dT |
| 55 | Strand for ligation | 5'- CGACTACGACGTGACTTTTAGTCAC GTCGTAGTCXAA-3' | X = 2'-deoxyinosine |

Figure 21c

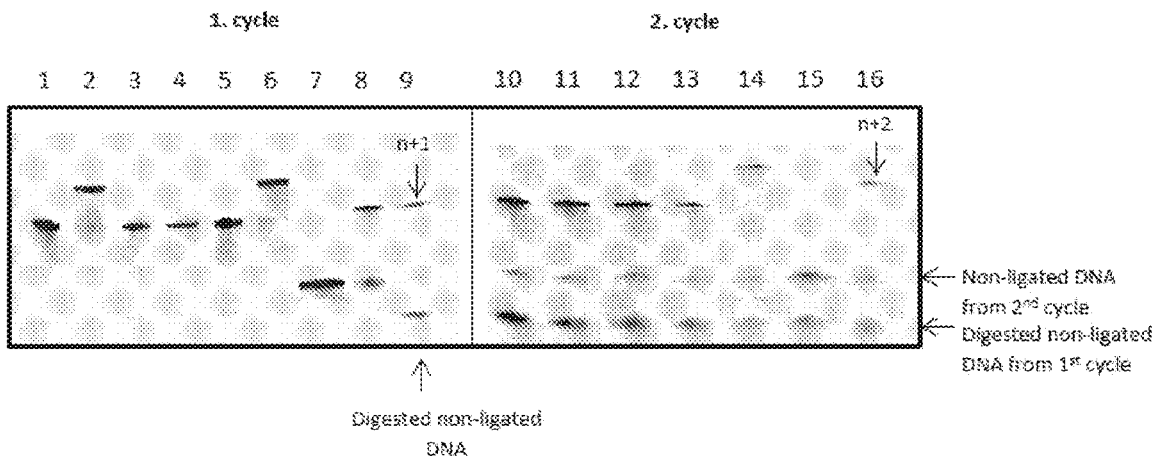

Figure 21d

| SEQ ID NO: | Oligonucleotide name | Sequence | Modification |
|---|---|---|---|
| 56 | Double hairpin model | 5'- CGACTACGACGTGACTTTTAGTCAC GTCGTAGTCXAGCTGCAGTCACCTGCYG CTTZTTGCAGCAGGTGACTGCAGCT-3' | X = 2'-deoxyinosine Y = Tamra-dT Z = Biotin-dT |
| 57 | Strand for ligation in the 1st cycle | 5'- CCGACTACGACGTGACTTTTAGTCAC GTCGTAGTCXGA-3' | X = 2'-deoxyinosine |
| 58 | Strand for ligation in the 2nd cycle | 5'- ACGAGTGACCTGGTTTTTTTTTTTTTT TTTTTTTTTTTTTTTTTTTACCAGGTCACT CXTG-3' | X = 2'-deoxyinosine |

| SEQ ID NO: | Oligonucleotide name | Sequence | Modification |
|---|---|---|---|
| 59 | Single hairpin model | 5'-AGTCACGTCGTAGTCXAGCTGCAGTCACCTGCYGCTTZTTGCAGCAGGTGACTGCAGC-3' | X = 2'-deoxyinosine<br>Y = Tamra-dT<br>Z = Biotin-dT |
| 60 | Inosine strand for ligation | 5'- AGTCACGTCGTAGTCXAA-3' | X = 2'-deoxyinosine |
| 51 | Helper strand for ligation | 5'- TCGACTACGACGTGACT-3' | |

Figure 33a

| Sample ID | Sequence | SEQ ID NO: |
|---|---|---|
| A (BRAPA control) | 5'-Alexa647-AGTCACGTCGTAGTCIAGCTGCAGTCACCTGCTGCTTTTT*T*T*T*T*T*TTTTGCAGCAGGTGACTGCAGC | SEQ ID NO: 61 |
| B (BRAPA modified 1) | 5'-Alexa647-AGTCACGTCGTAGTCIAGCTGCAGTCACCTGCTGCTTTTT*T*T*T*T*T*TTTTGCAGCAGGTGACTGCAGC | SEQ ID NO: 61 |
| C (BRAPA modified 2) | 5'-Alexa647-AGTCACGTCGTAGTCIAGCTGCAGTCACCTGCTGCTTTTT*T*T*T*T*T*TTTTGCAGCAGGTGACTGCAGC | SEQ ID NO: 61 |
| D (Oligomer control) | 5'-Alexa647-AGTCACGTCGTAGTCIAGCTGCAGTCACCTGCTGCTTTTTTTTTTTTTTGCAGCAGGTGACTGCAGC | SEQ ID NO: 62 |
| * = phosphorothioate bond; I = 2'-deoxyinosine | | |

Figure 33b

| Sample ID | Sequence | SEQ ID NO: |
|---|---|---|
| A (BRAPA control) | 5'-Alexa647-AGTCACGTCGTAGTCIAGCTGCAGTCACCTGCTGCTTZTTGCAGCAGGTGACTGCAGC-3' | SEQ ID NO: 63 |
| B (BRAPA modified 1) | 5'-Alexa647-AGTCACGTCGTAGTCIAGCTGCAGTCACCTGCTGCTTZTTGCAGCAGGTGACTGCAGC-3' | SEQ ID NO: 63 |
| C (BRAPA modified 2) | 5'-Alexa647-AGTCACGTCGTAGTCIAGCTGCAGTCACCTGCTGCTTZTTGCAGCAGGTGACTGCAGC-3' | SEQ ID NO: 63 |
| D (Oligomer control) | 5'-Alexa647-AGTCACGTCGTAGTCIAGCTGCAGTCACCTGCTGCTTYTTGCAGCAGGTGACTGCAGC-3' | SEQ ID NO: 64 |
| Z = 5''-thiophosphate-Sp9-Sp9-Sp9-5-methylC, Y = 5''-phosphate-Sp9-Sp9-Sp9-5-methylC; Sp9 = Spacer 9; I = 2'-deoxyinosine | | |

Figure 38a

| Sample ID | Sample description (experimental outcome) | Cleavage step | Ligation step |
|---|---|---|---|
| A (positive) | Cleavage (+)<br>Ligation (+) | + inosine<br>+ Endonuclease V | + helper strand<br>+ Ligase |
| B (ligation negative control) | Cleavage (+)<br>Ligation (-) | + inosine<br>+ Endonuclease V | + helper strand<br>- Ligase |
| C (cleavage negative control 1) | Cleavage (-)<br>Ligation (N/A) | + inosine<br>- Endonuclease V | N/A |
| D (cleavage negative control 2) | Cleavage (-)<br>Ligation (N/A) | - inosine<br>+ Endonuclease V | N/A |

Figure 38b

| Sample ID | Sequence | SEQ ID NO: |
|---|---|---|
| A (positive samples) | 5'-Alexa647-AGTCACGTCGTAGTCIAGCTGCAGTCACCTGCTGCTTZTTGCAGCAGGTGACTGCAGCT-3' | SEQ ID NO: 65 |
| B (ligation negative control) | 5'-Alexa647-AGTCACGTCGTAGTCIAGCTGCAGTCACCTGCTGCTTZTTGCAGCAGGTGACTGCAGCT-3' | SEQ ID NO: 65 |
| C (cleavage negative control 1) | 5'-Alexa647-AGTCACGTCGTAGTCIAGCTGCAGTCACCTGCTGCTTZTTGCAGCAGGTGACTGCAGCT-3' | SEQ ID NO: 65 |
| D (cleavage negative control 2) | 5'-Alexa647-AGTCACGTCGTAGTCGAGCTGCAGTCACCTGCTGCTTZTTGCAGCAGGTGACTGCAGCT-3' | SEQ ID NO: 66 |
| Z = 5''-thiophosphate-Sp9-Sp9-Sp9-5-methylC; Sp9 = Spacer 9;<br>I = 2'-deoxyinosine | | |

| DNA | Sequence | SEQ ID NO: |
|---|---|---|
| Inosine strand | 5'-Alexa647-AGTCACGTCGTAGTCIAA-3' | SEQ ID NO: 67 |
| Helper strand | 5'-TCGACTACGACGTGACT-3' | SEQ ID NO: 51 |
| I = 2'-deoxyinosine | | |

METHODS AND REAGENTS FOR SYNTHESISING POLYNUCLEOTIDE MOLECULES

RELATED APPLICATIONS

This Application is a continuation of U.S. application Ser. No. 16/479,141, filed Jul. 18, 2019 which is a National Stage filing under 35 U.S.C. 371 of international application number PCT/GB2018/050165, filed Jan. 19, 2018, which claims the benefit of United Kingdom application number 1700937.4, filed Jan. 19, 2017, each of which is herein incorporated by reference in its entirety.

FIELD OF THE INVENTION

The invention relates to new methods for synthesising polynucleotide molecules according to a predefined nucleotide sequence. The invention also relates to methods for the assembly of synthetic polynucleotides following synthesis, as well as systems and kits for performing the synthesis and/or assembly methods.

BACKGROUND TO THE INVENTION

Two primary methods currently exist for the synthesis and assembly of polynucleotide molecules, particularly DNA.

Phosphoramidite chemistry is a synthetic approach that assembles monomers of chemically activated T, C, A or G into oligonucleotides of approximately 100/150 bases in length via a stepwise process. The chemical reaction steps are highly sensitive and the conditions alternate between fully anhydrous (complete absence of water), aqueous oxidative and acidic conditions (Roy and Caruthers, Molecules, 2013, 18, 14268-14284). If the reagents from the previous reaction step have not been completely removed this will be detrimental to future steps of synthesis. Accordingly, this synthesis method is limited to the production of polynucleotides of length of approximately 100 nucleotides.

The polymerase synthetic approach uses a polymerase to synthesise a complementary strand to a DNA template using T, C, A and G triphosphates. The reaction conditions are aqueous and mild and this approach can be used to synthesise DNA polynucleotides which are many thousands of bases in length. The main disadvantage of this method is that single- and double-stranded DNA cannot be synthesised de novo by this method, it requires a DNA template from which a copy is made. (Kosuri and Church, Nature Methods, 2014, 11, 499-507).

Thus previous methods cannot be used to synthesise double-stranded DNA de novo without the aid of a pre-existing template molecule which is copied.

The inventors have developed new methodologies by which single- and double-stranded polynucleotide molecules can be synthesised de novo in a stepwise manner without the need to copy a pre-existing template molecule. Such methods also avoid the extreme conditions associated with phosphoramidite chemistry techniques and in contrast are carried out under mild, aqueous conditions around neutral pH. Such methods also enable de novo synthesis of single- or double-stranded polynucleotide molecules with a potential $10^8$ improvement on current synthesis methods with nucleotide lengths of >100 mers to full genomes, providing a wide range of possibly applications in synthetic biology.

SUMMARY OF THE INVENTION

The invention provides an in vitro method of synthesising a double-stranded polynucleotide molecule having a predefined sequence, the method comprising performing cycles of synthesis wherein in each cycle a first polynucleotide strand is extended by the incorporation of a nucleotide of the predefined sequence, and then the second polynucleotide strand which is hybridized to the first strand is extended by the incorporation of a nucleotide thereby forming a nucleotide pair with the incorporated nucleotide of the first strand. Preferably, the methods are for synthesising DNA.

In any of the methods of the invention described herein the methods may provide for the synthesis of a single-stranded polynucleotide molecule wherein following synthesis of the double-stranded polynucleotide molecule having a predefined sequence one strand of the double-stranded polynucleotide molecule is removed, or copied and/or amplified, to provide the single-stranded polynucleotide molecule.

In any of the methods of the invention described herein the methods provide for the synthesis of a double-stranded or single-stranded oligonucleotide. Thus all references herein to the synthesis of a double-stranded polynucleotide using any of the methods of the invention apply mutatis mutandis to the synthesis of a double-stranded oligonucleotide.

In methods of the invention each cycle may comprise extending the first strand by incorporating the nucleotide of the predefined sequence together with an attached reversible blocking group followed by extending the second strand, wherein the reversible blocking group is removed before or after the second strand is extended. In any such method, in each cycle the nucleotides may be incorporated into a scaffold polynucleotide.

The invention provides a method as described above and herein, wherein each cycle comprises:

(1) providing a scaffold polynucleotide;
(2) incorporating into the scaffold polynucleotide by the action of a polymerase a nucleotide of the predefined sequence, the nucleotide comprising a reversible terminator group which prevents further extension by polymerase;
(3) cleaving the scaffold polynucleotide at a cleavage site;
(4) ligating a ligation polynucleotide to the cleaved scaffold polynucleotide, the ligation polynucleotide comprising a partner nucleotide for the nucleotide of the predefined sequence of (2), wherein upon ligation the nucleotide of the predefined sequence pairs with the partner nucleotide; and
(5) removing the reversible terminator group from the nucleotide of the predefined sequence of (2).

In methods involving a scaffold polynucleotide the scaffold polynucleotide may be provided comprising a synthesis strand and a support strand hybridized thereto, wherein the synthesis strand comprises a primer strand portion and a helper strand portion. In any such methods the helper strand portion may be removed from the scaffold polynucleotide prior to any one, more or all steps of incorporating into the scaffold polynucleotide the nucleotide of the predefined sequence.

In any such method involving a scaffold polynucleotide the synthesis strand may be the first strand and the support strand may be the second strand.

In any such method the support strand may be extended by ligating to the support strand a ligation polynucleotide, wherein in each cycle of synthesis the ligation polynucleotide comprises the nucleotide forming the nucleotide pair with the predefined nucleotide incorporated into the first strand in that cycle.

The ligation polynucleotide may be single-stranded or double-stranded. Preferably, the ligation polynucleotide is double-stranded.

In methods wherein the ligation polynucleotide is double-stranded, the ligation polynucleotide may preferably comprise a support strand and a helper strand. The helper strand may be removed from the scaffold polynucleotide before the step of incorporating into the scaffold polynucleotide a nucleotide of the predefined sequence in the next synthesis cycle, in such methods the helper strand is removed after the ligation step.

The invention provides a method as described above, wherein step (1) comprises providing a scaffold polynucleotide comprising a synthesis strand and a support strand hybridized thereto, wherein the synthesis strand comprises a primer strand portion, and the support strand comprises a universal nucleotide; wherein step (3) comprises cleaving the scaffold polynucleotide at a cleavage site, the site defined by a sequence comprising the universal nucleotide in the support strand, wherein cleavage comprises cleaving the support strand and removing the universal nucleotide; and wherein in step (4) the ligation polynucleotide comprises a support strand comprising a universal nucleotide which contributes to/defines a cleavage site for use in the next cycle, and wherein the ligation polynucleotide is ligated to the support strand of the cleaved scaffold polynucleotide.

The invention provides a method as described above, comprising:
(1) providing a scaffold polynucleotide comprising a synthesis strand and a support strand hybridized thereto, wherein the synthesis strand comprises a primer strand portion and a helper strand portion separated by a single-strand break, and the support strand comprises a universal nucleotide;
(2) incorporating a first nucleotide of the predefined sequence into the synthesis strand by the action of polymerase, the first nucleotide comprising a reversible terminator group which prevents further extension by polymerase;
(3) cleaving the scaffold polynucleotide at a cleavage site, the site defined by a sequence comprising the universal nucleotide in the support strand, wherein cleavage comprises cleaving the support strand and removing the universal nucleotide to provide in the synthesis strand an overhanging end comprising the first nucleotide;
(4) ligating a double-stranded ligation polynucleotide to the cleaved scaffold polynucleotide, the ligation polynucleotide comprising a support strand, a helper strand and a complementary ligation end, the ligation end comprising in the support strand a universal nucleotide and a partner nucleotide for the first nucleotide (which overhangs the helper strand), and in the helper strand a terminal nucleotide lacking a phosphate group, wherein upon ligation of the support strand of the ligation polynucleotide and the support strand of the cleaved scaffold polynucleotide first nucleotide pairs with the partner nucleotide,
(5) removing the reversible terminator group from the first nucleotide;
(6) incorporating the next nucleotide of the predefined nucleotide sequence into the synthesis strand of the scaffold polynucleotide by the action of polymerase, the next nucleotide comprising a reversible terminator group which prevents further extension by polymerase;
(7) cleaving the scaffold polynucleotide at a cleavage site, the site defined by a sequence comprising a universal nucleotide in the support strand, wherein cleavage comprises cleaving the support strand and removing the universal nucleotide to provide in the synthesis strand an overhanging end comprising the next nucleotide;
(8) ligating a double-stranded ligation polynucleotide to the cleaved scaffold polynucleotide, the ligation polynucleotide comprising a support strand, a helper strand and a complementary ligation end, the ligation end comprising in the support strand a universal nucleotide and a partner nucleotide for the next nucleotide which overhangs the helper strand, and in the helper strand a terminal nucleotide lacking a phosphate group, wherein upon ligation of the support strand of the ligation polynucleotide and the support strand of the cleaved scaffold polynucleotide the next nucleotide pairs with the partner nucleotide;
(9) removing the reversible terminator group from the next nucleotide; and
(10) repeating steps 6 to 9 multiple times to provide the double-stranded polynucleotide having a predefined nucleotide sequence.

In any such method in a given synthesis cycle the universal nucleotide occupies position n in: (a) the support strand of the scaffold polynucleotide in steps 1 and 6, wherein position n is the nucleotide position in the support strand which is opposite the position in the synthesis strand which will be occupied by the nucleotide of the predefined sequence upon its incorporation in that cycle, and (b) the support strand of the ligation polynucleotide in steps 4 and 8, wherein position n is the nucleotide position in the support strand which is opposite the position in the synthesis strand which will be occupied by the next nucleotide of the predefined sequence upon its incorporation in the next synthesis cycle; wherein position n−1 is the next nucleotide position in the support strand relative to the position occupied by the universal nucleotide in the direction distal to the helper strand/proximal to the primer strand; and wherein the support strand of the scaffold polynucleotide is cleaved between positions n and n−1 in steps 3 and 7.

Alternatively, in any such method in a given synthesis cycle the universal nucleotide occupies position n+1 in: (a) the support strand of the scaffold polynucleotide in steps 1 and 6, wherein position n is the nucleotide position in the support strand which is opposite the position in the synthesis strand which will be occupied by the nucleotide of the predefined sequence upon its incorporation in that cycle, and (b) the support strand of the ligation polynucleotide in steps 4 and 8, wherein position n is the nucleotide position in the support strand which is opposite the position in the synthesis strand which will be occupied by the next nucleotide of the predefined sequence upon its incorporation in the next synthesis cycle; wherein position n−1 is the next nucleotide position in the support strand relative to position n in the direction distal to the helper strand/proximal to the primer strand, and wherein position n+1 is the next nucleotide position in the support strand relative to position n in the direction proximal to the helper strand/distal to the primer strand; and wherein the support strand of the scaffold polynucleotide is cleaved between positions n and n−1 in steps 3 and 7.

Alternatively still, in any such method in a given synthesis cycle the universal nucleotide occupies position n in: (a) the support strand of the scaffold polynucleotide in steps 1 and 6, wherein position n is the nucleotide position in the support strand which is opposite the position in the synthesis strand which will be occupied by the nucleotide of the predefined sequence upon its incorporation in that cycle, and (b) the support strand of the ligation polynucleotide in steps 4 and 8, wherein position n is the nucleotide position in the support strand which is opposite the position in the synthesis strand which will be occupied by the next nucleotide of the predefined sequence upon its incorporation in the next synthesis cycle; wherein position n−1 is the next nucleotide position in the support strand relative to the position occupied by the universal nucleotide in the direction distal to the helper strand/proximal to the primer strand, and wherein position n−2 is the next nucleotide position in the support strand relative to position n−1 in the direction distal to the helper strand/proximal to the primer strand; and wherein the support strand of the scaffold polynucleotide is cleaved between positions n−1 and n−2 in steps 3 and 7.

In any such method described above and herein wherein the universal nucleotide occupies position n and wherein the support strand of the scaffold polynucleotide is cleaved between positions n and n−1, performance of the method may comprise:
   a) in steps (1)/(6) the universal nucleotide in the support strand is positioned opposite the terminal nucleotide of the helper strand adjacent the single-strand break and is paired therewith (position n);
   b) in step (2)/(6) the first/next nucleotide is incorporated into the synthesis strand at a position opposite the universal nucleotide in the support strand (position n), whereupon the first/next nucleotide pairs with the universal nucleotide in place of the terminal nucleotide of the helper strand;
   c) in step (3)/(7) the support strand is cleaved at a position between the universal nucleotide position (position n) and the nucleotide next to the universal nucleotide position in the support strand (position n−1, in the direction distal to the helper strand/proximal to the primer strand), wherein cleavage generates a single-nucleotide overhang in the scaffold polynucleotide comprising the first/next nucleotide overhanging the support strand; and
   d) in step (4)/(8), the ligation end of the ligation polynucleotide comprises a single-nucleotide overhang wherein:
      i. the universal nucleotide in the support strand is positioned opposite the terminal nucleotide of the helper strand and is paired therewith;
      ii. the universal nucleotide is positioned next to the terminal nucleotide of the support strand (position n);
      iii. the terminal nucleotide of the support strand (position n−1) overhangs the terminal nucleotide of the helper strand and is the partner nucleotide for the first/next nucleotide of step (2)/(6).

In any such method described above and herein wherein the universal nucleotide occupies position n+1 and wherein the support strand of the scaffold polynucleotide is cleaved between positions n and n−1, performance of the method may comprise:
   a) in step (1) the scaffold polynucleotide is provided in the support strand with a nucleotide (position n) which is the partner nucleotide for the first nucleotide of step (2) and is paired with the terminal nucleotide of the helper strand, and the universal nucleotide in the support strand is positioned next to the partner nucleotide (position n+1, in the direction proximal to the helper strand/distal to the primer strand);
   b) in step (2)/(6) the first/next nucleotide is incorporated into the synthesis strand at the position opposite the partner nucleotide in the support strand (position n), whereupon the first/next nucleotide pairs with the partner nucleotide in place of the terminal nucleotide of the helper strand;
   c) in step (3)/(7) the support strand is cleaved at a position between the first nucleotide (position n) and the second nucleotide (position n−1) from the universal nucleotide in the support strand in the direction distal to the helper strand/proximal to the primer strand, wherein cleavage removes the universal nucleotide and creates a single-nucleotide overhang in the scaffold polynucleotide comprising the first/next nucleotide overhanging the support strand;
   d) in step (4)/(8), the complementary ligation end of the ligation polynucleotide comprises a single-nucleotide overhang wherein:
      i. the universal nucleotide in the support strand is positioned opposite the penultimate nucleotide of the helper strand (position n+1) and is paired therewith;
      ii. the universal nucleotide is positioned next to the penultimate nucleotide of the support strand (position n);
      iii. the penultimate nucleotide of the support strand is paired with the terminal nucleotide of the helper strand and is a partner nucleotide for the next nucleotide in step (6) of the next synthesis cycle; and
      iv. the terminal nucleotide of the support strand (position n−1) overhangs the terminal nucleotide of the helper strand and is a partner nucleotide for the first nucleotide of step (2), or is a partner nucleotide for the newly-incorporated nucleotide of step (6) of the current synthesis cycle.

In any such method described above and herein wherein the universal nucleotide occupies position n and wherein the support strand of the scaffold polynucleotide is cleaved between positions n−1 and n−2, performance of the method may comprise:
   a) in steps (1)/(6) the universal nucleotide in the support strand of the scaffold polynucleotide is positioned opposite the terminal nucleotide of the helper strand adjacent the single-strand break and is paired therewith (position n);
   b) in step (2)/(6), the first/next nucleotide is incorporated into the synthesis strand at a position opposite the universal nucleotide in the support strand, whereupon the first/next nucleotide pairs with the universal nucleotide in place of the terminal nucleotide of the helper strand;
   c) in step (3)/(7) the support strand is cleaved at a position between the first nucleotide (position n−1) and the second nucleotide (position n−2) from the universal nucleotide in the support strand in the direction distal to the helper strand/proximal to the primer strand, wherein cleavage removes the universal nucleotide and creates a double-nucleotide overhang in the scaffold polynucleotide comprising the first/next nucleotide overhanging the support strand wherein the terminal nucleotide of the synthesis strand is the incorporated first/next nucleotide;
   d) in step (4)/(8) the complementary ligation end of the ligation polynucleotide comprises a double-nucleotide overhang wherein:
      i. the universal nucleotide in the support strand is positioned (position n) opposite the terminal nucleotide of the helper strand and is paired therewith;
      ii. the universal nucleotide is positioned next to the penultimate nucleotide of the support strand (position n−1); and iii. the penultimate nucleotide of the support strand (position n−1) overhangs the terminal nucleotide of the helper strand (position n−2) and is the partner nucleotide for the first/next nucleotide in step (2)/(6).

In an alternative embodiment the invention provides a method as described above and herein, wherein:
  a) in step (1) the scaffold polynucleotide is provided in the support strand with a nucleotide (position n) which is the partner nucleotide for the first nucleotide of step (2), and the universal nucleotide in the support strand is positioned at position n+2 (in the direction proximal to the helper strand/distal to the primer strand);
  b) in step (2)/(6) the first/next nucleotide is incorporated into the synthesis strand at the position opposite the partner nucleotide in the support strand (position n), whereupon the first/next nucleotide pairs with the partner nucleotide;
  c) in step (3)/(7) the support strand is cleaved at a position between the second nucleotide (position n) and the third nucleotide (position n−1) from the universal nucleotide in the support strand in the direction distal to the helper strand/proximal to the primer strand, wherein cleavage removes the universal nucleotide and creates a single-nucleotide overhang in the scaffold polynucleotide comprising the first/next nucleotide overhanging the support strand;
  d) in step (4)/(8), the complementary ligation end of the ligation polynucleotide comprises a single-nucleotide overhang wherein:
    i. the universal nucleotide is positioned at position n+2 in the support strand opposite a nucleotide in the helper strand and is paired therewith;
    ii. the penultimate nucleotide of the support strand is paired with the terminal nucleotide of the helper strand and is a partner nucleotide for the next nucleotide in step (6) of the next synthesis cycle (position n); and
    iii. the terminal nucleotide of the support strand (position n−1) overhangs the terminal nucleotide of the helper strand and is a partner nucleotide for the first nucleotide of step (2), or is a partner nucleotide for the newly-incorporated nucleotide of step (6) of the current synthesis cycle.

In a modification of this method described immediately above, in step (1) the universal nucleotide in the support strand is positioned at position n+3 (in the direction proximal to the helper strand/distal to the primer strand), and in step (4)/(8) the complementary ligation end of the ligation polynucleotide is provided with the universal nucleotide in the support strand positioned at position n+3. Alternatively, in step (1) the universal nucleotide in the support strand is positioned at position n+3+x (in the direction proximal to the helper strand/distal to the primer strand), and in step (4)/(8) the complementary ligation end of the ligation polynucleotide is provided with the universal nucleotide in the support strand positioned at position n+3+x, wherein x is a whole number between 1 and 10 or more.

In a further alternative embodiment the invention provides a method as described above and herein, wherein:
  a) in step (1) the scaffold polynucleotide is provided in the support strand with a nucleotide (position n) which is the partner nucleotide for the first nucleotide of step (2), and the universal nucleotide in the support strand is positioned at position n+1 (in the direction proximal to the helper strand/distal to the primer strand);
  b) in step (2)/(6) the first/next nucleotide is incorporated into the synthesis strand at the position opposite the partner nucleotide in the support strand (position n), whereupon the first/next nucleotide pairs with the partner nucleotide;
  c) in step (3)/(7) the support strand is cleaved at a position between the second nucleotide (position n−1) and the third nucleotide (position n−2) from the universal nucleotide in the support strand in the direction distal to the helper strand/proximal to the primer strand, wherein cleavage removes the universal nucleotide and creates a double-nucleotide overhang in the scaffold polynucleotide comprising the first/next nucleotide overhanging the support strand;
  d) in step (4)/(8), the complementary ligation end of the ligation polynucleotide comprises a double-nucleotide overhang and wherein:
    i. the universal nucleotide in the support strand is positioned at position n+1 opposite a nucleotide in the helper strand and is paired therewith;
    ii. the penultimate nucleotide of the support strand (position n−1) overhangs the terminal nucleotide of the helper strand and is a partner nucleotide for the first nucleotide of step (2), or is a partner nucleotide for the newly-incorporated nucleotide of step (6) of the current synthesis cycle; and
    iii. the nucleotide at position n of the support strand is paired with the terminal nucleotide of the helper strand and is a partner nucleotide for the next nucleotide in step (6) of the next synthesis cycle.

In a modification of this method described immediately above, in step (1) the universal nucleotide in the support strand is positioned at position n+2 (in the direction proximal to the helper strand/distal to the primer strand), and in step (4)/(8) the complementary ligation end of the ligation polynucleotide is provided with the universal nucleotide in the support strand positioned at position n+2. Alternatively, in step (1) the universal nucleotide in the support strand is positioned at position n+2+x (in the direction proximal to the helper strand/distal to the primer strand), and in step (4)/(8) the complementary ligation end of the ligation polynucleotide is provided with the universal nucleotide in the support strand positioned at position n+2+x, wherein x is a whole number between 1 and 10 or more.

In any of the methods described above and herein, a nucleotide which pairs with a first/next nucleotide of the predefined sequence may be a nucleotide which is complementary with the first/next nucleotide, preferably naturally complementary.

In any of the methods described above and herein, step (1)/(6) may comprise providing a scaffold polynucleotide comprising a synthesis strand and a support strand hybridized thereto, wherein the synthesis strand is provided without a helper strand portion.

In any of the methods described above and herein, in any one or more cycles of synthesis, or in all cycles of synthesis, after the step of ligating the double-stranded ligation polynucleotide to the cleaved scaffold polynucleotide and before the step of incorporating the next nucleotide of the predefined nucleotide sequence into the synthesis strand of the scaffold polynucleotide, the helper strand portion of the synthesis strand may be removed from the scaffold polynucleotide. In any such method the helper strand portion of the synthesis strand may be removed from the scaffold polynucleotide by: (i) heating the scaffold polynucleotide to a temperature of about 80° C. to about 95° C. and separating the helper strand portion from the scaffold polynucleotide, (ii) treating the scaffold polynucleotide with urea solution, such as 8M urea and separating the helper strand portion from the scaffold polynucleotide, (iii) treating the scaffold polynucleotide with formamide or formamide solution, such as 100% formamide and separating the helper strand portion from the scaffold polynucleotide, or (iv) contacting the scaffold polynucleotide with a single-stranded polynucleotide molecule which comprises a region of nucleotide sequence which is complementary with the sequence of the helper strand portion, thereby competitively inhibiting the hybridisation of the helper strand portion to the scaffold polynucleotide.

In any such method described above and herein wherein the universal nucleotide occupies position n and wherein the support strand of the scaffold polynucleotide is cleaved between positions n and n−1, each cleavage step may comprise a first step comprising removing the universal nucleotide thus forming an abasic site, and a second step comprising cleaving the support strand at the abasic site. In any such method the first step may be performed with a nucleotide-excising enzyme. The nucleotide-excising enzyme may be a 3-methyladenine DNA glycosylase enzyme. The nucleotide-excising enzyme may be human alkyladenine DNA glycosylase (hAAG). In any such method the second step may be performed with a chemical which is a base. The base may be NaOH. In any such method the second step may be performed with an organic chemical having abasic site cleavage activity. The organic chemical may be N,N'-dimethylethylenediamine. In any such method the second step may be performed with an enzyme having abasic site lyase activity such as Endonuclease VIII.

In any such method described above and herein wherein the universal nucleotide occupies position n+1 and wherein the support strand of the scaffold polynucleotide is cleaved between positions n and n−1, or in any such method described above and herein wherein the universal nucleotide occupies position n and wherein the support strand of the scaffold polynucleotide is cleaved between positions n−1 and n−2, the cleavage step may comprise cleaving the support strand with an enzyme. The enzyme may cleave the support strand after the nucleotide which is next to the universal nucleotide in the direction proximal to the primer strand portion, thereby creating the overhanging end in the synthesis strand comprising the first/next nucleotide. Such an enzyme may be Endonuclease V.

In any of the methods described above and herein, both strands of the synthesised double-stranded polynucleotide may be DNA strands. The synthesis strand and the support strand may be DNA strands. In such cases incorporated nucleotides are preferably dNTPs, preferably dNTPs comprising a reversible terminator group. In any such method any one or more or all of the incorporated nucleotides comprising a reversible terminator group may comprise 3'-O-allyl-dNTPs or 3'-O-azidomethyl-dNTPs.

In any of the methods described above and herein, a first strand of the synthesised double-stranded polynucleotide may be a DNA strand and the second strand of the synthesised double-stranded polynucleotide may be an RNA strand. The synthesis strand may be an RNA strand and the support strand may be a DNA strand. In such cases incorporated nucleotides are preferably NTPs, preferably NTPs comprising a reversible terminator group. In any such method any one or more or all of the incorporated nucleotides comprising a reversible terminator group may be 3'-O-allyl-NTPs or 3'-O-azidomethyl-NTPs.

In any of the methods described above and herein involving incorporation of a nucleotide into a synthesis strand comprising DNA e.g. incorporation of one or more dNTPs, the enzyme may be a polymerase, preferably a DNA polymerase, more preferably a modified DNA polymerase having an enhanced ability to incorporate a dNTP comprising a reversible terminator group compared to an unmodified polymerase. The polymerase may be a variant of the native DNA polymerase from *Thermococcus* species 9° N, preferably species 9° N-7.

In any of the methods described above and herein involving incorporation of a nucleotide into a synthesis strand comprising RNA e.g. incorporation of one or more NTPs, the enzyme may be a polymerase, preferably an RNA polymerase such as T3 or T7 RNA polymerase, more preferably a modified RNA polymerase having an enhanced ability to incorporate an NTP comprising a reversible terminator group compared to an unmodified polymerase.

In any of the methods described above and herein, a first strand of the synthesised double-stranded polynucleotide may be a DNA strand and the second strand of the synthesised double-stranded polynucleotide may be an RNA strand. Alternatively, a first strand of the synthesised double-stranded polynucleotide may be an RNA strand and the second strand of the synthesised double-stranded polynucleotide may be a DNA strand.

In any of the methods described above and herein, the step of removing the reversible terminator group from the first/next nucleotide may be performed with tris(carboxyethyl)phosphine (TCEP).

In any of the methods described above and herein, the step of ligating a double-stranded ligation polynucleotide to the cleaved scaffold polynucleotide is preferably performed with a ligase enzyme. The ligase enzyme may be a T3 DNA ligase or a T4 DNA ligase.

In any of the methods described above and herein, in step (1) and/or (6) the helper strand and the portion of the support strand hybridized thereto may be connected by a hairpin loop.

In any of the methods described above and herein, in step (1) the synthesis strand comprising the primer strand portion and the portion of the support strand hybridized thereto may be connected by a hairpin loop.

In any of the methods described above and herein, in step (1) and/or (6):
 a) the helper strand and the portion of the support strand hybridized thereto may be connected by a hairpin loop; and
 b) the synthesis strand comprising the primer strand portion and the portion of the support strand hybridized thereto may be connected by a hairpin loop.

In any of the methods described above and herein, at least one or more or all of the ligation polynucleotides may be provided as a single molecule comprising a hairpin loop connecting the support strand and the helper strand at the end opposite the overhanging end. In any of the methods described above and herein, the ligation polynucleotides of each synthesis cycle may be provided as single molecules each comprising a hairpin loop connecting the support strand and the helper strand at the end opposite the overhanging end.

In any of the methods described above and herein, in step (1) the synthesis strand comprising the primer strand portion and the portion of the support strand hybridized thereto may be tethered to a common surface. The primer strand portion and the portion of the support strand hybridized thereto may each comprise a cleavable linker, wherein the linkers may be cleaved to detach the double-stranded polynucleotide from the surface following synthesis.

In any of the methods described above and herein, in step (1) the primer strand portion of the synthesis strand and the portion of the support strand hybridized thereto may be connected by a hairpin loop, and wherein the hairpin loop is tethered to a surface.

In any of the methods described above and herein, a hairpin loop may be tethered to a surface via a cleavable linker, wherein the linker may be cleaved to detach the double-stranded polynucleotide from the surface following synthesis. The cleavable linker may be a UV cleavable linker.

In any of the methods described above and herein, the surface to which polynucleotides are attached may be the surface of a microparticle or a planar surface.

In any of the methods described above and herein, the surface to which polynucleotides are attached may comprise a gel. The surface comprises a polyacrylamide surface, such as about 2% polyacrylamide, preferably wherein the polyacrylamide surface is coupled to a solid support such as glass.

In any of the methods described above and herein, the synthesis strand comprising the primer strand portion and the portion of the support strand hybridized thereto may tethered to the common surface via one or more covalent bonds. The one or more covalent bonds may be formed between a functional group on the common surface and a functional group on the scaffold molecule, wherein the functional group on the scaffold molecule may be an amine group, a thiol group, a thiophosphate group or a thioamide group. The functional group on the common surface may be a bromoacetyl group, optionally wherein the bromoacetyl group is provided on a polyacrylamide surface derived using N-(5-bromoacetamidylpentyl) acrylamide (BRAPA).

In any of the methods described above and herein, the step of removing the reversible terminator group from a nucleotide of the predefined sequence may be performed before the cleavage step, or before the ligation step.

In any of the methods described above and herein, reactions relating to any of the synthesis cycles described above and herein may be performed in droplets within a microfluidic system. The microfluidic system may be an electrowetting system. The microfluidic system may be an electrowetting-on-dielectric system (EWOD).

In a related aspect, the invention further provides the use of a universal nucleotide in an in vitro method of synthesising a double-stranded polynucleotide having a predefined sequence, wherein the universal nucleotide is used to create a polynucleotide cleavage site during each cycle of synthesis, wherein in each synthesis cycle said use comprises: providing a scaffold polynucleotide comprising a synthesis strand and a support strand hybridized thereto, wherein the synthesis strand comprises a primer strand portion and optionally a helper strand portion separated from the primer strand portion by a single-strand break, and wherein the universal nucleotide is provided in the support strand; incorporating into the synthesis strand by polymerase a new nucleotide of the predefined sequence comprising a reversible terminator group, wherein the new nucleotide occupies a position in the scaffold polynucleotide in proximity with the universal nucleotide so as to define the polynucleotide cleavage site comprising the universal nucleotide; cleaving the scaffold polynucleotide at the cleavage site whereupon the universal nucleotide is removed from the scaffold polynucleotide, a cleaved end is created in the scaffold polynucleotide and an overhanging end is created in the synthesis strand comprising the new nucleotide; wherein the cleaved end acts as a ligation acceptor site for a ligation polynucleotide having a support strand and a helper strand hybridized thereto, the support strand comprising a nucleotide for pairing with the new nucleotide in the synthesis strand of the scaffold polynucleotide and further comprising a new universal nucleotide for use in the next cycle of synthesis. Such use of a universal nucleotide in a method of synthesising a double-stranded polynucleotide having a predefined sequence may be implemented using any of the specific methods defined and described above and herein.

In a related aspect, the invention further provides an in vitro method of extending a synthesis strand of a polynucleotide molecule with a predefined nucleotide, the method comprising: providing a scaffold polynucleotide comprising the synthesis strand and a support strand hybridized thereto, wherein the synthesis strand comprises a primer strand portion and optionally a helper strand portion separated from the primer strand portion by a single-strand break, and wherein the universal nucleotide is provided in the support strand; incorporating into the synthesis strand by polymerase the predefined nucleotide comprising a reversible terminator group, wherein the predefined nucleotide occupies a position in the scaffold polynucleotide in proximity with the universal nucleotide so as to define the polynucleotide cleavage site comprising the universal nucleotide; cleaving the scaffold polynucleotide at the cleavage site whereupon the universal nucleotide is removed from the scaffold polynucleotide, a cleaved end is created in the scaffold polynucleotide and an overhanging end is created in the synthesis strand comprising the predefined nucleotide; wherein the cleaved end acts as a ligation acceptor site for a ligation polynucleotide having a support strand and a helper strand hybridized thereto, the support strand comprising a nucleotide for pairing with the predefined nucleotide in the synthesis strand of the scaffold polynucleotide and further comprising a new universal nucleotide for use in the next cycle of synthesis. In any such method of extending a synthesis strand of a polynucleotide molecule with a predefined nucleotide, the method may be implemented using any of the specific methods defined and described above and herein.

In a related aspect, the invention further provides an in vitro method of synthesising a double-stranded polynucleotide having a predefined sequence, the method comprising cycles of synthesis and wherein each synthesis cycle comprises: providing a scaffold polynucleotide comprising a synthesis strand and a support strand hybridized thereto, wherein the synthesis strand comprises a primer strand portion and optionally a helper strand portion separated from the primer strand portion by a single-strand break, and wherein the universal nucleotide is provided in the support strand; incorporating into the synthesis strand by polymerase a new nucleotide of the predefined sequence comprising a reversible terminator group, wherein the new nucleotide occupies a position in the scaffold polynucleotide in proximity with the universal nucleotide so as to define a polynucleotide cleavage site comprising the universal nucleotide; cleaving the scaffold polynucleotide at the cleavage site whereupon the universal nucleotide is removed from the scaffold polynucleotide, a cleaved end is created in the scaffold polynucleotide and an overhanging end is created in the synthesis strand comprising the new nucleotide; ligating to the cleaved end a ligation polynucleotide having a support strand and a helper strand hybridized thereto, the support strand comprising a nucleotide for pairing with the new nucleotide in the synthesis strand of the scaffold polynucleotide and further comprising a new universal nucleotide for use in the next cycle of synthesis; removing the reversible terminator group from the new nucleotide after the cleavage or ligation step to create a new scaffold polynucleotide for use in the next synthesis cycle; and optionally removing the helper strand after the ligation step and before the incorporation step of the next cycle. In any such method of synthesising a double-stranded polynucleotide having a predefined sequence, the method may be implemented using any of the specific methods defined and described above and herein.

In a related aspect, the invention further provides an in vitro method of ligating a ligation polynucleotide comprising a universal nucleotide to a double-stranded polynucleotide during a cycle of synthesising a double-stranded polynucleotide having a predefined sequence, wherein during the synthesis cycle the double-stranded polynucleotide is extended with a predefined nucleotide and a partner therefor; the method comprising providing a scaffold polynucleotide comprising a synthesis strand and a support strand hybridized thereto, wherein the synthesis strand comprises a primer strand portion and optionally a helper strand portion separated from the primer strand portion by a single-strand break, and wherein a universal nucleotide is provided in the support strand; incorporating into the synthesis strand by polymerase a new nucleotide of the predefined sequence comprising a reversible terminator group, wherein the new nucleotide occupies a position in the scaffold polynucleotide in proximity with the universal nucleotide so as to define a polynucleotide cleavage site comprising the universal nucleotide; cleaving the scaffold polynucleotide at the cleavage site whereupon the universal nucleotide is removed from the scaffold polynucleotide, a cleaved end is created in the scaffold polynucleotide and an overhanging end is created in the synthesis strand comprising the new nucleotide; ligating to the cleaved end a ligation polynucleotide having a support strand and a helper strand hybridized thereto, the support strand comprising a nucleotide for pairing with the new nucleotide in the synthesis strand of the scaffold polynucleotide and further comprising a new universal nucleotide for use in the next cycle of synthesis; removing the reversible terminator group from the new nucleotide after the cleavage or ligation step to create a new scaffold polynucleotide for use in the next synthesis cycle; and optionally removing the helper strand after the ligation step and before the incorporation step of the next cycle. In any such method of ligating a ligation polynucleotide comprising a universal nucleotide to a double-stranded polynucleotide during a cycle of synthesising a double-stranded polynucleotide having a predefined sequence, the method may be implemented using any of the specific methods defined and described above and herein.

In any of the methods described above and herein, following synthesis the strands of the double-stranded polynucleotides may be separated to provide a single-stranded polynucleotide having a predefined sequence.

In any of the methods described above and herein, following synthesis the double-stranded polynucleotide or a region thereof is amplified, preferably by PCR.

The invention also provides a method of assembling a polynucleotide having a predefined sequence, the method comprising performing any of the synthesis methods described above and herein to synthesise a first polynucleotide having a predefined sequence and one or more additional polynucleotides having a predefined sequence and joining together the first and the one or more additional polynucleotides. The first and the one or more additional polynucleotides may preferably comprise different predefined sequences. The first polynucleotide and the one or more additional polynucleotides may be double-stranded or may be single-stranded. The first polynucleotide and the one or more additional polynucleotides may first be cleaved to create compatible termini and then joined together, e.g. by ligation. The first polynucleotide and the one or more additional polynucleotides may be cleaved by a restriction enzyme at a cleavage site to create compatible termini.

Any of the in vitro methods for synthesising a double-stranded polynucleotide having a predefined sequence as described above and herein, and/or any of the in vitro methods of assembling a polynucleotide having a predefined sequence as described above and herein may be performed in droplets within a microfluidic system. In any such methods, the assembly methods may comprise assembly steps which comprise providing a first droplet comprising a first synthesised polynucleotide having a predefined sequence and a second droplet comprising an additional one or more synthesised polynucleotides having a predefined sequence, wherein the droplets are brought in contact with each other and wherein the synthesised polynucleotides are joined together thereby assembling a polynucleotide comprising the first and additional one or more polynucleotides. In any such methods the synthesis steps may be performed by providing a plurality of droplets each droplet comprising reaction reagents corresponding to a step of the synthesis cycle, and sequentially delivering the droplets to the scaffold polynucleotide in accordance with the steps of the synthesis cycles. In any such methods, following delivery of a droplet and prior to the delivery of a next droplet, a washing step may be carried out to remove excess reaction reagents. In any such methods the microfluidic system may be an electrowetting system. In any such methods the microfluidic system may be an electrowetting-on-dielectric system (EWOD). In any such methods the synthesis and assembly steps may be performed within the same system.

The invention additionally provides a polynucleotide synthesis system for carrying out any of the synthesis and/or assembly methods described above and herein, comprising (a) an array of reaction areas, wherein each reaction area comprises at least one scaffold polynucleotide; and (b) means for the delivery of the reaction reagents to the reaction areas and optionally, (c) means to cleave the synthesised double-stranded polynucleotide from the scaffold polynucleotide. Such a system may further comprise means for providing the reaction reagents in droplets and means for delivering the droplets to the scaffold polynucleotide in accordance with the synthesis cycles.

The invention further provides a kit for use with any of the systems described above and herein, and for carrying out any of the synthesis methods described above and herein, the kit comprising volumes of reaction reagents corresponding to the steps of the synthesis cycles.

The invention also provides a method of making a polynucleotide microarray, wherein the microarray comprises a plurality of reaction areas, each area comprising one or more polynucleotides having a predefined sequence, the method comprising:
a) providing a surface comprising a plurality of reaction areas, each area comprising one or more double-stranded anchor or scaffold polynucleotides, and
b) performing cycles of synthesis according to any of the methods described above and herein at each reaction area, thereby synthesising at each area one or more double-stranded polynucleotides having a predefined sequence.

In such methods, following synthesis the strands of the double-stranded polynucleotides may be separated to provide a microarray wherein each area comprises one or more single-stranded polynucleotides having a predefined sequence.

The invention also relates to a nucleotide molecule construct comprising a polynucleotide molecule having a sequence as defined in any one of SEQ ID NOS: 1 to 67.

The invention also relates to a nucleotide molecule construct comprising a polynucleotide molecule having a sequence as defined in any one of SEQ ID NOS: 1 to 67 wherein each polynucleotide sequence as defined in any one of SEQ ID NOS: 1 to 67 is modified with the respective modification(s) shown in the Figures, if present, as well as terminal modifications described herein.

DESCRIPTION OF THE FIGURES

Relevant Figures presented herein and described below show some or all of the steps of a cycle of synthesis using methods of the invention as well as means for performing aspects of the methods, such as oligonucleotides, surfaces, surface attachment chemistries, linkers etc. These Figures as well as all descriptions thereof and all associated methods, reagents and protocols are presented for illustration only and are not to be construed as limiting.

Relevant Figures, such as e.g. FIGS. 1, 2, 3a, 3b, 3c, 6a, 7a, 8a etc. show some or all of the steps of a cycle of synthesis including incorporation of a nucleotide (e.g., a nucleotide comprising a reversible terminator group), cleavage (e.g., cleaving the scaffold polynucleotide into a first portion and a second portion, wherein the first portion comprises an universal nucleotide, and the second portion comprises the incorporated nucleotide), ligation (e.g., ligating to the second portion of the cleaved scaffold polynucleotide comprising the incorporated nucleotide, a polynucleotide construct comprising a single-stranded portion, wherein the single-stranded portion comprises a partner nucleotide that is complementary to the incorporated nucleotide) and deprotection (e.g., removing the reversible terminator group from the incorporated nucleotide).

FIG. 1. Scheme of Exemplary Method Version 1.

Scheme showing a first synthesis cycle according to exemplary method version 1, comprising a cycle of provision of a scaffold polynucleotide, incorporation, cleavage, ligation and deprotection. The scheme shows the incorporation of a thymine nucleotide in the first synthesis cycle (101, 102) and its pairing opposite a partner adenine nucleotide (104), as well as the provision of a scaffold polynucleotide (106) for use in the next synthesis cycle. This pair is shown for illustration purposes only and is not limiting, it can be any pair depending on the required predefined sequence. Nucleotide Z can be any nucleotide. Nucleotide X can be any appropriate nucleotide. The Figure also shows reference signs corresponding to a second synthesis cycle.

Figure 2:
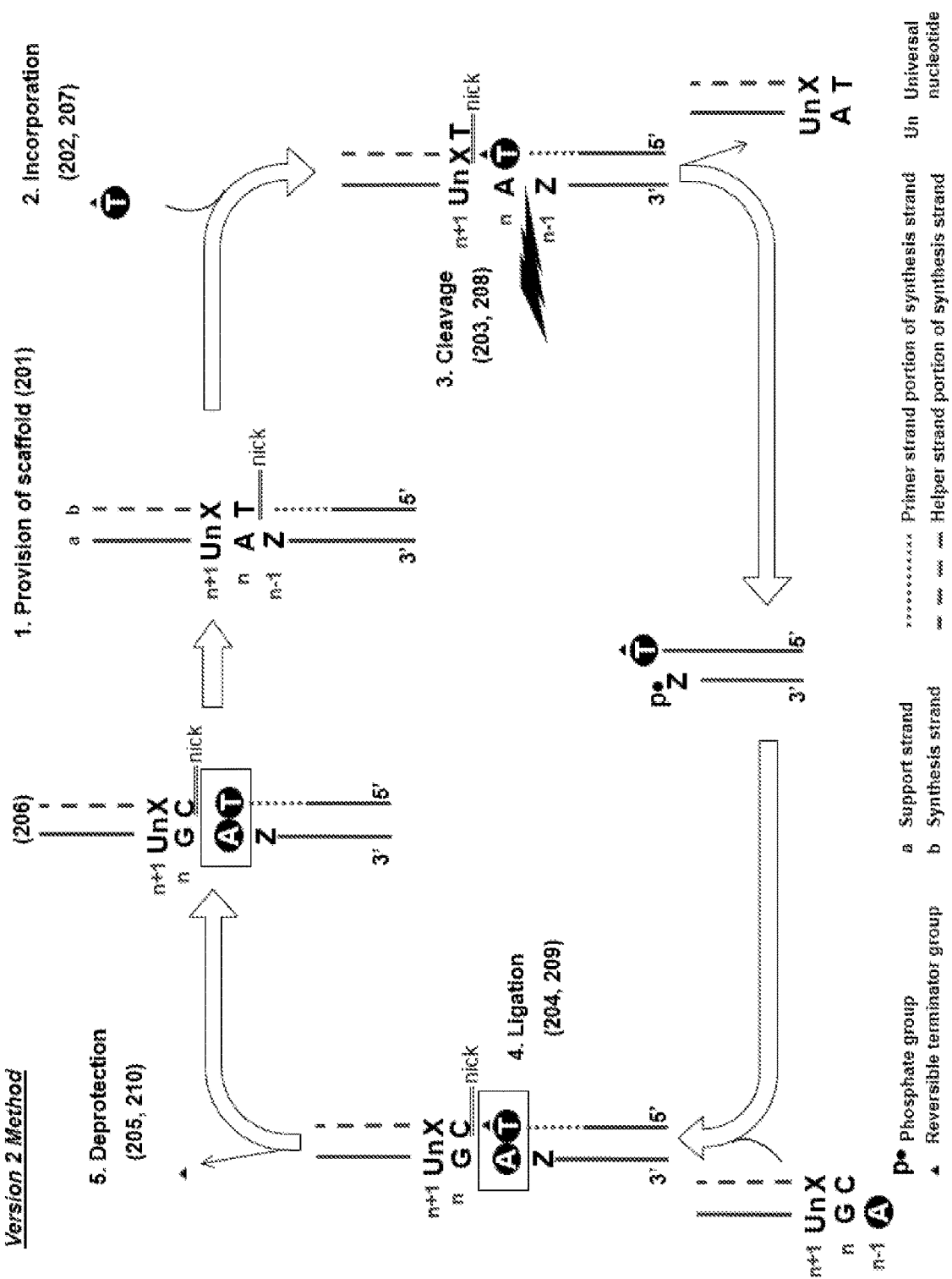

FIG. 2. Scheme of Exemplary Method Version 2.

Scheme showing a first synthesis cycle according to exemplary method version 2, comprising a cycle of provision of a scaffold polynucleotide, incorporation, cleavage, ligation and deprotection. The scheme shows the incorporation in the first cycle (201, 202) of a thymine nucleotide and its pairing opposite a partner adenine nucleotide (204), as well as the provision of a scaffold polynucleotide (206) comprising a guanine for pairing with a cytosine in the next synthesis cycle. These pairs are shown for illustration purposes only and are not limiting, they can be any pairs depending on the required predefined sequence. Nucleotide Z can be any nucleotide. Nucleotide X can be any appropriate nucleotide. The Figure also shows reference signs corresponding to a second synthesis cycle.

Figure 3A:
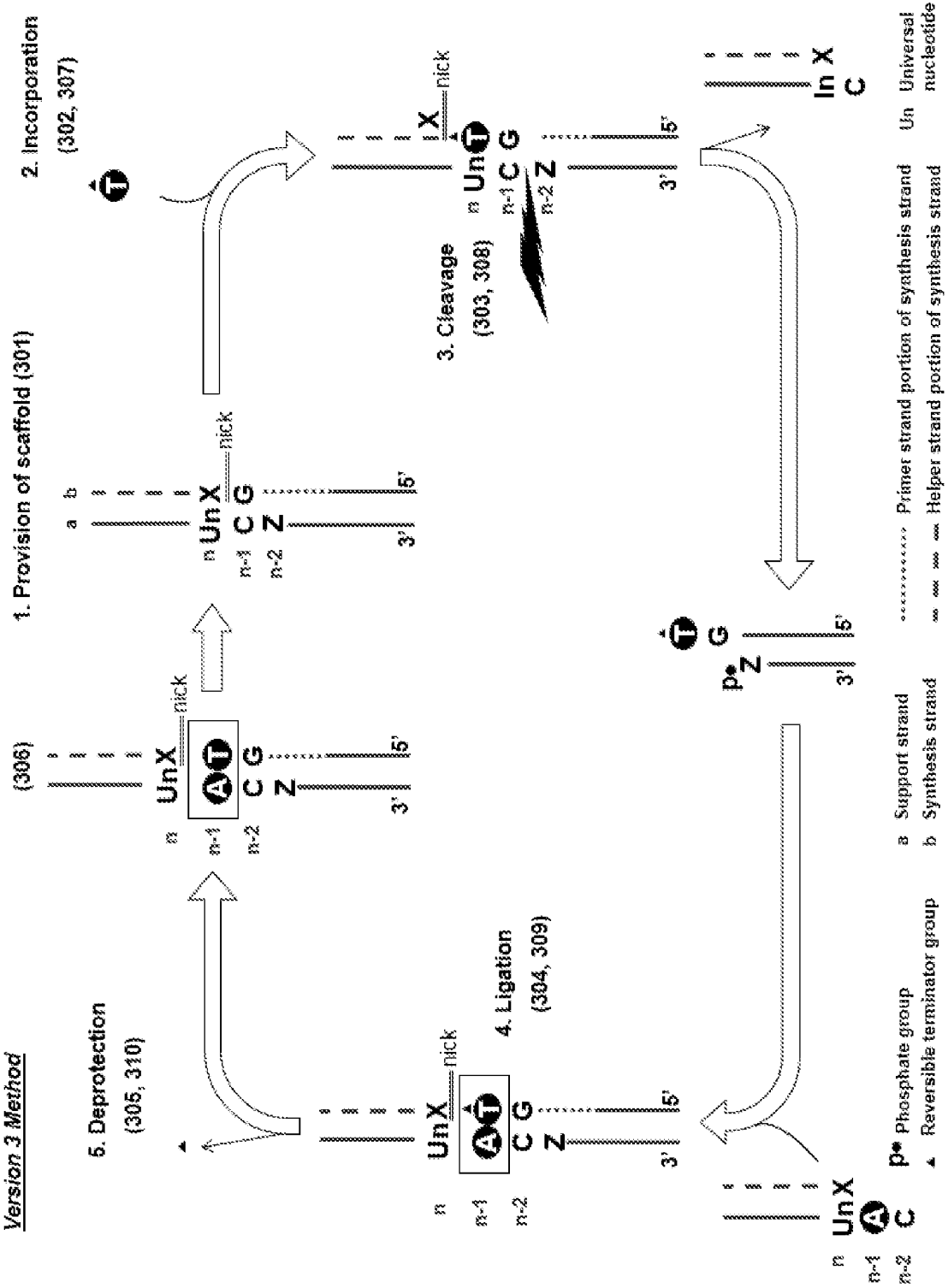

FIG. 3a. Scheme of Exemplary Method Version 3.

Scheme showing a first synthesis cycle according to exemplary method version 3, comprising a cycle of provision of a scaffold polynucleotide, incorporation, cleavage, ligation and deprotection. The scheme shows the incorporation in the first cycle (301, 302) of a thymine nucleotide and its pairing opposite a partner adenine nucleotide (304), as well as the provision of a scaffold polynucleotide (306) for use in the next synthesis cycle. This pair is shown for illustration purposes only and is not limiting, it can be any pair depending on the required predefined sequence. The scheme also shows a cytosine-guanine pair as a component of the scaffold polynucleotide and which is not part of the predefined sequence. This pair is also shown for illustration purposes only and is not limiting, it can be any pair. Nucleotide Z can be any nucleotide. Nucleotide X can be any appropriate nucleotide.

FIG. 3b. Scheme of Exemplary Method Version 4.

Scheme showing a first synthesis cycle according to exemplary method version 4, comprising a cycle of provision of a scaffold polynucleotide, incorporation, cleavage, ligation and deprotection. The scheme shows the incorporation in the first cycle (401, 402) of a thymine nucleotide and its pairing opposite a partner universal nucleotide (404), as well as the provision of a scaffold polynucleotide (406) comprising a guanine for pairing with a cytosine in the next synthesis cycle. These pairs are shown for illustration purposes only and are not limiting, they can be any pairs depending on the required predefined sequence. Nucleotides X, Y and Z can be any nucleotide.

Figure 3C:
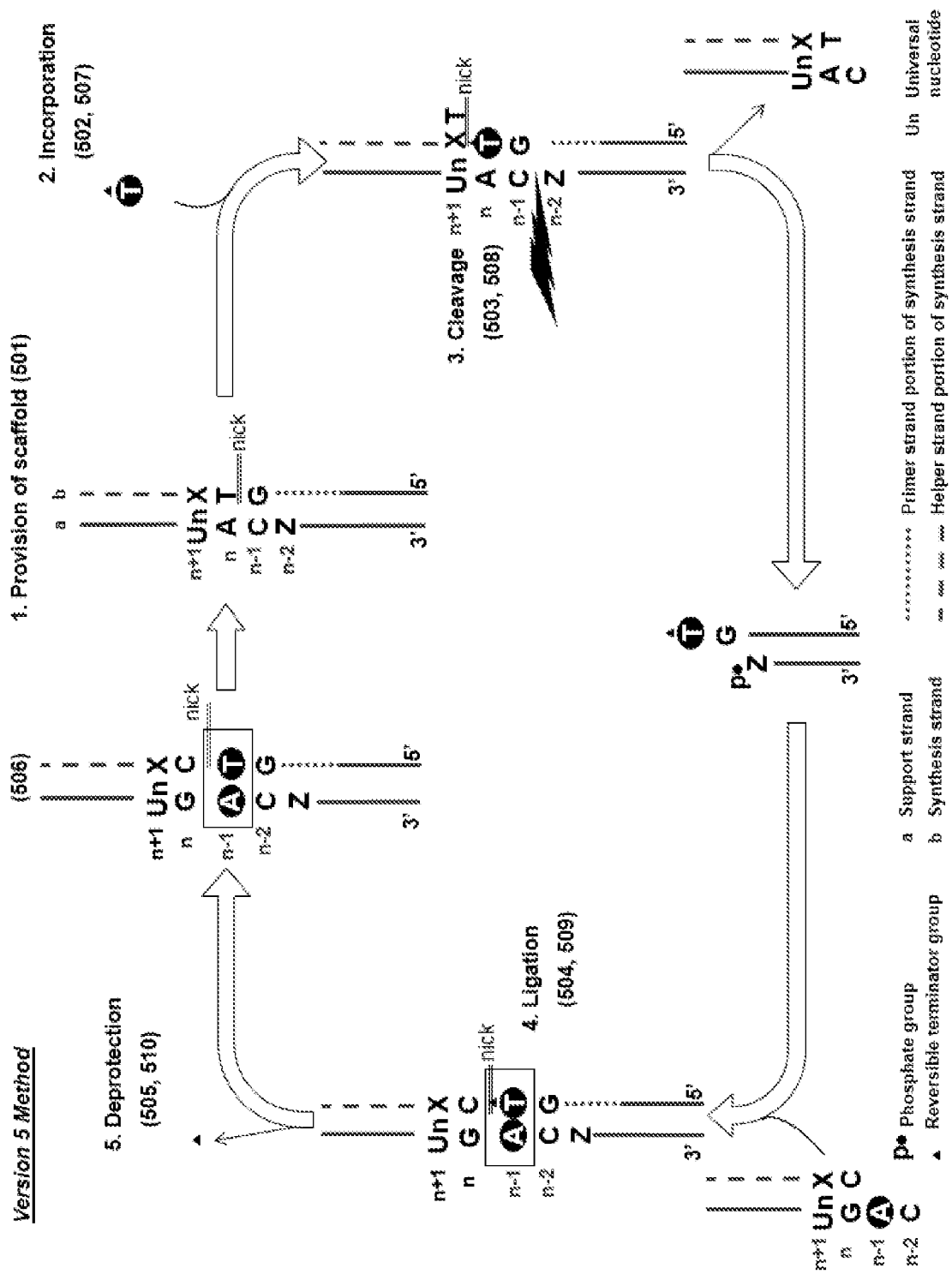

FIG. 3c. Scheme of Exemplary Method Version 5.

Scheme showing a first synthesis cycle according to exemplary method version 5, comprising a cycle of provision of a scaffold polynucleotide, incorporation, cleavage, ligation and deprotection. The scheme shows the incorporation in the first cycle (501, 502) of a thymine nucleotide and its pairing opposite a partner adenine nucleotide (504), as well as the provision of a scaffold polynucleotide (506) comprising a guanine for pairing with a cytosine in the next synthesis cycle. The scheme also shows a cytosine-guanine pair (position n–2) as a component of the scaffold polynucleotide and which is not part of the predefined sequence. These pairs are shown for illustration purposes only and are not limiting, they can be any pairs depending on the required predefined sequence. Nucleotides X, Y and Z can be any nucleotide.

FIGS. 4a-4h. Scheme Showing Surface Immobilization of Scaffold Polynucleotides.

Schemes show possible example hairpin loop configurations of scaffold polynucleotides and their immobilisation to surfaces.

Figures 4A, 4B, 4C, 4D, 4E, 4F, 4G, 4H:
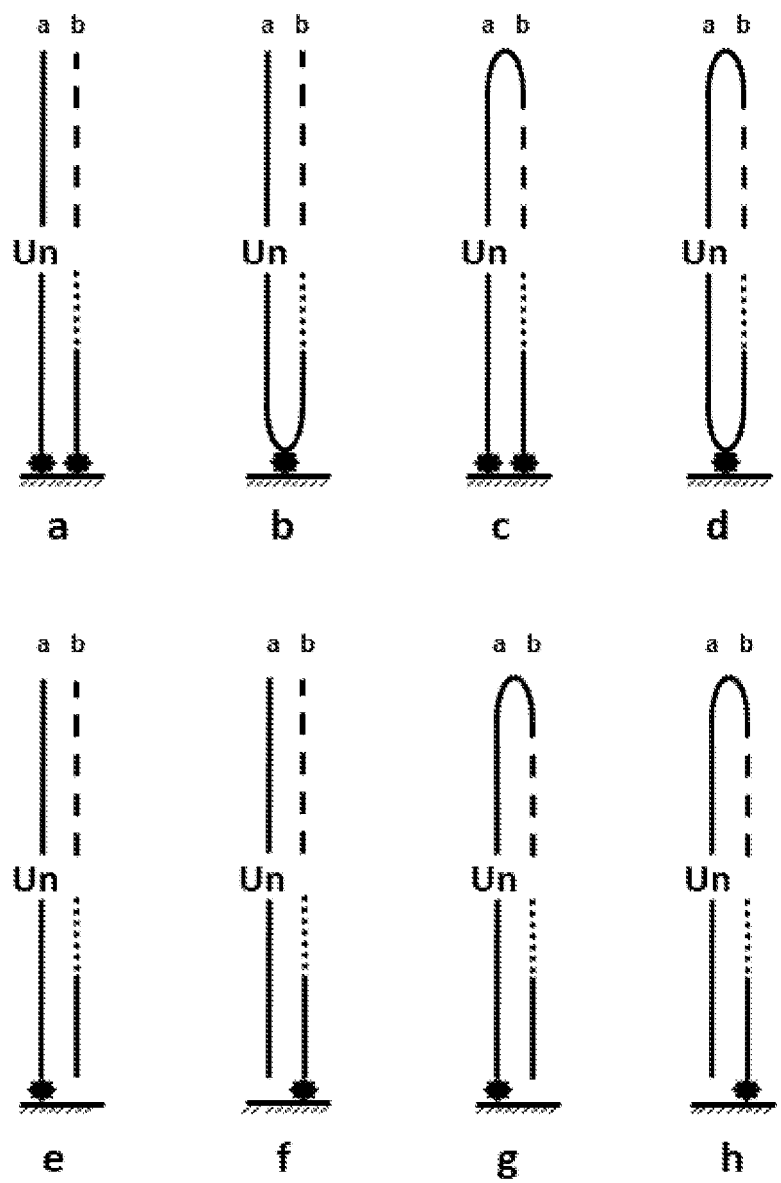
Figure 4I:
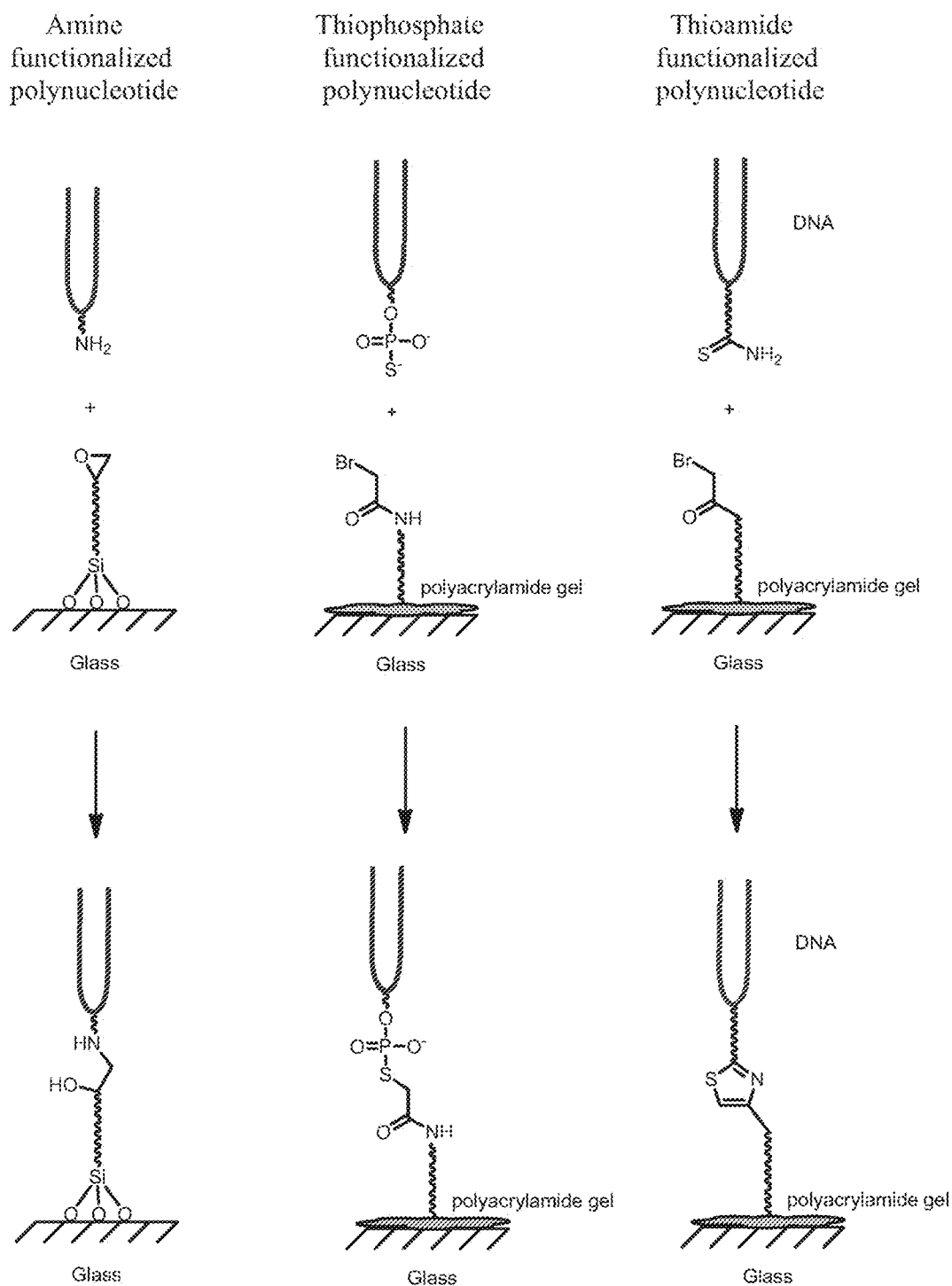

FIGS. 4i-4j. Scheme Showing Surface Immobilization of Scaffold Polynucleotides.

Schemes show examples of surface chemistries for attaching polynucleotides to surfaces. The examples show double-stranded embodiments wherein both strands are connected via a hairpin, but the same chemistries may be used for attaching one or both strands of an unconnected double-stranded polynucleotide.

FIGS. 5a-5h. Absence of Helper Strand—Incorporation.

FIG. 5a) Scheme showing incorporation step highlighted in dashed box.

FIG. 5b) Evaluation of DNA polymerases for incorporation of 3'-O-modified-dTTPs opposite inosine. The Figure depicts a gel showing results of incorporation of 3'-O-modified-dTTPs by various DNA polymerases (Bst, Deep Vent (Exo-), Therminator I and Therminator IX) in presence of $Mn^{2+}$ ions at 50° C. Lane 1: Incorporation of 3'-O-allyldTTPs using Bst DNA polymerase. Lane 2: Incorporation of 3'-O-azidomethyl-dTTPs using Bst DNA polymerase. Lane 3: Incorporation of 3'-O-allyl-dTTPs using Deep vent (exo-) DNA polymerase. Lane 4: Incorporation of 3'-O-azidomethyl-dTTPs using Deep vent (exo-) DNA polymerase. Lane 5: Incorporation of 3'-O-allyl-dTTPs using Terminator I DNA polymerase. Lane 6: Incorporation of 3'-O-azidomethyl-dTTPs using Terminator I DNA polymerase. Lane 7: Incorporation of 3'-O-allyl-dTTPs using Terminator IX DNA polymerase. Lane 8: Incorporation of 3'-O-azidomethyl-dTTPs using Terminator IX DNA polymerase.

FIG. 5c) Evaluation of DNA polymerases for incorporation of 3'-O-modified-dTTPs opposite inosine. Results of incorporation using various DNA polymerases.

FIG. 5d) Evaluation of the temperature on the incorporation using Terminator IX DNA polymerase. The Figure depicts a gel showing results of incorporation of 3'-modified-dTTP opposite inosine in presence of $Mn^{2+}$ ions using Terminator IX DNA polymerase at various temperatures. Lane 1: Incorporation of 3'-O-allyl-dTTPs at 37° C. Lane 2: Incorporation of 3'-O-azidomethyl-dTTPs at 37° C. Lane 3: Incorporation of 3'-O-allyl-dTTPs at 50° C. Lane 4: Incorporation of 3'-O-azidomethyl-dTTPs at 50° C. Lane 5: Incorporation of 3'-O-allyl-dTTPs at 65° C. Lane 6: Incorporation of 3'-O-azidomethyl-dTTPs at 65° C.

FIG. 5e) Evaluation of the temperature on the incorporation using Terminator IX DNA polymerase. Results of incorporation performed at different temperatures.

FIG. 5f) Evaluation of the presence of $Mn^{2+}$ on the incorporation using Terminator IX DNA polymerase. The Figure depicts a gel showing results of incorporation of 3'-O-modified-dTTP opposite inosine at 65° C. Lane S: Standards. Lane 1: Incorporation of 3'-O-allyl-dTTPs without $Mn^{2+}$ ions. Lane 2: Incorporation of 3'-O-azidomethyl-dTTPs without $Mn^{2+}$ ions. Lane 3: Incorporation of 3'-O-allyl-dTTPs in presence of $Mn^{2+}$ ions. Lane 4: Incorporation of 3'-O-azidomethyl-dTTPs in presence of $Mn^{2+}$ ions.

FIG. 5g) Evaluation of the presence of $Mn^{2+}$ on the incorporation using Terminator IX DNA polymerase. Results of incorporation in presence and absence of $Mn^{2+}$ ions.

FIG. 5h) Oligonucleotides used for study of the incorporation step.

FIGS. 6a-6e. Absence of Helper Strand—Cleavage.

Figure 6A:
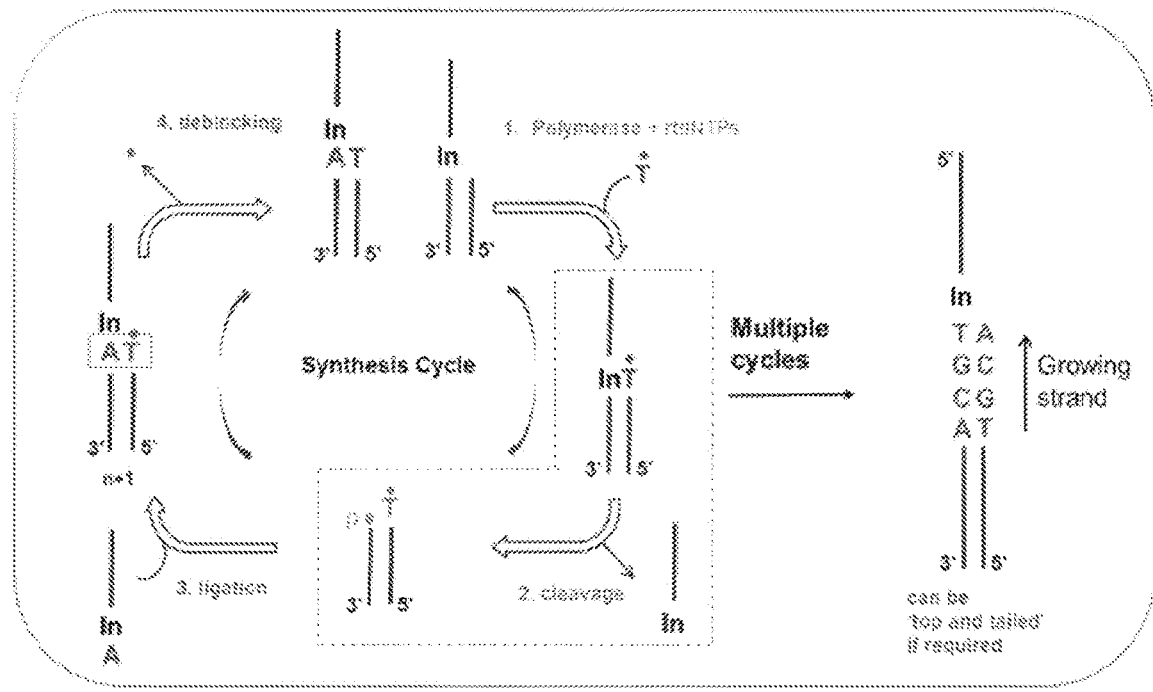

FIG. 6a) Scheme showing cleavage of hybridized polynucleotide strands in the absence of a helper strand. Cleavage step is highlighted in dashed box.

Figure 6B:
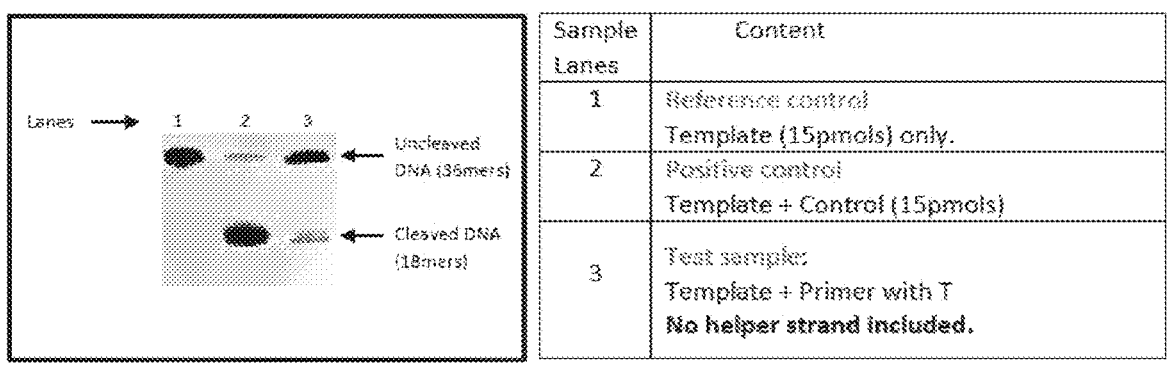

FIG. 6b) Gel showing cleavage of oligonucleotide with hAAG and 0.2M NaOH (strong base) at 37° C. and room temperature 24° C. respectively. Lane 1. Starting oligonucleotide. Lane 2 which was a positive control that contained both full length strands showed a higher yield of cleaved to uncleaved DNA ratio of 90%:10%. Lane 3 which included the cleavage reaction without a helper strand showed a low percentage yield of cleaved to uncleaved DNA ratio of 10%:90%.

FIG. 6c) Gel showing cleavage of oligonucleotide with hAAG and Endo VIII at 37° C. Lane 2 which was a positive control that contained both full length strands showed a higher yield of cleaved to uncleaved DNA ratio of ~90%: 10%. Lane 3 which included the cleavage reaction without a helper strand showed a low percentage yield of cleaved to uncleaved DNA ratio of ~7%:93%.

FIG. 6d) A summary of cleavage of oligonucleotide with hAAG/Endo VIII and hAAG/Chemical base.

FIG. 6e) Oligonucleotides used for study of the cleavage step.

FIGS. 7a-7c. Absence of Helper Strand—Ligation.

FIG. 7a) Scheme showing ligation of hybridized polynucleotide strands in the absence of a helper strand. Ligation step highlighted in dashed box.

FIG. 7b) Gel showing ligation of Oligonucleotides with Quick T4 DNA ligase at room temperature (24° C.) in the absence of a helper strand. Lane 1 contained a mixture of the 36 mers TAMRA single stranded oligos and 18 mers TAMRA single stranded oligos. These oligos served reference bands.

FIG. 7c) Oligonucleotides used for study of the ligation step.

Figures 8A, 8B:
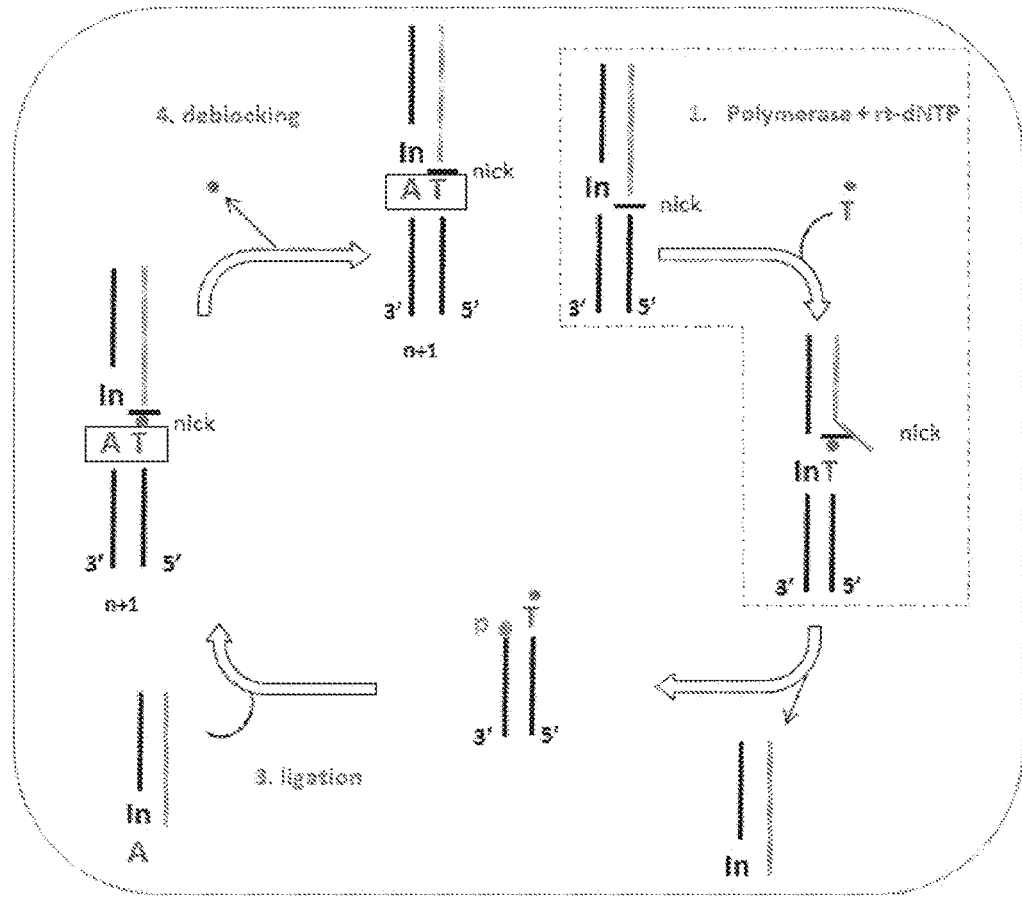

FIGS. 8a-8b. Version 1 Chemistry with Helper Strand—Incorporation.

FIG. 8a) Scheme showing incorporation step highlighted in dashed box.

FIG. 8b) Oligonucleotides applicable for study of the incorporation step.

FIGS. 9a-9f. Version 1 Chemistry with Helper Strand—Cleavage.

Figure 9A:
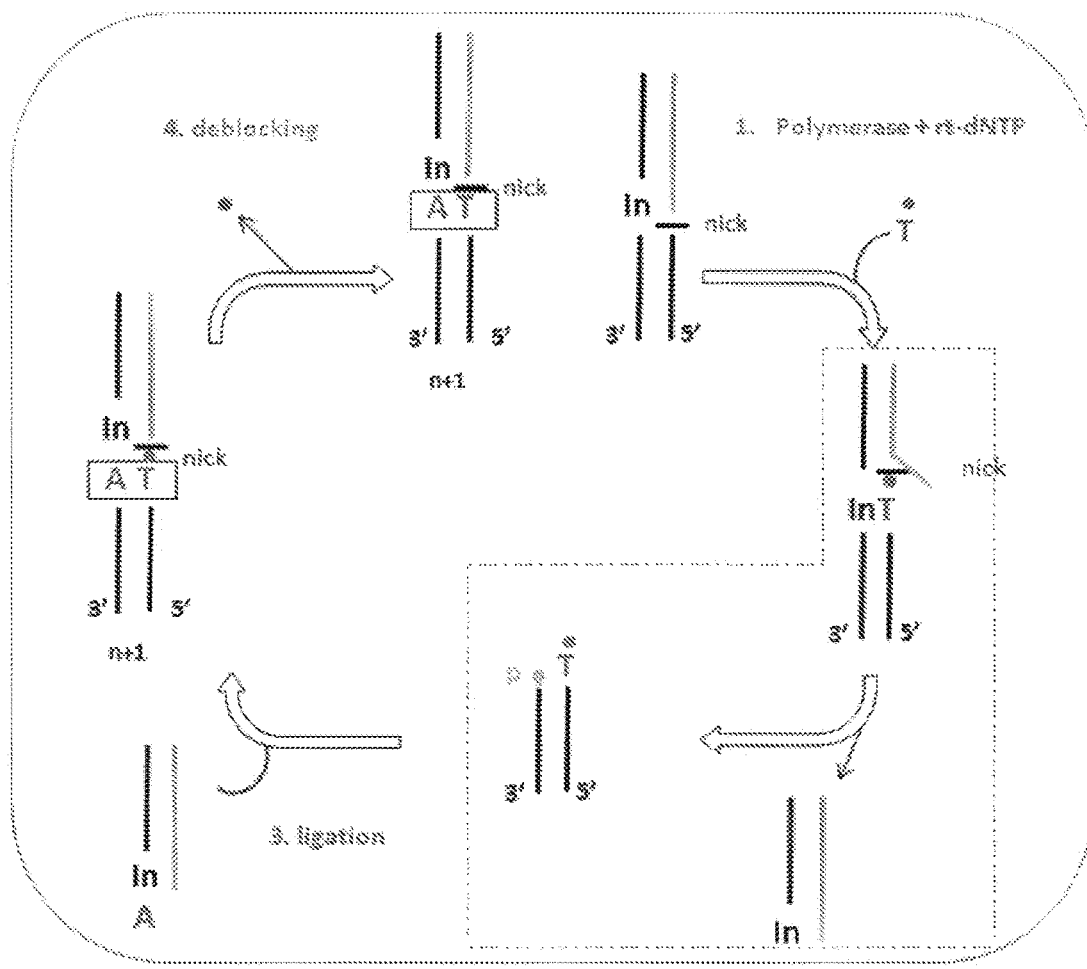

FIG. 9a) Scheme showing cleavage of hybridized polynucleotide strands in the absence of a helper strand. Cleavage step is highlighted in dashed box.

Figure 9B:
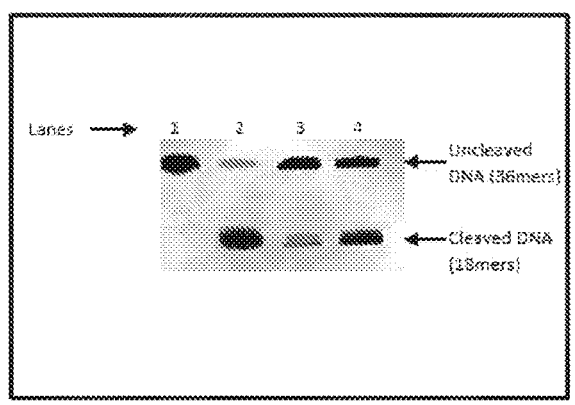

FIG. 9b) Gel showing cleavage of Oligonucleotide with hAAG and 0.2M NaOH (strong base) at 37° C. and room temperature 24° C. respectively. Lane 1. Starting oligonucleotide. Lane 2 which was a positive control that contained both full length strands showed a higher yield of cleaved to uncleaved DNA ratio of 90%:10%. Lane 3 which included the cleavage reaction without a helper strand showed a low percentage yield of cleaved to uncleaved DNA ratio of 10%:90%. Lane 4 which included the cleavage reaction with a helper strand showed an equal percentage yield of cleaved to uncleaved DNA ratio of 50%:50%.

FIG. 9c) Evaluation of Endonuclease VIII for cleavage of abasic sites. Gel shows cleavage of oligonucleotide with hAAG and Endo VIII at 37° C. Lane 2 which was a positive control that contained both full length strands showed a higher yield of cleaved to uncleaved DNA ratio of ~90%: 10%. Lane 3 which included the cleavage reaction without a helper strand showed a low percentage yield of cleaved to uncleaved DNA ratio of ~7%:93%. Lane 4 which included the cleavage reaction with a helper strand showed an low percentage yield of cleaved to uncleaved DNA ratio of 10%:90%.

FIG. 9d) Evaluation of N,N'-dimethylethylenediamine for cleavage of abasic sites. Gel shows cleavage of oligonucleotide with hAAG and 100 mM N,N'-dimethylethylenediamine at 37° C. Lane 1. Starting oligonucleotide. Lane 2 which was a positive control that contained both full length strands showed a 100% cleaved DNA. Lane 3 which included the cleavage reaction with a helper strand showed a higher percentage yield of cleaved to uncleaved DNA ratio of 90%:10%.

FIG. 9e) A summary of cleavage of oligonucleotide with hAAG/Endo VIII, hAAG/chemical base and hAAG/alternative chemical base.

FIG. 9f) Oligonucleotides used for study of the cleavage step.

FIGS. 10a-10d. Version 1 Chemistry with Helper Strand—Ligation.

Figure 10A:
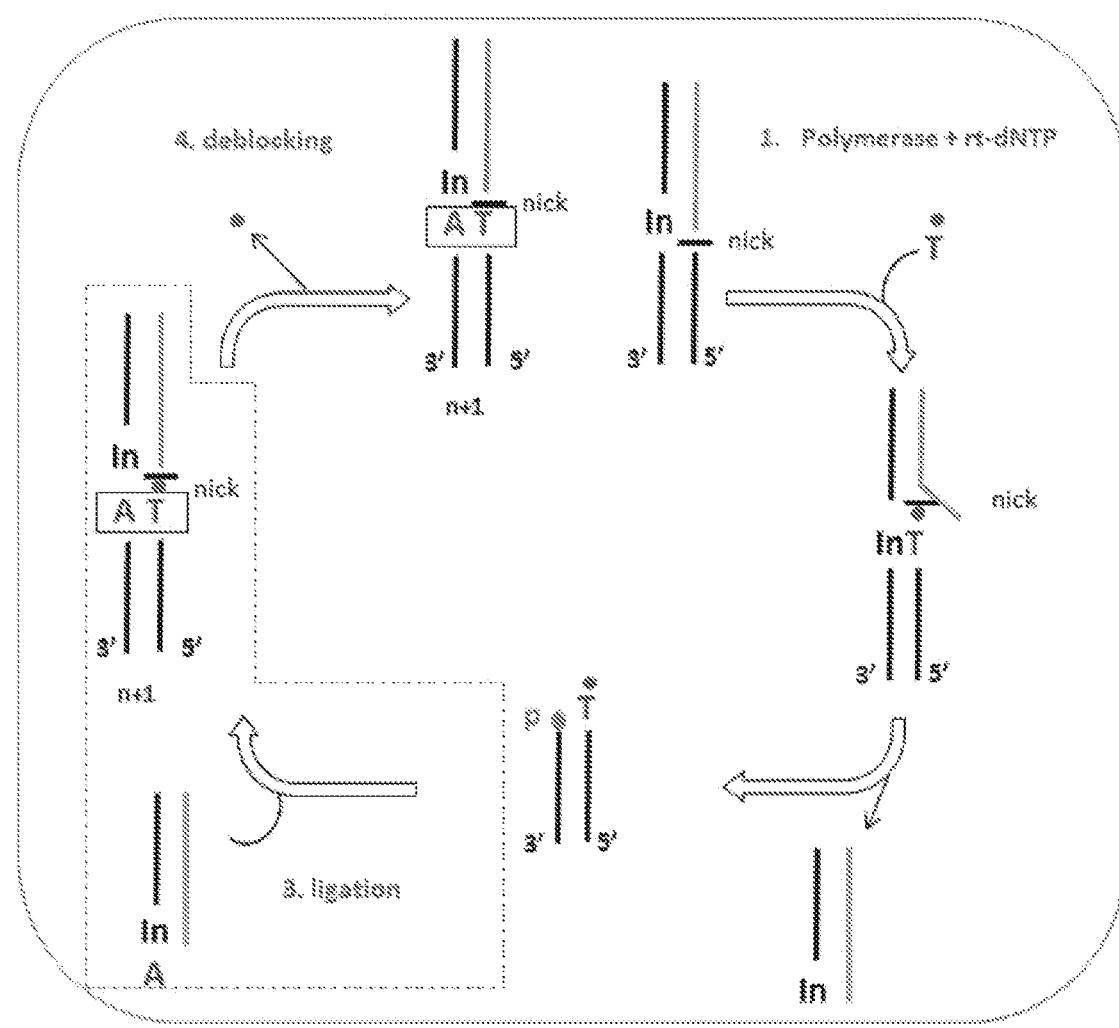

FIG. 10a) Scheme showing ligation of hybridized polynucleotide strands in the presence of a helper strand. Ligation step highlighted in dashed box.

FIG. 10b) Gel showing ligation of oligonucleotides with Quick T4 DNA ligase at room temperature (24° C.) in the presence of a helper strand. Lane 1 contained a mixture of the 36 mers TAMRA single stranded oligos and 18 mers TAMRA single stranded oligos. These oligos served reference bands. In lane 2 there was an observable ligation product of expected band size 36 mers after 20 minutes.

FIG. 10c) Gel showing ligation of oligonucleotides with Quick T4 DNA ligase at room temperature (24° C.) after overnight incubation in the presence of a helper strand. Lane 1 contained a mixture of the 36 mers TAMRA single stranded oligos and 18 mers TAMRA single stranded oligos. These oligos served as reference bands. In lane 2 there was an observable completely ligated product of expected band size of 36 mers.

FIG. 10d) Oligonucleotides used for study of the ligation step.

FIGS. 11a-11j. Version 2 Chemistry with Helper Strand—Incorporation.

Figure 11A:
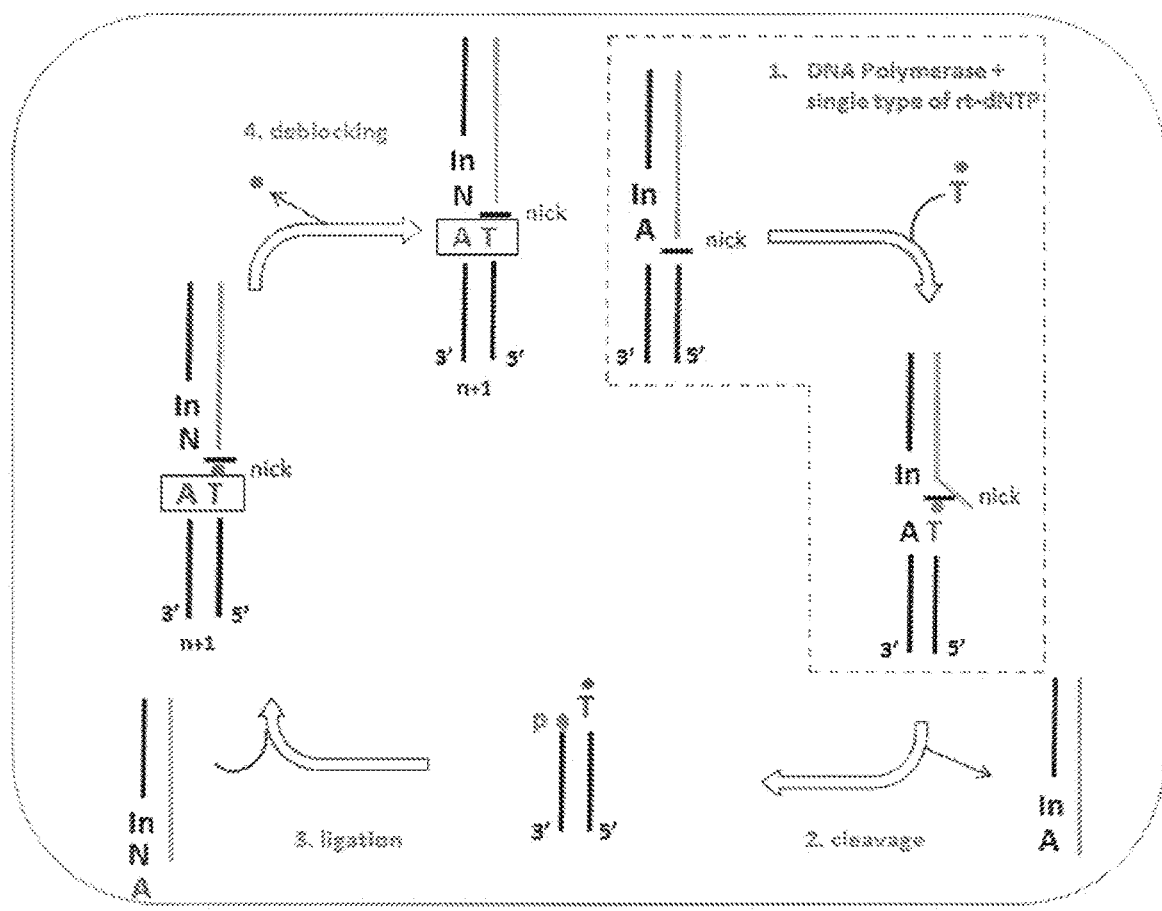

FIG. 11a) Scheme showing incorporation step highlighted in orange dashed box

Figure 11B:
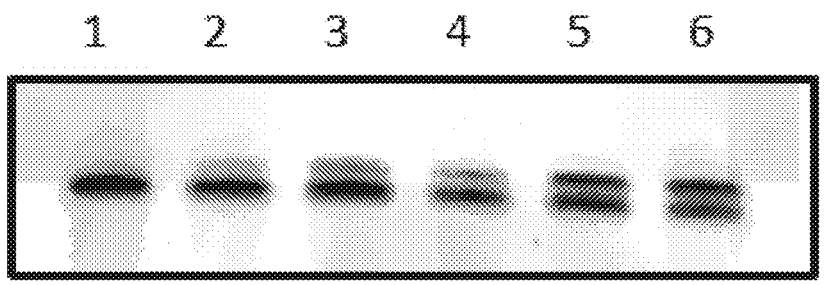

FIG. 11b) Gel showing results of incorporation of 3'-O-modified-dTTPs by Therminator IX DNA polymerase at 27° C. Lane 1: Starting material. Lane 2: Incorporation after 1 minute, conversion 5%. Lane 3: Incorporation after 2 minutes, conversion 10%. Lane 4: Incorporation after 5 minutes, conversion 20%. Lane 5: Incorporation after 10 minutes, conversion 30%. Lane 6: Incorporation after 20 minutes, conversion 35%.

Figure 11C:
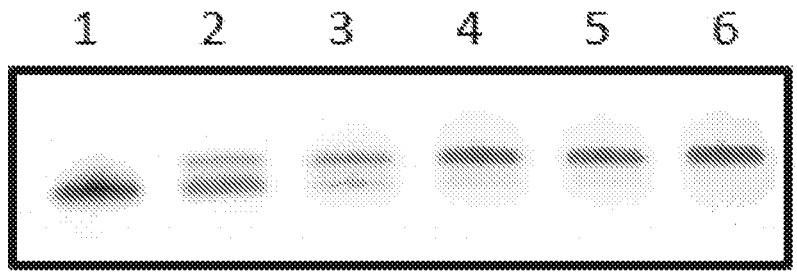

FIG. 11c) The Figure depicts a gel showing results of incorporation of 3'-O-modified-dTTPs by Therminator IX DNA polymerase at 37° C. Lane 1: Starting material. Lane 2: Incorporation after 1 minute, conversion 30%. Lane 3: Incorporation after 2 minutes, conversion 60%. Lane 4: Incorporation after 5 minutes, conversion 90%. Lane 5: Incorporation after 10 minutes, conversion 90%. Lane 6: Incorporation after 20 minutes, conversion 90%.

Figure 11D:
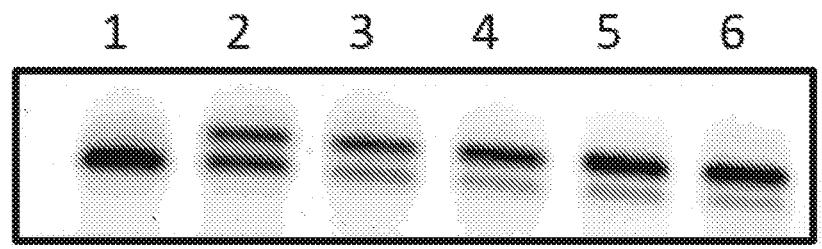

FIG. 11d) Gel showing results of incorporation of 3'-O-modified-dTTPs by Therminator IX DNA polymerase at 47° C. Lane 1: Starting material. Lane 2: Incorporation after 1 minute, conversion 30%. Lane 3: Incorporation after 2 minutes, conversion 65%. Lane 4: Incorporation after 5 minutes, conversion 90%. Lane 5: Incorporation after 10 minutes, conversion 90%. Lane 6: Incorporation after 20 minutes, conversion 90%.

Figure 11E:
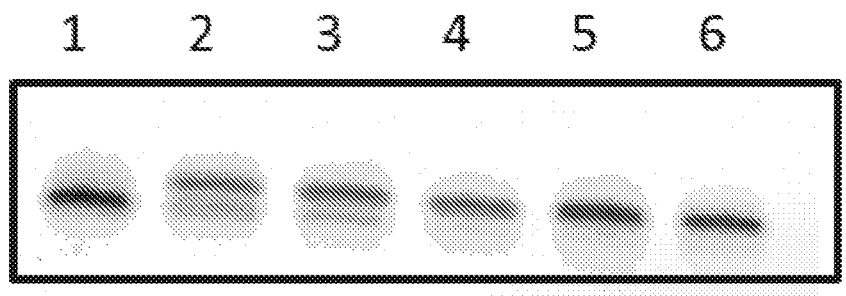

FIG. 11e) Gel showing results of incorporation of 3'-O-modified-dTTPs by Therminator IX DNA polymerase at 27° C. Lane 1: Starting material. Lane 2: Incorporation after 1 minute, conversion 70%. Lane 3: Incorporation after 2 minutes, conversion 85%. Lane 4: Incorporation after 5 minutes, conversion 92%. Lane 5: Incorporation after 10 minutes, conversion 96%. Lane 6: Incorporation after 20 minutes, conversion 96%.

Figure 11F:
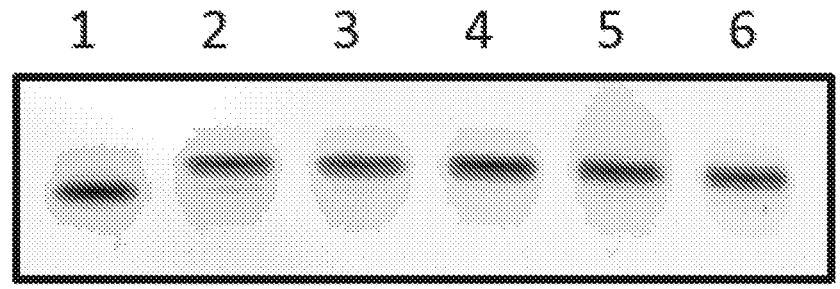

FIG. 11f) Gel showing results of incorporation of 3'-O-modified-dTTPs by Therminator IX DNA polymerase at 37° C. Lane 1: Starting material. Lane 2: Incorporation after 1 minute, conversion 85%. Lane 3: Incorporation after 2 minutes, conversion 95%. Lane 4: Incorporation after 5 minutes, conversion 96%. Lane 5: Incorporation after 10 minutes, conversion 96%. Lane 6: Incorporation after 20 minutes, conversion 96%.

FIG. 11g) Gel showing results of incorporation of 3'-O-modified-dTTPs by Therminator IX DNA polymerase at 47° C. Lane 1: Starting material. Lane 2: Incorporation after 1 minute, conversion 85%. Lane 3: Incorporation after 2 minutes, conversion 90%. Lane 4: Incorporation after 5 minutes, conversion 96%. Lane 5: Incorporation after 10 minutes, conversion 96%. Lane 6: Incorporation after 20 minutes, conversion 96%.

FIG. 11h) Summary of incorporation of 3'-O-azidomethyl-dTTP at various temperatures and presence of $Mn^{2+}$ ions.

FIG. 11i) Gel showing results of incorporation of 3'-O-modified-dNTPs opposite complementary base by Therminator IX DNA polymerase in presence of $Mn^{2+}$ at 37° C. Lane 1: Starting material. Lane 2: Incorporation of 3'-O-azidomethyl-dTTP for 5 minutes. Lane 3: Incorporation of 3'-O-azidomethyl-dATP for 5 minutes. Lane 4: Incorporation of 3'-O-azidomethyl-dCTP for 5 minutes. Lane 5: Incorporation of 3'-O-azidomethyl-dGTP for 5 minutes.

FIG. 11j) Oligonucleotides used for study of the incorporation step.

FIGS. 12a-12d. Version 2 Chemistry with Helper Strand—Cleavage.

Figure 12A:
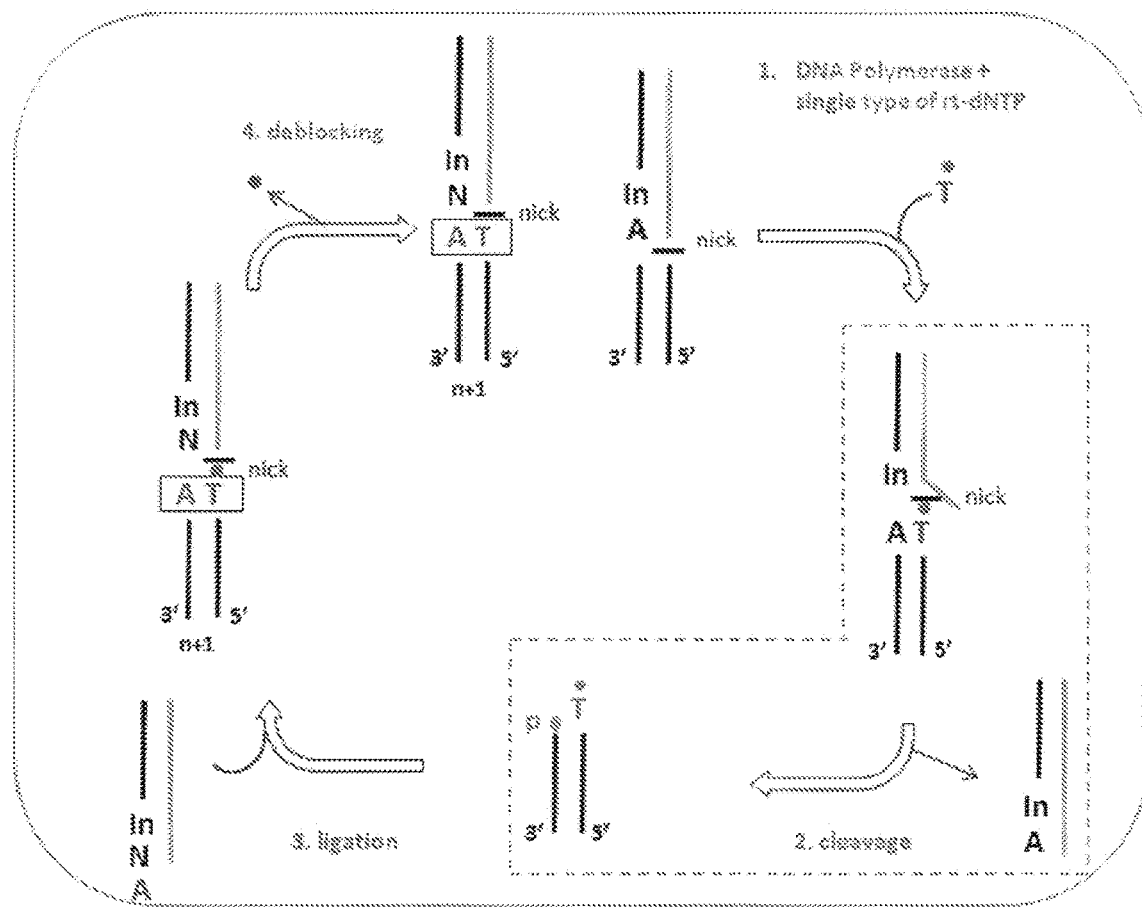

FIG. 12a) Scheme showing cleavage of hybridized polynucleotide strand in the presence of a helper strand. Cleavage step is highlighted in orange dashed box.

Figure 12B:
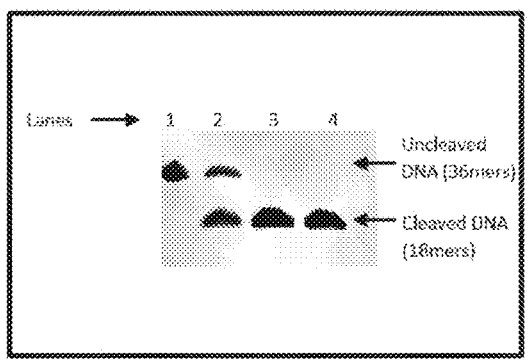

FIG. 12b) Gel shows cleavage of Oligonucleotide with Endo V at 37° C. Lane 1. Starting oligonucleotide. Lane 2 which was a positive control that contained both full length strands showed a yield of cleaved to uncleaved DNA ratio of 80%:20%. Lane 3 which included the cleavage reaction without a helper strand showed a much higher yield of cleaved DNA of >99%. Lane 4 which included the cleavage reaction with a helper strand also showed a DNA cleavage yield of >99%.

FIG. 12c) A summary of cleavage study with Endonuclease V.

FIG. 12d) Oligonucleotides used for study of the cleavage step.

Figures 13A, 13B:
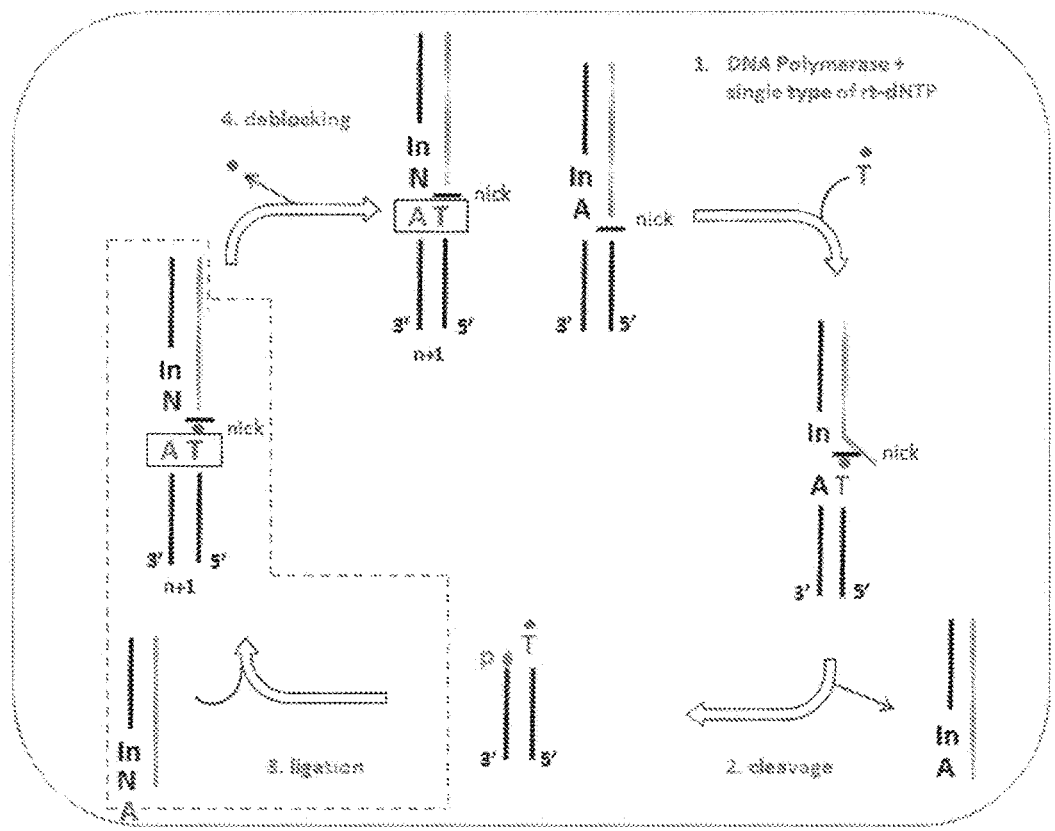

FIGS. 13a-13b. Version 2 Chemistry with Helper Strand—Ligation.

FIG. 13a) Scheme showing ligation of hybridized polynucleotide strands in the absence of a helper strand. Ligation step highlighted in orange dashed box.

FIG. 13b) Oligonucleotides for study of the ligation step.

FIGS. 14a-14i. Version 2 Chemistry with Helper Strand—Deprotection.

Figure 14A:
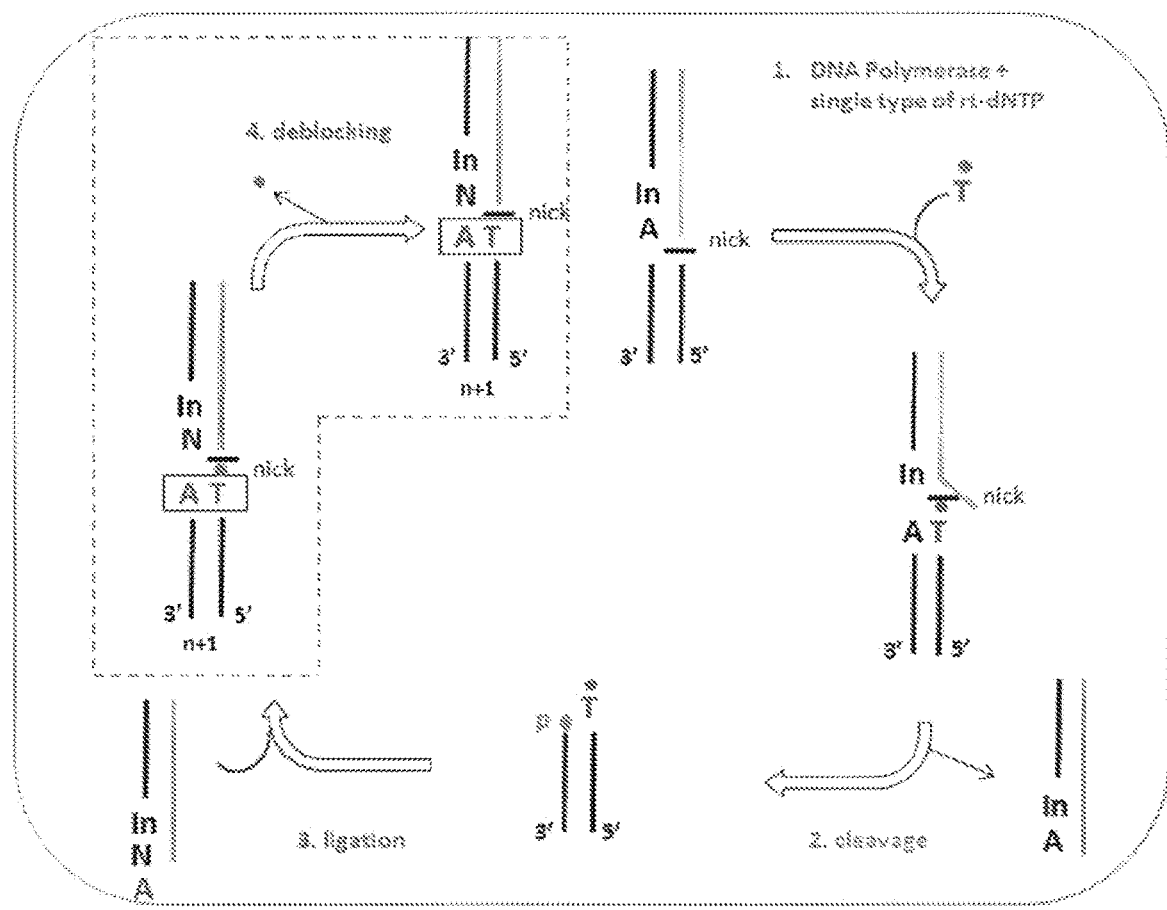

FIG. 14a) Scheme showing deprotection step highlighted in orange dashed box.

Figure 14B:
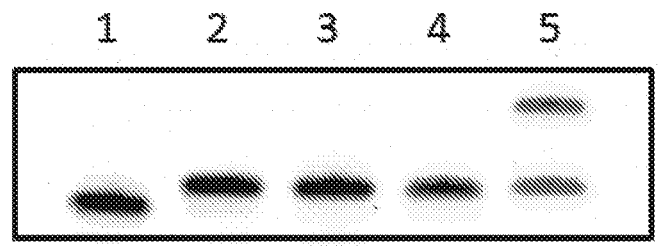

FIG. 14b) The Figure depicts a gel showing results of 3'-O-azidomethyl group deprotection by 50 mM TCEP after incorporation of 3'-O-azidomethyl-dTTP. Lane 1: Starting primer Lane 2: Incorporation of 3'-O-azidomethyl-dTTPs in presence $Mn^{2+}$. Lane 3: Extension of the product in lane 2 by addition of all natural dNTPs. Lane 4: Deprotection of the product (0.5 µM) in lane 2 by 50 mM TCEP. Lane 5: Extension of the product in lane 4 by addition of all natural dNTPs.

Figure 14C:
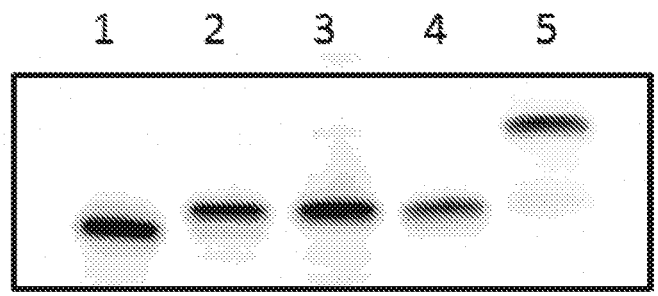

FIG. 14c) The Figure depicts a gel showing results of 3'-O-azidomethyl group deprotection by 300 mM TCEP after incorporation of 3'-O-azidomethyl-dTTP. Lane 1: Starting primer. Lane 2: Incorporation of 3-O-azidomethyl-dTTPs in presence $Mn^{2+}$. Lane 3: Extension of the product in lane 2 by addition of all natural dNTPs. Lane 4: Deprotection of the product (0.5 µM) in lane 2 by 300 mM TCEP. Lane 5: Extension of the product in lane 4 by addition of all natural dNTPs.

Figure 14D:
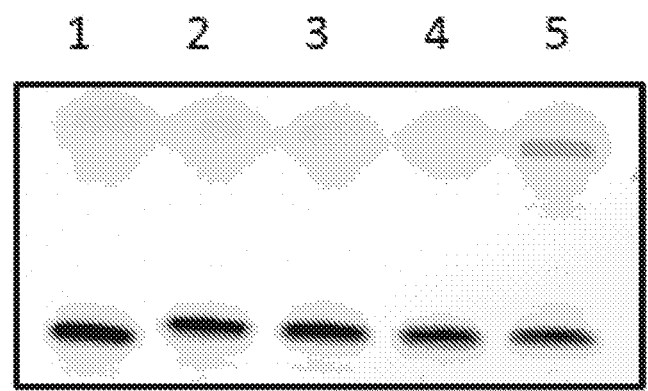

FIG. 14d) The Figure depicts a gel showing results of 3'-O-azidomethyl group deprotection by 50 mM TCEP after incorporation of 3'-O-azidomethyl-dCTP. Lane 1: Starting primer. Lane 2: Incorporation of 3-O-azidomethyl-dCTPs in presence $Mn^{2+}$. Lane 3: Extension of the product in lane 2 by addition of all natural dNTPs. Lane 4: Deprotection of the product (0.5 µM) in lane 2 by 300 mM TCEP. Lane 5: Extension of the product in lane 4 by addition of all natural dNTPs.

Figure 14E:
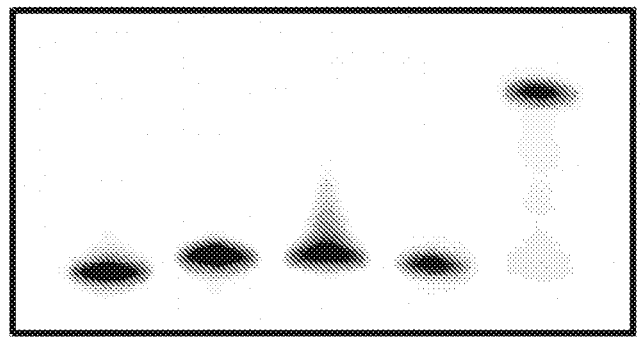

FIG. 14e) The Figure depicts a gel showing results of 3'-O-azidomethyl group deprotection by 300 mM TCEP after incorporation of 3'-O-azidomethyl-dCTP. Lane 1: Starting primer
Lane 2: Incorporation of 3-O-azidomethyl-dCTPs in presence $Mn^{2+}$. Lane 3: Extension of the product in lane 1 by addition of all natural dNTPs. Lane 4: Deprotection of the product (0.5 µM) in lane 1 by 300 mM TCEP. Lane 5: Extension of the product in lane 3 by addition of all natural dNTPs.

Figure 14F:
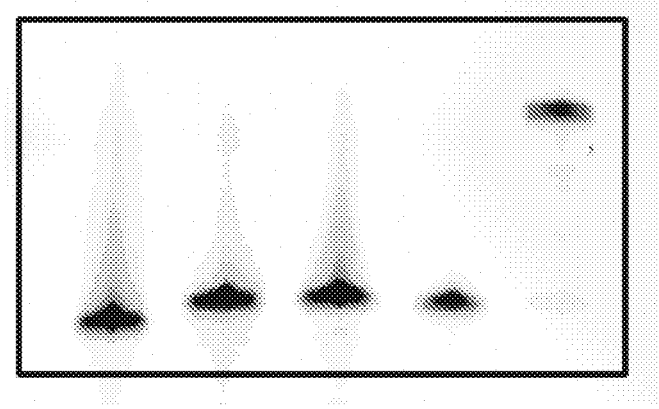

FIG. 14f) The Figure depicts a gel showing results of 3'-O-azidomethyl group deprotection by 300 mM TCEP after incorporation of 3'-O-azidomethyl-dATP.

Lane 1: Starting primer
Lane 2: Incorporation of 3-O-azidomethyl-dATPs in presence $Mn^{2+}$. Lane 3: Extension of the product in lane 2 by addition of all natural dNTPs. Lane 4: Deprotection of the product (0.5 µM) in lane 2 by 300 mM TCEP. Lane 5: Extension of the product in lane 4 by addition of all natural dNTPs.

Figure 14G:
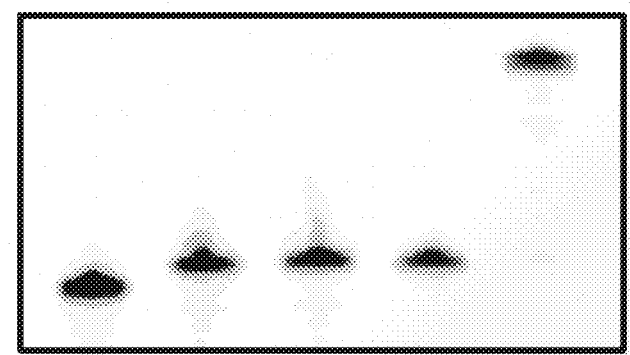

FIG. 14g) The Figure depicts a gel showing results of 3'-O-azidomethyl group deprotection by 300 mM TCEP after incorporation of 3'-O-azidomethyl-dGTP. Lane 1: Starting primer.
Lane 2: Incorporation of 3-O-azidomethyl-dGTPs in presence $Mn^{2+}$. Lane 3: Extension of the product in lane 2 by addition of all natural dNTPs. Lane 4: Deprotection of the product (0.5 µM) in lane 2 by 300 mM TCEP. Lane 5: Extension of the product in lane 4 by addition of all natural dNTPs.

FIG. 14h) Efficiency of deprotection by TCEP on 0.2 µM DNA.

FIG. 14i) Oligonucleotides used for study of the cleavage step.

Figure 15A:
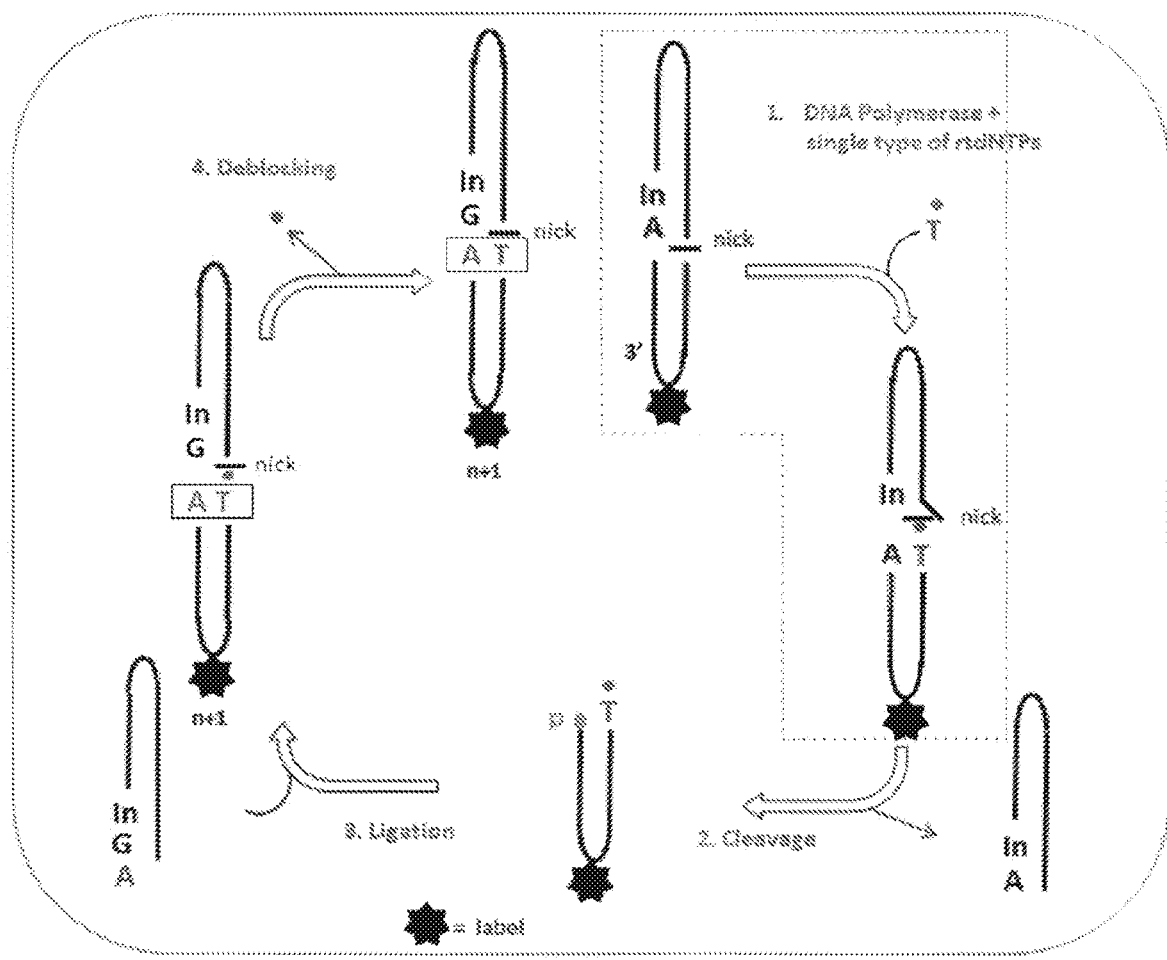
Figures 15B, 15C:
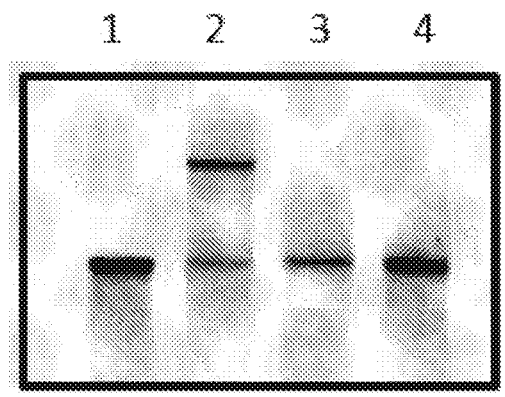

FIGS. 15a-15c. Version 2 Chemistry with Double Hairpin Model—Incorporation.

FIG. 15a) Scheme showing incorporation step highlighted in dashed box.

FIG. 15b) Evaluation of DNA polymerases for incorporation of 3'-O-modified-dTTPs opposite its natural counterpart. The Figure depicts a gel showing results of incorporation of 3'-O-modified-dTTPs by Terminator IX DNA polymerase at 37° C. Lane 1: Starting material. Lane 2: Incorporation of natural dNTP mix. Lane 3: Incorporation of 3'-O-azidomethyl-dTTP by Terminator IX DNA polymerase. Lane 4: Extension of the product in lane 3 by addition of all natural dNTPs.

FIG. 15c) Evaluation of DNA polymerases for incorporation of 3'-O-modified-dTTPs opposite its natural counterpart. Oligonucleotides applicable for study of the incorporation step.

Figure 16A:
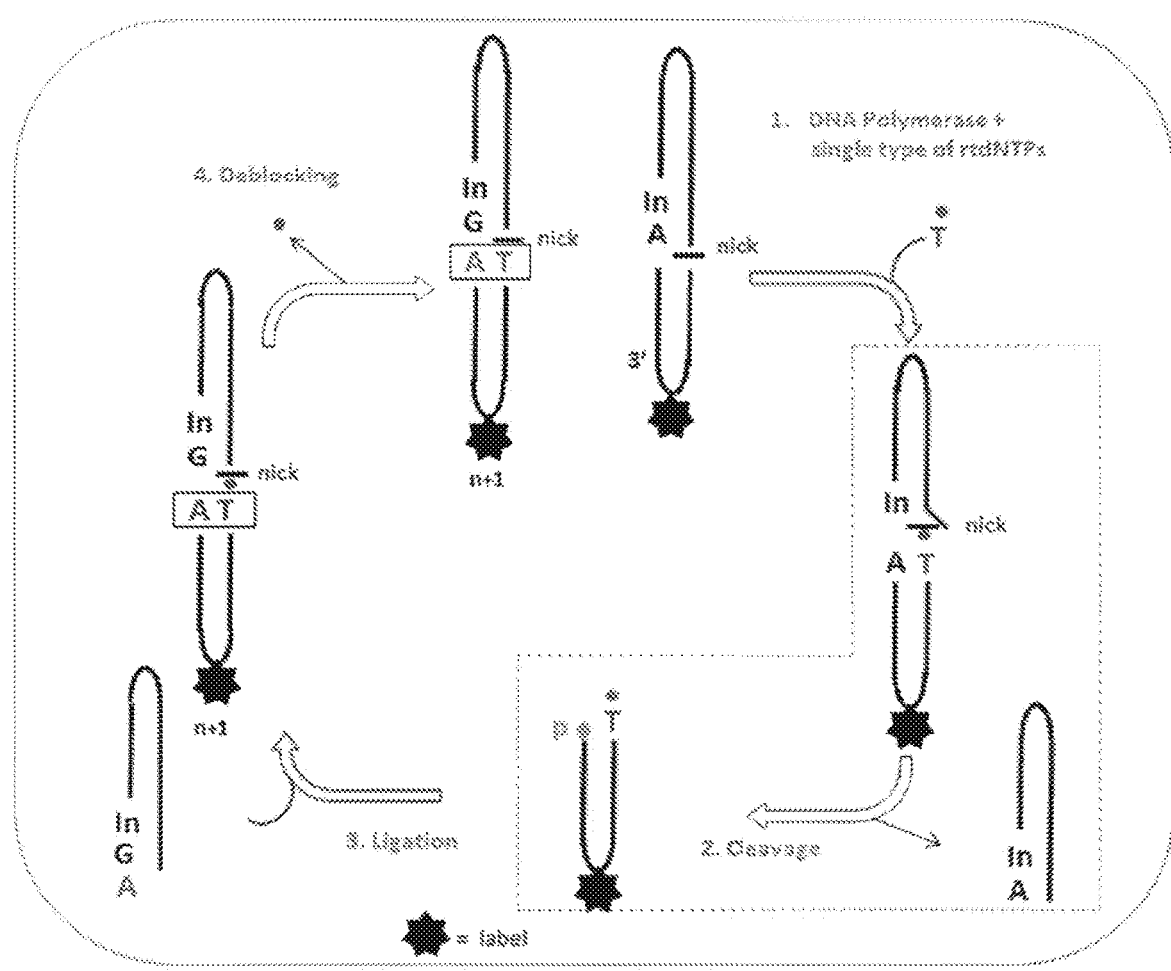

FIGS. 16a-16c. Version 2 Chemistry with Double Hairpin Model—Cleavage.

FIG. 16a) Scheme showing cleavage of a hairpin Oligonucleotide. Cleavage step is highlighted in dashed box.

FIG. 16b) Gel showing cleavage of Hairpin Oligonucleotide with Endo V at 37° C. Lane 1. Starting hairpin oligonucleotide. Lane 2 which was the cleaved hairpin oligonucleotide after 5 minutes showed a high yield of digested DNA with a ratio of ~98%. Lane 3 which was the cleaved hairpin oligonucleotide after 10 minutes showed a high yield of digested DNA with a ratio of ~99%. Lane 4 which was the cleaved hairpin oligonucleotide after 30 minutes showed a high yield of digested DNA with a ratio of ~99% and in lane 5 which was the cleaved hairpin oligonucleotide after 1 hr showed a high yield of digested DNA with a ratio of ~99%.

FIG. 16c) Oligonucleotides used for study of the cleavage step.

Figure 17A:
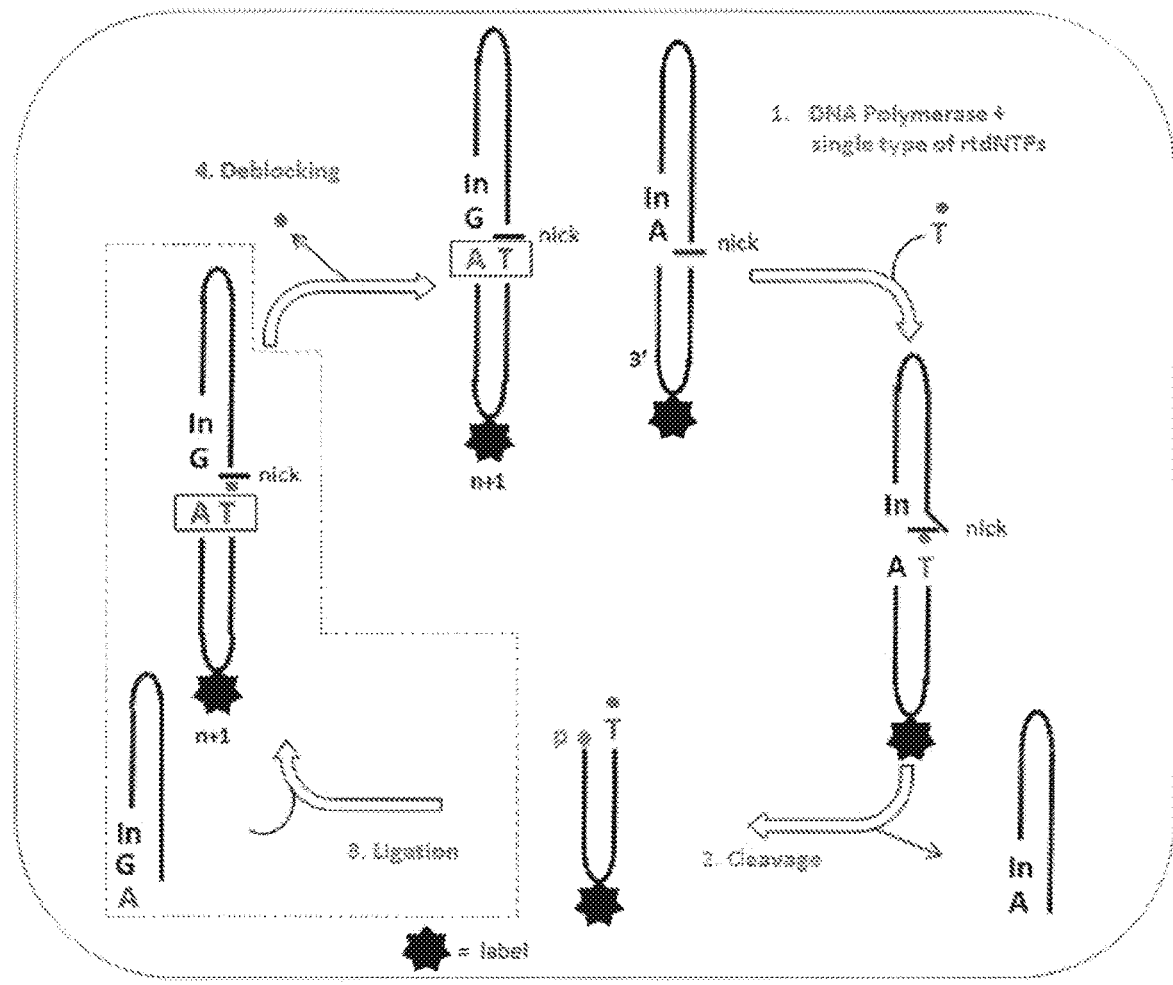

FIGS. 17a-17c. Version 2 Chemistry with Double Hairpin Model—Ligation.

FIG. 17a) Scheme showing ligation of hybridized hairpins. Ligation step highlighted in dashed box.

FIG. 17b) The gel shows ligation of Hairpin Oligonucleotides with Blunt/TA DNA ligase at room temperature (24° C.) in the presence of a helper strand. Lane 1 contained a starting hairpin Oligonucleotide. Lane 2 which was the ligated hairpin oligonucleotide after 1 minute showed a high yield of ligated DNA product with a ratio of ~85%. Lane 3 which was the ligated hairpin oligonucleotide after 2 minutes showed a high yield of digested DNA with a ratio of ~85%. Lane 4 which was the ligated hairpin oligonucleotide after 3 minutes showed a high yield of ligated DNA product with a ratio of ~85%. Lane 5 which was the ligated hairpin oligonucleotide after 4 minutes showed a high yield of ligated DNA product with a ratio of ~>85%.

FIG. 17c) Hairpin Oligonucleotides used for study of the Ligation step.

Figure 18A:
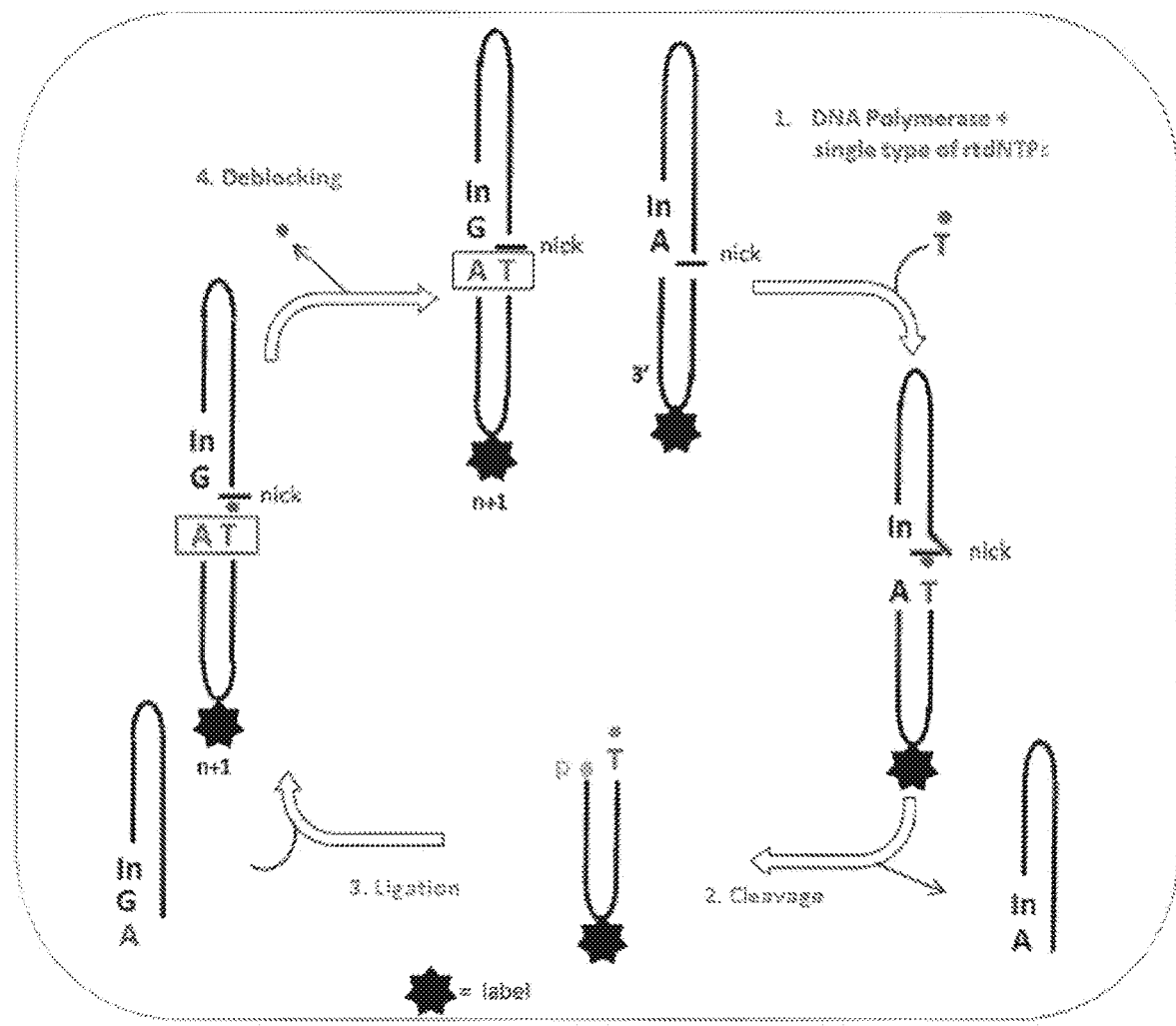
Figure 18B:
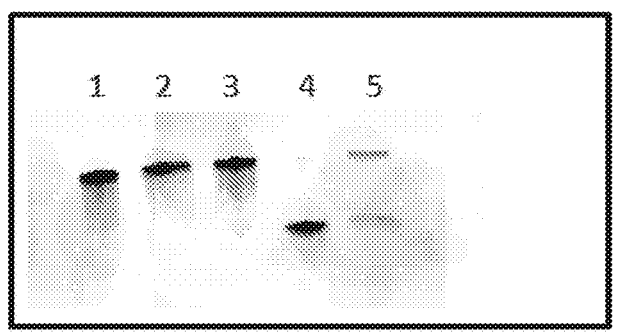

FIGS. 18a-18c. Version 2 Chemistry—Complete Cycle on Double Hairpin Model.

FIG. 18a) Scheme showing full cycle involving enzymatic incorporation, cleavage, ligation and deprotection steps.

FIG. 18b) Evaluation of DNA polymerases for incorporation of 3'-O-modified-dTTPs opposite its natural counterpart. The Figure depicts a gel showing results of incorporation of 3'-O-modified-dTTPs by Terminator IX DNA polymerase at 37° C. Lane 1: Starting material. Lane 2: Incorporation of 3'-O-azidomethyl-dTTP by Terminator IX DNA polymerase. Lane 3: Extension of the product in lane 2 by addition of all natural dNTPs. Lane 4: Cleavage of the product in lane 2 by Endonuclease V. Lane 5: Ligation of the product in lane 4 by blunt TA ligase kit.

FIG. 18c) Oligonucleotides applicable for study of the incorporation step.

Figures 19A, 19B:
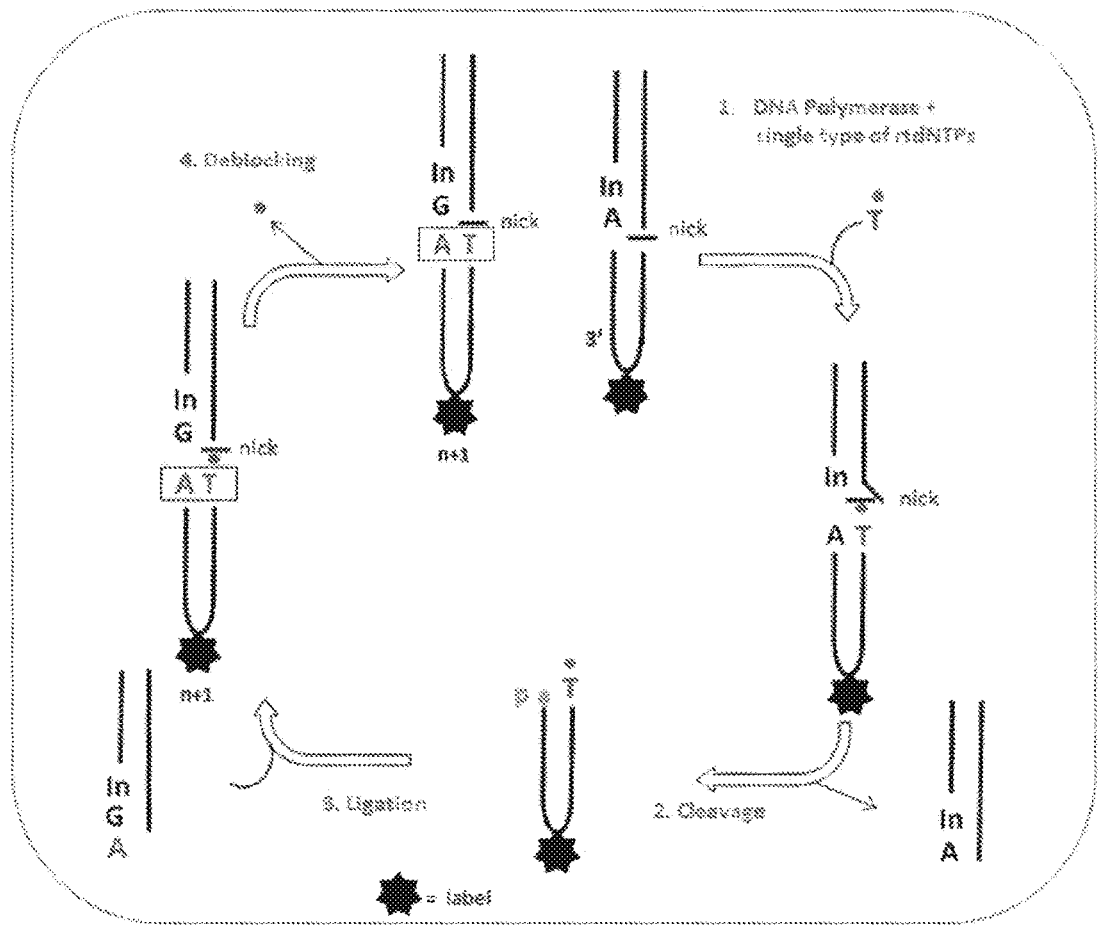

FIGS. 19a-19c. Version 2 Chemistry—Complete Cycle on Single Hairpin Model using Helper Strand.

FIG. 19a) Scheme showing full cycle involving enzymatic incorporation, cleavage, ligation and deprotection steps.

FIG. 19b) Oligonucleotides applicable for study of the incorporation step.

Figures 20A, 20B:
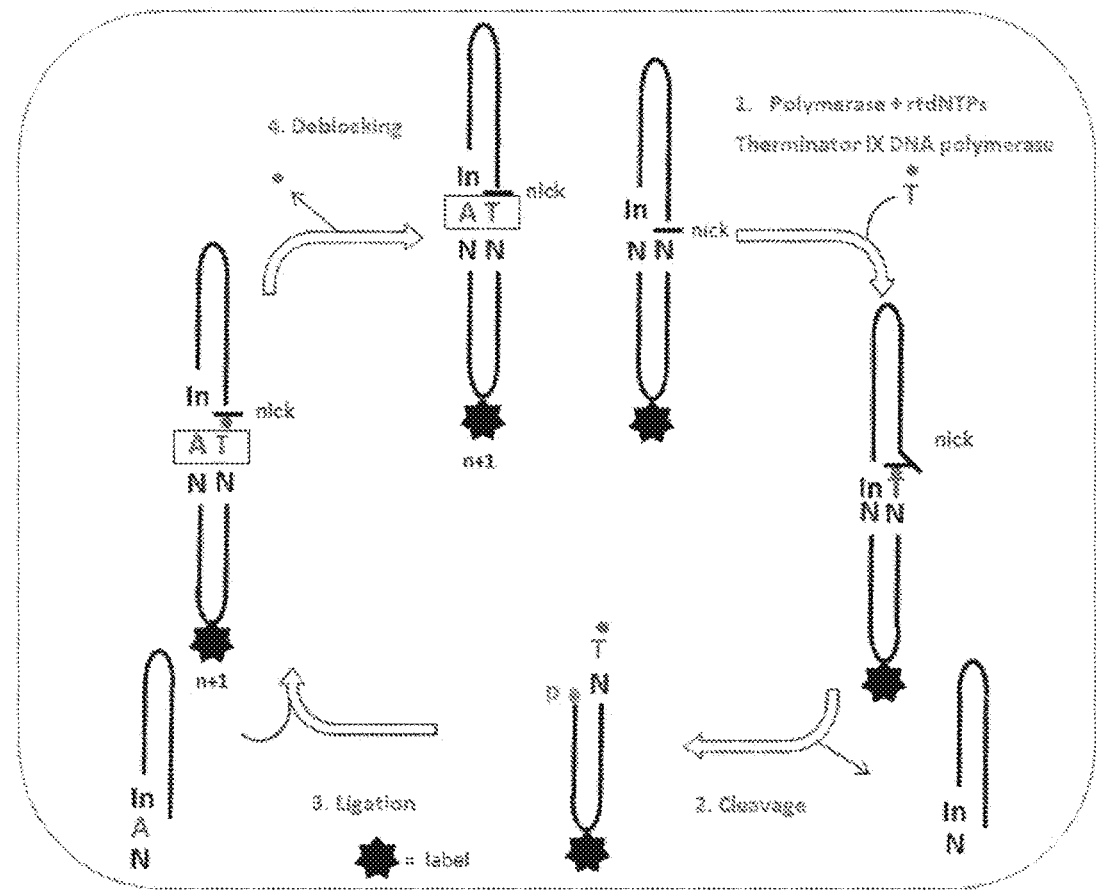

FIGS. 20a-20b. Version 3 Chemistry—Complete Cycle on Double-Hairpin Model.

FIG. 20a) Scheme showing full cycle involving enzymatic incorporation, cleavage, ligation and deprotection steps.

FIG. 20b) Oligonucleotides applicable for study of the incorporation step.

FIGS. 21a-21d. Version 2 Chemistry—Complete Two-Cycle on Double-Hairpin Model.

Figure 21A:
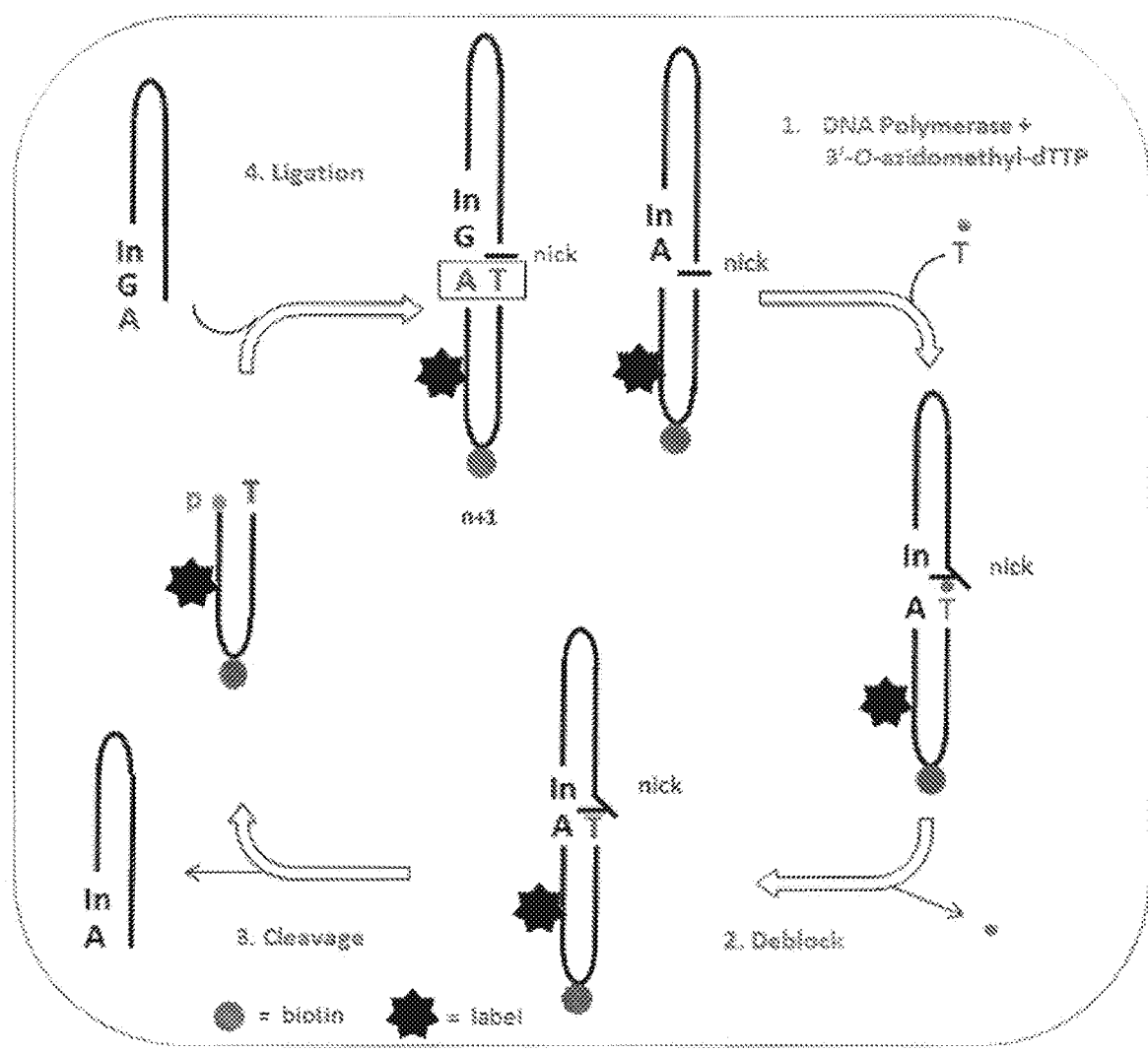

FIG. 21a) Scheme showing the first full cycle involving enzymatic incorporation, deprotection, cleavage and ligation steps.

Figure 21B:
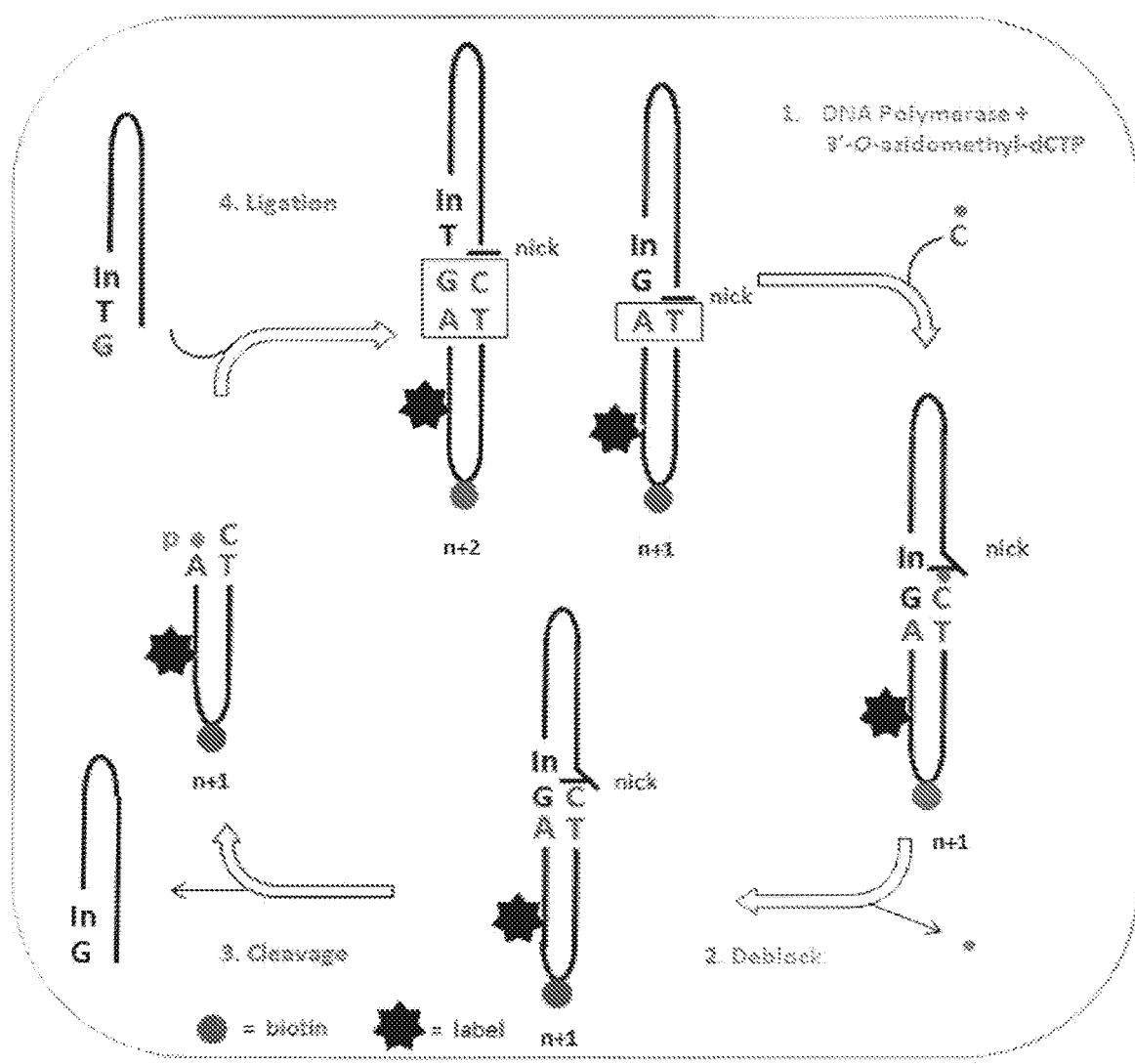

FIG. 21b) Scheme showing the second full cycle, following the first full cycle, involving enzymatic incorporation, deprotection, cleavage and ligation steps.

FIG. 21c) The Figure depicts a gel showing full two-cycle experiment comprising: incorporation, deprotection, cleavage and ligation steps.

Lane 1. Starting material.
Lane 2. Extension of starting material with natural dNTPs.
Lane 3. Incorporation of 3'-O-azidomethyl-dTTP by Therminator IX DNA polymerase.
Lane 4. Extension of the product in lane 3 by addition of all natural dNTPs.
Lane 5. Deprotection of the product in lane 3 by TCEP.
Lane 6. Extension of the product in lane 5 by addition of all natural dNTPs.
Lane 7. Cleavage of the product in lane 5 by Endonuclease V.
Lane 8. Ligation of the product in lane 7 by blunt TA ligase kit.
Lane 9. Cleavage of the product in lane 8 by Lambda exonuclease.
Lane 10. Starting material for second cycle—the same material as in lane 9.
Lane 11. Incorporation of 3'-O-azidomethyl-dTTP by Therminator IX DNA polymerase.
Lane 12. Extension of the product in lane 11 by addition of all natural dNTPs.
Lane 13. Deprotection of the product in lane 11 by TCEP.
Lane 14. Extension of the product in lane 13 by addition of all natural dNTPs.
Lane 15. Cleavage of the product in lane 13 by Endonuclease V.
Lane 16. Ligation of the product in lane 15 by blunt TA ligase kit.

FIG. 21d) Oligonucleotides used for study.

FIG. 22.

Example showing a mechanism of release from a scaffold polynucleotide of a polynucleotide of predefined sequence, as synthesised in accordance with the methods described herein.

FIG. 23.

Schematic of an exemplary method for the synthesis of RNA according to the invention. The exemplary method shows synthesis in the absence of a helper strand.

FIG. 24.

Schematic of an exemplary method for the synthesis of RNA according to the invention. The exemplary method shows synthesis in the presence of a helper strand.

FIG. 25.

Schematic of an exemplary method for the synthesis of RNA according to the invention. The exemplary method shows synthesis in the presence of a helper strand.

FIG. 26.

Schematic of the 1st full cycle of an exemplary method for the synthesis of DNA according to synthesis method version 2 with single hairpin model, involving a step of denaturing the helper strand prior to the incorporation step.

FIG. 27.

Schematic of the 2nd full cycle of an exemplary method for the synthesis of DNA according to synthesis method version 2 with single hairpin model, involving a step of denaturing the helper strand prior to the incorporation step.

FIG. 28.

Schematic of the 3rd full cycle of an exemplary method for the synthesis of DNA according to synthesis method version 2 with single hairpin model, involving a step of denaturing the helper strand prior to the incorporation step.

FIG. 29.

Oligonucleotides used in the experiments detailed in Example 9.

FIG. 30.

Gel showing reaction products corresponding to a full three-cycle experiment as detailed in Example 9.

The Figure depicts a gel showing the results of a full three-cycle experiment comprising: incorporation, deblock, cleavage and ligation steps.

Lane 1: Starting material.
Lane 2. Extension of starting material with natural dNTPs
Lane 3: Incorporation of 3'-O-azidomethyl-dTTP by Therminator X DNA polymerase.
Lane 4: Extension of the product in lane 3 by addition of all natural dNTPs.¬
Lane 5: Deblock of the product in lane 3 by TCEP
Lane 6: Extension of the product in lane 5 by addition of all natural dNTPs.¬
Lane 7: Cleavage of the product in lane 5 by Endonuclease V.
Lane 8: Ligation of the product in lane 7 by T3 DNA ligase
Lane 9: Starting material for 2nd cycle—the same material as in lane 9
Lane 10: Extension of the product in lane 9 by addition of all natural dNTPs.
Lane 11: Incorporation of 3'-O-azidomethyl-dTTP by Therminator X DNA polymerase.
Lane 12: Extension of the product in lane 11 by addition of all natural dNTPs.
Lane 13: Deblock of the product in lane 11 by TCEP
Lane 14: Extension of the product in lane 13 by addition of all natural dNTPs.
Lane 15: Cleavage of the product in lane 13 by Endonuclease V
Lane 16: Ligation of the product in lane 15 by T3 DNA ligase
Lane 17: Starting material for 3rd cycle—the same material as in lane 16
Lane 18: Extension of the product in lane 17 by addition of all natural dNTPs.
Lane 19: Incorporation of 3'-O-azidomethyl-dTTP by Therminator X DNA polymerase.
Lane 20: Extension of the product in lane 19 by addition of all natural dNTPs.
Lane 21: Deblock of the product in lane 19 by TCEP
Lane 22: Extension of the product in lane 21 by addition of all natural dNTPs.
Lane 23: Cleavage of the product in lane 21 by Endonuclease V
Lane 24: Ligation of the product in lane 23 by T3 DNA ligase

FIG. 31.

Fluorescence signals from polyacrylamide gel surfaces spiked with different amount of BRAPA exposed to FITC-PEG-SH and FITC-PEG-COOH.

FIG. 32.

Measured fluorescence signals from fluorescein channel on polyacrylamide gel surfaces spiked with different amount of BRAPA that are exposed to FITC-PEG-SH and FITC-PEG-COOH.

FIGS. 33a-33b.

FIG. 33a) Shows sequences of hairpin DNA without linker immobilised on different samples.

FIG. 33b) Shows sequences of hairpin DNA with linker immobilised on different samples.

FIG. 34.

Fluorescence signals from hairpin DNA oligomers with and without linker immobilised onto bromoacetyl functionalised polyacrylamide surfaces.

FIG. 35.

Measured fluorescence from hairpin DNA oligomers with and without linker immobilised onto bromoacetyl functionalised polyacrylamide surfaces.

FIG. 36.

Fluorescence signals from hairpin DNA oligomers with and without linker immobilised onto bromoacetyl functionalised polyacrylamide surfaces following incorporation of triphosphates.

Figure 37A:
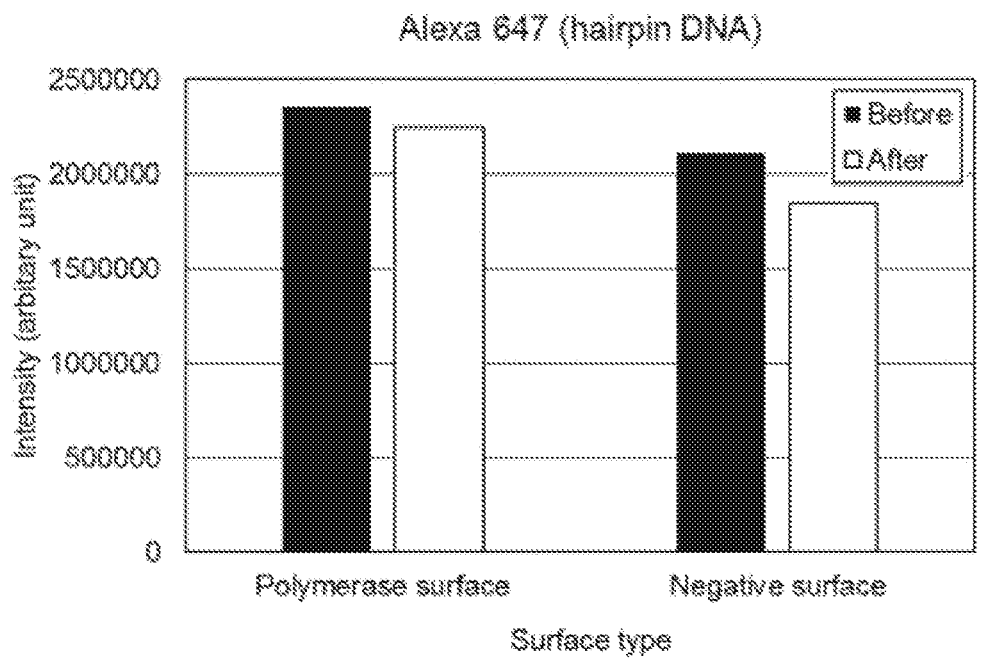
Figure 37B:
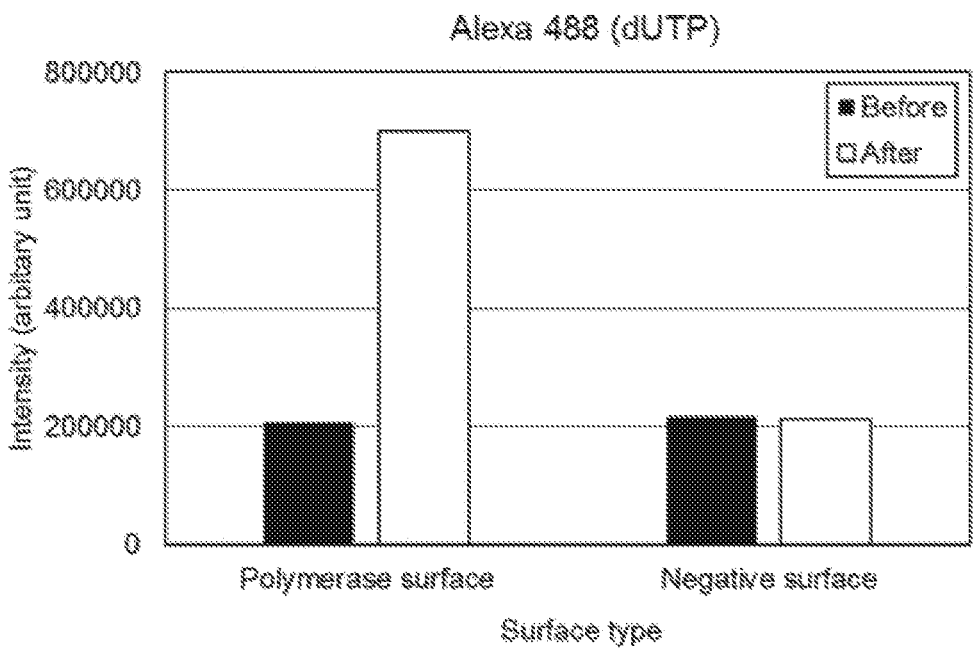

FIGS. 37a-37b.

Measured fluorescence from hairpin DNA oligomers with and without linker immobilised onto bromoacetyl functionalised polyacrylamide surfaces following incorporation of triphosphates.

FIGS. 38a-38b.

FIG. 38a) Experimental overview and outcome for each reaction step as detailed in Example 12.

FIG. 38b) Oligonucleotides used in the experiments detailed in Example 12.

FIG. 39.

Shows fluorescence signals from hairpin DNA oligomers before and after cleavage reactions (Example 12).

FIG. 40.

Shows measured fluorescence signals from hairpin DNA oligomers before and after cleavage reactions (Example 12).

FIG. 41.

Shows the sequences for the inosine-containing strand and the complimentary 'helper' strand for ligation reactions (Example 12).

FIG. 42.

Results relating to fluorescence signals from hairpin DNA oligomers corresponding to the monitoring of ligation reactions (Example 12).

FIG. 43.

Results relating to measured fluorescence from hairpin DNA oligomers corresponding to the monitoring of ligation reactions (Example 12).

INTERPRETATION OF FIGURES

Figure 1:
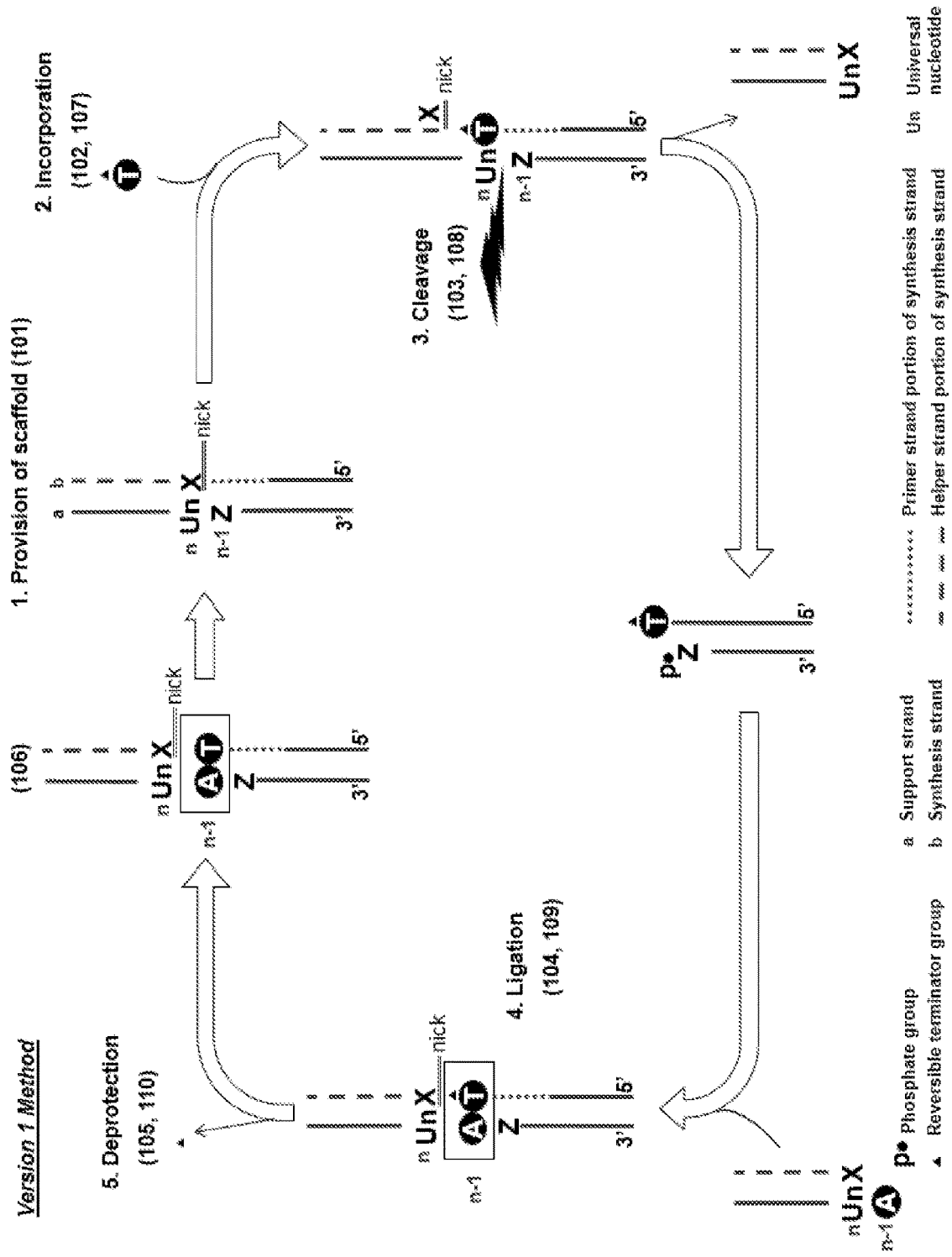

The structures depicted in FIGS. 4, 5a, 6a, 7a, 8a, 9a, 10a, 11a, 12a, 13a, 14a, 15a, 16a, 17a, 18a, 19a, 20a, 21a, 21b, 22, 23, 24, 25, 26, 27, and 28 are to be interpreted consistently with those depicted in FIGS. 1, 2 and 3a. Thus in these Figures, each left hand strand of a double-stranded scaffold polynucleotide molecule relates to the support strand (corresponding to strand "a" in FIGS. 1, 2 and 3a); each right hand strand of a double-stranded scaffold polynucleotide molecule relates to the synthesis strand (corresponding to strand "b" in FIGS. 1, 2 and 3a); all scaffold polynucleotide molecules comprise a lower synthesis strand which corresponds to a strand comprising a primer strand portion (corresponding to the solid and dotted line of strand "b" in FIGS. 1, 2 and 3a); certain scaffold polynucleotide molecules (e.g. in FIGS. 8a and 16a) are shown, prior to incorporation of the new nucleotide, with an upper synthesis strand which corresponds to a strand comprising a helper strand portion (corresponding to the dashed line of strand "b" in FIGS. 1, 2 and 3a); certain scaffold polynucleotide molecules (e.g. in FIGS. 5a, 6a and 7a) are shown with no helper strand portion (corresponding to an absence of the dashed line of strand "b" in FIGS. 1, 2 and 3a); and certain scaffold polynucleotide molecules (e.g. in FIGS. 26, 27 and 28) are shown, after the ligation step, with an upper synthesis strand which corresponds to a strand comprising a helper strand portion (corresponding to the dashed line of strand "b" in FIGS. 1, 2 and 3a) and wherein the helper strand portion is removed prior to incorporation of the new nucleotide in the next synthesis cycle.

In addition, in these Figures, where relevant, each new nucleotide is shown to be incorporated together with a reversible terminator group, labelled rtNTP and depicted as a small circular structure (corresponding to the small triangular structure in FIGS. 1, 2 and 3a) and terminal phosphate groups are labelled "p" and depicted as a small elliptical structure.

FIGS. 4c, 4d, 4g, 4h, 15a, 16a, 17a, 18a, 20a, 21a, 21b, and 22 show scaffold polynucleotide molecules wherein strands comprising a helper strand portion and support strands are connected by a hairpin loop. FIGS. 4b, 15a, 16a, 17a, 18a, 19a, 20a, 21a, 21b, 22, 26, 27, and 28 show scaffold polynucleotide molecules wherein strands comprising a primer strand portion and support strands are connected by a hairpin loop.

Figures such as FIGS. 20a and 21a show scaffold polynucleotide molecules wherein the strand comprising a helper strand portion (upper right strand) and the support strand (upper left strand) is connected by a hairpin loop and, in the same molecule, the strand comprising the primer strand portion (lower right strand) and the support strand (lower left strand) are connected by a hairpin loop.

DETAILED DESCRIPTION OF THE INVENTION

The present invention provides methods for the de novo synthesis of polynucleotide molecules according to a predefined nucleotide sequence. Synthesised polynucleotides are preferably DNA and are preferably double-stranded polynucleotide molecules. The invention provides advantages compared with existing synthesis methods. For example, all reaction steps may be performed in aqueous conditions at mild pH, extensive protection and deprotection procedures are not required. Furthermore, synthesis is not dependent upon the copying of a pre-existing template strand comprising the predefined nucleotide sequence.

The present inventors have determined that the use of a universal nucleotide, as defined herein, allows a newly-incorporated nucleotide to be correctly paired with its desired partner nucleotide during each cycle of synthesis. The use of a universal nucleotide allows for the creation of a cleavage site within the region of de novo synthesis, which facilitates cleavage and repeat cycles of synthesis. The invention provides versatile methods for synthesising polynucleotides, and for assembling large fragments comprising such synthesised polynucleotides.

Certain embodiments of the synthesis methods of the invention will be described in more general detail herein by reference to exemplary methods including five method versions. Method versions are also described in specific detail in the Examples. It is to be understood that all exemplary methods, including the five method versions, are not intended to be limiting on the invention. The invention provides an in vitro method of synthesising a double-stranded polynucleotide molecule having a predefined sequence, the method comprising performing cycles of synthesis wherein in each cycle a first polynucleotide strand is extended by the incorporation of a nucleotide of the predefined sequence, and then the second polynucleotide strand which is hybridized to the first strand is extended by the incorporation of a nucleotide thereby forming a nucleotide pair with the incorporated nucleotide of the first strand. Preferably, the methods are for synthesising DNA. Specific methods described herein are provided as embodiments of the invention.

Reaction Conditions

In one aspect the invention provides a method for synthesising a double-stranded polynucleotide having a predefined sequence.

In one aspect the invention provides a method for synthesising a double-stranded polynucleotide having a predefined sequence.

In some embodiments, synthesis is carried out under conditions suitable for hybridization of nucleotides within double-stranded polynucleotides. Polynucleotides are typically contacted with reagents under conditions which permit the hybridization of nucleotides to complementary nucleotides. Conditions that permit hybridization are well-known in the art (for example, Sambrook et al., 2001, Molecular Cloning: a laboratory manual, 3rd edition, Cold Spring Harbour Laboratory Press; and Current Protocols in Molecular Biology, Greene Publishing and Wiley-Interscience, New York (1995)).

Incorporation of nucleotides into polynucleotides can be carried out under suitable conditions, for example using a polymerase (e.g., Therminator IX polymerase) to incorporate modified nucleotides (e.g., 3'-O-modified-dNTPs) at a suitable temperature (e.g., ~65° C.) in the presence of a suitable buffered solution. In one embodiment, the buffered solution can comprise 2 mM Tris-HCl, 1 mM $(NH_4)_2SO_4$, 1 mM KCl, 0.2 mM $MgSO_4$ and 0.01% Triton® X-100.

Cleavage of polynucleotides can be carried out under suitable conditions, for example using a polynucleotide cleaving enzyme (e.g., endonuclease) at a temperature that is compatible with the enzyme (e.g., 37° C.) in the presence of a suitable buffered solution. In one embodiment, the buffered solution can comprise 5 mM potassium acetate, 2 mM Tris-acetate, 1 mM magnesium acetate and 0.1 mM DTT.

Ligation of polynucleotides can be carried out under suitable conditions, for example using a ligase (e.g., T4 DNA ligase) at a temperature that is compatible with the enzyme (e.g., room temperature) in the presence of a suitable buffered solution. In one embodiment, the buffered solution can comprise 4.4 mM Tris-HCl, 7 mM $MgCl_2$, 0.7 mM dithiothreitol, 0.7 mM ATP, 5% polyethylene glycol (PEG6000).

Deprotection can be carried out under suitable conditions, for example using a reducing agent (e.g., TCEP). For example, deprotection can be performed using TCEP in Tris buffer (e.g., at a final concentration of 300 mM).

Anchor Polynucleotides and Scaffold Polynucleotides

Double-stranded polynucleotides having a predefined sequence are synthesized by methods of the invention by incorporation of pre-defined nucleotides into a pre-existing polynucleotide, referred to herein as a scaffold polynucleotide, which may be attached to or capable of being attached to a surface as described herein. As described in more detail herein a scaffold polynucleotide forms a support structure to accommodate the newly-synthesised polynucleotide and, as will be apparent from the description herein, does not comprise a pre-existing template strand which is copied as in conventional methods of synthesis. A scaffold polynucleotide may be referred to as an anchor polynucleotide if the scaffold polynucleotide is attached to a surface. Surface attachment chemistries for attaching a scaffold polynucleotide to a surface to form an anchor polynucleotide are described in more detail herein.

In one embodiment a scaffold polynucleotide comprises a synthesis strand hybridized to a complementary support strand. The synthesis strand comprises a polymerase primer strand portion and optionally a helper strand portion separated by a single-strand break or "nick" (e.g. FIGS. 1 to 3a). Both the primer strand portion and the helper strand portion of the synthesis strand may be provided hybridized to the complementary support strand. Alternatively, the helper strand portion of the synthesis strand may be provided separately. The primer strand portion of the synthesis strand may be provided first, followed by the support strand and helper strand. Alternatively components of the scaffold polynucleotide may be provided separately. For example, the support strand may be provided first, followed by the primer strand portion of the synthesis strand and then the helper strand. The support strand may be provided first, followed by the helper strand portion of the synthesis strand and then the primer strand. The helper strand portion may be provided before a cleavage step. The helper strand portion may be omitted from a scaffold polynucleotide prior to incorporation of a new predefined nucleotide. The helper strand portion may be removed from a scaffold polynucleotide prior to incorporation of a new predefined nucleotide, e.g. by denaturation, as describe in more detail herein. Upon mixing of the components in suitable conditions the scaffold polynucleotide forms upon hybridization of the separate components.

New synthesis is initiated by polymerase at the site of the single-strand break. Thus polymerase will act to extend the terminal nucleotide of the primer strand portion at the site of the single-strand break. The single-stranded break or "nick" between the helper strand portion of the synthesis strand and the primer strand portion of the synthesis strand is typically achieved by providing both portions of the synthesis strand as separate molecules which will align following hybridization with the support strand. The (5') terminal nucleotide of the helper strand at the single-stranded break site is typically provided lacking a phosphate group. The lack of a terminal phosphate group prevents the terminal nucleotide of the helper strand portion ligating with the terminal nucleotide of the primer strand portion at the single-stranded break site, thus maintaining the single-stranded break. Creation and maintenance of the single-stranded break could be effected by other means. For example, the terminal nucleotide of the helper strand portion may be provided with a suitable blocking group which prevents ligation with the primer strand portion. Preferably the helper strand is provided lacking a terminal phosphate group at the single-stranded break site.

A scaffold polynucleotide may be provided with each of the support and synthesis strands unconnected at adjacent ends. A scaffold polynucleotide may be provided with both support and synthesis strands connected at adjacent ends, such as via a hairpin loop, at both ends of the scaffold polynucleotide. A scaffold polynucleotide may be provided with both support and synthesis strands connected at adjacent ends, such as via a hairpin loop, at one end of the scaffold polynucleotide or any other suitable linker.

Scaffold polynucleotides with or without hairpins may be immobilized to a solid support or surface as described in more detail herein (see FIG. 4).

The terms "hairpin" or "hairpin loop" are commonly used in the current technical field. The term "hairpin loop" is also often referred to as a "stem loop". Such terms refer to a region of secondary structure in a polynucleotide comprising a loop of unpaired nucleobases which form when one strand of a polynucleotide molecule hybridizes with another section of the same strand due to intramolecular base pairing. Thus hairpins can resemble U-shaped structures. Examples of such structures are shown in FIG. 4.

Nucleotides and Universal Nucleotides

Nucleotides which can be incorporated into synthetic polynucleotides by any of the methods described herein may be nucleotides, nucleotide analogues and modified nucleotides. Nucleotides, nucleotide analogues and modified nucleotides can be incorporated into synthetic polynucleotides by any of the methods described herein.

In any of the synthesis methods of the invention defined and described herein, nucleotides are preferably incorporated as nucleotides comprising a reversible terminator group as described herein.

Nucleotides may comprise natural nucleobases or non-natural nucleobases. Nucleotides may contain a natural nucleobase, a sugar and a phosphate group. Natural nucleobases comprise adenosine (A), thymine (T), uracil (U), guanine (G) and cytosine (C). One of the components of the nucleotide may be further modified.

Nucleotide analogues are nucleotides that are modified structurally either in the base, sugar or phosphate or combination therein and that are still acceptable to a polymerase enzyme as a substrate for incorporation into an oligonucleotide strand.

A non-natural nucleobase may be one which will bond, e.g. hydrogen bond, to some degree to all of the nucleobases in the target polynucleotide. A non-natural nucleobase is preferably one which will bond, e.g. hydrogen bond, to some degree to nucleotides comprising the nucleosides adenosine (A), thymine (T), uracil (U), guanine (G) and cytosine (C).

A non-natural nucleotide may be a peptide nucleic acid (PNA), a locked nucleic acid (LNA) and an unlocked nucleic acid (UNA), a bridged nucleic acid (BNA) or a morpholino, a phosphorothioate or a methylphosphonate.

A non-natural nucleotide may comprise a modified sugar and/or a modified nucleobase. Modified sugars include but are not limited to 2'-O-methylribose sugar. Modified nucleobases include but are not limited to methylated nucleobases. Methylation of nucleobases is a recognised form of epigenetic modification which has the capability of altering the expression of genes and other elements such as microRNAs. Methylation of nucleobases occurs at discrete loci which are predominately dinucleotide consisting of a CpG motif, but may also occur at CHH motifs (where H is A, C, or T). Typically, during methylation a methyl group is added to the fifth carbon of cytosine bases to create methylcytosine. Thus modified nucleobases include but are not limited to 5-methylcytosine.

Nucleotides of the predefined sequence may be incorporated opposite partner nucleotides to form a nucleotide pair. A partner nucleotide may be a complementary nucleotide. A complementary nucleotide is a nucleotide which is capable of bonding, e.g. hydrogen bonding, to some degree to the nucleotides of the predefined sequence.

Typically, a nucleotide of the predefined sequence is incorporated into a polynucleotide opposite a naturally complementary partner nucleobase. Thus adenosine may be incorporated opposite thymine and vice versa. Guanine may be incorporated opposite cytosine and vice versa. Alternatively, a nucleotide of the predefined sequence may be incorporated opposite a partner nucleobase to which it will bond, e.g. hydrogen bond, to some degree.

Alternatively a partner nucleotide may be a non-complementary nucleotide. A non-complementary nucleotide is a nucleotide which is not capable of bonding, e.g. hydrogen bonding, to the nucleotide of the predefined sequence. Thus a nucleotide of the predefined sequence may be incorporated opposite a partner nucleotide to form a mismatch, provided that the synthesised polynucleotide overall is double-stranded and wherein the first strand is attached to the second strand by hybridization.

The term "opposite" is to be understood as relating to the normal use of the term in the field of nucleic acid biochemistry, and specifically to conventional Watson-Crick base-pairing. Thus a first nucleic acid molecule of sequence 5'-ACGA-3' may form a duplex with a second nucleic acid molecule of sequence 5'-TCGT-3' wherein the G of the first molecule will be positioned opposite the C of the second molecule and will hydrogen bond therewith. A first nucleic acid molecule of sequence 5'-ATGA-3' may form a duplex with a second nucleic acid molecule of sequence 5'-TCGT-3', wherein the T of the first molecule will mismatch with the G of the second molecule but will still be positioned opposite therewith and will act as a partner nucleotide. This principle applies to any nucleotide partner pair relationship disclosed herein, including partner pairs comprising universal nucleotides.

In all of the methods described herein a position in the support strand, and the opposite position in the synthesis strand, is assigned the position number "n". This position refers to the position of a nucleotide in the support strand of a scaffold polynucleotide which in any given synthesis cycle is opposite the position in the synthesis strand which will be occupied by a newly-incorporated nucleotide of predefined sequence upon incorporation at step (2). It also refers to the position in the support strand of a ligation polynucleotide at step (4) which position is opposite the position in the synthesis strand which will be occupied by a newly-incorporated nucleotide of predefined sequence upon incorporation in the next synthesis cycle at step (6). Both the position in the support strand and the opposite position in the synthesis strand may be referred to as positon n. For reference see FIGS. 1, 2, 3a, 3b and 3c.

The term "in proximity with", relating to the positioning in the scaffold polynucleotide of a newly-incorporated nucleotide of predefined sequence and its partner relative to the placement of the universal nucleotide, is to be understood as relating to the normal use of the term in the context of the invention. Thus in methods, such as method version 1 described herein, wherein a newly-incorporated nucleotide of predefined sequence (occupying position "n") initially has a universal nucleotide as its partner (thus also occupying position n), then the newly-incorporated nucleotide is positioned "opposite" the universal nucleotide as described above. This is one example of a newly-incorporated nucleotide being positioned in proximity with the universal nucleotide. Alternatively, a newly-incorporated nucleotide of predefined sequence (occupying position n) may initially have a different nucleotide as its partner, and the universal nucleotide may occupy a different position, such as position n+1 as in method version 2 described herein. In this case the newly-incorporated nucleotide is positioned in proximity with the universal nucleotide but not opposite the universal nucleotide. In alternative methods, the universal nucleotide may be removed from position n incrementally by one position to occupy positions e.g. n+2, n+3, n+3+x wherein x is a whole number between 1 and 10 or more etc. In such alternative methods the newly-incorporated nucleotide is still positioned in proximity with the universal nucleotide, provided that a cleavage site defined by the universal nucleotide may be created and provided that the overhang structures described herein may be generated upon cleavage allowing for the subsequent ligation of the ligation polynucleotide.

Nucleotides and nucleotide analogues may preferably be provided as nucleoside triphosphates. Thus in any of the methods of the invention in order to synthesise DNA polynucleotides, nucleotides may be incorporated from 2'-deoxyribonucleoside-5'-O-triphosphates (dNTPs), e.g. via the action of a DNA polymerase enzyme. In any of the methods of the invention in order to synthesise RNA polynucleotides, nucleotides may be incorporated ribonucleoside-5'-O-triphosphates (NTPs), e.g. via the action of a RNA polymerase enzyme. Triphosphates can be substituted by tetraphosphates or pentaphosphates (generally oligophosphate). These oligophosphates can be substituted by other alkyl or acyl groups:

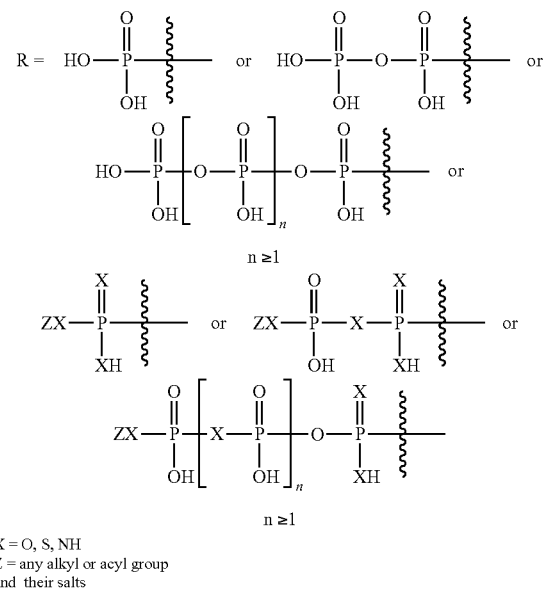

X = O, S, NH
Z = any alkyl or acyl group
and their salts

Methods of the invention may use a universal nucleotide. A universal nucleotide may be used as a component of the support strand of a scaffold molecule to facilitate a newly-incorporated nucleotide to be correctly paired with its desired partner nucleotide during each cycle of synthesis. A universal nucleotide may also be incorporated into the synthesis strand as a component of the predefined nucleotide sequence if desired.

A universal nucleotide is one wherein the nucleobase will bond, e.g. hydrogen bond, to some degree to the nucleobase of any nucleotide of the predefined sequence. A universal nucleotide is preferably one which will bond, e.g. hydrogen bond, to some degree to nucleotides comprising the nucleosides adenosine (A), thymine (T), uracil (U), guanine (G) and cytosine (C). The universal nucleotide may bond more strongly to some nucleotides than to others. For instance, a universal nucleotide (I) comprising the nucleoside, 2'-deoxyinosine, will show a preferential order of pairing of I-C>I-A>I-G approximately =I-T.

Examples of possible universal nucleotides are inosines or nitro-indoles. The universal nucleotide preferably comprises one of the following nucleobases: hypoxanthine, 4-nitroindole, 5-nitroindole, 6-nitroindole, 3-nitropyrrole, nitroimidazole, 4-nitropyrazole, 4-nitrobenzimidazole, 5-nitroindazole, 4-aminobenzimidazole or phenyl (C6-aromatic ring.

The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 4-nitroindole 2'-deoxyribonucleoside, 4-nitroindole ribonucleoside, 5-nitroindole 2' deoxyribonucleoside, 5-nitroindole ribonucleoside, 6-nitroindole 2' deoxyribonucleoside, 6-nitroindole ribonucleoside, 3-nitropyrrole 2' deoxyribonucleoside, 3-nitropyrrole ribonucleoside, an acyclic sugar analogue of hypoxanthine, nitroimidazole 2' deoxyribonucleoside, nitroimidazole ribonucleoside, 4-nitropyrazole 2' deoxyribonucleoside, 4-nitropyrazole ribonucleoside, 4-nitrobenzimidazole 2' deoxyribonucleoside, 4-nitrobenzimidazole ribonucleoside, 5-nitroindazole 2' deoxyribonucleoside, 5-nitroindazole ribonucleoside, 4-aminobenzimidazole 2' deoxyribonucleoside, 4-aminobenzimidazole ribonucleoside, phenyl C-ribonucleoside or phenyl C-2'-deoxyribosyl nucleoside.

Some examples of universal bases are shown below:

inosine base analogues

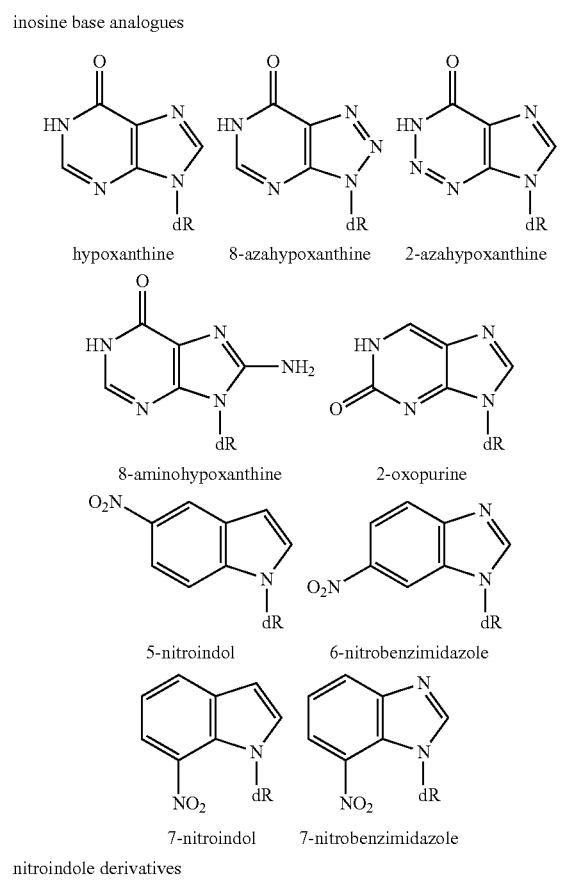

nitroindole derivatives

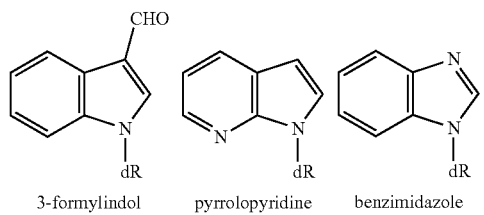

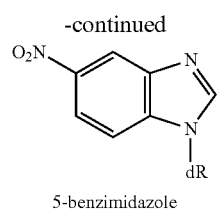

5-benzimidazole nitropyrrol and nitrobenzene derivatives

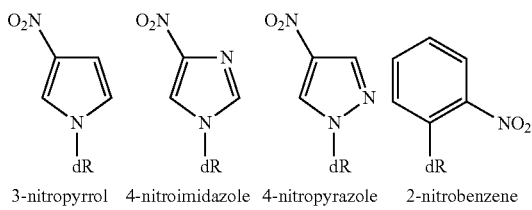

3-nitropyrrol    4-nitroimidazole    4-nitropyrazole    2-nitrobenzene nucleoside analogue

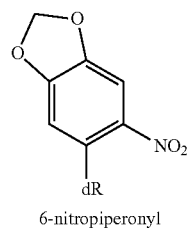

6-nitropiperonyl

Universal nucleotides incorporating cleavable bases may also be used, including photo- and enzymatically-cleavable bases, some examples of which are shown below.

Photocleavable Bases:

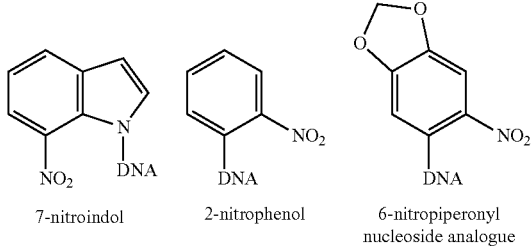

7-nitroindol    2-nitrophenol    6-nitropiperonyl nucleoside analogue

Base Analogues Cleavable by Endonuclease III:

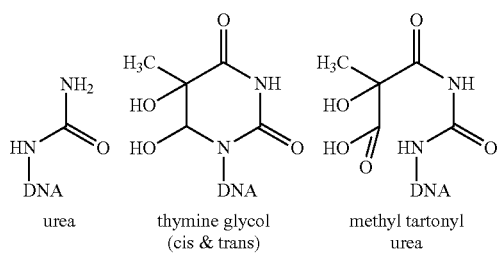

urea    thymine glycol (cis & trans)    methyl tartonyl urea

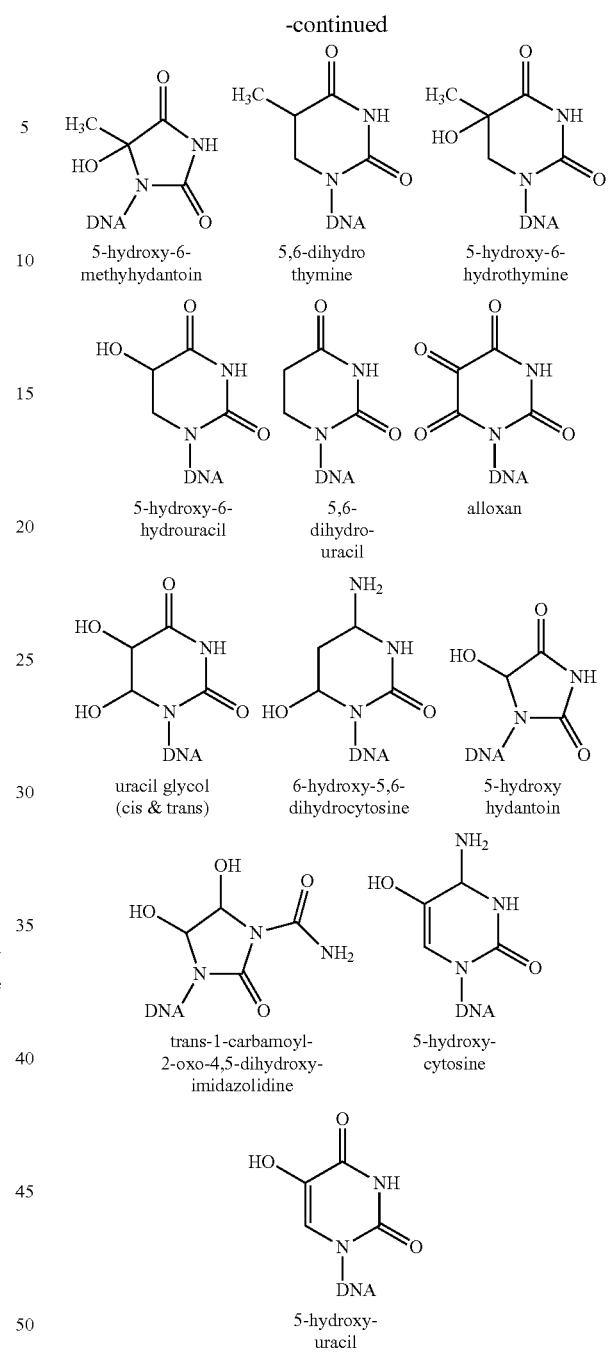

5-hydroxy-6-methyhydantoin    5,6-dihydro thymine    5-hydroxy-6-hydrothymine 5-hydroxy-6-hydrouracil    5,6-dihydro-uracil    alloxan uracil glycol (cis & trans)    6-hydroxy-5,6-dihydrocytosine    5-hydroxy hydantoin trans-1-carbamoyl-2-oxo-4,5-dihydroxy-imidazolidine    5-hydroxy-cytosine 5-hydroxy-uracil Base Analogues Cleavable by Formamidopyrimidine DNA Glycosylase (Fpg):

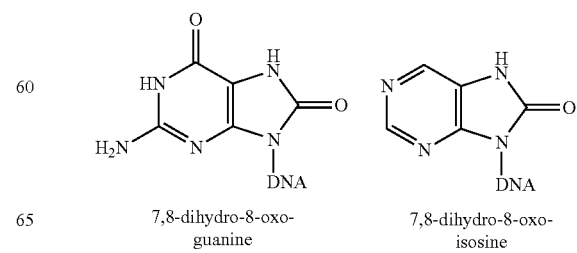

7,8-dihydro-8-oxo-guanine    7,8-dihydro-8-oxo-isosine

-continued

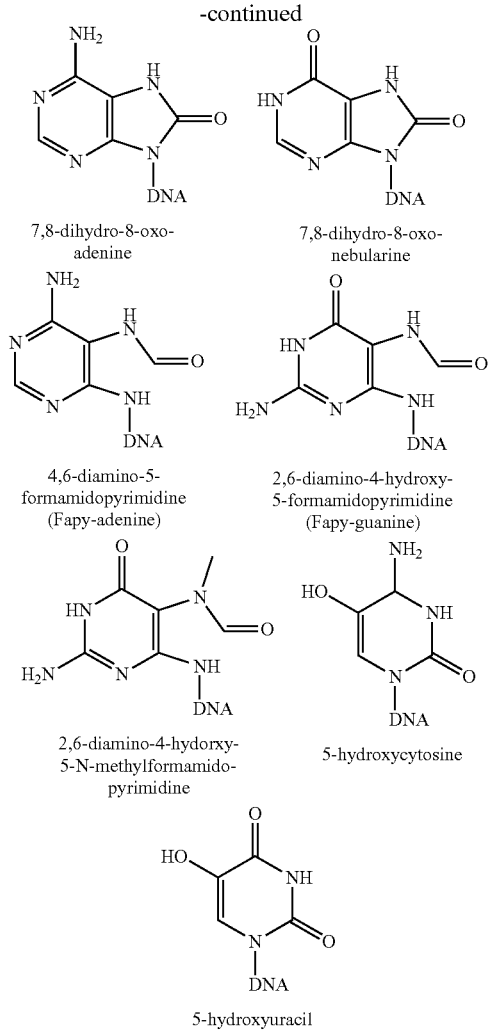

7,8-dihydro-8-oxo-adenine 7,8-dihydro-8-oxo-nebularine 4,6-diamino-5-formamidopyrimidine (Fapy-adenine)

2,6-diamino-4-hydroxy-5-formamidopyrimidine (Fapy-guanine)

2,6-diamino-4-hydorxy-5-N-methylformamido-pyrimidine 5-hydroxycytosine

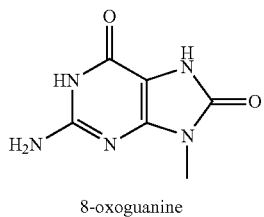

5-hydroxyuracil

Base Analogues Cleavable by 8-Oxoguanine DNA Glycosylase (hOGG1):

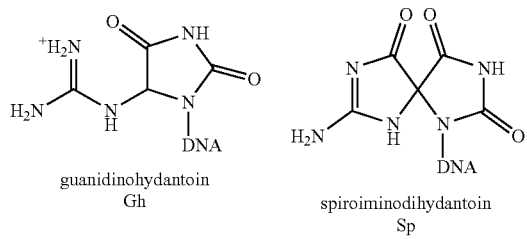

8-oxoguanine

Base Analogues Cleavable by hNeil1:

guanidinohydantoin Gh spiroiminodihydantoin Sp

-continued

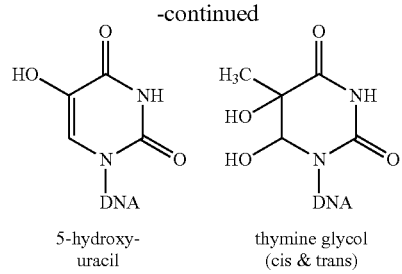

5-hydroxy-uracil thymine glycol (cis & trans)

Base Analogues Cleavable by Thymine DNA Glycosylase (TDG):

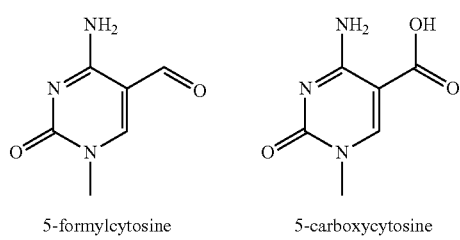

5-formylcytosine 5-carboxycytosine

Base Analogues Cleavable by Human Alkyladenine DNA Glycosylase (hAAG):

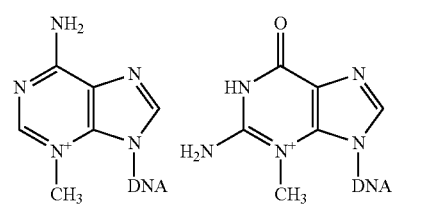

3-methyladenine 3-methylguanine

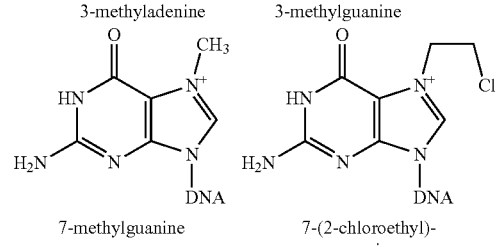

7-methylguanine 7-(2-chloroethyl)-guanine

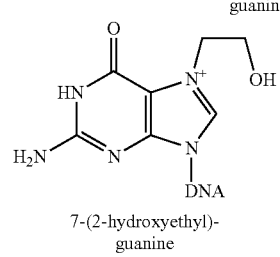

7-(2-hydroxyethyl)-guanine

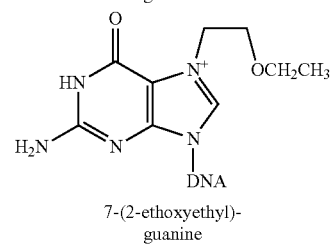

7-(2-ethoxyethyl)-guanine

-continued

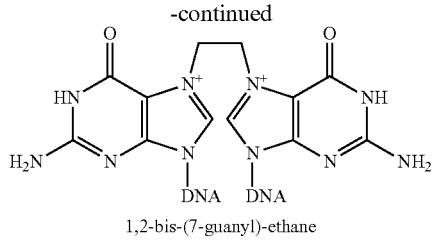

1,2-bis-(7-guanyl)-ethane

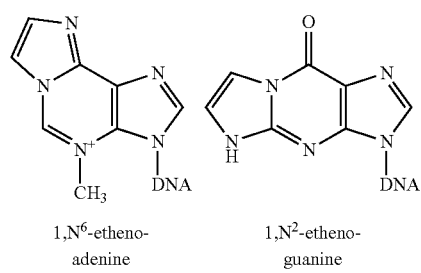

1,N⁶-etheno-adenine     1,N²-etheno-guanine

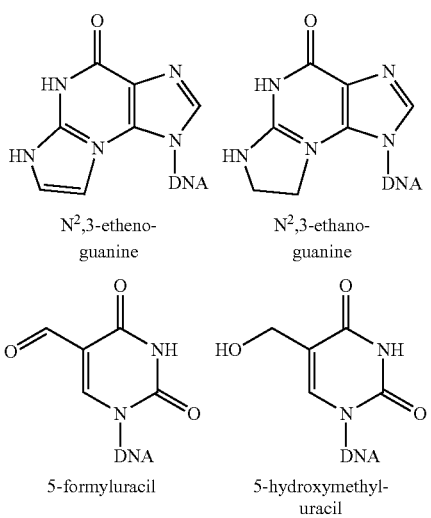

N²,3-etheno-guanine     N²,3-ethano-guanine 5-formyluracil     5-hydroxymethyl-uracil

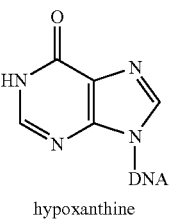

hypoxanthine

Base Cleavable by Uracil DNA Glycosylase:

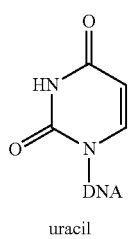

uracil

Bases Cleavable by Human Single-Strand-Selective Monofunctional Uracil-DNA Glycosylase (SMUG1):

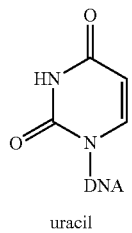

uracil

Bases Cleavable by 5-Methylcytosine DNA Glycosylase (ROS1):

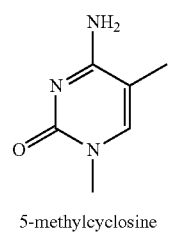

5-methylcyclosine (see S. S. David, S. D. Williams *Chemical reviews* 1998, 98, 1221-1262 and M. I. Ponferrada-Marín, T. Roldán-Arjona, R. R. Ariza' *Nucleic Acids Res* 2009, 37, 4264-4274).

In any of the methods involving scaffold polynucleotides, the universal nucleotide most preferably comprises 2'-deoxyinosine.

Examples of epigenetic bases which may be incorporated using any of the synthesis methods described herein include the following:

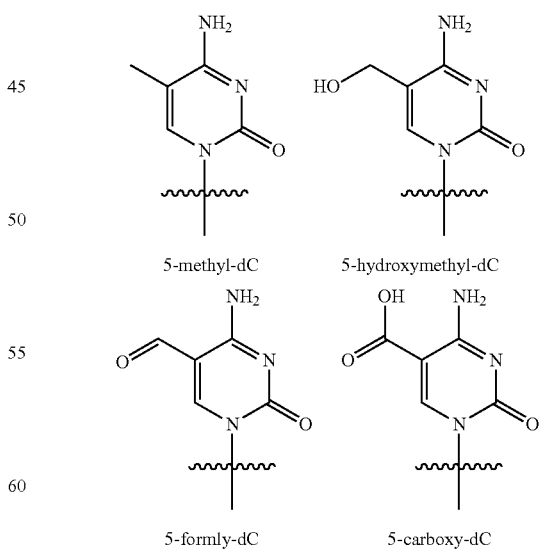

5-methyl-dC     5-hydroxymethyl-dC 5-formly-dC     5-carboxy-dC

Examples of modified bases which may be incorporated using any of the synthesis methods described herein include the following:

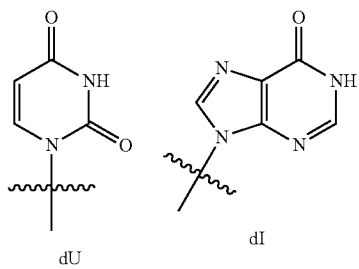 [SMILES: *n1ccc(=O)[nH]c1=O ; *n1cnc2c(=O)[nH]cnc21]

Examples of halogenated bases which may be incorporated using any of the synthesis methods described herein include the following:

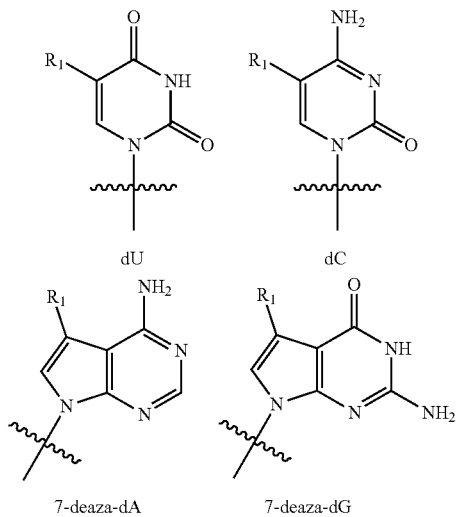

where R1=F, Cl, Br, I, alkyl, aryl, fluorescent label, aminopropargyl, aminoallyl.

Examples of amino-modified bases, which may be useful in e.g. attachment/linker chemistry, which may be incorporated using any of the synthesis methods described herein include the following:

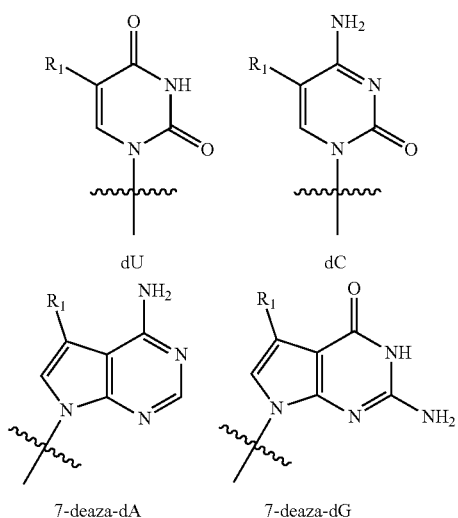

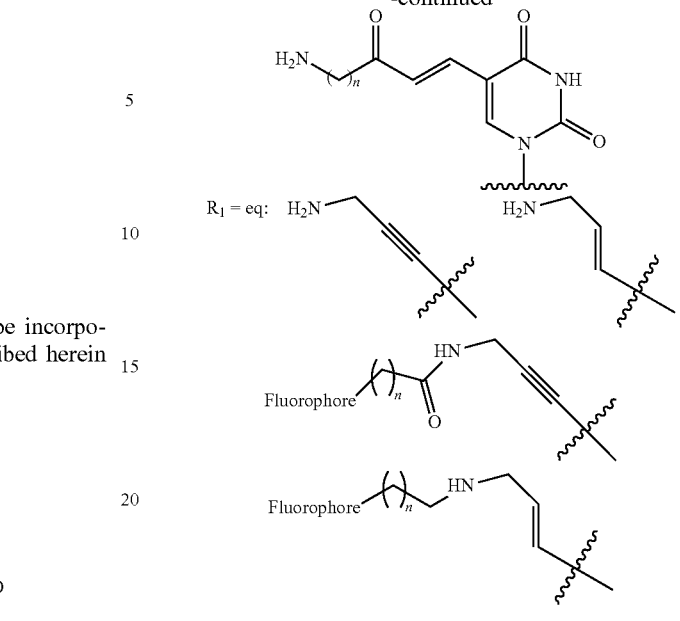

where base=A, T, G or C with alkyne or alkene linker.

Examples of modified bases, which may be useful in e.g. click chemistry, which may be incorporated using any of the synthesis methods described herein include the following:

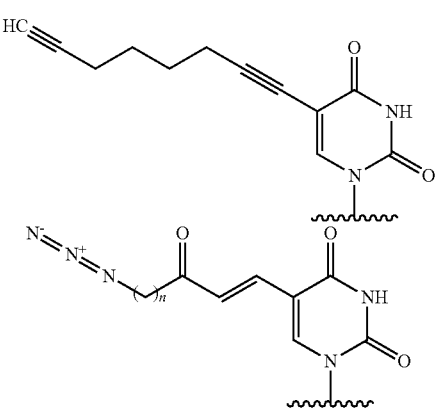

Examples of biotin-modified bases which may be incorporated using any of the synthesis methods described herein include the following:

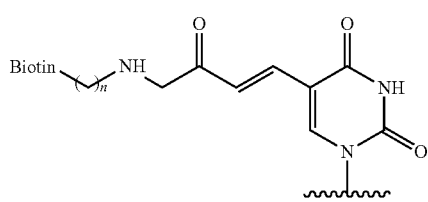

where base=A, T, G or C with alkyne or alkene linker.

Examples of bases bearing fluorophores and quenchers which may be incorporated using any of the synthesis methods described herein include the following:

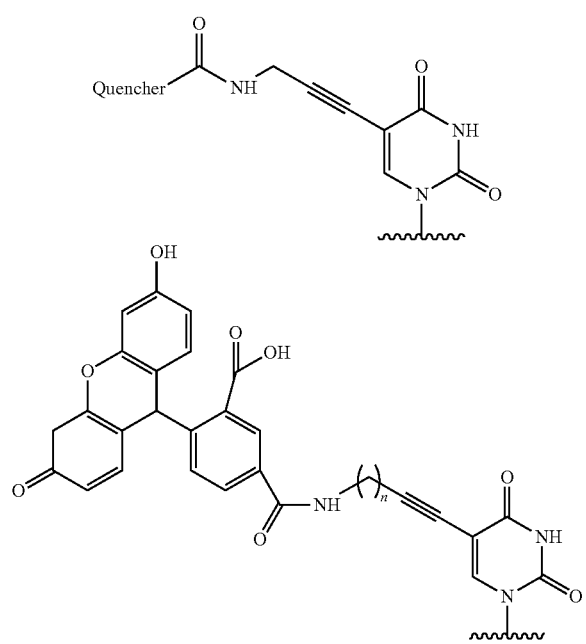

Nucleotide-Incorporating Enzymes

Any suitable enzyme may be employed to incorporate a predefined nucleotide using the methods described herein. Thus in all methods defined and described herein referring to the use a polymerase, the polymerase may be substituted with another enzyme capable of performing the same function as a polymerase in the context of the methods of the invention.

Preferably, a polymerase enzyme may be employed in the methods described herein. Polymerase enzymes may be chosen based on their ability to incorporate modified nucleotides, in particular nucleotides having attached reversible terminator groups, as described herein. In the exemplary methods described herein all polymerases which act on DNA must not have 3' to 5' exonuclease activity. Preferably, the polymerase will have strand displacement activity.

Thus preferably the polymerase is a modified polymerase having an enhanced ability to incorporate a nucleotide comprising a reversible terminator group compared to an unmodified polymerase. The polymerase is more preferably a genetically engineered variant of the native DNA polymerase from *Thermococcus* species 9° N, preferably species 9° N-7. One such example of a modified polymerase is Therminator IX DNA polymerase available from New England BioLabs. This enzyme has an enhanced ability to incorporate 3'-O-modified dNTPs.

Examples of other polymerases that can be used for incorporation of reversible terminator dNTPs in any of the methods of the invention are Deep Vent (exo-), Vent (Exo-), 9° N DNA polymerase, Therminator DNA polymerase, Therminator IX DNA polymerase, Klenow fragment (Exo-), Bst DNA polymerase, Bsu DNA polymerase, *Sulfolobus* DNA polymerase I, and Taq Polymerase.

Examples of other polymerases that can be used for incorporation of reversible terminator NTPs in any of the methods of the invention are T3 RNA polymerase, T7 RNA polymerase, and SP6 RNA polymerase.

Reversible Blocking Groups

All methods defined and described herein refer to a reversible blocking group or reversible terminator group. Such groups act to prevent further extension by the enzyme in a given synthesis cycle so that only a nucleotide of predefined sequence may controllably be used to extend the synthesis strand, and thus non-specific nucleotide incorporation is prevented. Any functionality which achieves this effect may be used in any of the methods defined and described herein. Reversible blocking groups/reversible terminator groups attached to nucleotides and deblocking steps are preferred means for achieving this effect. However this effect may be achieved by alternative means as appropriate.

Any suitable reversible blocking group may be attached to a nucleotide to prevent further extension by the enzyme following the incorporation of a nucleotide in a given cycle and to limit incorporation to one nucleotide per cycle. In any the methods of the invention the reversible blocking group is preferably a reversible terminator group which acts to prevent further extension by a polymerase enzyme. Examples of reversible terminators are provided below.

Propargyl Reversible Terminators:

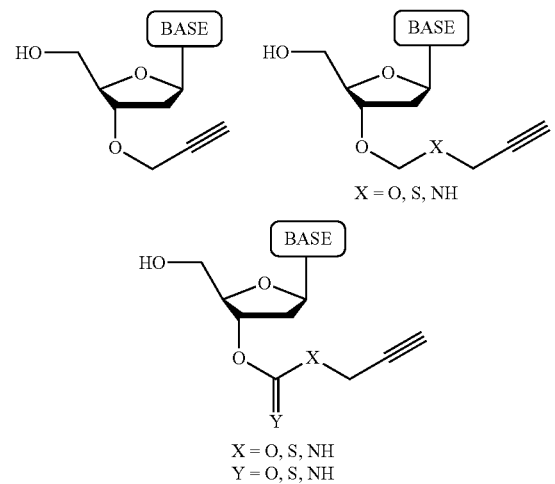

Allyl Reversible Terminators:

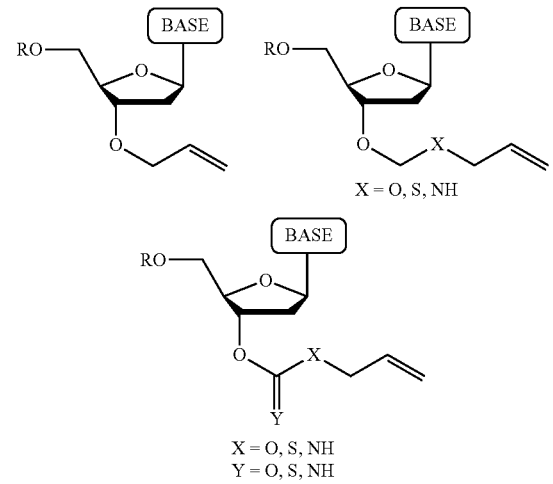

Cyclooctene Reversible Terminators:
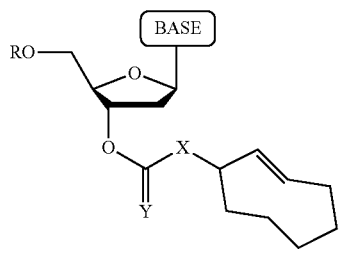
X = O, S, NH
Y = O, S, NH
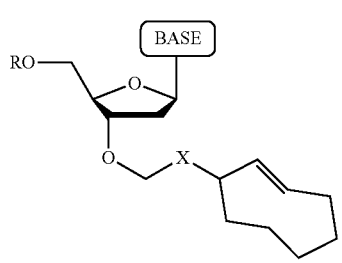
X = O, S, NH
Y = O, S, NH
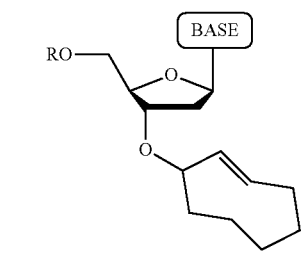
Cyanoethyl Reversible Terminators:
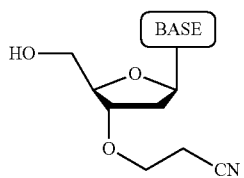 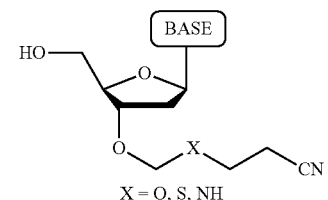
X = O, S, NH
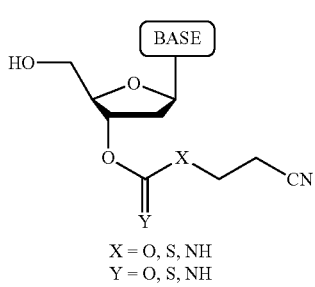
X = O, S, NH
Y = O, S, NH
Nitrobenzyl Reversible Terminators:
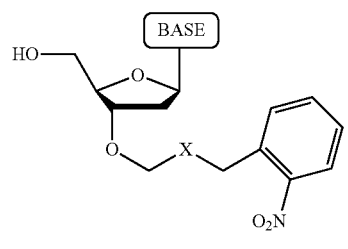
X = O, S, NH
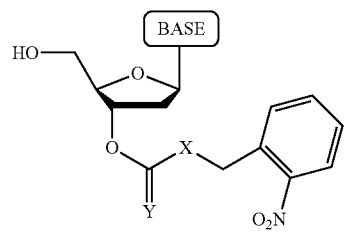
X = O, S, NH
Y = O, S, NH
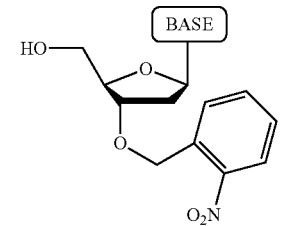
Disulfide Reversible Terminators:
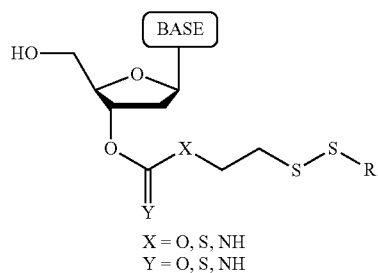
X = O, S, NH
Y = O, S, NH
Azidomethyl Reversible Terminators:
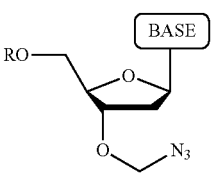 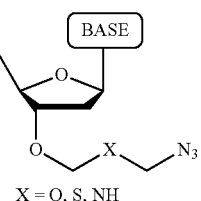
X = O, S, NH 45
-continued

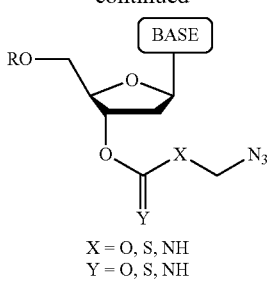

X = O, S, NH
Y = O, S, NH

Aminoalkoxy Reversible Terminators:

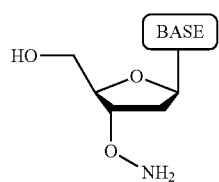

Nucleoside triphosphates with bulky groups attached to the base can serve as substitutes for a reversible terminator group on 3'-hydroxy group and can block further incorporation. This group can be deprotected by TCEP or DTT producing natural nucleotides.

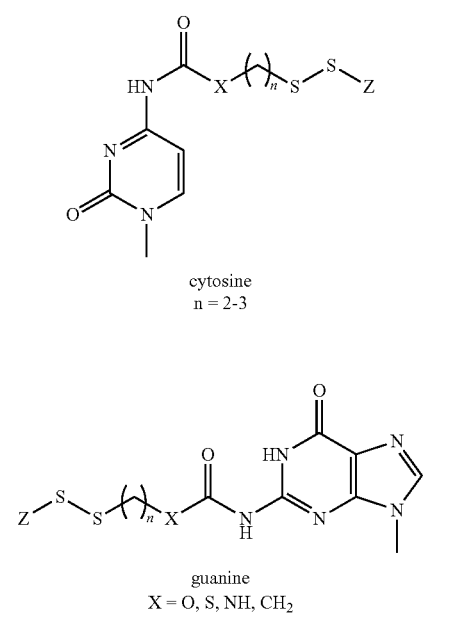

46
-continued

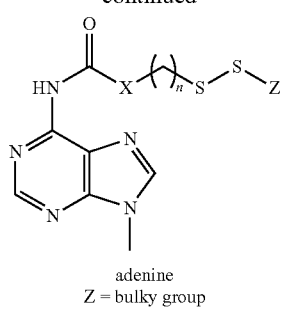

adenine
Z = bulky group

For synthesising DNA polynucleotides according to any of the methods of the invention preferred modified nucleosides are 3'-O-modified-2'-deoxyribonucleoside-5'-O-triphosphate. For synthesising RNA polynucleotides according to any of the methods of the invention preferred modified nucleosides are 3'-O-modified-ribonucleoside-5'-O-triphosphate.

Preferred modified dNTPs are modified dNTPs which are 3'-O-allyl-dNTPs and 3'-O-azidomethyl-dNTPs.

3'-O-allyl-dNTPs are shown below.

3'-O-allyl-dTTP:

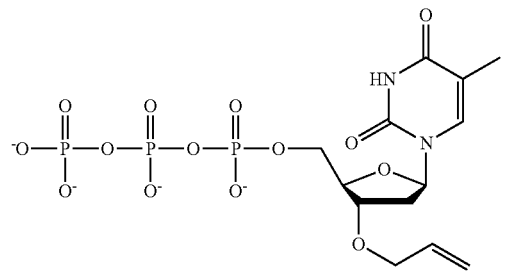

3'-O-allyl-dCTP:

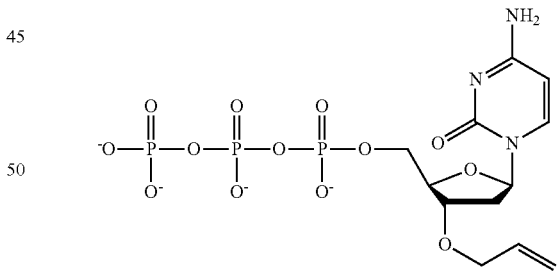

3'-O-allyl-dATP:

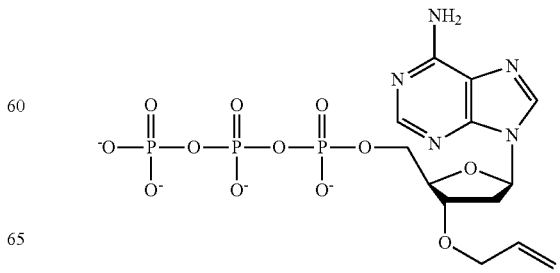

3'-O-allyl-dGTP:

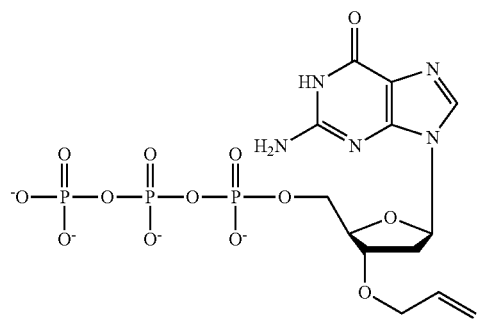

3'-O-azidomethyl-dNTPs are shown below.

3'-O-azidomethyl-dTTP:

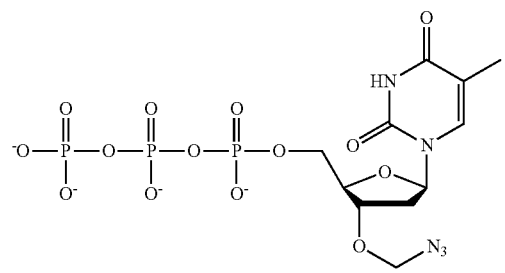

3'-O-azidomethyl-dCTP:

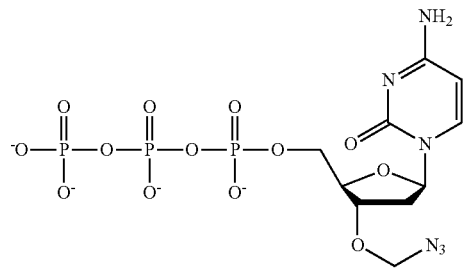

3'-O-azidomethyl-dATP:

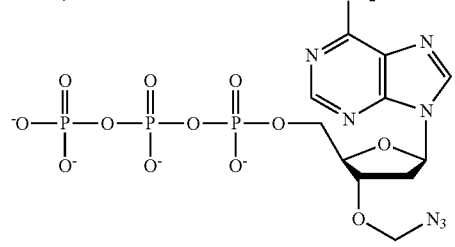

3'-O-azidomethyl-dGTP:

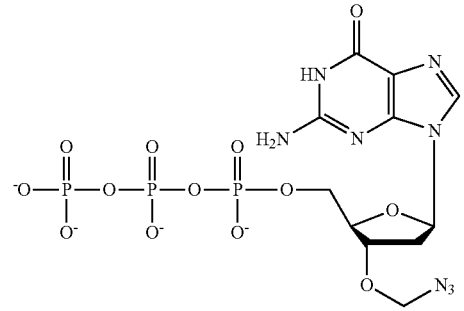

Methods of the invention described and defined herein may refer to a deprotection or deblocking step. Such a step involves removal of the reversible blocking group (e.g. the reversible terminator group) by any suitable means, or otherwise reversing the functionality of the blocking/terminator group to inhibit further extension by the enzyme/polymerase.

Any suitable reagent may be used to remove the reversible terminator group at the deprotection step.

A preferred deprotecting reagent is tris(carboxyethyl)phosphine (TCEP). TCEP may be used to remove reversible terminator groups from 3'-O-allyl-nucleotides (in conjunction with $Pd^0$) and 3'-O-azidomethyl-nucleotides following incorporation.

Examples of deprotecting reagents are provided below.
Propargyl Reversible Terminators:
Treatment by Pd catalysts—$Na_2PdCl_4$, $PdCl_2$.
Ligands can be used e. g.: Triphenylphosphine-3,3',3"-trisulfonic acid trisodium salt.
Allyl Reversible Terminators:
Treatment by Pd catalysts—$Na_2PdCl_4$, $PdCl_2$.
Ligands can be used e. g.: Triphenylphosphine-3,3',3"-trisulfonic acid trisodium salt.
Azidomethyl Reversible Terminators:
Treatment by thiol (mercaptoethanol or dithiothreitol), or Tris (2-carboxyethyl)phosphine—TCEP.
Cyanoethyl Reversible Terminators:
Treatment by fluoride—ammonium fluoride, tetrabutylammonium fluoride (TBAF).
Nitrobenzyl Reversible Terminators:
Exposure to UV light
Disulfide Reversible Terminators:
Treatment by thiol (mercaptoethanol or dithiothreitol), or Tris (2-carboxyethyl)phosphine—TCEP.
Aminoalkoxy Reversible Terminators:
Treatment by nitrite ($NO_2^-$, $HNO_2$) pH=5.5

A reversible blocking group (e.g., a reversible terminator group) can be removed by a step performed immediately after the incorporation step and before the cleavage step, provided that unwanted reagent from the incorporation step is removed to prevent further incorporation following removal of the reversible terminator group. A reversible blocking group (e.g., a reversible terminator group) can be removed by a step performed immediately after the cleavage step and before the ligation step. A reversible blocking group (e.g., a reversible terminator group) can be removed by a step performed immediately after the ligation step.

Synthetic Polynucleotide

The polynucleotide having a predefined sequence synthesised according to the methods described herein is double-stranded. The synthesised polynucleotide overall is double-stranded and wherein the first strand is attached to the second strand by hybridization. Mismatches and regions of non-hybridization may be tolerated, provided that overall the first strand is attached to the second strand by hybridization.

The double-stranded polynucleotide having a predefined sequence synthesised according to the methods described herein may be retained as a double-stranded polynucleotide. Alternatively the two strands of the double-stranded polynucleotide may be separated to provide a single-stranded polynucleotide having a predefined sequence. Conditions that permit separation of two strands of a double-stranded polynucleotide (melting) are well-known in the art (for example, Sambrook et al., 2001, Molecular Cloning: a laboratory manual, 3rd edition, Cold Spring Harbour Laboratory Press; and Current Protocols in Molecular Biology, Greene Publishing and Wiley-Interscience, New York (1995)).

The double-stranded polynucleotide having a predefined sequence synthesised according to the methods described herein may be amplified following synthesis. Any region of the double-stranded polynucleotide may be amplified. The whole or any region of the double-stranded polynucleotide may be amplified together with the whole or any region of the scaffold polynucleotide. Conditions that permit amplification of a double-stranded polynucleotide are well-known in the art (for example, Sambrook et al., 2001, Molecular Cloning: a laboratory manual, 3rd edition, Cold Spring Harbour Laboratory Press; and Current Protocols in Molecular Biology, Greene Publishing and Wiley-Interscience, New York (1995)). Thus any of the synthesis methods described herein may further comprise an amplification step wherein the double-stranded polynucleotide having a predefined sequence, or any region thereof, is amplified as described above. Amplification may be performed by any suitable method, such as polymerase chain reaction (PCR), polymerase spiral reaction (PSR), loop mediated isothermal amplification (LAMP), nucleic acid sequence based amplification (NASBA), self-sustained sequence replication (3SR), rolling circle amplification (RCA), strand displacement amplification (SDA), multiple displacement amplification (MDA), ligase chain reaction (LCR), helicase dependent amplification (HDA), ramification amplification method (RAM) etc. Preferably, amplification is performed by polymerase chain reaction (PCR).

The double-stranded or single-stranded polynucleotide having a predefined sequence synthesised according to the methods described herein can be any length. For example, the polynucleotides can be at least 10, at least 50, at least 100, at least 150, at least 200, at least 250, at least 300, at least 350, at least 400, at least 450 or at least 500 nucleotides or nucleotide pairs in length. For example, the polynucleotides may be from about 10 to about 100 nucleotides or nucleotide pairs, about 10 to about 200 nucleotides or nucleotide pairs, about 10 to about 300 nucleotides or nucleotide pairs, about 10 to about 400 nucleotides or nucleotide pairs and about 10 to about 500 nucleotides or nucleotide pairs in length. The polynucleotides can be up to about 1000 or more nucleotides or nucleotide pairs, up to about 5000 or more nucleotides or nucleotide pairs in length or up to about 100000 or more nucleotides or nucleotide pairs in length.

Cleavage of Scaffold Polynucleotide

In methods requiring the presence of scaffold polynucleotides and steps of cleavage prior to ligation, the selection of the reagent to perform the cleavage step will depend upon the particular method employed. The cleavage site is defined by the specific position of the universal nucleotide in the support strand and the requirement for a single- or double-nucleotide overhang in the scaffold polynucleotide once cleaved. Configuration of the desired cleavage site and selection of the appropriate cleavage reagent will therefore depend upon the specific chemistry employed in the method, as will readily be apparent by reference to the exemplary methods described herein.

Some examples of DNA cleaving enzymes recognizing modified bases is shown in the Table below:

| DNA glycosylase/ Endo-nuclease | Main substrate | Cleavage site | Termini created from the cleavage | |
|---|---|---|---|---|
| | | | 5'-end | 3'-end |
| APE1 | AP site | $1^{st}$ phosphodiester bond 5' to the lesion | Deoxyribose-5'-phosphate | OH |
| Endo-nuclease III | AP site, thymine glycol | $1^{st}$ phosphodiester bond 3' to the lesion | phosphate | 3'-phospho-α,β-unsaturated aldehyde |
| Endo-nuclease IV | AP site | $1^{st}$ phosphodiester bond 5' to the lesion | Deoxyribose-5'-phosphate | OH |
| Endo-nuclease V | Inosine | $2^{nd}$ phosphodiester bond 3' to the lesion | phosphate | OH |
| Endo-nuclease VIII | AP site, thymine glycol | $1^{st}$ phosphodiester bond 5' and 3' to the lesion | phosphate | phosphate |
| FpG | 8-oxoguanine | $1^{st}$ phosphodiester bond 5' and 3' to the lesion | phosphate | phosphate |
| hOGG1 | 8-oxoguanine | $1^{st}$ phosphodiester bond 3' to the lesion | phosphate | 3'-phospho-α,β-unsaturated aldehyde |
| hNeil1 | Oxidized purines | $1^{st}$ phosphodiester bond 5' and 3' to the lesion | phosphate | phosphate |
| ROS1 | 5-methylcytosine | $1^{st}$ phosphodiester bond 5' and 3' to the lesion | phosphate | phosphate |
| Uracil DNA glycosylase | Uracil | N-glycosidic bond | AP site (no break) | |
| hSMUG | Uracil | N-glycosidic bond | AP site (no break) | |
| hAAG | Inosine | N-glycosidic bond | AP site (no break) | |

Ligation Polynucleotide

In methods requiring the presence of scaffold polynucleotides and steps of ligation following cleavage, the selection of the configuration and structure of the ligation polynucleotide will also depend upon the particular method employed. The ligation polynucleotide generally comprises a support strand as described herein and a helper strand as described herein. The support strand and the helper strand used in the ligation polynucleotide can be the same or different from those used in the initial scaffold polynucleotide construct. For example, the requirement for a single- or double-nucleotide overhang in the support strand of the ligation end of the ligation polynucleotide will depend upon the method employed. The appropriate structure can readily be achieved by reference to the exemplary methods described herein.

The ligation end of the ligation polynucleotide is typically provided with a non-phosphorylated terminal nucleotide in the helper strand adjacent the overhang. This prevents ligation of the helper strand portion of the synthesis strand to the primer strand portion of the synthesis strand and thus maintains the single-strand break in the synthesis strand. Alternative means for preventing ligation in the synthesis strands could be employed. For example blocking moieties could be attached to the terminal nucleotide in the helper strand. Moreover, the helper stand may be removed from the scaffold molecule, e.g. by denaturation, prior to incorporation of the next predefined nucleotide in the next synthesis cycle, as described further herein.

Ligation

In methods of the invention which involve a ligation step, ligation may be achieved using any suitable means. Preferably, the ligation step will be performed by a ligase enzyme. The ligase may be a modified ligase with enhanced activity for single-base overhang substrates. The ligase may be a T3 DNA ligase or a T4 DNA ligase. The ligase may a blunt TA ligase. For example a blunt TA ligase is available from New England BioLabs (NEB). This is a ready-to-use master mix solution of T4 DNA Ligase, ligation enhancer, and optimized reaction buffer specifically formulated to improve ligation and transformation of both blunt-end and single-base overhang substrates. Molecules, enzymes, chemicals and methods for ligating (joining) single- and double-stranded polynucleotides are well known to the skilled person.

Solid Phase Synthesis

Synthetic polynucleotides produced in accordance with the synthesis methods of the invention may preferably be synthesised using solid phase or reversible solid phase techniques. A variety of such techniques is known in the art and may be used. Before initiating synthesis of a new double-stranded polynucleotide of predefined sequence, scaffold polynucleotides may be immobilized to a surface e.g. a planar surface such as glass, a gel-based material, or the surface of a microparticle such as a bead or functionalised quantum dot. The material comprising the surface may itself be bound to a substrate. For example, scaffold polynucleotides may be immobilized to a gel-based material such as e.g. polyacrylamide, and wherein the a gel-based material is bound to a supporting substrate such as glass.

Polynucleotides may be immobilized or tethered to surfaces directly or indirectly. For example they may be attached directly to surfaces by chemical bonding. They may be indirectly tethered to surfaces via an intermediate surface, such as the surface of a microparticle or bead e.g. as in SPRI or as in electrowetting systems, as described below. Cycles of synthesis may then be initiated and completed whilst the scaffold polynucleotide incorporating the newly-synthesised polynucleotide is immobilized.

In such methods a double-stranded scaffold polynucleotide may be immobilized to a surface prior to the incorporation of the first nucleotide of the predefined sequence. Such an immobilized double-stranded scaffold polynucleotide may therefore act as an anchor to tether the double-stranded polynucleotide of the predefined sequence to the surface during and after synthesis.

Only one strand of such a double-stranded anchor/scaffold polynucleotide may be immobilized to the surface at the same end of the molecule. Alternatively both strands of a double-stranded anchor/scaffold polynucleotide may each be immobilized to the surface at the same end of the molecule. A double-stranded anchor/scaffold polynucleotide may be provided with each strand connected at adjacent ends, such as via a hairpin loop at the opposite end to the site of initiation of new synthesis, and connected ends may be immobilized on a surface (for example as depicted schematically in FIG. 4).

In methods involving a scaffold polynucleotide, as described herein, the scaffold polynucleotide may be attached to a surface prior to the incorporation of the first nucleotide in the predefined sequence. Thus the synthesis strand comprising the primer strand portion and the portion of the support strand hybridized thereto may both be separately attached to a surface, as depicted in FIGS. 4(a) and (c). The synthesis strand comprising the primer strand portion and the portion of the support strand hybridized thereto may be connected at adjacent ends, such as via a hairpin loop, e.g. at the opposite end to the site of initiation of new synthesis, and connected ends may be tethered to a surface, as depicted in FIGS. 4(b) and (d). One or other of the synthesis strand comprising the primer strand portion and the portion of the support strand hybridized thereto may be attached separately to a surface, as depicted in FIG. 4(e) to (h). Preferably the synthesis strand comprising the primer strand portion and the portion of the support strand hybridized thereto is attached to a surface.

Solid Phase Synthesis on Planar Surfaces

Before initiating synthesis of a new double-stranded polynucleotide of predefined sequence synthetic anchor/scaffold polynucleotides can be synthesised by methods known in the art, including those described herein, and tethered to a surface.

Pre-formed polynucleotides can be tethered to surfaces by methods commonly employed to create nucleic acid microarrays attached to planar surfaces. For example, anchor/scaffold polynucleotides may be created and then spotted or printed onto a planar surface. Anchor/scaffold polynucleotides may be deposited onto surfaces using contact printing techniques. For example, solid or hollow tips or pins may be dipped into solutions comprising pre-formed scaffold polynucleotides and contacted with the planar surface. Alternatively, oligonucleotides may be adsorbed onto micro-stamps and then transferred to a planar surface by physical contact. Non-contact printing techniques include thermic printing or piezoelectric printing wherein sub-nanolitre size microdroplets comprising pre-formed scaffold polynucleotides may be ejected from a printing tip using methods similar to those used in inkjet and bubblejet printing.

Single-stranded oligonucleotides may be synthesised directly on planar surfaces such as using so-called "on-chip" methods employed to create microarrays. Such single-stranded oligonucleotides may then act as attachment sites to immobilize pre-formed anchor/scaffold polynucleotides.

On-chip techniques for generating single-stranded oligonucleotides include photolithography which involves the use of UV light directed through a photolithographic mask to selectively activate a protected nucleotide allowing for the subsequent incorporation of a new protected nucleotide. Cycles of UV-mediated deprotection and coupling of pre-determined nucleotides allows the in situ generation of an oligonucleotide having a desired sequence. As an alternative to the use of a photolithographic mask, oligonucleotides may be created on planar surfaces by the sequential deposition of nucleobases using inkjet printing technology and the use of cycles of coupling, oxidation and deprotection to generate an oligonucleotide having a desired sequence (for a review see Kosuri and Church, Nature Methods, 2014, 11, 499-507).

In any of the synthesis methods described herein, including methods involving reversible immobilisation as described below, surfaces can be made of any suitable material. Typically a surface may comprise silicon, glass or polymeric material. A surface may comprise a gel surface, such as a polyacrylamide surface, such as about 2% polyacrylamide, optionally a polyacrylamide surface derived using N-(5-bromoacetamidylpentyl) acrylamide (BRAPA), preferably the polyacrylamide surface is coupled to a solid support, such as glass.

Reversible Immobilization

Synthetic polynucleotides having a predefined sequence can be synthesised in accordance with the invention using binding surfaces and structures, such as microparticles and beads, which facilitate reversible immobilization. Solid phase reversible immobilization (SPRI) methods or modified methods are known in the art and may be employed (e.g. see DeAngelis M. M. et al. (1995) Solid-Phase Reversible Immobilization for the Isolation of PCR Products, Nucleic Acids Research, 23(22): 4742-4743).

Surfaces can be provided in the form of microparticles, such as paramagnetic beads. Paramagnetic beads can agglomerate under the influence of a magnetic field. For example, paramagnetic surfaces can be provided with chemical groups, e.g. carboxyl groups, which in appropriate attachment conditions will act as binding moieties for nucleic acids, as described in more detail below. Nucleic acids can be eluted from such surfaces in appropriate elution conditions. Surfaces of microparticles and beads can be provided with UV-sensitive polycarbonate. Nucleic acids can be bound to the activated surface in the presence of a suitable immobilization buffer.

Microparticles and beads may be allowed to move freely within a reaction solution and then reversibly immobilized, e.g. by holding the bead within a microwell or pit etched into a surface. A bead can be localised as part of an array e.g. by the use of a unique nucleic acid "barcode" attached to the bead or by the use of colour-coding.

Thus before initiating synthesis of a new double-stranded polynucleotide of predefined sequence, anchor/scaffold polynucleotides in accordance with the invention can be synthesised and then reversibly immobilized to such binding surfaces. Polynucleotides synthesised by methods of the invention can be synthesised whilst reversibly immobilized to such binding surfaces.

Microfluidic Techniques and Systems

The surface may be part of an electrowetting-on-dielectric system (EWOD). EWOD systems provide a dielectric-coated surface which facilitates microfluidic manipulation of very small liquid volumes in the form of microdroplets (e.g. see Chou, W-L., et al. (2015) Recent Advances in Applications of Droplet Microfluidics, Micromachines, 6: 1249-1271). Droplet volumes can programmably be created, moved, partitioned and combined on-chip by electrowetting techniques. Thus electrowetting systems provide alternative means to reversibly immobilize polynucleotides during and after synthesis.

Polynucleotides having a predefined sequence may be synthesised in solid phase by methods described herein, wherein polynucleotides are immobilized on an EWOD surface and required steps in each cycle facilitated by electrowetting techniques. For example, in methods involving scaffold polynucleotides and requiring incorporation, cleavage, ligation and deprotection steps, reagents required for each step, as well as for any required washing steps to remove used and unwanted reagent, can be provided in the form of microdroplets transported under the influence of an electric field via electrowetting techniques.

Other microfluidic platforms are available which may be used in the synthesis methods of the invention. For example, the emulsion-based microdroplet techniques which are commonly employed for nucleic acid manipulation can be used. In such systems microdroplets are formed in an emulsion created by the mixing of two immiscible fluids, typically water and an oil. Emulsion microdroplets can be programmably be created, moved, partitioned and combined in microfluidic networks. Hydrogel systems are also available. In any of the synthesis methods described herein microdroplets may be manipulated in any suitable compatible system, such as EWOD systems described above and other microfluidic systems, e.g. microfluidic systems comprising architectures based on components comprising elastomeric materials.

Microdroplets may be of any suitable size, provided that they are compatible with the synthesis methods herein. Microdroplet sizes will vary depending upon the particular system employed and the relevant architecture of the system. Sizes may thus be adapted as appropriate. In any of the synthesis methods described herein droplet diameters may be in the range from about 150 nm to about 5 mm. Droplet diameters below 1 µm may be verified by means known in the art, such as by techniques involving capillary jet methods, e.g. as described in Gañán-Calvo et al. (Nature Physics, 2007, 3, pp 737-742)

Surface Attachment Chemistries

Although oligonucleotides will typically be attached chemically, they may also be attached to surfaces by indirect means such as via affinity interactions. For example, oligonucleotides may be functionalised with biotin and bound to surfaces coated with avidin or streptavidin.

For the immobilization of polynucleotides to surfaces (e.g. planar surfaces), microparticles and beads etc., a variety of surface attachment methods and chemistries are available. Surfaces may be functionalised or derivatized to facilitate attachment. Such functionalisations are known in the art. For example, a surface may be functionalised with a polyhistidine-tag (hexa histidine-tag, 6×His-tag, His6 tag or His-Tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide), polynucleotide binding proteins, peptides, proteins, antibodies or antibody fragments. The surface may be functionalised with a molecule or group which specifically binds to the anchor/scaffold polynucleotide.

Some examples of chemistries suitable for attaching polynucleotides to surfaces are shown in FIG. 4i and FIG. 4j.

In any of the methods described herein the scaffold polynucleotide comprising the synthesis strand comprising the primer strand portion and the portion of the support strand hybridized thereto may be tethered to a common surface via one or more covalent bonds. The one or more covalent bonds may be formed between a functional group on the common surface and a functional group on the scaffold molecule. The functional group on the scaffold molecule may be e.g. an amine group, a thiol group, a thiophosphate group or a thioamide group. The functional group on the common surface may be a bromoacetyl group, optionally wherein the bromoacetyl group is provided on a polyacrylamide surface derived using N-(5-bromoacetamidylpentyl) acrylamide (BRAPA).

In any of the methods of the invention a scaffold polynucleotide may be attached to a surface, either directly or indirectly, via a linker. Any suitable linker which is biocompatible and hydrophilic in nature may be used.

A linker may be a linear linker or a branched linker.

A linker may comprise a hydrocarbon chain. A hydrocarbon chain may comprise from 2 to about 2000 or more carbon atoms. The hydrocarbon chain may comprise an alkylene group, e.g. C2 to about 2000 or more alkylene groups. The hydrocarbon chain may have a general formula of —(CH$_2$)$_n$— wherein n is from 2 to about 2000 or more. The hydrocarbon chain may be optionally interrupted by one or more ester groups (i.e. —C(O)—O—) or one or more amide groups (i.e. —C(O)—N(H)—).

Any linker may be used selected from the group comprising PEG, polyacrylamide, poly(2-hydroxyethyl methacrylate), Poly-2-methyl-2-oxazoline (PMOXA), zwitterionic polymers, e.g. poly(carboxybetaine methacrylate) (PCBMA), poly[N-(3-sulfopropyl)-N-methacryloxyethyl-N,N dimethyl ammonium betaine] (PSBMA), glycopolymers, and polypeptides.

A linker may comprise a polyethylene glycol (PEG) having a general formula of —(CH$_2$—CH$_2$—O)n-, wherein n is from 1 to about 600 or more.

A linker may comprise oligoethylene glycol-phosphate units having a general formula of —[(CH$_2$—CH$_2$—O)$_n$—PO$_2^-$—O]$_m$— where n is from 1 to about 600 or more and m could be 1-200 or more.

Any of the above-described linkers may be attached at one end of the linker to a scaffold molecule as described herein, and at the other end of the linker to a first functional group wherein the first functional group may provide a covalent attachment to a surface. The first functional group may be e.g. an amine group, a thiol group, a thiophosphate group or a thioamide group as further described herein. The surface may be functionalised with a further functional group to provide a covalent bond with the first functional group. The further functional group may be e.g. a 2-bromoacetamido group as further described herein. Optionally a bromoacetyl group is provided on a polyacrylamide surface derived using N-(5-bromoacetamidylpentyl) acrylamide (BRAPA). The further functional group on the surface may be a bromoacetyl group, optionally wherein the bromoacetyl group is provided on a polyacrylamide surface derived using N-(5-bromoacetamidylpentyl) acrylamide (BRAPA) and the first functional group may be e.g. an amine group, a thiol group, a thiophosphate group or a thioamide group as appropriate. The surface to which polynucleotides are attached may comprise a gel. The surface comprises a polyacrylamide surface, such as about 2% polyacrylamide, preferably the polyacrylamide surface is coupled to a solid support such as glass.

In any of the methods of the invention a scaffold polynucleotide may optionally be attached to a linker via a branching nucleotide incorporated into the scaffold polynucleotide. Any suitable branching nucleotide may be used with any suitable compatible linker.

Prior to initiating synthesis cycles of the invention, scaffold polynucleotides may be synthesised with one or more branching nucleotides incorporated into the scaffold polynucleotide. The exact position at which the one or more branching nucleotides are incorporated into the scaffold polynucleotide, and thus where a linker may be attached, may vary and may be chosen as desired. The position may e.g. be at the terminal end of a support strand and/or a synthesis strand or e.g. in the loop region which connects the support strand to the synthesis strand in embodiments which comprise a hairpin loop.

During synthesis of the scaffold polynucleotide the one or more branching nucleotides may be incorporated into the scaffold polynucleotide with a blocking group which blocks a reactive group of the branching moiety. The blocking group may then be removed (deblocked) prior to the coupling to the branching moiety of the linker, or a first unit (molecule) of the linker if a linker comprises multiple units.

During synthesis of the scaffold polynucleotide the one or more branching nucleotides may be incorporated into the scaffold polynucleotide with a group suitable for use in a subsequent "click chemistry" reaction to couple to the branching moiety the linker, or a first unit of the linker if a linker comprises multiple units. An example of such a group is an acetylene group.

Some non-limiting exemplary branching nucleotides are shown below.

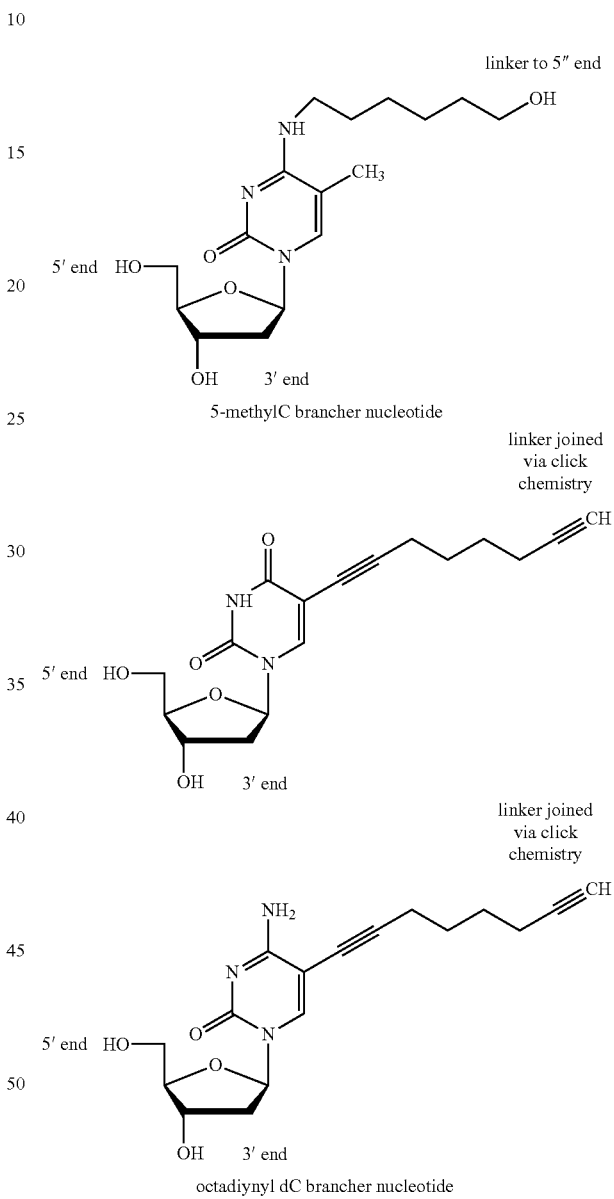

A linker may optionally comprise one or more spacer molecules (units), such as e.g. an Sp9 spacer, wherein the first spacer unit is attached to the branching nucleotide.

The linker may comprise one or more further spacer groups attached to the first spacer group. For example, the linker may comprise multiple e.g. Sp9 spacer groups. A first spacer group is attached to the branching moiety and then one or more further spacer groups are sequentially added to extend a spacer chain comprising multiple spacer units connected with phosphate groups therebetween.

Shown below are some non-limiting examples of spacer units (Sp3, Sp9 and Sp13) which could comprise the first spacer unit attached to a branching nucleotide, or a further spacer unit to be attached to an existing spacer unit already attached to the branching nucleotide.

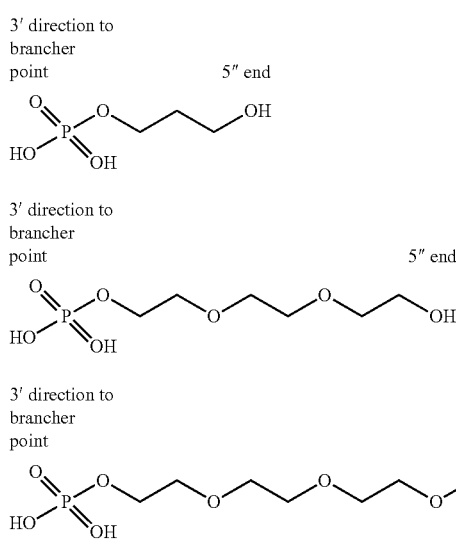

SpC3

Sp9 unit

Sp18 unit

A linker may comprise one or more ethylene glycol units.

A linker may comprise an oligonucleotide, wherein multiple units are nucleotides.

In the structures depicted above the term 5" is used to differentiate from the 5' end of the nucleotide to which the branching moiety is attached, wherein 5' has its ordinary meaning in the art. By 5" it is intended to mean a position on the nucleotide from which a linker can be extended. The 5" position may vary. The 5" position is typically a position in the nucleobase of the nucleotide. The 5" position in the nucleobase may vary depending on the nature of the desired branching moiety, as depicted in the structures above.

Microarrays

Any of the polynucleotide synthesis methods described herein may be used to manufacture a polynucleotide microarray (Trevino, V. et al., Mol. Med. 2007 13, pp 527-541). Thus anchor or scaffold polynucleotides may be tethered to a plurality of individually addressable reaction sites on a surface and polynucleotides having a predefined sequence may be synthesised in situ on the microarray.

Following synthesis, at each reaction area the polynucleotide of predefined sequence may be provided with a unique sequence. The anchor or scaffold polynucleotides may be provided with barcode sequences to facilitate identification.

Other than the method of synthesising the polynucleotides of predefined sequence, microarray manufacture may be performed using techniques commonly used in this technical field, including techniques described herein. For example, anchor or scaffold polynucleotides may be tethered to surfaces using known surface attachment methods and chemistries, including those described herein.

Following synthesis of the polynucleotides of predefined sequence, there may be provided a final cleavage step to remove any unwanted polynucleotide sequence from untethered ends.

Polynucleotides of predefined sequence may be provided at reaction sites in double-stranded form. Alternatively, following synthesis double-stranded polynucleotides may be separated and one strand removed, leaving single-stranded polynucleotides at reaction sites. Selective tethering of strands may be provided to facilitate this process. For example, in methods involving a scaffold polynucleotide the synthesis strand may be tethered to a surface and the support strand may be untethered, or vice versa. The synthesis strand may be provided with a non-cleavable linker and the support strand may be provided with a cleavable linker, or vice versa. Separation of strands may be performed by conventional methods, such as heat treatment.

Assembly of Synthetic Polynucleotides

A polynucleotide having a predefined sequence synthesised by methods described herein, and optionally amplified by methods described herein, may be joined to one or more other such polynucleotides to create larger synthetic polynucleotides.

Joining of multiple polynucleotides can be achieved by techniques commonly known in the art. A first polynucleotide and one or more additional polynucleotides synthesised by methods described herein may be cleaved to create compatible termini and then polynucleotides joined together by ligation. Cleavage can be achieved by any suitable means. Typically, restriction enzyme cleavage sites may be created in polynucleotides and then restriction enzymes used to perform the cleavage step, thus releasing the synthesised polynucleotides from any anchor/scaffold polynucleotide. Cleavage sites could be designed as part of the anchor/scaffold polynucleotides. Alternatively, cleavage sites could be created within the newly-synthesised polynucleotide as part of the predefined nucleotide sequence.

Assembly of polynucleotides is preferably performed using solid phase methods. For example, following synthesis a first polynucleotide may be subject to a single cleavage at a suitable position distal to the site of surface immobilization. The first polynucleotide will thus remain immobilized to the surface, and the single cleavage will generate a terminus compatible for joining to another polynucleotide. An additional polynucleotide may be subject to cleavage at two suitable positions to generate at each terminus a compatible end for joining to other polynucleotides, and at the same time releasing the additional polynucleotide from surface immobilization. The additional polynucleotide may be compatibly joined with the first polynucleotide thus creating a larger immobilized polynucleotide having a predefined sequence and having a terminus compatible for joining to yet another additional polynucleotide. Thus iterative cycles of joining of preselected cleaved synthetic polynucleotides may create much longer synthetic polynucleotide molecules. The order of joining of the additional polynucleotides will be determined by the required predefined sequence.

Thus the assembly methods of the invention may allow the creation of synthetic polynucleotide molecules having lengths in the order of one or more Mb.

The assembly and/or synthesis methods of the invention may be performed using apparatuses known in the art. Techniques and apparatuses are available which allow very small volumes of reagents to be selectively moved, partitioned and combined with other volumes in different locations of an array, typically in the form of droplets Electrowetting techniques, such as electrowetting-on-dielectric (EWOD), may be employed, as described above. Suitable electrowetting techniques and systems that may be employed in the invention that are able to manipulate droplets are disclosed for example in U.S. Pat. Nos. 8,653,832, 8,828,336, US20140197028 and US20140202863.

Cleavage from the solid phase may be achieved by providing cleavable linkers in one or both the primer strand portion and the portion of the support strand hybridized thereto. The cleavable linker may be e.g. a UV cleavable linker.

Figure 22:
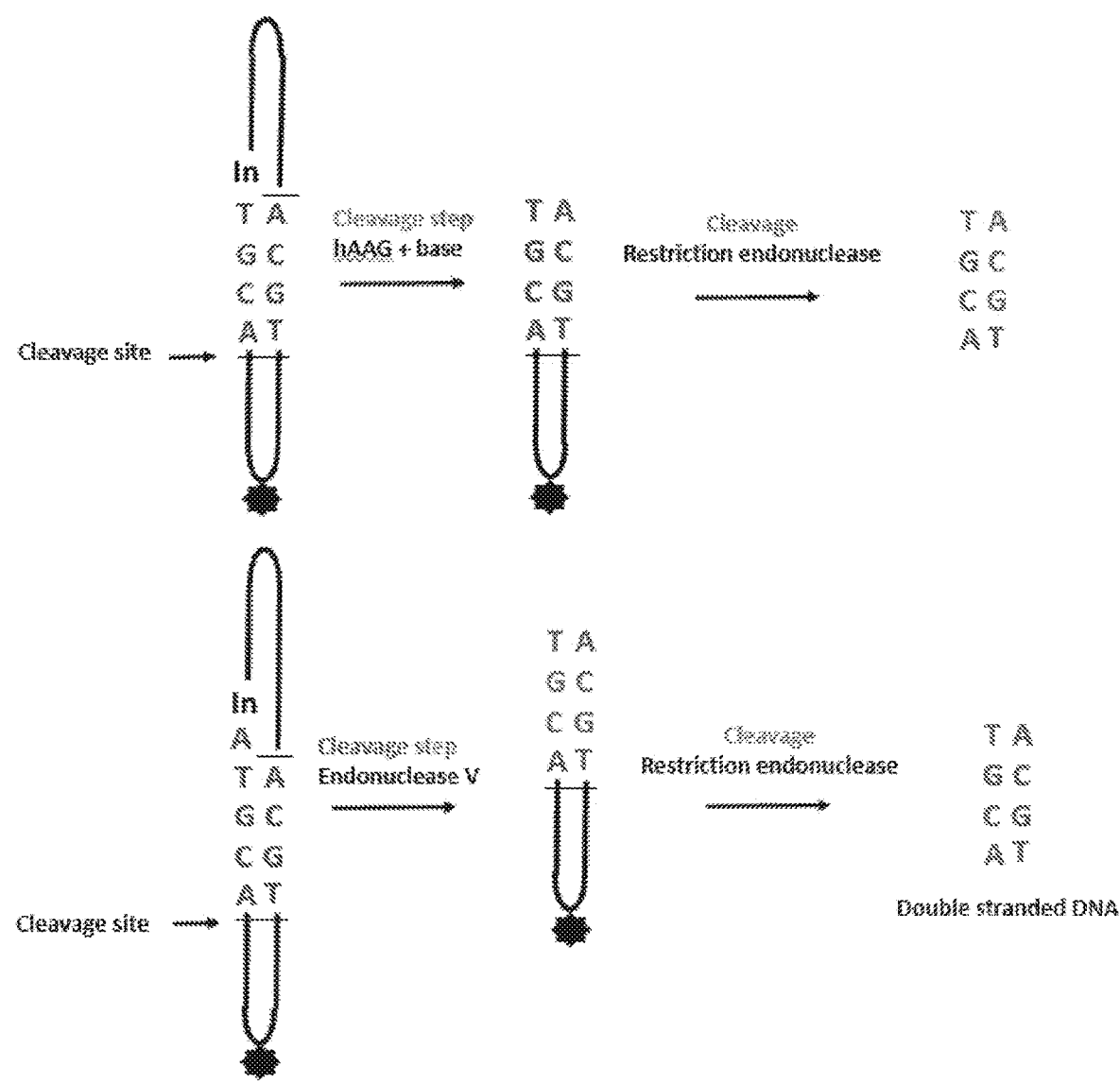

Examples of cleavage methods involving enzymatic cleavage are shown in FIG. 22. The schematic shows a scaffold polynucleotide attached to a surface (via black diamond structures) and comprising a polynucleotide of predefined sequence. The scaffold polynucleotide comprises top and bottom hairpins. In each case the top hairpin can be cleaved using a cleavage step utilizing the universal nucleotide to define a cleavage site. The bottom hairpin can be removed by a restriction endonuclease via a site that is engineered into the scaffold polynucleotide or engineered into the newly-synthesised polynucleotide of predefined sequence.

Thus polynucleotides having a predefined sequence may be synthesised whilst immobilized to an electrowetting surface, as described above. Synthesised polynucleotides may be cleaved from the electrowetting surface and moved under the influence of an electric field in the form of a droplet. Droplets may be combined at specific reaction sites on the surface where they may deliver cleaved synthesised polynucleotides for ligation with other cleaved synthesised polynucleotides. Polynucleotides can then be joined, for example by ligation. Using such techniques populations of different polynucleotides may be synthesised and attached in order according to the predefined sequence desired. Using such systems a fully automated polynucleotide synthesis and assembly system may be designed. The system may be programmed to receive a desired sequence, supply reagents, perform synthesis cycles and subsequently assemble desired polynucleotides according to the predefined sequence desired.

Systems and Kits

The invention also provides polynucleotide synthesis systems for carrying out any of the synthesis methods described and defined herein, as well as any of the subsequent amplification and assembly steps described and defined herein.

Typically, synthesis cycle reactions will be carried out by incorporating nucleotides of predefined sequence into scaffold polynucleotide molecules which are tethered to a surface by means described and defined herein. The surface may be any suitable surface as described and defined herein.

In one embodiment, reactions to incorporate nucleotides of predefined sequence into a scaffold polynucleotide molecule involve performing any of the synthesis methods on a scaffold polynucleotide within a reaction area.

A reaction area is any area of a suitable substrate to which a scaffold polynucleotide molecule is attached and wherein reagents for performing the synthesis methods may be delivered.

In one embodiment a reaction area may be a single area of a surface comprising a single scaffold polynucleotide molecule wherein the single scaffold polynucleotide molecule can be addressed with reagents.

In another embodiment a reaction area may be a single area of a surface comprising multiple scaffold polynucleotide molecules, wherein the scaffold polynucleotide molecules cannot be individually addressed with reagent in isolation from each other. Thus in such an embodiment the multiple scaffold polynucleotide molecules in the reaction area are exposed to the same reagents and conditions and may thus give rise to synthetic polynucleotide molecules having the same or substantially the same nucleotide sequence.

In one embodiment a synthesis system for carrying out any of the synthesis methods described and defined herein may comprise multiple reaction areas, wherein each reaction area comprises one or more attached scaffold polynucleotide molecules and wherein each reaction area may be individually addressed with reagent in isolation from each of the other reaction areas. Such a system may be configured e.g. in the form of an array, e.g. wherein reaction areas are formed upon a substrate, typically a planar substrate.

A system having a substrate comprising a single reaction area or comprising multiple reaction areas may be comprised within e.g. an EWOD system or a microfluidic system and the systems configured to deliver reagents to the reaction site. EWOD and microfluidic systems are described in more detail herein. For example an EWOD system may be configured to deliver reagents to the reaction site(s) under electrical control. A microfluidic system, such as comprising microfabricated architecture e.g. as formed from elastomeric or similar material, may be configured to deliver reagents to the reaction site(s) under fluidic pressure and/or suction control or by mechanical means. Reagents may be delivered by any suitable means, for example via carbon nanotubes acting as conduits for reagent delivery. Any suitable system may be envisaged.

EWOD, microfluidic and other systems may be configured to deliver any other desired reagents to reaction sites, such as enzymes for cleaving a synthesised double-stranded polynucleotide from the scaffold polynucleotide following synthesis, and/or reagents for cleaving a linker to release an entire scaffold polynucleotide from the substrate and/or reagents for amplifying a polynucleotide molecule following synthesis or any region or portion thereof, and/or reagents for assembling larger polynucleotide molecules from smaller polynucleotide molecules which have been synthesised according to the synthesis methods of the invention.

The invention also provides kits for carrying out any of the synthesis methods described and defined herein. A kit may contain any desired combination of reagents for performing any of the synthesis and/or assembly methods of the invention described and defined herein. For example, a kit may comprise any one or more volume(s) of reaction reagents comprising scaffold polynucleotides, volume(s) of reaction reagents corresponding to any one or more steps of the synthesis cycles described and defined herein, volume(s) of reaction reagents comprising nucleotides comprising reversible blocking groups or reversible terminator groups, volume(s) of reaction reagents for amplifying one or more polynucleotide molecules following synthesis or any region or portion thereof, volume(s) of reaction reagents for assembling larger polynucleotide molecules from smaller polynucleotide molecules which have been synthesised according to the synthesis methods of the invention, volume(s) of reaction reagents for cleaving a synthesised double-stranded polynucleotide from the scaffold polynucleotide following synthesis, and volume(s) of reaction reagents for cleaving one or more linkers to release entire scaffold polynucleotides from a substrate.

Exemplary Methods

Exemplary methods of synthesising a polynucleotide or an oligonucleotide molecule according to the invention are described herein, including in the appended claims. Reference signs in the text below correspond with those in FIGS. 1, 2, 3a, 3b and 3c.

In each exemplary method described below, the structures described in each step may be referred to by reference to specific Figures with the aid of reference signs as appropriate. However, such references are not intended to be limited to the structures shown in the Figures, and the description of the relevant structures correspond to the description thereof as provided herein in its entirety, including as illustrated.

Five non-limiting exemplary methods, method versions 1 to 5, are described below (see e.g. FIGS. 1 to 3c respectively). In step (1) of each of these exemplary methods a scaffold polynucleotide (see structure depicted in step 1 of each of FIGS. 1 to 3c) is provided (101, 201, 301, 401, 501) comprising a synthesis strand (see strand labelled "b" in structure depicted in step 1 of each of FIGS. 1 to 3c) hybridized to a complementary support strand (see strand labelled "a" in structure depicted in step 1 of each of FIGS. 1 to 3c).

The scaffold polynucleotide is double-stranded and provides a support structure to accommodate the region of synthetic polynucleotide as it is synthesised de novo. The scaffold polynucleotide comprises a synthesis strand comprising a polymerase primer strand portion (see dotted portion of strand labelled "b" in structure depicted in step 1 of each of FIGS. 1 to 3c) and a helper strand portion (see dashed portion of strand labelled "b" in structure depicted in step 1 of each of FIGS. 1 to 3c) separated by a single-strand break or "nick". As described in more detail herein, in any of the exemplary method versions 1 to 5 and variants thereof described herein the helper strand may be removed prior to the incorporation step (2), e.g. by denaturation. Both the primer strand portion and the helper strand portion of the synthesis strand are provided hybridized to a complementary support strand. The primer strand portion of the synthesis strand provides a primer sequence for use in the initiation of synthesis by a polymerase enzyme. Synthesis is initiated at the site of the single-strand break. Thus polymerase will act to extend the terminal nucleotide of the primer strand portion at the site of the single-strand break. This terminal nucleotide will therefore typically define a 3' terminus of the primer strand portion to allow extension by polymerase enzymes which catalyse extension in a 5' to 3' direction. The opposite terminus of the synthesis strand comprising the primer strand portion will consequently typically define a 5' terminus, and the terminal nucleotide of the support strand adjacent the 5' terminus of the synthesis strand will consequently typically define the 3' terminus of the support strand.

The terminal nucleotide of the helper strand portion of the synthesis strand, which is positioned at the site of the single-strand break, will typically define a 5' terminus of the helper strand portion and consequently the opposite terminus of the helper strand portion of the synthesis strand will typically define the 3' terminus of the synthesis strand.

The single-stranded break or "nick" between the helper strand portion and the primer strand portion of the synthesis strand is typically achieved by providing the (5') terminal nucleotide of the helper strand without a phosphate group. The break is typically achieved by assembling the scaffold polynucleotide from separate components comprising: (i) the support strand; (ii) the helper strand portion of the synthesis strand having a non-phosphorylated (5') terminal nucleotide; and (iii) the synthesis strand portion comprising the primer sequence. Upon mixing of the components in suitable conditions the scaffold polynucleotide forms upon hybridization of the separate components.

In step (2) of the methods a first nucleotide in the predefined nucleotide sequence is incorporated into the synthesis strand by the action of polymerase (102, 202, 302, 402, 502). The first nucleotide is provided with a reversible terminator group (depicted as the small triangle of the incorporated nucleotide in step 2 of each of FIGS. 1 to 3c) which prevents further extension by the polymerase. Thus in step (2) only a single nucleotide is incorporated.

Nucleotides comprising any suitable reversible terminator group could be used. Preferred nucleotides with reversible terminator groups are 3'-O-allyl-dNTPs and/or 3'-O-azidomethyl-dNTPs as described herein.

In each of the five methods a universal nucleotide (labelled "Un" in the structures depicted in each of FIGS. 1 to 3c) is provided in the support strand which aids in the incorporation of a nucleotide of the predefined sequence and/or facilitates cleavage of the scaffold polynucleotide (103, 203, 303, 403, 503). The role of the universal nucleotide will be apparent from the detailed description of each method below.

Synthesis Method Version 1

In a first exemplary version of the synthesis method of the invention a new nucleotide is incorporated into a double-stranded scaffold polynucleotide opposite a universal nucleotide positioned in the support strand (steps 1 and 2 of FIG. 1; 101, 102). In each cycle of synthesis the scaffold polynucleotide is cleaved at a cleavage site defined by a sequence comprising the universal nucleotide (step 3 of FIG. 1; 103). A single-nucleotide overhang comprising the newly-incorporated nucleotide is generated in the cleaved scaffold polynucleotide (see structure depicted in the middle of the lower part of FIG. 1). Ligation of a ligation polynucleotide (see structure depicted at the far left of the lower part of FIG. 1) to the cleaved scaffold polynucleotide incorporates a partner nucleotide into the scaffold polynucleotide and allows the newly-incorporated nucleotide to pair with the partner nucleotide (step 4 of FIG. 1; 104), thus completing a synthesis cycle.

In the first exemplary version of the synthesis method of the invention a scaffold polynucleotide is provided in step (1) as described above (101). In this method the universal nucleotide in the support strand of the scaffold polynucleotide is positioned opposite the terminal nucleotide of the helper strand at the single-strand break site (labelled "X" in the structures of FIG. 1), and is paired therewith (see structure depicted in step 1 of FIG. 1).

In step (2) the first nucleotide of the predefined sequence is incorporated (102) opposite the universal nucleotide such that the universal nucleotide pairs with the first nucleotide upon its incorporation. Thus in this configuration the universal nucleotide is positioned in the support strand in steps (1) and (2) at position "n" with respect to the incorporated first nucleotide in the synthesis strand, as depicted in FIG. 1 (step 3).

During extension, polymerase will act to "invade" the helper strand (if present) and displace the terminal nucleotide of the helper strand. The incorporated first nucleotide will occupy the position previously occupied by the displaced terminal nucleotide of the helper strand (step 3 of FIG. 1).

In step (3) of the method the scaffold polynucleotide is cleaved (103) at a cleavage site. The cleavage site is defined by a sequence comprising the universal nucleotide in the support strand. Cleavage comprises cleaving the support strand to provide in the synthesis strand an overhanging end comprising the first nucleotide. Cleavage results in a double-stranded break in the scaffold polynucleotide. The synthesis strand is already provided with a single-stranded break or "nick" in this exemplary method, thus only cleavage of the support strand is necessary to provide a double-stranded break in the scaffold polynucleotide.

In this exemplary method version, cleavage generates an overhang in the synthesis strand which overhangs the support strand. The overhanging end of the synthesis strand at the cleavage site comprises only a single unhybridized nucleotide which is the incorporated first nucleotide. Typically the overhanging first nucleotide will define a 3' terminus of the synthesis strand overhanging the 5' terminus of the support strand in the cleaved scaffold polynucleotide (see structure depicted in the middle of the lower part of FIG. 1).

In this method the universal nucleotide occupies position "n" in the support strand prior to the cleavage step. To obtain such a single-nucleotide overhang when the universal nucleotide occupies position "n" in the support strand, the support strand is cleaved at a specific position relative to the universal nucleotide. The support strand of the scaffold polynucleotide is cleaved between nucleotide positions "n" and "n−1".

By "n" it is meant the nucleotide position in the support strand which is occupied by, or has been occupied by, the universal nucleotide paired with the nucleotide of the predefined sequence incorporated in that given cycle. Thus at the cleavage step, position "n" in the support strand is opposite the position occupied by the nucleotide of the predefined sequence incorporated in that cycle, i.e. the terminal nucleotide of the primer strand portion of the synthesis strand. By "n−1" it is meant the next nucleotide position in the support strand relative to the position which is occupied by, or has been occupied by, the universal nucleotide, in the direction distal to the helper strand/proximal to the primer strand (nucleotide labelled "z" at position n−1, as shown schematically in step 3 of FIG. 1). Thus at the cleavage step, position "n−1" in the support strand is opposite the position occupied by the penultimate nucleotide of the primer strand portion of the synthesis strand (as depicted in step 3 of FIG. 1; 103).

Upon cleavage of the support strand between nucleotide positions n and n−1, the universal nucleotide, helper strand and portion of the support strand which is hybridized to the helper strand are removed from the remaining scaffold polynucleotide (see structure depicted at the far right of the lower part of FIG. 1), thus generating a single-nucleotide overhang comprising the first nucleotide in the synthesis strand overhanging the support strand in the cleaved scaffold polynucleotide.

A phosphate group should continue to be attached to the terminal nucleotide of the support strand at the site of the overhang (as depicted in the structure shown in the middle of the lower part of FIG. 1). This ensures that the support strand of the ligation polynucleotide can be ligated to the support strand of the cleaved scaffold polynucleotide in the ligation step.

Thus in method version 1 the universal nucleotide occupies position n in the support strand and the support strand is cleaved between nucleotide positions n and n−1.

Preferably, the support strand is cleaved by cleavage of the phosphodiester bond between nucleotide positions n and n−1 (the first phosphodiester bond of the support strand relative to the position of the universal nucleotide, in the direction distal to the helper strand/proximal to the primer strand).

The support strand may be cleaved by cleavage of one ester bond of the phosphodiester bond between nucleotide positions n and n−1.

Preferably the support strand is cleaved by cleavage of the first ester bond relative to nucleotide position n. This will have the effect of retaining a terminal phosphate group on the support strand of the cleaved scaffold polynucleotide at the cleavage position.

Cleavage of the support strand between nucleotide positions n and n−1 as described above may be performed by the action of an enzyme.

Cleavage of the support strand between nucleotide positions n and n−1 as described above may be performed as a two-step process.

The first cleavage step may comprise removing the universal nucleotide from the support strand thus forming an abasic site at position n, and the second cleavage step may comprise cleaving the support strand at the abasic site, between positions n and n−1.

One mechanism of cleaving the support strand at a cleavage site defined by a sequence comprising a universal nucleotide which is occupying position n in the support strand is described in Example 2. The mechanism described is exemplary and other mechanisms could be employed, provided that the single-nucleotide overhang described above is achieved.

In the first cleavage step the universal nucleotide is removed from the support strand whilst leaving the sugar-phosphate backbone intact. This can be achieved by the action of an enzyme which can specifically excise a single universal nucleotide from a double-stranded polynucleotide. In the exemplified methods the universal nucleotide is inosine and inosine is excised from the support strand by the action of an enzyme, thus forming an abasic site. In the exemplified method the enzyme is a 3-methyladenine DNA glycosylase enzyme, specifically human alkyladenine DNA glycosylase (hAAG). Other enzymes, molecules or chemicals could be used provided that an abasic site is formed.

In the second cleavage step the support strand is cleaved at the abasic site by making a single-strand break. In the exemplified methods the support strand is cleaved by the action of a chemical which is a base, such as NaOH. Alternatively, an organic chemical such as N,N'-dimethylethylenediamine may be used. Alternatively, an enzyme having abasic site lyase activity, such as Endonuclease VIII, may be used. Other enzymes, molecules or chemicals could be used provided that the support strand is cleaved at the abasic site as described.

Thus in embodiments wherein the universal nucleotide is at position n of the support strand and the support strand is cleaved between positions n and n−1, a first cleavage step may be performed with a nucleotide-excising enzyme. An example of such an enzyme is a 3-methyladenine DNA glycosylase enzyme, such as human alkyladenine DNA glycosylase (hAAG). The second cleavage step may be performed with a chemical which is a base, such as NaOH. The second step may be performed with an organic chemical having abasic site cleavage activity such as N,N'-dimethylethylenediamine. The second step may performed with an enzyme having abasic site lyase activity such as Endonuclease VIII.

In step (4) of the method a double-stranded ligation polynucleotide is ligated (104) to the cleaved scaffold polynucleotide. The ligation polynucleotide comprises a support strand and a helper strand. The ligation polynucleotide further comprises a complementary ligation end comprising in the support strand a universal nucleotide and a single overhanging nucleotide which is the partner nucleotide for the first nucleotide of the predefined sequence. The ligation polynucleotide further comprises in the helper strand adjacent the overhang a terminal nucleotide lacking a phosphate group (see the position labelled "X" in the structure depicted at the far left of the lower part of FIG. 1). The complementary ligation end is configured so that it will compatibly join with the overhanging end of the cleaved scaffold polynucleotide product of step (3) when subjected to suitable ligation conditions. Upon ligation of the support strands, the first nucleotide becomes paired with its partner nucleotide.

Thus in step (4) of this exemplary method (104), in the complementary ligation end of the ligation polynucleotide the universal nucleotide in the support strand is positioned opposite the terminal nucleotide of the helper strand and is paired therewith. The universal nucleotide is positioned (position n) next to the terminal nucleotide of the support strand. By position n in the ligation polynucleotide it is meant that when the ligation end of the ligation polynucleotide is ligated to the cleaved scaffold polynucleotide the universal nucleotide will be positioned in the support strand such that it will pair with the next nucleotide to be incorporated in step (6), i.e. in the next synthesis cycle, as depicted in FIG. 1 (106, 107). In the complementary ligation end of the ligation polynucleotide of step (4) the terminal nucleotide of the support strand is the partner nucleotide for the first nucleotide of step (2) and overhangs the terminal nucleotide of the helper strand.

In the ligation polynucleotide the helper strand is provided such that the terminal nucleotide adjacent the overhang lacks a phosphate group. Typically, as described above, this non-phosphorylated terminal nucleotide of the helper strand will define the 5' terminus of the helper strand.

In step (4), upon ligation of the support strand of the ligation polynucleotide and the support strand of the cleaved scaffold polynucleotide (104), the first nucleotide in the synthesis strand pairs with its partner nucleotide in the support strand.

Ligation of the support strands may be performed by any suitable means. Ligation will result in the joining of the support strands only, with the maintenance of a single-stranded break between the first nucleotide in the synthesis strand, i.e. in the primer strand portion, and the terminal nucleotide of the helper strand adjacent the first nucleotide.

Ligation may typically be performed by enzymes having ligase activity. For example, ligation may be performed with T3 DNA ligase or T4 DNA ligase. The use of such enzymes will result in the maintenance of the single-stranded break in the synthesis strand, since the terminal nucleotide of the helper strand cannot act as a substrate for ligase due to the absence of a terminal phosphate group.

Ligation of the ligation polynucleotide to the cleaved scaffold polynucleotide completes a first synthesis cycle whereupon the scaffold polynucleotide of step (1) is effectively re-constituted except that the first nucleotide of the predefined nucleotide sequence is incorporated into the polynucleotide opposite its partner nucleotide. In this exemplary method, at the end of a given synthesis cycle, during cycles of synthesis, the universal nucleotide will occupy position n+1 in the support strand relative to the position occupied by the universal nucleotide in the support strand in the previous cycle. At the same time, at the end of a given synthesis cycle the universal nucleotide will occupy position n in the support strand relative to the position in the synthesis strand which will be occupied by the next nucleotide of the predefined nucleotide sequence to be incorporated in the next cycle. Thus at the end of a given synthesis cycle a modified scaffold molecule is provided (106) for use in the next synthesis cycle, wherein the universal nucleotide is once again positioned in the support strand to facilitate incorporation of the next nucleotide of the predefined nucleotide sequence and cleavage of the support strand in the next synthesis cycle.

In this exemplary method version of the invention, as well as with versions 2 and 3, to allow the next nucleotide to be incorporated in the next synthesis cycle, the reversible terminator group must be removed from the first nucleotide (deprotection step; 105). This can be performed at various stages of the first cycle. Typically it will be performed as step (5) of the method, after ligation step (4), as shown in step 5 of FIG. 1; (105). However, the deprotection step could be performed at any step after incorporation of the new nucleotide. Regardless of which stage the deprotection step is performed, polymerase and residual unincorporated first nucleotides should first be removed in order to prevent multiple incorporation of first nucleotides. Polymerase and unincorporated first nucleotides are preferably removed prior to the cleavage step (step (3)). Thus, removal of the reversible terminator group from the first nucleotide could be performed prior to the cleavage step (step (3)), prior to the ligation step (step (4)), or after the ligation step (as step (5)).

Removal of the reversible terminator group from the first nucleotide can be performed by any suitable means. For example, removal can be performed by the use of a chemical, such as tris(carboxyethyl)phosphine (TCEP).

In method version 1, second and subsequent synthesis cycles may be performed as described above for the first synthesis cycle.

Thus in step (6) the scaffold polynucleotide provided for the next synthesis cycle (106) is the product of the ligation step (4) and deprotection step (5) of the first synthesis cycle. In step (6) the next nucleotide in the predefined nucleotide sequence is incorporated (107) into the synthesis strand of the scaffold polynucleotide by the action of polymerase, as described above for step (2) of the first cycle. The next nucleotide also comprises a reversible terminator group which prevents further extension in that cycle by polymerase. The helper strand may optionally be removed prior to incorporation step (6), as described further herein.

As in step (2) of the first synthesis cycle of method version 1, in step (6) the next nucleotide is incorporated opposite a universal nucleotide which is positioned in the support strand such that it pairs with the next nucleotide upon its incorporation. In this configuration the universal nucleotide is again positioned at position "n" relative to the incorporated next nucleotide in the synthesis strand. Furthermore, as described above for the first synthesis cycle, in step (6) of the next synthesis cycle the universal nucleotide will occupy position "n+1" in the support strand relative to the position occupied by the universal nucleotide in the support strand in step (2) of the previous cycle. This is achieved because in the ligation polynucleotide of the previous synthesis cycle the universal nucleotide was positioned to be opposite to and paired with the terminal non-phosphorylated nucleotide of the helper strand.

In step (7) the scaffold polynucleotide is cleaved (108) at a cleavage site, the site defined by a sequence comprising the universal nucleotide in the support strand. Cleavage comprises cleaving the support strand and removing the universal nucleotide to provide in the synthesis strand a single-nucleotide overhanging end comprising the next nucleotide in the predefined nucleotide sequence as the terminal nucleotide of the overhang. The single-nucleotide overhang of the synthesis strand overhangs the terminal nucleotide of the support strand in the cleaved scaffold polynucleotide. The cleavage steps may be performed as described above for step (3) of the first cycle.

In step (8) of the next cycle a double-stranded ligation polynucleotide is ligated (109) to the cleaved scaffold polynucleotide. The ligation polynucleotide comprises a support strand and a helper strand. The ligation polynucleotide further comprises a complementary ligation end comprising in the support strand a universal nucleotide and a single overhanging nucleotide which is a partner nucleotide for the next nucleotide of the predefined nucleotide sequence. The ligation polynucleotide further comprises in the helper strand adjacent the overhang a terminal nucleotide lacking a phosphate group. The complementary ligation end is configured so that it will compatibly join with the overhanging end of the cleaved scaffold polynucleotide product of step (7) when subjected to suitable ligation conditions. Upon ligation of the support strands the next nucleotide of the predefined nucleotide sequence becomes paired with its partner nucleotide.

The ligation polynucleotide of step (8) of the next and subsequent synthesis cycles may be configured, and the ligation step may be performed, as described above for step (4) of the first synthesis cycle.

Thus in step (8) upon ligation (109) the universal nucleotide in the support strand is positioned opposite the terminal nucleotide of the helper strand, and is paired therewith. The universal nucleotide in the support strand is positioned at position "n" with respect to the next nucleotide to be incorporated in the next cycle. Furthermore, as described above, following step (8) the universal nucleotide will occupy position "n+1" in the support strand relative to the position occupied by the universal nucleotide in the support strand prior to the commencement of step (6).

Deprotection of the reversible terminator group in the next and subsequent cycles (110) may be performed as described above with respect to the first synthesis cycle.

Synthesis cycles are repeated for as many times as necessary to synthesise the double-stranded polynucleotide having the predefined nucleotide sequence.

Synthesis Method Version 2.

In a second exemplary version of the synthesis method of the invention a new nucleotide is incorporated into a double-stranded scaffold polynucleotide opposite a complementary nucleotide positioned in the support strand (steps 1 and 2 of FIG. 2; 201, 202). In each cycle of synthesis the scaffold polynucleotide is cleaved at a cleavage site defined by a sequence comprising the universal nucleotide (step 3 of FIG. 2; 203). A single-nucleotide overhang comprising the newly-incorporated nucleotide is generated in the cleaved scaffold polynucleotide (see structure depicted in the middle of the lower part of FIG. 2).

Ligation of a ligation polynucleotide to the cleaved scaffold polynucleotide (204) incorporates a partner nucleotide into the scaffold polynucleotide and allows the newly-incorporated nucleotide to pair with the partner nucleotide, thus completing a full synthesis cycle. Ligation of the ligation polynucleotide (see structure depicted at the far left of the lower part of FIG. 2) to the cleaved scaffold polynucleotide (204) also incorporates into the scaffold polynucleotide a nucleotide which is capable of pairing with the next nucleotide to be incorporated in the next cycle (step 4 of FIG. 2).

In the second exemplary version of the synthesis method of the invention a scaffold polynucleotide is provided in step (1) as described above (201). In this method a nucleotide which is capable of pairing with the first nucleotide of step (2) is provided in the support strand of the scaffold polynucleotide and is positioned opposite the terminal nucleotide of the helper strand at the single-strand break site, and is paired therewith. The complementary nucleotide is positioned in the support strand in at position "n" with respect to the incorporated first nucleotide in the synthesis strand, as depicted in step 1 of FIG. 2.

In step (2) the first nucleotide of the predefined sequence is incorporated (202) opposite the complementary nucleotide such that the complementary nucleotide pairs with the first nucleotide upon its incorporation.

In step (1) of the second version of the synthesis method the scaffold polynucleotide is also provided with a universal nucleotide in the support strand. In this method the universal nucleotide is positioned (position "n+1") in the support strand opposite to and paired with the penultimate nucleotide in the helper strand at the single-strand break site, i.e. typically at the 5' terminus of the helper strand (see structure depicted in step 1 of FIG. 2).

During extension, polymerase will act to "invade" the helper strand, if present, and displace the terminal nucleotide of the helper strand and the incorporated first nucleotide will occupy the position previously occupied by the displaced terminal nucleotide of the helper strand. Following incorporation of the first nucleotide, the universal nucleotide will be positioned in the support strand at position "n+1" with respect to the first nucleotide in the synthesis strand at the single-stranded break site, as depicted in the structure of step 3 of FIG. 2.

In step (3) of the method the scaffold polynucleotide is cleaved (203) at a cleavage site. The cleavage site is defined by a sequence comprising the universal nucleotide in the support strand. Cleavage comprises cleaving the support strand to provide in the synthesis strand an overhanging end comprising the first nucleotide of the predefined nucleotide sequence. Cleavage results in a double-stranded break in the scaffold polynucleotide. The synthesis strand is already provided with a single-stranded break or "nick", thus only cleavage of the support strand is necessary to provide a double-stranded break in the scaffold polynucleotide.

In this exemplary method version cleavage generates an overhang in the synthesis strand which overhangs the support strand. The overhanging end of the synthesis strand comprises only a single unhybridized nucleotide which is the incorporated first nucleotide. Typically the overhanging first nucleotide will define a 3' terminus of the synthesis strand overhanging the 5' terminus of the support strand in the cleaved scaffold polynucleotide, as depicted in the structure shown in the middle of the lower part of FIG. 2.

In this method the universal nucleotide occupies position "n+1" in the support strand. To obtain such a single-nucleotide overhang when the universal nucleotide occupies the "n+1" position in the support strand, the support strand is cleaved in step 3 between nucleotide positions "n" and "n−1".

By "n" in exemplary method version 2 it is meant the nucleotide position in the support strand which is the next nucleotide position in the support strand relative to the position which is occupied by the universal nucleotide, in the direction distal to the helper strand/proximal to the primer strand. Thus at the cleavage step position "n" in the support strand is opposite the position occupied by the nucleotide of the predefined sequence incorporated in that cycle, i.e. the terminal nucleotide of the primer strand portion of the synthesis strand/proximal to the primer strand. By "n−1" it is meant the second nucleotide position in the support strand relative to the position which is occupied by the universal nucleotide, in the direction distal to the helper strand/proximal to the primer strand (nucleotide labelled "z" in FIG. 2). Thus at the cleavage step, position "n−1" in the support strand is opposite the position occupied by the penultimate nucleotide of the primer strand portion of the synthesis strand. In this configuration the universal nucleotide occupies position "n+1". In this method the universal nucleotide at position "n+1" is opposite the penultimate nucleotide in the helper strand portion of the synthesis strand relative to the nick (as depicted in step 3 of FIG. 2).

Upon cleavage of the support strand (203), the universal nucleotide, helper strand (if present) and portion of the support strand which is hybridized to the helper strand are removed from the remaining scaffold polynucleotide (see structure depicted at the far right of the lower part of FIG. 2) thus generating a single-nucleotide overhang comprising the first nucleotide of the predefined nucleotide sequence in the synthesis strand overhanging the support strand in the cleaved scaffold polynucleotide (see structure depicted in the middle of the lower part of FIG. 2).

A phosphate group should continue to be attached to the terminal nucleotide of the support strand at the site of the overhang (as depicted in the structure shown in the middle of the lower part of FIG. 2). This ensures that the support strand of the ligation polynucleotide can be ligated to the support strand of the cleaved scaffold polynucleotide in the ligation step.

Thus in method version 2 the support strand is cleaved between nucleotide positions n and n−1.

Preferably, the support strand is cleaved by cleavage of the phosphodiester bond between nucleotide positions n and n−1 (the second phosphodiester bond of the support strand relative to the position of the universal nucleotide n+1, in the direction distal to the helper strand/proximal to the primer strand).

The support strand may be cleaved by cleavage of one ester bond of the phosphodiester bond between nucleotide positions n and n−1.

Preferably the support strand is cleaved by cleavage of the first ester bond relative to nucleotide position n. This will have the effect of retaining a terminal phosphate group on the support strand of the cleaved scaffold polynucleotide at the cleavage position.

Cleavage of the support strand between nucleotide positions n and n−1 as described above may be performed by the action of an enzyme such as Endonuclease V.

One mechanism of cleaving the support strand between nucleotide positions n and n−1 at a cleavage site defined by a sequence comprising a universal nucleotide which is occupying position n+1 in the support strand is described in Example 3. The mechanism described is exemplary and other mechanisms could be employed, provided that the single-nucleotide overhang described above is achieved.

In this exemplary mechanism an endonuclease enzyme is employed. In the exemplified method the enzyme is Endonuclease V. Other enzymes, molecules or chemicals could be used provided that the single-nucleotide overhang described above is formed.

In step (4) of the method a ligation polynucleotide is ligated (204) to the cleaved scaffold polynucleotide. The ligation polynucleotide comprises a support strand and a helper strand. The ligation polynucleotide further comprises a complementary ligation end comprising in the support strand a universal nucleotide and an overhanging nucleotide which is the partner nucleotide for the first nucleotide. The ligation polynucleotide further comprises in the helper strand adjacent the overhang a terminal nucleotide lacking a phosphate group (see structure depicted at the far left of the lower part of FIG. 2). The complementary ligation end is configured so that it will compatibly join with the overhanging end of the cleaved scaffold polynucleotide product of step (3) when subjected to suitable ligation conditions. Upon ligation of the support strands the first nucleotide becomes paired with its partner nucleotide.

In this method, the universal nucleotide in the support strand of the ligation polynucleotide is positioned in the complementary ligation end opposite the penultimate nucleotide of the helper strand at the site of the single-stranded break site, and is hybridized thereto. The universal nucleotide in the support strand is positioned in the ligation polynucleotide at position "n+1" with respect to the next nucleotide of the predefined nucleotide sequence to be incorporated into the synthesis strand of step (6), i.e. in the next synthesis cycle as depicted schematically in FIG. 2. In the complementary ligation end of the ligation polynucleotide the penultimate nucleotide of the support strand is a partner nucleotide for the next nucleotide of step (6) and is paired with the terminal nucleotide of the helper strand. The terminal nucleotide of the support strand is a partner nucleotide for the first nucleotide of step (2). The terminal nucleotide of the support strand overhangs the terminal nucleotide of the helper strand.

In the ligation polynucleotide the helper strand is provided such that the terminal nucleotide adjacent the overhang lacks a phosphate group. Typically, as described above, this non-phosphorylated terminal nucleotide of the helper strand will define the 5' terminus of the helper strand.

In step (4), upon ligation of the support strand of the ligation polynucleotide and the support strand of the cleaved scaffold polynucleotide (204), the first nucleotide in the synthesis strand becomes paired with its partner nucleotide in the support strand.

Ligation of the support strands may be performed by any suitable means. Ligation will result in the joining of the support strands only, with the maintenance of a single-stranded break between the first nucleotide in the synthesis strand, i.e. in the primer strand portion, and the terminal nucleotide of the helper strand adjacent the first nucleotide.

As with method version 1, ligation in method version 2 may typically be performed by enzymes having ligase activity. For example, ligation may be performed with T3 DNA ligase or T4 DNA ligase. The use of such enzymes will result in the maintenance of the single-stranded break in the synthesis strand, since the terminal nucleotide of the helper strand cannot act as a substrate for ligase due to the absence of a terminal phosphate group.

Ligation of the ligation polynucleotide to the cleaved scaffold polynucleotide completes a first synthesis cycle whereupon the scaffold polynucleotide of step (1) is effectively re-constituted except that the first nucleotide of the predefined nucleotide sequence is incorporated into the polynucleotide opposite its partner nucleotide and a nucleotide which is a partner nucleotide for the next nucleotide to be incorporated in the next synthesis cycle is positioned in the support strand and is paired with the terminal nucleotide of the helper strand, as depicted in FIG. 2 (step 4). As in exemplary method version 1, in exemplary method version 2 at the end of a given synthesis cycle, during cycles of synthesis, the universal nucleotide will occupy position n+1 in the support strand relative to the position occupied by the universal nucleotide in the support strand in the previous cycle. At the same time, at the end of a given synthesis cycle the universal nucleotide will also occupy position n+1 in the support strand relative to the position in the synthesis strand which will be occupied by the next nucleotide of the predefined nucleotide sequence to be incorporated in the next cycle. Thus at the end of a given synthesis cycle a modified scaffold molecule is provided (206) for use in the next synthesis cycle, wherein the universal nucleotide is once again positioned in the support strand to facilitate cleavage of the support strand in the next synthesis cycle.

To allow the next nucleotide to be incorporated in the next synthesis cycle, the reversible terminator group must be removed from the first nucleotide (deprotection step; 205). This can be performed as described above for method version 1.

In exemplary method version 2, second and subsequent synthesis cycles may be performed as described above for the first synthesis cycle.

Thus in step (6) the scaffold polynucleotide provided for the next synthesis cycle (206) is the product of the ligation step (4) and deprotection step, e.g. step (5) of the first synthesis cycle (205). In step (6) the next nucleotide in the predefined nucleotide sequence is incorporated (207) into the synthesis strand of the scaffold polynucleotide by the action of polymerase, as described above for step (2) of the first cycle. The next nucleotide also comprises a reversible terminator group which prevents further extension in that cycle by polymerase.

As in step (2) of the first synthesis cycle of exemplary method version 2, in step (6) the next nucleotide of the predefined nucleotide sequence is incorporated (207) opposite its partner nucleotide which is positioned in the support strand such that it pairs with the next nucleotide upon its incorporation. In this configuration the universal nucleotide is positioned at position "n+1" with respect to the incorporated next nucleotide in the synthesis strand. Furthermore, as described above for the first synthesis cycle, in step (6) of the next synthesis cycle the universal nucleotide will also occupy position "n+1" in the support strand relative to the position occupied by the universal nucleotide in the support strand in step (2) of the previous cycle. This is achieved because in the ligation polynucleotide of the previous synthesis cycle the universal nucleotide was positioned to be opposite to and paired with the penultimate nucleotide of the helper strand.

In step (7) the scaffold polynucleotide is cleaved (208) at a cleavage site, the site defined by a sequence comprising the universal nucleotide in the support strand. Cleavage comprises cleaving the support strand and removing the universal nucleotide to provide in the synthesis strand a single-nucleotide overhanging end comprising the next nucleotide as the terminal nucleotide of the overhang in the remaining scaffold polynucleotide. The single-nucleotide overhang of the synthesis strand overhangs the terminal nucleotide of the support strand in the remaining cleaved scaffold polynucleotide. The cleavage steps may be performed as described above for step (3) of the first cycle.

In step (8) of the next cycle a double-stranded ligation polynucleotide is ligated (209) to the cleaved scaffold polynucleotide. The ligation polynucleotide comprises a support strand and a helper strand. The ligation polynucleotide further comprises a complementary ligation end comprising in the support strand a universal nucleotide and an overhanging nucleotide which is a partner nucleotide for the next nucleotide of the predefined nucleotide sequence. The ligation polynucleotide further comprises in the helper strand adjacent the overhang a terminal nucleotide lacking a phosphate group. The complementary ligation end is configured so that it will compatibly join with the overhanging end of the cleaved scaffold polynucleotide product of step (7) when subjected to suitable ligation conditions. Upon ligation of the support strands the next nucleotide of the predefined nucleotide sequence becomes paired with its partner nucleotide.

The ligation polynucleotide of step (8) of the next and subsequent synthesis cycles may be configured, and the ligation step may be performed, as described above for step (4) of the first synthesis cycle.

Thus in step (8) upon ligation (209) the universal nucleotide in the support strand is positioned opposite the penultimate nucleotide of the helper strand, and is paired therewith. The universal nucleotide in the support strand is positioned at position "n+1" with respect to the next nucleotide to be incorporated in the next cycle. Furthermore, as described above, following step (8) the universal nucleotide will occupy position "n+1" in the support strand relative to the position occupied by the universal nucleotide in the support strand prior to the commencement of step (6).

Deprotection of the reversible terminator group in the next cycle (210) may be performed as described above with respect to the first synthesis cycle.

Synthesis cycles are repeated for as many times as necessary to synthesise the double-stranded polynucleotide having the predefined nucleotide sequence.

Synthesis Method Version 3.

In a third exemplary version of the synthesis method of the invention a new nucleotide is incorporated into a double-stranded scaffold polynucleotide opposite a universal nucleotide positioned in the support strand (steps 1 and 2 of FIG. 3*a*; 301, 302). In each cycle of synthesis the scaffold polynucleotide is cleaved at a cleavage site defined by a sequence comprising the universal nucleotide (step 3 of FIG. 3*a*; 303). A double-nucleotide overhang comprising the newly-incorporated nucleotide is generated in the cleaved scaffold polynucleotide (see structure depicted in the middle of the lower part of FIG. 3*a*). Ligation of a ligation polynucleotide (see structure depicted at the far left of the lower part of FIG. 3*a*) to the cleaved scaffold polynucleotide incorporates a partner nucleotide into the scaffold polynucleotide and thus allows the newly-incorporated nucleotide to pair with the partner nucleotide (step 4 of FIG. 3*a*; 304), thus completing a full synthesis cycle.

In the third exemplary version of the synthesis method of the invention a scaffold polynucleotide is provided in step (1) as described above (301). In this method the universal nucleotide in the support strand of the scaffold polynucleotide is positioned opposite the terminal nucleotide of the helper strand at the single-strand break site, and is paired therewith (see structure depicted in step 1 of FIG. 3*a*).

In step (2) the first nucleotide is incorporated (302) opposite a universal nucleotide which is positioned in the support strand such that it pairs with the first nucleotide upon its incorporation. In this configuration the universal nucleotide is positioned at position "n" with respect to the incorporated first nucleotide in the synthesis strand, as depicted in FIG. 3a (step 3).

During extension, polymerase will act to "invade" the helper strand, if present, and displace the terminal nucleotide of the helper strand. The incorporated first nucleotide will occupy the position previously occupied by the displaced terminal nucleotide of the helper strand (step 3 of FIG. 3a).

In step (3) of the method the scaffold polynucleotide is cleaved (303) at a cleavage site. The cleavage site is defined by a sequence comprising the universal nucleotide in the support strand. Cleavage comprises cleaving the support strand to provide in the synthesis strand an overhanging end comprising the first nucleotide. Cleavage results in a double-stranded break in the scaffold polynucleotide. The synthesis strand is already provided with a single-stranded break or "nick", thus only cleavage of the support strand is necessary to provide a double-stranded break in the scaffold polynucleotide.

In this exemplary method version cleavage generates an overhang in the synthesis strand which overhangs the support strand. The overhanging end of the synthesis strand comprises two unhybridized nucleotides. The first overhanging unhybridized nucleotide is the terminal nucleotide of the synthesis strand of the cleaved scaffold polynucleotide and is the incorporated first nucleotide of the predefined nucleotide sequence. The second unhybridized nucleotide is the nucleotide next to the first nucleotide in the synthesis strand. Typically the overhanging first nucleotide will define a 3' terminus of the synthesis strand overhanging the 5' terminus of the support strand in the cleaved scaffold polynucleotide (see structure depicted in the middle of the lower part of FIG. 3a).

In this method the universal nucleotide occupies position "n" in the support strand. To obtain such a double-nucleotide overhang when the universal nucleotide occupies position "n" in the support strand, the support strand is cleaved between positions "n−1" and "n−2".

By "n" it is meant the nucleotide position in the support strand which is occupied by the universal nucleotide paired with the nucleotide of the predefined sequence incorporated in that given cycle. Thus at the cleavage step position "n" in the support strand is opposite the position occupied by the nucleotide of the predefined sequence incorporated in that given cycle, i.e. the terminal nucleotide of the primer strand portion of the synthesis strand. By "n−1" it is meant the next nucleotide position in the support strand relative to the position which is occupied by the universal nucleotide, in the direction distal to the helper strand/proximal to the primer strand. Thus at the cleavage step position "n−1" in the support strand is opposite the position occupied by the penultimate nucleotide of the primer strand portion of the synthesis strand. By "n−2" it is meant the second nucleotide position in the support strand relative to the position which is occupied by the universal nucleotide, in the direction distal to the helper strand/proximal to the primer strand (as depicted in step 3 of FIG. 3a; 303).

Thus upon cleavage of the support strand, the universal nucleotide, helper strand (if present) and portion of the support strand which is hybridized to the helper strand are removed from the remaining scaffold polynucleotide (see structure depicted at the far right of the lower part of FIG. 3a) thus generating the double-nucleotide overhang comprising the first nucleotide in the synthesis strand overhanging the remaining support strand.

A phosphate group should continue to be attached to the terminal nucleotide of the support strand at the site of the overhang (as depicted in the structure shown in the middle of the lower part of FIG. 3a). This ensures that the support strand of the ligation polynucleotide can be ligated to the support strand of the cleaved scaffold polynucleotide in the ligation step.

Thus the support strand is cleaved between nucleotide positions n−1 and n−2.

Preferably, the support strand is cleaved by cleavage of the phosphodiester bond between nucleotide positions n−1 and n−2 (the second phosphodiester bond of the support strand relative to the position of the universal nucleotide, in the direction distal to the helper strand/proximal to the primer strand).

The support strand may be cleaved by cleavage of one ester bond of the phosphodiester bond between nucleotide positions n−1 and n−2.

Preferably the support strand is cleaved by cleavage of the first ester bond relative to nucleotide position n−1. This will have the effect of retaining a terminal phosphate group on the support strand of the cleaved scaffold polynucleotide at the cleavage position.

Cleavage of the support strand between nucleotide positions n−1 and n−2 as described above may be performed by the action of an enzyme such as Endonuclease V.

One mechanism of cleaving the support strand at a cleavage site defined by a sequence comprising a universal nucleotide occupying position n in the support strand in order to generate a double-nucleotide overhang is described in Example 7. The mechanism described is exemplary and other mechanisms could be employed, provided that the double-nucleotide overhang described above is achieved.

In this exemplified mechanism an endonuclease enzyme is employed. In the exemplified method the enzyme is Endonuclease V. Other enzymes, molecules or chemicals could be used provided that the single-nucleotide overhang described above is formed.

In step (4) of the method a double-stranded ligation polynucleotide is ligated (304) to the cleaved scaffold polynucleotide. The ligation polynucleotide comprises a support strand and a helper strand. The ligation polynucleotide further comprises a complementary ligation end comprising in the support strand a universal nucleotide and an overhanging nucleotide which is the partner nucleotide for the first nucleotide. The ligation polynucleotide further comprises in the helper strand adjacent the overhang a terminal nucleotide lacking a phosphate group (see structure depicted at the far left of the lower part of FIG. 3a). The complementary ligation end is configured so that it will compatibly join with the overhanging end of the cleaved scaffold polynucleotide product of step (3) when subjected to suitable ligation conditions. Upon ligation of the support strands the first nucleotide becomes paired with its partner nucleotide.

In this method, the universal nucleotide in the support strand of the ligation polynucleotide is positioned in the complementary ligation end opposite the terminal nucleotide of the helper strand at the site of the single-strand break, and is paired therewith. The universal nucleotide in the support strand of the ligation polynucleotide is positioned at position "n" with respect to the next nucleotide of the predefined nucleotide sequence to be incorporated into the synthesis strand of step (6), i.e. in the next synthesis cycle, as depicted schematically in FIG. 3a. In the complementary ligation end of the ligation polynucleotide the penultimate nucleotide of the support strand is a partner nucleotide for the first nucleotide of step (2) and overhangs the terminal nucleotide of the helper strand.

In the ligation polynucleotide the helper strand is provided such that the terminal nucleotide adjacent the overhang lacks a phosphate group. Typically, as described above, this non-phosphorylated terminal nucleotide of the helper strand will define the 5' terminus of the helper strand.

In step (4), upon ligation of the support strand of the ligation polynucleotide and the support strand of the cleaved scaffold polynucleotide (304), the first nucleotide of the predefined nucleotide sequence in the synthesis strand becomes paired with its partner nucleotide in the support strand.

Ligation may typically be performed by enzymes having ligase activity. For example, ligation may be performed with T3 DNA ligase or T4 DNA ligase. The use of such enzymes will result in the maintenance of the single-stranded break in the synthesis strand, since the terminal nucleotide of the helper strand cannot act as a substrate for ligase due to the absence of a terminal phosphate group.

Ligation of the ligation polynucleotide to the cleaved scaffold polynucleotide completes a first synthesis cycle whereupon the scaffold polynucleotide of step (1) is effectively re-constituted except that the first nucleotide of the predefined nucleotide sequence is incorporated into the polynucleotide opposite its partner nucleotide.

As with method versions 1 and 2, ligation in method version 3 may typically be performed by enzymes having ligase activity. For example, ligation may be performed with T3 DNA ligase or T4 DNA ligase. The use of ligase enzymes will result in the maintenance of the single-stranded break in the synthesis strand, since the terminal nucleotide of the helper strand cannot act as a substrate for ligase due to the absence of a terminal phosphate group.

Ligation of the ligation polynucleotide to the cleaved scaffold polynucleotide completes a first synthesis cycle whereupon the scaffold polynucleotide of step (1) is effectively re-constituted except that the first nucleotide of the predefined nucleotide sequence is incorporated into the polynucleotide opposite its partner nucleotide, as depicted in FIG. 3a. As in exemplary method versions 1 and 2, in exemplary method version 3 at the end of a given synthesis cycle, during cycles of synthesis, the universal nucleotide will occupy position n+1 in the support strand relative to the position occupied by the universal nucleotide in the support strand in the previous cycle. At the same time, and as in exemplary method version 1, at the end of a given synthesis cycle the universal nucleotide will also occupy position n in the support strand relative to the position in the synthesis strand which will be occupied by the next nucleotide of the predefined nucleotide sequence to be incorporated in the next cycle. Thus at the end of a given synthesis cycle a modified scaffold molecule is provided (306) for use in the next synthesis cycle, wherein the universal nucleotide is once again positioned in the support strand to facilitate incorporation of the next nucleotide of the predefined nucleotide sequence and cleavage of the support strand in the next synthesis cycle.

To allow the next nucleotide of the predefined nucleotide sequence to be incorporated in the next synthesis cycle, the reversible terminator group must be removed from the first nucleotide (deprotection step; 305). This can be performed as described above for method version 1.

In exemplary method version 3, second and subsequent synthesis cycles may be performed as described above for the first synthesis cycle.

Thus in step (6) the scaffold polynucleotide provided for the next synthesis cycle (306) is the product of the ligation step (4) and deprotection step, e.g. step (5) of the first synthesis cycle. In step (6) the next nucleotide in the predefined nucleotide sequence is incorporated (307) into the synthesis strand of the scaffold polynucleotide by the action of polymerase, as described above for step (2) of the first cycle. The next nucleotide also comprises a reversible terminator group which prevents further extension in that cycle by polymerase.

As in step (2) of the first synthesis cycle of exemplary method version 3, in step (6) the next nucleotide is incorporated opposite a universal nucleotide which is positioned in the support strand such that it pairs with the next nucleotide upon its incorporation. In this configuration the universal nucleotide is again positioned at position "n" with respect to the incorporated next nucleotide in the synthesis strand. Furthermore, as described above for the first synthesis cycle, in step (6) of the next synthesis cycle the universal nucleotide will occupy position "n+1" in the support strand relative to the position occupied by the universal nucleotide in the support strand in step (2) of the previous cycle. This is achieved because in the ligation polynucleotide of the previous synthesis cycle the universal nucleotide was positioned to be opposite to and paired with the terminal non-phosphorylated nucleotide of the helper strand.

In step (7) the scaffold polynucleotide is cleaved (308) at a cleavage site, the site defined by a sequence comprising the universal nucleotide in the support strand. Cleavage comprises cleaving the support strand and removing the universal nucleotide to provide in the synthesis strand a double-nucleotide overhanging end comprising the next nucleotide as the terminal nucleotide of the overhang in the remaining scaffold polynucleotide. The double-nucleotide overhang of the synthesis strand overhangs the terminal nucleotide of the support strand in the remaining cleaved scaffold polynucleotide. The cleavage steps may be performed as described above for step (3) of the first cycle.

In step (8) of the next cycle a double-stranded ligation polynucleotide is ligated (309) to the cleaved scaffold polynucleotide. The ligation polynucleotide comprises a support strand and a helper strand. The ligation polynucleotide further comprises a complementary ligation end comprising in the support strand a universal nucleotide and an overhanging nucleotide which is the partner nucleotide for the next nucleotide of the predefined nucleotide sequence. The ligation polynucleotide further comprises in the helper strand adjacent the overhang a terminal nucleotide lacking a phosphate group. The complementary ligation end is configured so that it will compatibly join with the overhanging end of the cleaved scaffold polynucleotide product of step (7) when subjected to suitable ligation conditions. Upon ligation of the support strands the next nucleotide of the predefined nucleotide sequence becomes paired with its partner nucleotide, thus completing a further synthesis cycle.

The ligation polynucleotide of step (8) of the next and subsequent synthesis cycles may be configured, and the ligation step may be performed, as described above for step (4) of the first synthesis cycle.

Thus in step (8) upon ligation (309) the universal nucleotide in the support strand is positioned opposite the terminal nucleotide of the helper strand, and is paired therewith. The universal nucleotide in the support strand is positioned at position "n" with respect to the next nucleotide, as described above with respect to the first synthesis cycle. Furthermore, as described above, following step (8) the universal nucleotide will occupy position "n+1" in the support strand relative to the position occupied by the universal nucleotide in the support strand prior to the commencement of step (6).

Deprotection of the reversible terminator group in the next cycle (310) may be performed as described above with respect to the first synthesis cycle.

Synthesis cycles are repeated for as many times as necessary to synthesise the double-stranded polynucleotide having the predefined nucleotide sequence.

Synthesis Method Version 4

Synthesis method version 4 is a variation of synthesis method version 2. Thus as with synthesis method version 2, in synthesis method version 4 the newly-incorporated predefined nucleotide is incorporated into the synthesis strand opposite a partner nucleotide in the support strand at position n during steps (2)/(6), and the support strand is cleaved between positions n and n−1 during steps (3)/(7). Unlike synthesis method version 2 where the universal nucleotide occupies position n+1, in synthesis method version 4 the universal nucleotide occupies position n+2 in the direction proximal to the helper strand/distal to the primer strand. Thus, taking into account this difference, synthesis method version 4 may be described with reference to FIG. 3b and the description thereof in the context of the description above relating to method version 2. Further variations of this method are envisaged wherein in each variant method the support strand is cleaved between positions n and n−1 during steps (3)/(7) and wherein the universal nucleotide incrementally occupies a position in the support strand one position further removed from position n+2 respectively, such as position n+3 or position n+3+x wherein x is a whole number between 1 and 10 or more.

Thus the invention also provides an in vitro method of synthesising a double-stranded polynucleotide molecule having a predefined sequence as described above and herein, the method comprising performing cycles of synthesis wherein:

a) in step (1) the scaffold polynucleotide is provided in the support strand with a nucleotide (position n) which is the partner nucleotide for the first nucleotide of step (2), and the universal nucleotide in the support strand is positioned at position n+2 (in the direction proximal to the helper strand/distal to the primer strand);

b) in step (2)/(6) the first/next nucleotide is incorporated into the synthesis strand at the position opposite the partner nucleotide in the support strand (position n), whereupon the first/next nucleotide pairs with the partner nucleotide;

c) in step (3)/(7) the support strand is cleaved at a position between the second nucleotide (position n) and the third nucleotide (position n−1) from the universal nucleotide in the support strand in the direction distal to the helper strand/proximal to the primer strand, wherein cleavage removes the universal nucleotide and creates a single-nucleotide overhang in the scaffold polynucleotide comprising the first/next nucleotide overhanging the support strand;

d) in step (4)/(8), the complementary ligation end of the ligation polynucleotide comprises a single-nucleotide overhang wherein:

i. the universal nucleotide is positioned at position n+2 in the support strand opposite a nucleotide in the helper strand and is paired therewith;

ii. the penultimate nucleotide of the support strand is paired with the terminal nucleotide of the helper strand and is a partner nucleotide for the next nucleotide in step (6) of the next synthesis cycle (position n); and iii. the terminal nucleotide of the support strand (position n−1) overhangs the terminal nucleotide of the helper strand and is a partner nucleotide for the first nucleotide of step (2), or is a partner nucleotide for the newly-incorporated nucleotide of step (6) of the current synthesis cycle.

In a modification of this method described immediately above, in step (1) the universal nucleotide in the support strand is positioned at position n+3 (in the direction proximal to the helper strand/distal to the primer strand), and in step (4)/(8) the complementary ligation end of the ligation polynucleotide is provided with the universal nucleotide in the support strand positioned at position n+3. Alternatively, in step (1) the universal nucleotide in the support strand is positioned at position n+3+x (in the direction proximal to the helper strand/distal to the primer strand), and in step (4)/(8) the complementary ligation end of the ligation polynucleotide is provided with the universal nucleotide in the support strand positioned at position n+3+x, wherein x is a whole number between 1 and 10 or more.

As with method version 2, in method version 4 and variants thereof the helper strand portion may be omitted from a scaffold polynucleotide prior to incorporation of a new predefined nucleotide. The helper strand portion may be removed from a scaffold polynucleotide prior to incorporation of a new predefined nucleotide, e.g. by denaturation, as describe in more detail herein.

Synthesis Method Version 5

Synthesis method version 5 is a variation of synthesis method version 3. Thus as with synthesis method version 3, in synthesis method version 4 the newly-incorporated predefined nucleotide is incorporated into the synthesis strand opposite a partner universal nucleotide in the support strand at position n during steps (2)/(6), and the support strand is cleaved between positions n−1 and n−2 during steps (3)/(7). Unlike synthesis method version 3 where the universal nucleotide occupies position n, in synthesis method version 5 the universal nucleotide occupies position n+1 in the direction proximal to the helper strand/distal to the primer strand. Thus, taking into account this difference, synthesis method version 5 may be described with reference to FIG. 3c and the description thereof in the context of the description above relating to method version 3. Further variations of this method are envisaged wherein in each variant method the support strand is cleaved between positions n−1 and n−2 during steps (3)/(7) and wherein the universal nucleotide incrementally occupies a position in the support strand one position further removed from position n+1 respectively, such as position n+2, or position n+2+x wherein x is a whole number between 1 and 10 or more.

Thus the invention also provides an in vitro method of synthesising a double-stranded polynucleotide molecule having a predefined sequence as described above and herein, the method comprising performing cycles of synthesis wherein:

a) in step (1) the scaffold polynucleotide is provided in the support strand with a nucleotide (position n) which is the partner nucleotide for the first nucleotide of step (2), and the universal nucleotide in the support strand is positioned at position n+1 (in the direction proximal to the helper strand/distal to the primer strand);

b) in step (2)/(6) the first/next nucleotide is incorporated into the synthesis strand at the position opposite the partner nucleotide in the support strand (position n), whereupon the first/next nucleotide pairs with the partner nucleotide;

c) in step (3)/(7) the support strand is cleaved at a position between the second nucleotide (position n−1) and the third nucleotide (position n−2) from the universal nucleotide in the support strand in the direction distal to the helper strand/proximal to the primer strand, wherein cleavage removes the universal nucleotide and creates a double-nucleotide overhang in the scaffold polynucleotide comprising the first/next nucleotide overhanging the support strand;

d) in step (4)/(8), the complementary ligation end of the ligation polynucleotide comprises a double-nucleotide overhang and wherein:

i. the universal nucleotide in the support strand is positioned at position n+1 opposite a nucleotide in the helper strand and is paired therewith;

ii. the penultimate nucleotide of the support strand (position n−1) overhangs the terminal nucleotide of the helper strand and is a partner nucleotide for the first nucleotide of step (2), or is a partner nucleotide for the newly-incorporated nucleotide of step (6) of the current synthesis cycle; and iii. the nucleotide at position n of the support strand is paired with the terminal nucleotide of the helper strand and is a partner nucleotide for the next nucleotide in step (6) of the next synthesis cycle.

In a modification of this method described immediately above, in step (1) the universal nucleotide in the support strand is positioned at position n+2 (in the direction proximal to the helper strand/distal to the primer strand), and in step (4)/(8) the complementary ligation end of the ligation polynucleotide is provided with the universal nucleotide in the support strand positioned at position n+2. Alternatively, in step (1) the universal nucleotide in the support strand is positioned at position n+2+x (in the direction proximal to the helper strand/distal to the primer strand), and in step (4)/(8) the complementary ligation end of the ligation polynucleotide is provided with the universal nucleotide in the support strand positioned at position n+2+x, wherein x is a whole number between 1 and 10 or more.

As with method version 3, in method version 5 and variants thereof the helper strand portion may be omitted from a scaffold polynucleotide prior to incorporation of a new predefined nucleotide. The helper strand portion may be removed from a scaffold polynucleotide prior to incorporation of a new predefined nucleotide, e.g. by denaturation, as describe in more detail herein.

Synthesis Strand

In methods of synthesising a polynucleotide or oligonucleotide described herein including, but not limited to, method versions 1, 2 and 3 as described above, the scaffold polynucleotide is provided with a synthesis strand. During cycles of synthesis each new nucleotide of the predefined sequence is incorporated into the synthesis strand. A polymerase enzyme can be used to catalyse incorporation of each new nucleotide, nucleotide analogue/derivative or non-nucleotide. The synthesis strand comprises a primer strand portion and preferably comprises a helper strand portion.

Helper Strand

A helper strand may be provided in the scaffold polynucleotide to facilitate binding of cleavage enzyme(s) at the cleavage step. The helper strand may be omitted, provided that alternative means are provided to ensure binding of cleavage enzyme(s) at the cleavage step and to ensure ligation at the ligation step, if necessary. In preferred methods of the invention the synthesis strand is provided with a helper strand.

There are no special requirements for the parameters of length, sequence and structure of the helper strand, provided that the helper strand is suitable to facilitate binding of cleavage enzyme(s) at the cleavage step.

The helper strand may comprise nucleotides, nucleotide analogues/derivatives and/or non-nucleotides.

Preferably, within the region of sequence of the helper strand mismatches with the support strand should be avoided, GC- and AT-rich regions should be avoided, and in addition regions of secondary structure such as hairpins or bulges should be avoided.

The length of the helper strand may be 10 bases or more. Optionally, the length of the helper strand may be 15 bases or more, preferably 30 bases or more. However, the length of the helper strand may be varied, provided that the helper strand is capable of facilitating cleavage and/or ligation.

The helper strand must be hybridized to the corresponding region of the support strand. It is not essential that the entirety of the helper strand is hybridized to the corresponding region of the support strand, provided that the helper strand can facilitate binding of cleavage enzyme(s) at the cleavage step and/or binding of ligase enzyme at the ligation step. Thus, mismatches between the helper strand and the corresponding region of the support strand can be tolerated. The helper strand may be longer than the corresponding region of the support strand. The support strand may extend beyond the region which corresponds with the helper strand in the direction distal to the primer strand. The helper strand may be connected to the corresponding region of the support strand, e.g. via a hairpin.

The helper strand is preferably hybridized to the support strand such that the terminal nucleotide of the helper strand at the site of the nick occupies the next sequential nucleotide position in the synthesis strand relative to the terminal nucleotide of the primer strand at the site of the nick. Thus in this configuration there are no nucleotide position gaps between the helper strand and the primer strand. The helper strand and primer strand will nevertheless be physically separated due to the presence of the single-stranded break or nick. Preferably, the terminal nucleobase of the helper strand at the site of the nick is hybridized to its partner nucleotide in the support strand.

The nucleotide in the helper strand which pairs with the universal nucleotide may be any suitable nucleotide. Preferably, pairings which are likely to distort the helical structure of the molecule should be avoided. Preferably cytosine acts as a partner for the universal nucleotide. In a particularly preferred embodiment the universal nucleotide is inosine, or an analogue, variant or derivative thereof, and the partner nucleotide for the universal nucleotide in the helper strand is cytosine.

Removal of Helper Strand

In any of the synthesis methods described herein, including exemplary method versions 1, 2 and 3, in step (1) (i.e. in the first cycle) of providing a scaffold polynucleotide comprising a synthesis strand and a support strand hybridized thereto (101, 106, 201, 206, 301, 306), the synthesis strand may be provided without a helper strand. This may improve the binding of polymerase to the scaffold polynucleotide.

Furthermore, in any one or more cycles of synthesis, or in all cycles of synthesis, after the step of ligating the double-stranded ligation polynucleotide to the cleaved scaffold polynucleotide and before the step of incorporating the next nucleotide of the predefined nucleotide sequence into the synthesis strand of the scaffold polynucleotide, the helper strand portion of the synthesis strand may be removed from the scaffold polynucleotide. The helper strand portion of the synthesis strand may be removed from the scaffold polynucleotide by any suitable means including, but not limited to: (i) heating the scaffold polynucleotide to a temperature of about 80° C. to about 95° C. and separating the helper strand portion from the scaffold polynucleotide, (ii) treating the scaffold polynucleotide with urea solution, such as 8M urea and separating the helper strand portion from the scaffold polynucleotide, (iii) treating the scaffold polynucleotide with formamide or formamide solution, such as 100% formamide and separating the helper strand portion from the scaffold polynucleotide, or (iv) contacting the scaffold polynucleotide with a single-stranded polynucleotide molecule which comprises a region of nucleotide sequence which is complementary with the sequence of the helper strand portion, thereby competitively inhibiting the hybridisation of the helper strand portion to the scaffold polynucleotide.

In methods wherein the helper strand portion is removed from the scaffold polynucleotide after the step of ligating the double-stranded ligation polynucleotide to the cleaved scaffold polynucleotide and before the step of incorporating the next nucleotide of the predefined nucleotide sequence into the synthesis strand of the scaffold polynucleotide, the cleavage step will comprise cleaving the support strand in the absence of a double-stranded region provided by the helper strand. Any suitable enzyme may be chosen for performing such a cleavage step, such as selected from any suitable enzyme disclosed herein.

Primer Strand

The primer strand should be of sufficient length and should possess a sequence and structure such that it is suitable to allow a polymerase enzyme to initiate synthesis, i.e. catalyse the incorporation of a new nucleotide at the terminal end of the primer strand at the site of the nick.

The primer strand may comprise a region of sequence which can act to prime new polynucleotide synthesis (e.g. as shown by the dotted line in the structures depicted in each of FIGS. 1 to 3). The primer strand may consist of a region of sequence which can act to prime new polynucleotide synthesis, thus the entirety of the primer strand may be sequence which can act to prime new polynucleotide synthesis.

There are no special requirements for the parameters of length, sequence and structure of the primer strand, provided that the primer strand is suitable to prime new polynucleotide synthesis.

The primer strand may comprise nucleotides, nucleotide analogues/derivatives and/or non-nucleotides.

The skilled person is readily able to construct a primer strand which will be capable of priming new polynucleotide synthesis. Thus, within the region of sequence of the primer strand which can act to prime new polynucleotide synthesis mismatches with the support strand should be avoided, GC- and AT-rich regions should be avoided, and in addition regions of secondary structure such as hairpins or bulges should be avoided.

The length of the region of sequence of the primer strand which can act to prime new polynucleotide synthesis can be chosen by the skilled person depending on preference and the polymerase enzyme to be used. The length of this region may be 7 bases or more, 8 bases or more, 9 bases or more or 10 bases or more. Optionally the length of this region will be 15 bases or more, preferably 30 bases or more.

The primer strand must be hybridized to the corresponding region of the support strand. It is not essential that the entirety of the primer strand is hybridized to the corresponding region of the support strand, provided that the primer strand is capable of priming new polynucleotide synthesis. Thus, mismatches between the primer strand and the corresponding region of the support strand can be tolerated to a degree. Preferably, the region of sequence of the primer strand which can act to prime new polynucleotide synthesis should comprise nucleobases which are complementary to corresponding nucleobases in the support strand.

The primer strand may be longer than the corresponding region of the support strand. The support strand may extend beyond the region which corresponds with the primer strand in the direction distal to the helper strand. The primer strand may be connected to the corresponding region of the support strand, e.g. via a hairpin.

Support Strand

In methods of the invention including, but not limited to, method versions 1, 2 and 3, as described above, the scaffold polynucleotide is provided with a support strand. The support strand is hybridized to the synthesis strand. There are no special requirements for the parameters of length, sequence and structure of the support strand, provided that the support strand is compatible with the primer strand portion and, if included, the helper strand portion of the synthesis strand, as described above.

RNA Synthesis

Methods described for DNA synthesis may be adapted for the synthesis of RNA. In one adaptation the synthesis steps described for method versions 1-3 may be adapted. Thus in each of method versions 1-3 the support strand of the scaffold polynucleotide is a DNA strand, as described above. The primer strand portion of the synthesis strand of the scaffold polynucleotide is an RNA strand. The helper strand, if present, is preferably an RNA strand. The helper strand, if present, may be a DNA strand.

Nucleotides may be incorporated from ribonucleoside-5'-O-triphosphates (NTPs) which may be modified to comprise a reversible terminator group, as described above. Preferably 3'-O-modified-ribonucleoside-5'-O-triphosphates are used. Modified nucleotides are incorporated by the action of RNA polymerase.

Figure 23:
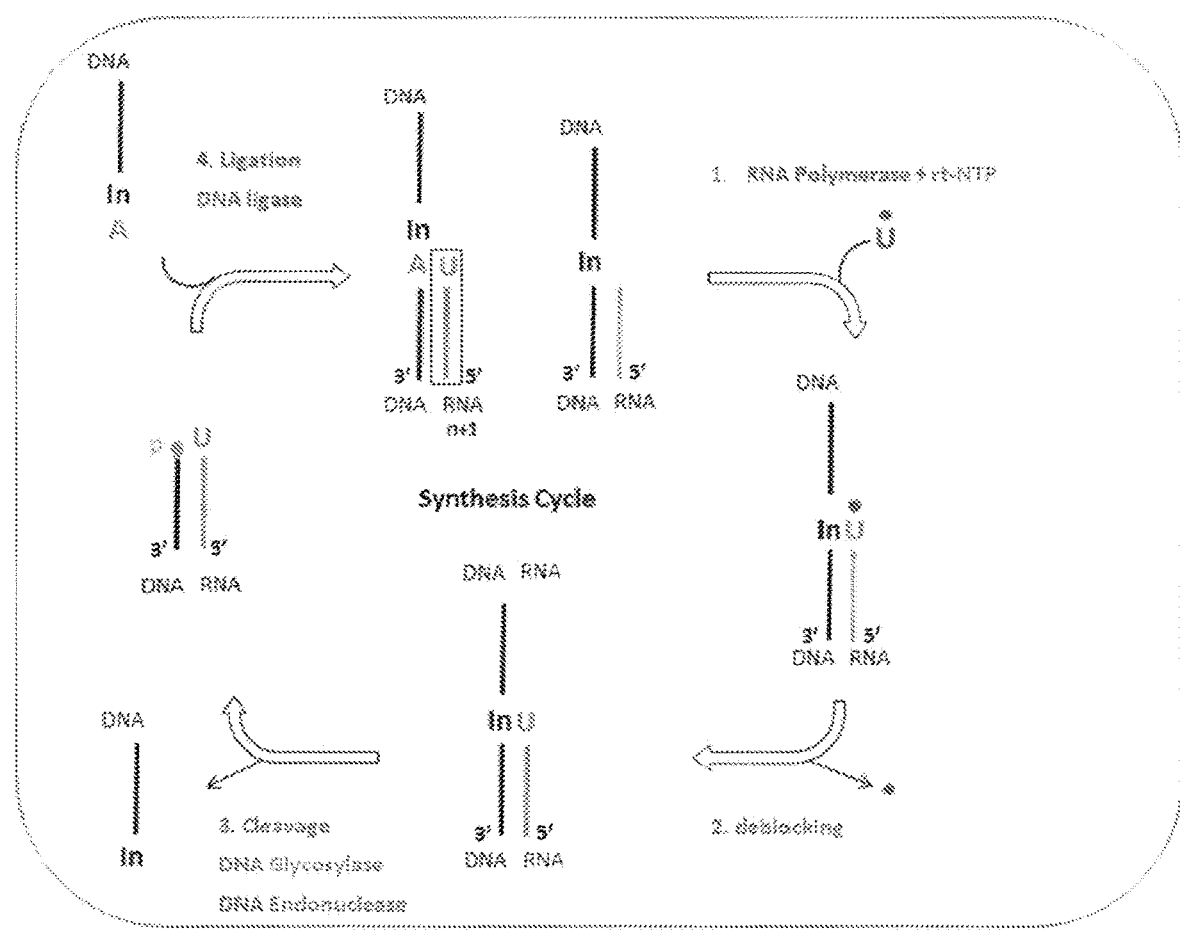
Figure 24:
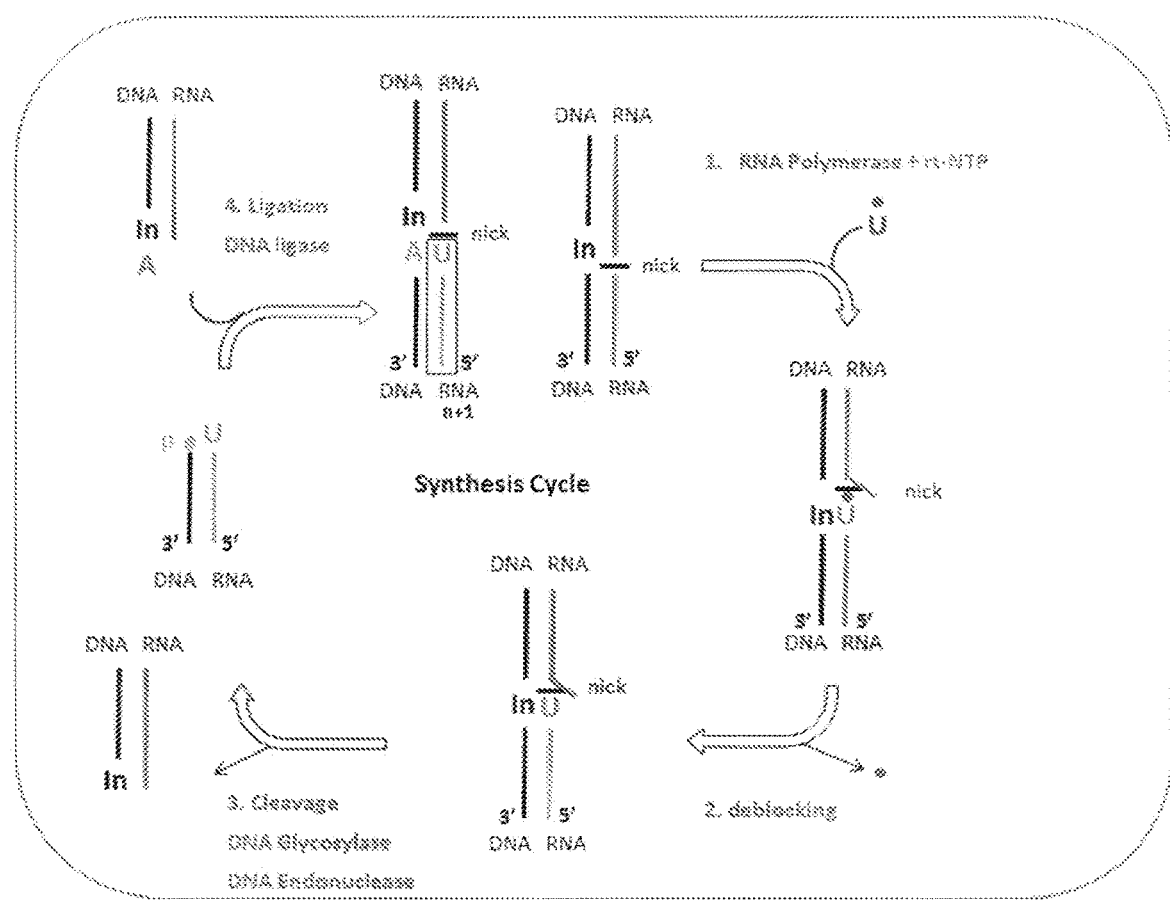
Figure 25:
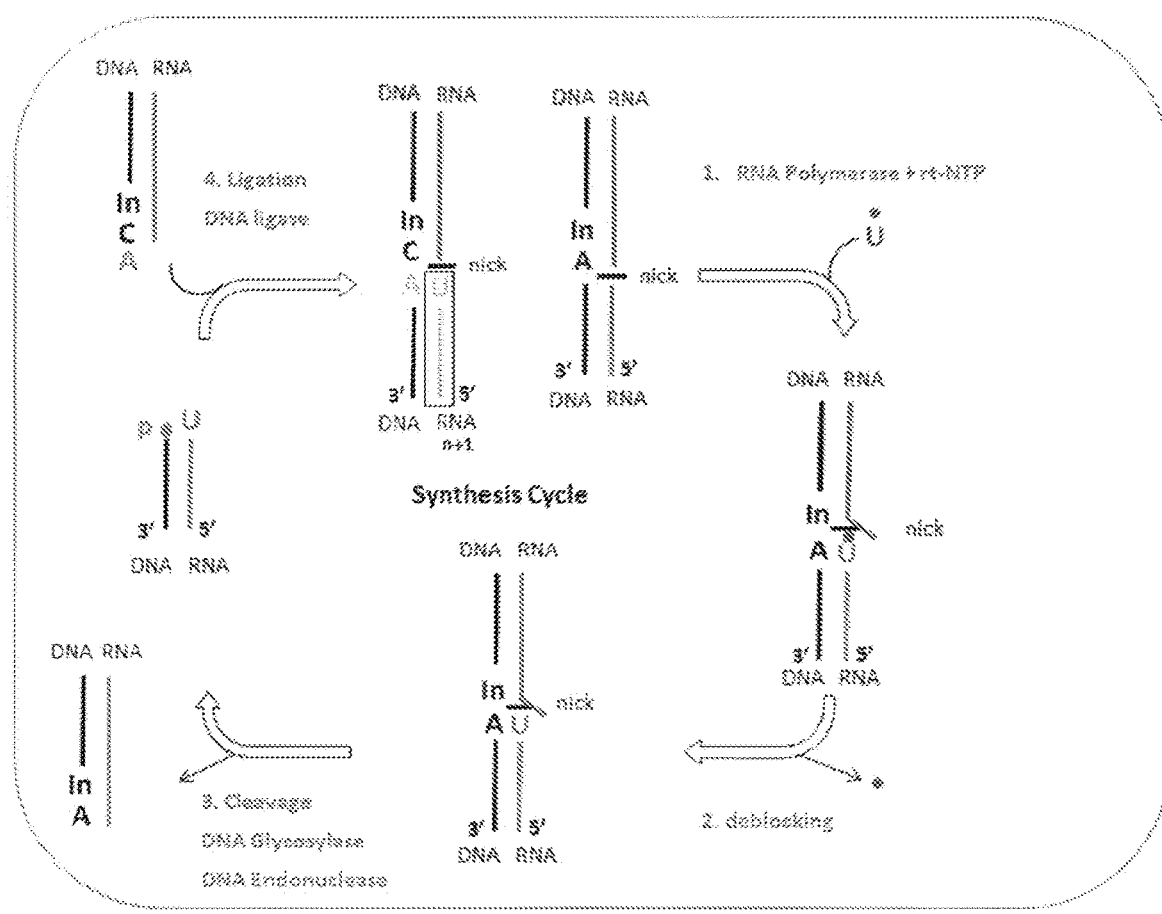

Thus the above descriptions relating to method versions 1-3 may be applied mutatis mutandis for RNA synthesis but adapted as described. Exemplary adapted reaction schemes relating to method versions 1 and 2 are shown in FIGS. 23 to 25. Method version 3 can be adapted in the same way. In any of the adapted methods for RNA synthesis, the above descriptions of support strand, primer strand, helper strand, ligation polynucleotide and universal nucleotide may be applied mutatis mutandis but adapted as described. Cleavage steps and cleavage positions as previously described may be applied mutatis mutandis since, the support strand which comprises the universal nucleotide is a DNA strand. In a preferred embodiment SplintR DNA ligase is used in the ligation step.

EXAMPLES

The following Examples illustrate certain embodiments of the methods for synthesising a polynucleotide or oligonucleotide according to the invention, as well as exemplary constructs used in the methods. The Examples do not limit the invention.

Example 1. Synthesis in the Absence of a Helper Strand

This example describes the synthesis of polynucleotides using 4 steps: incorporation of 3'-O-modified dNTPs on partial double-stranded DNA, cleavage, ligation and deprotection, with the first step taking place opposite a universal nucleotide, in this particular case inosine.

Step 1: Incorporation

The first step describes controlled addition of a 3'-O-protected single nucleotide to an oligonucleotide by enzymatic incorporation by DNA polymerase (FIG. 5a).

Materials and Methods

Materials 1. 3'-O-modified dNTPs were synthesised in-house according to the protocol described in PhD thesis Jian Wu: Molecular Engineering of Novel Nucleotide Analogues for DNA Sequencing by Synthesis, Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich (FIG. 5h). The stock solutions were prepared at a concentration of 100 μM.
3. Terminator IX DNA polymerase was used that has been engineered by New England BioLabs with enhanced ability to incorporate 3-O-modified dNTPs. However, any DNA polymerase that could incorporate modified dNTPs could be used.

Two Types of Reversible Terminators were Tested:

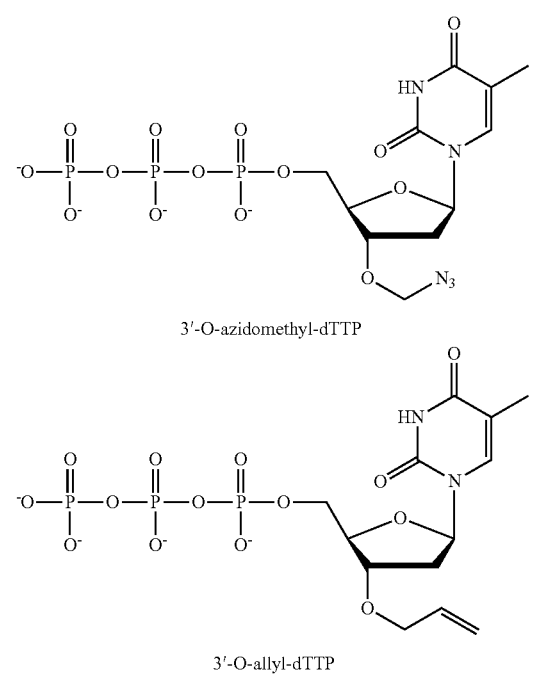

3'-O-azidomethyl-dTTP

3'-O-allyl-dTTP

Methods 1. 2 μl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.25 μl of sterile deionized water (ELGA VEOLIA) in 1.5 ml Eppendorf tube.
2. 0.5 μl of 10 μM primer (synthesised strand) (5 pmol, 1 equiv) (SEQ ID NO: 1, FIG. 5h) and 0.75 μl of 10 μM template (support strand) (6 pmol, 1.5 equiv) (SEQ ID NO: 2, FIG. 5h) were added to the reaction mixture.
3. 3'-O-modified-dTTP (2 μl of 100 μM) and $MnCl_2$ (1 μl of 40 mM) were added.
4. 1.5 μl of Therminator IX DNA polymerase (15 U, New England BioLabs) was then added. However, any DNA polymerase that could incorporate modified dNTPs could be used.
5. The reaction was incubated for 20 minutes at 65° C.
6. The reaction was stopped by addition of TBE-Urea sample buffer (Novex).
7. The reaction was separated on polyacrylamide gel (15%) with TBE buffer and visualized by ChemiDoc MP imaging system (BioRad).

Gel Electrophoresis and DNA Visualization:

1. 5 μl of reaction mixture was added to 5 μl of TBE-Urea sample buffer (Novex) in a sterile 1.5 ml Eppendorf tube and heated to 95° C. for 5 minutes using a heat ThermoMixer (Eppendorf).
2. 5 μl of the sample was then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. The gel was visualized by ChemiDoc MP (BioRad) using Cy3 LEDS. Visualization and analysis was carried out on the Image lab 2.0 platform.

Results

Customised engineered Therminator IX DNA polymerase from New England BioLabs is an efficient DNA polymerase able to incorporate 3'-O-modified-dNTPs opposite a universal nucleotide e.g. inosine (FIG. 5b-c).

Efficient incorporation opposite inosine occurred at a temperature of 65° C. (FIG. 5d-e).

Incorporation of 3'-O-modified-dTTPs opposite inosine requires the presence of $Mn^{2+}$ ions (FIG. 5f-g). Successful conversion is marked in bold in FIGS. 5 c, e, g and h.

Conclusion

Incorporation of 3-O-modified-dTTPs opposite inosine can be achieved with particularly high efficiency using customized engineered Therminator IX DNA polymerase from New England BioLabs, in the presence of $Mn^{2+}$ ions and at a temperature at 65° C.

Step 2: Cleavage

The second step describes a two-step cleavage of polynucleotides with either hAAG/Endo VIII or hAAG/chemical base (FIG. 6a).

Materials and Methods

Materials

1. Oligonucleotides utilized in Example 1 were designed in-house and synthesised by Sigma Aldrich (see table in FIG. 6(e) for sequences).
2. The oligonucleotides were diluted to a stock concentration of 100 uM using sterile distilled water (ELGA VEOLIA).

Methods

A cleavage reaction on oligonucleotides was carried out using the procedure below:

1. A pipette (Gilson) was used to transfer 410 sterile distilled water (ELGA VEOLIA) into a 1.5 ml Eppendorf tube.

2. 5 µl of 10× ThermoPol® reaction buffer NEB (20 mM Tris-HCl, 10 mM (NH$_4$)$_2$SO$_4$, 10 mM KCl, 2 mM MgSO$_4$, 0.1% Triton® X-100, pH 8.8) were then added into the same Eppendorf tube.
3. 1 µl each of oligonucleotides (FIG. 6e); template (SEQ ID NO: 3) or any fluorescently tagged long oligo strand, primer with T (SEQ ID NO: 4) and control (SEQ ID NO: 5) all at 5 pmols were added into the same tube.
4. 1 µl of Human Alkyladenine DNA Glycosylase (hAAG) NEB (10 units/µl) was added into the same tube.
5. Reaction mixture was then gently mixed by resuspension with a pipette, centrifuged at 13,000 rpm for 5 seconds and incubated at 37° C. for 1 hour.
6. Typically after incubation time had elapsed, the reaction was terminated by enzymatic heat inactivation (i.e. 65° C. for 20 minutes).

Purification under ambient conditions. The sample mixture was purified using the protocol outlined below:
1. 500 µl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 µl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.
6. For DNA elution, 50 µl of Buffer EB QIAGEN (10 mM Tris.CL, pH 8.5) was added to the centre of the column membrane and left to stand for 1 min at room temperature.
7. The tube was then centrifuged at 13000 rpm for 1 minutes. Eluted DNA concentration was measured and stored at −20° C. for subsequent use.

Measurement of purified DNA concentration was determined using the protocol below:
1. NanoDrop one (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop one was blanked by adding 2 µl of Buffer EB QIAGEN (10 mM Tris.CL, pH 8.5). Then step 2 was repeated after blanking.
4. DNA concentration was measured by adding 2 µl of the sample onto the pedestal and selecting the measure icon on the touch screen.

Cleavage of the generated abasic site was carried out using the procedure below:
1. 2 µl (10-100 ng/µl) DNA was added into a sterile 1.5 ml Eppendorf tube.
2. 40 µl (0.2M) NaOH or 1.5 µl Endo VIII NEB (10 units/µl) and 5 µl 10× Reaction Buffer NEB (10 mM Tris-HCl, 75 mM NaCl, 1 mM EDTA, pH 8 @ 25° C.) was also added into the same tube and gently mixed by resuspension and centrifugation at 13000 rpm for 5 sec.
3. The resulting mixture was incubated at room temperature for 5 minutes for the NaOH treated sample while Endo VIII reaction mixture was incubated at 37° C. for 1 hr.
4. After incubation time had elapsed, the reaction mixture was purified using steps 1-7 of purification protocol as outlined above.

Gel Electrophoresis and DNA Visualization:
1. 5 µl of DNA and TBE-Urea sample buffer (Novex) was added into a sterile 1.5 ml Eppendorf tube and heated to 95° C. for 2 minutes using a heat thermoblock (Eppendorf).
2. The DNA mixtures were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. Detection and visualization of DNA in the gel was carried out with ChemiDoc MP (BioRad) using Cy3 LEDS. Visualization and analysis was carried out on the Image lab 2.0 platform.

Results and Conclusion

The cleavage reaction without a helper strand showed a low percentage yield of cleaved to uncleaved DNA ratio of ~7%:93% (FIG. 6b-d).

Cleavage results showed that in this specific example, and based on the specific reagents used, a low yield of cleaved DNA is obtained in the absence of a helper strand in comparison to the positive control. In addition the use of a chemical base for cleavage of the abasic site was less time-consuming compared to EndoVIII cleavage.

Step 3: Ligation

The third step describes ligation of polynucleotides with DNA ligase in the absence of a helper strand. A diagrammatic illustration is shown in FIG. 7.

Materials and Methods

Materials
1. Oligonucleotides utilized in Example 1 were designed in-house and synthesised by Sigma Aldrich (see table in FIG. 7c for sequences).
2. The oligonucleotides were diluted to a stock concentration of 100 uM using sterile distilled water (ELGA VEOLIA).

Methods

Ligation reaction on oligonucleotides was carried out using the procedure below:
1. A pipette (Gilson) was used to transfer 160 sterile distilled water (ELGA VEOLIA) into a 1.5 ml Eppendorf tube.
2. 10 µl of 2× Quick Ligation Reaction buffer NEB (132 mM Tris-HCl, 20 mM MgCl$_2$, 2 mM dithiothreitol, 2 mM ATP, 15% Polyethylene glycol (PEG6000) and pH 7.6 at 25° C.) was then added into the same Eppendorf tube.
3. 1 µl each of oligonucleotides (FIG. 7c); TAMRA or any fluorescently tagged phosphate strand (SEQ ID NO: 7), primer with T (SEQ ID NO: 8) and inosine strand (SEQ ID NO: 9), all at 5 pmols, was added into the same tube.
4. 1 µl of Quick T4 DNA Ligase NEB (400 units/µl) was added into the same tube.

5. The reaction mixture was then gently mixed by resuspension with a pipette, centrifuged at 13,000 rpm for 5 seconds and incubated at room temperature for 20 minutes.
6. Typically after incubation time had elapsed, reaction was terminated with the addition of TBE-Urea sample Buffer (Novex).
7. The reaction mixture was purified using the protocol outlined in purification steps 1-7 as described above.

Measurement of purified DNA concentration was determined using the protocol below:
1. NanoDrop one (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop one was blanked by adding 2 µl of Buffer EB QIAGEN (10 mM Tris.CL, pH 8.5), then step 2 was repeated after blanking.
4. DNA concentration was measured by adding 2 µl of the sample onto the pedestal and selecting the measure icon on the touch screen.
5. Purified DNA was run on a polyacrylamide gel and visualized in accordance with the procedure in steps 5-8 described above. No change in conditions or reagents was introduced.

Results and Conclusion

In this specific example, and based on the specific reagents used, ligation of oligonucleotides with DNA ligase, in this particular case quick T4 DNA ligase, at room temperature (24° C.) in the absence of a helper strand results in a reduced amount of ligation product (FIG. 7b).

Example 2. Version 1 Chemistry with a Helper Strand

This example describes the synthesis of polynucleotides using 4 steps: incorporation of 3'-O-modified dNTPs from a nick site, cleavage, ligation and deprotection, with the first step taking place opposite a universal nucleotide, in this particular case inosine. The method uses a helper strand which improves the efficiency of the ligation and cleavage steps.

Step 1: Incorporation

The first step describes controlled addition of 3'-O-protected single nucleotide to oligonucleotide by enzymatic incorporation using DNA polymerase (FIG. 8a).

Materials and Methods

Materials
1. 3'-O-modified dNTPs were synthesised in-house according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich. The stock solutions were prepared at a concentration of 100 µM. Oligonucleotides are shown in FIG. 8b.
3. Terminator IX DNA polymerase was used that has been engineered by New England BioLabs with enhanced ability to incorporate 3-O-modified dNTPs.

Two Types of Reversible Terminators were Tested:

3'-O-azidomethyl-dTTP:

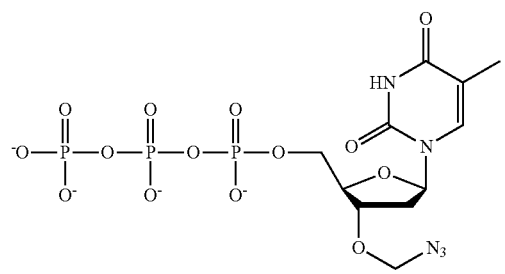

3'-O-allyl-dTTP:

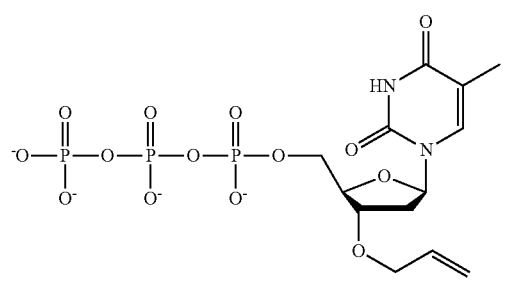

Methods
1. 2 µl of 10× Thermopol® buffer (20 mM Tris-HCl, 10 mM (NH$_4$)$_2$SO$_4$, 10 mM KCl, 2 mM MgSO$_4$, 0.1% Triton® X-100, pH 8.8, New England BioLabs) was mixed with 10.25 µl of sterile deionized water (ELGA VEOLIA) in 1.5 ml Eppendorf tube.
2. 0.5 µl of 10 µM primer (5 pmol, 1 equiv) (SEQ ID NO: 10, Table in FIG. 8(b)), 0.75 µl of 10 µM template (6 pmol, 1.5 equiv) (SEQ ID NO: 11, Table in FIG. 8(b)), 2 µl of 10 µM of helper strand (SEQ ID NO: 12, Table in FIG. 8(b)) were added to the reaction mixture.
3. 3'-O-modified-dTTP (2 µl of 100 µM) and MnCl$_2$ (1 µl of 40 mM) were added.
4. 1.5 µl of Therminator IX DNA polymerase (15 U, New England BioLabs) was then added.
5. The reaction was incubated for 20 minutes at 65° C.
6. The reaction was stopped by addition of TBE-Urea sample buffer (Novex).
7. The reaction was separated on polyacrylamide gel (15%) TBE buffer and visualized by ChemiDoc MP imaging system (BioRad).

Gel Electrophoresis and DNA Visualization:
1. 5 µl of reaction mixture was added to 5 µl of TBE-Urea sample buffer (Novex) in a sterile 1.5 ml Eppendorf tube and heated to 95° C. for 5 minutes using a heat ThermoMixer (Eppendorf).
2. 5 µl of the sample were then loaded into the wells of a 15% TBE-Urea gel 1.0 mm×10 well (Invitrogen) which contained preheated 1×TBE buffer Thermo Scientific (89 mM Tris, 89 mM Boric acid and 2 mM EDTA).
3. X-cell sure lock module (Novex) was fastened in place and electrophoresis performed at the following conditions; 260V, 90 Amps for 40 minutes at room temperature.

4. The gel was visualized by ChemiDoc MP (BioRad) using Cy3 LEDS. Visualization and analysis was carried out on the Image lab 2.0 platform.

The incorporation step can be studied according to the protocol described above.

Step 2: Cleavage

The second step describes a two-step cleavage of polynucleotides with either hAAG/Endo VIII or hAAG/chemical base (×2) (FIG. 9a).

Materials and Methods

Materials

1. Oligonucleotides utilized in Example 2 were designed in-house and synthesised by Sigma Aldrich (see FIG. 9f for sequences).
2. The oligonucleotides were diluted to a stock concentration of 100 uM using sterile distilled water (ELGA VEOLIA).

Methods

Cleavage reaction on oligonucleotides was carried out using the procedure below:

1. A pipette (Gilson) was used to transfer 410 sterile distilled water (ELGA VEOLIA) into a 1.5 ml Eppendorf tube.
2. 5 µl of 10× ThermoPol® Reaction buffer NEB (20 mM Tris-HCl, 10 mM $(NH_4)_2SO_4$, 10 mM KCl, 2 mM $MgSO_4$, 0.1% Triton® X-100, pH 8.8) was then added into the same Eppendorf tube.
3. 1 µl each of oligonucleotides (FIG. 9f); template (SEQ ID NO: 13) or any fluorescently tagged long oligo strand, primer with T (SEQ ID NO: 14), control (SEQ ID NO: 15) and helper strand (SEQ ID NO: 16), all at 5 pmols, were added into the same tube.
4. 1 µl of Human Alkyladenine DNA Glycosylase (hAAG) NEB (10 units/µl) was added into the same tube.
5. In the reaction using alternative base, 1 µl of Human Alkyladenine DNA Glycosylase (hAAG) NEB (100 units/µl) was added.
6. Reaction mixture was then gently mixed by resuspension with a pipette, centrifuged at 13,000 rpm for 5 seconds and incubated at 37° C. for 1 hour.
7. Typically after incubation time had elapsed, the reaction was terminated by enzymatic heat inactivation (i.e. 65° C. for 20 minutes).

Purification under ambient conditions. The sample mixture was purified using the protocol outlined below:

1. 500 µl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 µl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.
6. For DNA elution, 50 µl of Buffer EB QIAGEN (10 mM Tris.CL, pH 8.5) was added to the centre of the column membrane and left to stand for 1 min at room temperature.
7. The tube was then centrifuged at 13000 rpm for 1 minute. Eluted DNA concentration was measured and stored at −20° C. for subsequent use.

Measurement of purified DNA concentration was determined using the protocol below:

1. NanoDrop one (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop one was blanked by adding 2 µl of Buffer EB QIAGEN (10 mM Tris.CL, pH 8.5). Then step 2 was repeated after blanking.
4. DNA concentration was measured by adding 2 µl of the sample onto the pedestal and selecting the measure icon on the touch screen.

Cleavage of generated abasic site was carried out using the procedure below:

1. 2 µl (10-100 ng/µl) DNA was added into a sterile 1.5 ml Eppendorf tube.
2. 40 µl (0.2M) NaOH or 1.5 µl Endo VIII NEB (10 units/µl) and 5 µl 10× Reaction Buffer NEB (10 mM Tris-HCl, 75 mM NaCl, 1 mM EDTA, pH 8 @ 25° C.) was also added into the same tube and gently mixed by resuspension and centrifugation at 13000 rpm for 5 sec.
3. The resulting mixture was incubated at room temperature for 5 minutes for the 0.2 M NaOH treated sample while Endo VIII reaction mixture was incubated at 37° C. for 1 hr.
4. After incubation time had elapsed, the reaction mixture was purified using steps 1-7 of purification protocol as stated above.

Cleavage of generated abasic site using alternative basic chemical was carried out using the procedure below:

1. 1 µl (10-100 ng/µl) DNA was added into a sterile 1.5 ml Eppendorf tube. 2 µl of N,N' dimethylethylenediamine Sigma (100 mM) which had been buffered at room temperature with acetic acid solution sigma (99.8%) to pH 7.4 was then added into the same tube.
2. 20 µl of sterile distilled water (ELGA VEOLIA) was added into the tube and gently mixed by resuspension and centrifugation at 13000 rpm for 5 sec.
3. The resulting mixture was incubated at 37° C. for 20 minutes.
4. After incubation time had elapsed, the reaction mixture was purified using steps 1-7 of the purification protocol stated above.

Gel Electrophoresis and DNA Visualization:

1. 5 µl of DNA and TBE-Urea sample buffer (Novex) was added into a sterile 1.5 ml Eppendorf tube and heated to 95° C. for 2 minutes using a heat thermoblock (Eppendorf).
2. The DNA mixtures were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. Detection and visualization of DNA in the gel was carried out with ChemiDoc MP (BioRad) using Cy3 LEDS. Visualization and analysis was carried out on the Image lab 2.0 platform.

Results

Cleavage efficiency at a cleavage site comprising a universal nucleotide, in this particular case inosine, by hAAG DNA glycosylase was significantly increased from 10% in absence of helper strand to 50% in presence of helper strand (FIG. 9b). hAAG and Endonuclease VIII cleave inosine with lower efficiency (10%) than hAAG and NaOH (50%). Chemical cleavage using 0.2M NaOH was shown to be preferable for cleavage of AP sites than Endonuclease VIII in the described system using nicked DNA (FIG. 9c). Mild N,N'-dimethylethylenediamine at neutral pH has high efficiency to cleave abasic sites as 0.2M NaOH, and therefore it is preferable compared with Endonuclease VIII and NaOH (FIGS. 9d-e).

Conclusion

Three methods were evaluated for cleavage of DNA containing inosine. One full enzymatic method—hAAG/Endonuclease VIII, and two methods combining chemical and enzymatic cleavage—hAAG/NaOH and hAAG/dimethylethylamine were studied for DNA cleavage in Example 2.

hAAG/NaOH results showed a much higher yield of cleaved DNA (50%) in the presence of a helper strand in comparison to the absence of a helper strand (10%). In these specific examples, and based on the specific reagents used, helper strands increase yield of DNA cleavage.

Enzymatic cleavage using Endonuclease VIII as a substitute for NaOH was less efficient (10%) compared to NaOH (50%) in the presence of a helper strand.

The inclusion of an alternative mild chemical base N,N'-dimethylethylenediamine led to high cleavage efficiency of AP sites, as efficient as for NaOH, and, together with addition of 10× hAAG enzyme, had a significant increase on cleaved DNA (see FIG. 9e).

Step 3: Ligation

The third step describes ligation of polynucleotides with DNA ligase in the presence of a helper strand. A diagrammatic illustration is shown in FIG. 10a.

Materials and Methods

Materials

1. Oligonucleotides were designed in-house and synthesised by Sigma Aldrich (see FIG. 10d for sequences).
2. The oligonucleotides were diluted to a stock concentration of 100 uM using sterile distilled water (ELGA VEOLIA).

Methods

Ligation reaction on oligonucleotides was carried out using the procedure below:

1. A pipette (Gilson) was used to transfer 160 sterile distilled water (ELGA VEOLIA) into a 1.5 ml Eppendorf tube.
2. 10 µl of 2× Quick Ligation Reaction buffer NEB (132 mM Tris-HCl, 20 mM MgCl$_2$, 2 mM dithiothreitol, 2 mM ATP, 15% Polyethylene glycol (PEG6000) and pH 7.6 at 25° C.) was then added into the same Eppendorf tube.
3. 1 µl each of oligonucleotides (FIG. 10d); TAMRA or any fluorescently tagged phosphate strand (SEQ ID NO: 18), primer with T (SEQ ID NO: 19) and inosine strand (SEQ ID NO: 20) and helper strand (SEQ ID NO: 21), all at of 5 pmols, was added into the same tube.
4. 1 µl of Quick T4 DNA Ligase NEB (400 units/µl) was added into the same tube.
5. Reaction mixture was then gently mixed by resuspension with a pipette, centrifuged at 13,000 rpm for 5 seconds and incubated at room temperature for 20 minutes.
6. Typically after incubation time had elapsed, reaction was terminated with the addition of TBE-Urea sample Buffer (Novex).
7. The reaction mixture was purified using the protocol outlined in purification steps 1-7 as described above.

Measurement of purified DNA concentration was determined using the protocol below:

1. NanoDrop one (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop one was blanked by adding 2 µl of Buffer EB QIAGEN (10 mM Tris.CL, pH 8.5). Then step 2 was repeated after blanking.
4. DNA concentration was measured by adding 2 µl of the sample onto the pedestal and selecting the measure icon on the touch screen.
5. Purified DNA was run on a polyacrylamide gel and visualized in accordance with the procedure in steps 5-8 above. No change in conditions or reagents was introduced.

Results and Conclusion

In this specific example, and based on the specific reagents used, reduced ligation activity is observed in the absence of a helper strand (FIG. 10b), whereas ligation proceeds with high efficiency in presence of a helper strand (FIG. 10c) and the product is formed in high yield.

Example 3. Version 2 Chemistry with a Helper Strand

This example describes the synthesis of polynucleotides using 4 steps: incorporation of 3'-O-modified dNTPs on partial double-stranded DNA; cleavage, ligation and deprotection with the first step of incorporation taking place opposite a naturally complementary nucleotide which is positioned in the support strand adjacent to a universal nucleotide, in this particular case inosine.

Step 1: Incorporation

Materials and Methods

Materials

The first step describes controlled addition of 3'-O-protected single nucleotide to oligonucleotide by enzymatic incorporation by DNA polymerase (FIG. 11a).

1. 3'-O-modified dNTPs were synthesised in-house according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich (FIG. 11j). The stock solutions are prepared in concentration of 100 µM.
3. Terminator IX DNA polymerase was used that has been engineered by New England BioLabs with enhanced ability to incorporate 3-O-modified dNTPs.

3'-O-azidomethyl reversible terminators of all dNTPs were tested independently for incorporation:

3'-O-azidomethyl-dTTP:

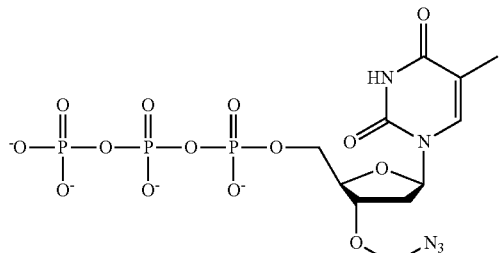

3'-O-azidomethyl-dCTP:

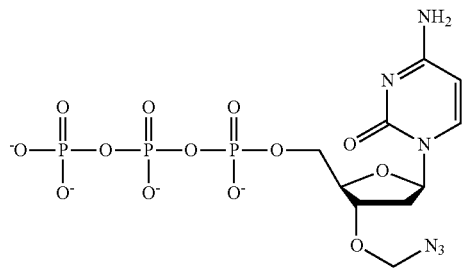

3'-O-azidomethyl-dATP:

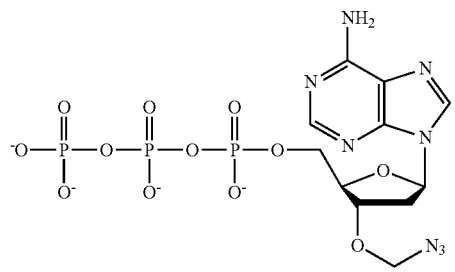

3'-O-azidomethyl-dGTP:

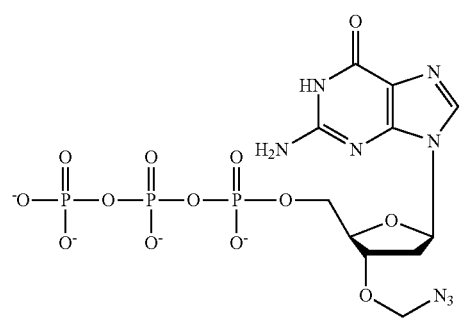

Methods
1. 2 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.25 µl of sterile deionized water (ELGA VEOLIA) in 1.5 ml Eppendorf tube.
2. 0.5 µl of 10 µM primer (5 pmol, 1 equiv) (SEQ ID NO: 22, FIG. 11j) and 0.75 µl of 10 µM template-A/G/T/C (6 pmol, 1.5 equiv) (SEQ ID NOS: 23 to 26, FIG. 11j) and 1 µl of 10 µM helper strand-T/C/A/G (10 pmol, 2 equiv) (SEQ ID NOS: 27 to 30, FIG. 11j) were added to the reaction mixture.
3. 3'-O-modified-dTTP/dCTP/dATP/dGTP (2 µl of 100 µM) and $MnCl_2$ (1 µl of 40 mM) were added.
4. 1.5 µl of Therminator IX DNA polymerase (15 U, New England BioLabs) was then added.
5. The reaction was incubated for 20 minutes at 65° C.
6. The reaction was stopped by addition of TBE-Urea sample buffer (Novex).
7. The reaction was separated on polyacrylamide gel (15%) TBE buffer and visualized by ChemiDoc MP imaging system (BioRad).

Gel Electrophoresis and DNA Visualization:
1. 5 µl of reaction mixture was added to 5 µl of TBE-Urea sample buffer (Novex) in a sterile 1.5 ml Eppendorf tube and heated to 95° C. for 5 minutes using a heat ThermoMixer (Eppendorf).
2. 5 µl of the sample were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. The gel was visualized by ChemiDoc MP (BioRad) using Cy3 LEDS. Visualization and analysis was carried out on the Image lab 2.0 platform.

Results and Conclusions

Regarding the evaluation of the temperature on the incorporation of 3-O-azidomethyl-dTTP using Therminator IX DNA polymerase, the results indicate that incorporation of 3'-O-azidomethyl-dTTP in the presence of a helper strand for ligation goes to 90% after 5 minutes. 10% of primer remains unextended after 20 minutes at 37° C. and 47° C.

Therminator IX DNA polymerase at 2 mM $Mn^{2+}$ ions and a temperature of 37° C. provide good conditions for incorporation of 3'-O-modified-dNTPs opposite a complementary base in DNA with high efficiency in the presence of the helper strand (from the ligation step from the previous cycle).

Step 2: Cleavage

The second step describes a one-step cleavage of polynucleotides with Endonuclease V (FIG. 12a).

Materials and Methods
Materials
1. Oligonucleotides utilized in Example 3 were designed in-house and synthesised by Sigma Aldrich (see table in FIG. 12d for sequences).
2. The oligonucleotides were diluted to a stock concentration of 100 uM using sterile distilled water (ELGA VEOLIA).

Methods

Cleavage reaction on oligonucleotides was carried out using the procedure below:
1. A pipette (Gilson) was used to transfer 41 µl sterile distilled water (ELGA VEOLIA) into a 1.5 ml Eppendorf tube.
2. 5 µl of 10× Reaction Buffer® NEB (50 mM Potassium Acetate, 20 mM Tris-acetate, 10 mM Magnesium Acetate, 1 mM DTT, pH 7.9 @ 25° C.) was then added into the same Eppendorf tube.
3. 1 µl each of oligonucleotides (FIG. 12d); Template (SEQ ID NO: 31) or any fluorescently tagged long oligo strand, Primer with T (SEQ ID NO: 32) and control (SEQ ID NO: 33) and helper strand (SEQ ID NO: 34), all at 5 pmols, were added into the same tube.
4. 1 µl of Human Endonuclease V (Endo V) NEB (10 units/µl) was added into the same tube.

5. Reaction mixture was then gently mixed by resuspension with a pipette, centrifuged at 13,000 rpm for 5 seconds and incubated at 37° C. for 1 hour.
6. Typically after incubation time had elapsed, reaction was terminated by enzymatic heat inactivation (i.e. 65° C. for 20 minutes).

The sample mixture was purified using the protocol outlined below:
1. 500 μl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 μl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.
6. For DNA elution, 50 μl of Buffer EB QIAGEN (10 mM Tris.CL, pH 8.5) was added to the centre of the column membrane and left to stand for 1 min at room temperature.
7. The tube was then centrifuged at 13000 rpm for 1 minutes. Eluted DNA concentration was measured and stored at −20° C. for subsequent use.

Measurement of purified DNA concentration was determined using the protocol below:
1. NanoDrop one (Thermo Scientific) was equilibrated by adding 2 μl of sterile distilled water (ELGA VEOLIA) onto the pedestal.
2. After equilibration, the water was gently wiped off using a lint-free lens cleaning tissue (Whatman).
3. NanoDrop one was blanked by adding 2 μl of Buffer EB QIAGEN (10 mM Tris.CL, pH 8.5). Then step 2 was repeated after blanking.
4. DNA concentration was measured by adding 2 μl of the sample onto the pedestal and selecting the measure icon on the touch screen.

Gel Electrophoresis and DNA Visualization:
1. 5 μl of DNA and TBE-Urea sample buffer (Novex) was added into a sterile 1.5 ml Eppendorf tube and heated to 95° C. for 2 minutes using a heat thermoblock (Eppendorf).
2. The DNA mixtures were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. Detection and visualization of DNA in the gel was carried out with Chemidoc MP (BioRad) using Cy3 LEDS. Visualization and analysis was carried out on the Image lab 2.0 platform.

Results and Conclusions

Cleavage results from Example 3 showed that a significantly high yield of cleaved DNA could be obtained with Endonuclease V in the presence or absence of the helper strand (FIG. 12c).

Step 3: Ligation

The third step describes ligation of polynucleotides with DNA ligase in the presence of a helper strand. A diagrammatic illustration is shown in FIG. 13a.

Materials and Methods

Materials
1. Oligonucleotides utilized in Example 3 were designed in-house and synthesised by Sigma Aldrich (see table in FIG. 13b for sequences).
2. The oligonucleotides were diluted to a stock concentration of 100 uM using sterile distilled water (ELGA VEOLIA).

Methods

Ligation reaction on oligonucleotides was carried out using the procedure below
1. A pipette (Gilson) was used to transfer 16 μl sterile distilled water (ELGA VEOLIA) into a 1.5 ml Eppendorf tube.
2. 10 μl of 2× Quick Ligation Reaction buffer NEB (132 mM Tris-HCl, 20 mM MgCl$_2$, 2 mM dithiothreitol, 2 mM ATP, 15% Polyethylene glycol (PEG6000) and pH 7.6 at 25° C.) was then added into the same Eppendorf tube.
3. 1 μl each of oligonucleotides (FIG. 13b); TAMRA or any fluorescently tagged phosphate strand (SEQ ID NO: 35), primer with T (SEQ ID NO: 36) and inosine strand (SEQ ID NO: 37) and helper strand (SEQ ID NO: 38) all having an amount of 5 pmols was added into the same tube.
4. 1 μl of Quick T4 DNA Ligase NEB (400 units/μ1) was added into the same tube.
5. Reaction mixture was then gently mixed by resuspension with a pipette, centrifuged at 13,000 rpm for 5 seconds and incubated at room temperature for 20 minutes.
6. Typically after the incubation time had elapsed, the reaction was terminated with the addition of TBE-Urea sample Buffer (Novex).
7. The reaction mixture was purified using the protocol outlined in purification steps 1-7 as described above.

Measurement of purified DNA concentration was determined using the protocol below:
1. NanoDrop one (Thermo Scientific) was equilibrated by adding 2 μl of sterile distilled water (ELGA VEOLIA) onto the pedestal.
2. After equilibration, the water was gently wiped off using a lint-free lens cleaning tissue (Whatman).
3. NanoDrop one was blanked by adding 2 μl of Buffer EB QIAGEN (10 mM Tris.CL, pH 8.5). Then step 2 was repeated after blanking.
4. DNA concentration was measured by adding 2 μl of the sample onto the pedestal and selecting the measure icon on the touch screen.
5. Purified DNA was run on a polyacrylamide gel and visualized in accordance with the procedure in steps 5-8 described above. No change in conditions or reagents was introduced.

Gel Electrophoresis and DNA Visualization:
1. 5 μl of DNA and TBE-Urea sample buffer (Novex) was added into a sterile 1.5 ml Eppendorf tube and heated to 95° C. for 2 minutes using a heat thermoblock (Eppendorf).
2. The DNA mixtures were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).

3. X-cell sure lock module (Novex) was fastened in place and electrophoresis performed at the following conditions; 260V, 90 Amps for 40 minutes at room temperature.
4. Detection and visualization of DNA in the gel was carried out with ChemiDoc MP (BioRad) using Cy3 LEDS. Visualization and analysis was carried out on the Image lab 2.0 platform.

Step 4: Deprotection

Deprotection step (FIG. 14a) was studied on DNA model bearing 3'-O-azidomethyl group that is introduced to DNA by incorporation of 3'-O-azidomethyl-dNTPs by Therminator IX DNA polymerase. Deprotection was carried out by tris(carboxyethyl)phosphine (TCEP) and monitored by extension reaction when mixture of all natural dNTPs is added to the solution of the purified deprotected DNA.

Materials and Methods

Materials

1. Oligonucleotides utilized in Example 3 were designed in-house and synthesised by Sigma Aldrich (see FIG. 14i for sequences).
2. The oligonucleotides were diluted to a stock concentration of 100 uM using sterile distilled water (ELGA VEOLIA).
3. Enzymes were purchased from New England BioLabs.

Methods 1. 2 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.25 µl of sterile deionized water (ELGA VEOLIA) in 1.5 ml Eppendorf tube.
2. 1 µl of 10 µM primer (10 pmol, 1 equiv) (SEQ ID NO: 39, FIG. 14i) and 1.5 µl of either 10 µM template-A/G/T/C (15 pmol, 1.5 equiv) (SEQ ID NOS: 40 to 43, FIG. 14i) were added to the reaction mixture.
3. 3'-O-modified-dTTP/dCTP/dATP/dGTP (2 µl of 100 µM) and $MnCl_2$ (1 µl of 40 mM) were added.
4. 1.5 µl of Therminator IX DNA polymerase (15 U, New England BioLabs) was then added.
5. The reaction was incubated for 5 minutes at 37° C.
6. 4 µL of the sample was taken out and mixed with 0.5 ul of 5 mM dNTP mix and allowed to react for 10 minutes for control reaction.
7. 40 µl of the 500 mM TCEP in 1M TRIS buffer pH 7.4 was added to the reaction mixture and allowed to react for 10 minutes at 37° C.
8. The reaction mixture was purified using QIAGEN Nucleotide removal kit eluting by 20 µL of 1× Thermopol® buffer.
9. 1 µL of 5 mM dNTP mix and 1 µL of DeepVent (exo-) DNA polymerase were added to the purified reaction mixture and allowed to react 10 minutes.
10. The reaction was stopped by addition of TBE-Urea sample buffer (Novex).
11. The reaction was separated on polyacrylamide gel (15%) TBE buffer and visualized by ChemiDoc MP imaging system (BioRad).

Results and Conclusion 50 mM TCEP was not sufficient to cleave 3'-O-azidomethyl group with high efficiency on 0.2 µM DNA model (FIG. 14h). In contrast, 300 mM TCEP successfully cleaved 3'-O-azidomethyl group with 95% efficiency on 0.2 µM DNA model (FIG. 14h).

Example 4. Version 2 Chemistry with Double Hairpin Model

This Example describes the synthesis of polynucleotides using 4 steps on a two-hairpin model: incorporation of 3'-O-modified dNTPs from a nick site; cleavage, ligation and deprotection with the first step taking place opposite a naturally complementary nucleotide which is positioned in the support strand adjacent to a universal nucleotide, in this particular case inosine.

Step 1: Incorporation

The first step describes controlled addition of 3'-O-protected single nucleotide to oligonucleotide by enzymatic incorporation by DNA polymerase (FIG. 15a).

Materials and Methods

Materials 1. 3'-O-modified dNTPs were synthesised in-house according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich (FIG. 15c). The stock solutions were prepared in concentration of 100 µM.
3. Therminator IX DNA polymerase was used that has been engineered by New England BioLabs with enhanced ability to incorporate 3-O-modified dNTPs.

3'-O-azidomethyl-dTTP was tested for incorporation:

3'-O-azidomethyl-dTTP:

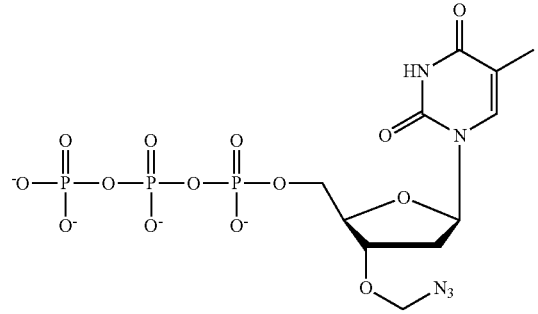 [SMILES: Cc1cn([C@H]2C[C@@H](OCN=[N+]=[N-])[C@@H](COP(=O)([O-])OP(=O)([O-])OP(=O)([O-])[O-])O2)c(=O)[nH]c1=O]

Method 1. 2 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 10.25 µl of sterile deionized water (ELGA VEOLIA) in 1.5 ml Eppendorf tube.
2. 0.5 µl of 10 µM hairpin oligonucleotide (5 pmol, 1 equiv) (SEQ ID NO: 44, FIG. 15c) was added to the reaction mixture.
3. 3'-O-modified-dTTP (2 µl of 100 µM) and $MnCl_2$ (1 µl of 40 mM) were added.
4. 1.5 µl of Therminator IX DNA polymerase (15 U, New England BioLabs) was then added.
5. The reaction was incubated for 20 minutes at 65° C.
6. The reaction was stopped by addition of TBE-Urea sample buffer (Novex).
7. The reaction was separated on polyacrylamide gel (15%) TBE buffer and visualized by ChemiDoc MP imaging system (BioRad).

Gel Electrophoresis and DNA Visualization:

1. 5 µl of reaction mixture was added to 5 µl of TBE-Urea sample buffer (Novex) in a sterile 1.5 ml Eppendorf tube and heated to 95° C. for 5 minutes using a heat ThermoMixer (Eppendorf).
2. 5 μl of the sample were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. The gel was visualized by ChemiDoc MP (BioRad) using Cy3 LEDS. Visualization and analysis was carried out on the Image lab 2.0 platform.

Results

DNA polymerases incorporate 3'-O-modified-dTTPs opposite its naturally complementary base in a hairpin construct.

Step 2: Cleavage

The second step describes a one-step cleavage of a hairpin model in this particular case with Endonuclease V (FIG. 16a).

Materials and Methods

Materials

1. Oligonucleotides utilized in Example 4 were designed in-house and synthesised by Sigma Aldrich (see FIG. 16c for sequences).
2. The oligonucleotides were diluted to a stock concentration of 100 uM using sterile distilled water (ELGA VEOLIA).

Methods

Cleavage reaction on hairpin oligonucleotides was carried out using the procedure below:
1. A pipette (Gilson) was used to transfer 430 sterile distilled water (ELGA VEOLIA) into a 1.5 ml Eppendorf tube.
2. 5 μl of 10× Reaction Buffer® NEB (50 mM potassium acetate, 20 mM Tris-acetate, 10 mM magnesium acetate, 1 mM DTT, pH 7.9 @ 25° C.) was then added into the same Eppendorf tube.
3. 1 μl of hairpin oligonucleotide (SEQ ID NO: 45, FIG. 16c) having an amount of 5 pmols was added into the same tube.
4. 1 μl of Human Endonuclease V (Endo V) NEB (30 units/μl) was added into the same tube.
5. The reaction mixture was then gently mixed by resuspension with a pipette, centrifuged at 13,000 rpm for 5 seconds and incubated at 37° C. for 1 hour.
6. Typically after incubation time had elapsed, the reaction was terminated by enzymatic heat inactivation (i.e. 65° C. for 20 minutes).

The sample mixture was purified using the protocol outlined below:
1. 500 μl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 μl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.
6. For DNA elution, 50 μl of Buffer EB QIAGEN (10 mM Tris.CL, pH 8.5) was added to the centre of the column membrane and left to stand for 1 min at room temperature.
7. The tube was then centrifuged at 13000 rpm for 1 minute. Eluted DNA concentration was measured and stored at −20° C. for subsequent use.

Measurement of purified DNA concentration was determined using the protocol below:
1. NanoDrop One (Thermo Scientific) was equilibrated by adding 2 μl of sterile distilled water (ELGA VEOLIA) onto the pedestal.
2. After equilibration, the water was gently wiped off using a lint-free lens cleaning tissue (Whatman).
3. NanoDrop One was blanked by adding 2 μl of Buffer EB QIAGEN (10 mM Tris.CL, pH 8.5). Then step 2 was repeated after blanking.
4. DNA concentration was measured by adding 2 μl of the sample onto the pedestal and selecting the measure icon on the touch screen.

Gel Electrophoresis and DNA Visualization:

1. 5 μl of DNA and TBE-Urea sample buffer (Novex) was added into a sterile 1.5 ml Eppendorf tube and heated to 95° C. for 2 minutes using a heat ThermoMixer (Eppendorf).
2. The DNA mixtures were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. Detection and visualization of DNA in the gel was carried out with ChemiDoc MP (BioRad) using Cy3 LEDS. Visualization and analysis was carried out on the Image lab 2.0 platform.

Results and Conclusion

Cleavage results from Example 4 showed that a significantly high yield of digested hairpin DNA was obtained with Endonuclease V at 37° C. (FIG. 16b).

Step 3: Ligation

The third step describes ligation of a hairpin model with DNA ligase. Diagrammatic illustration is shown in FIG. 17a.

Materials and Methods

Materials

1. Oligonucleotides utilized in Example 4 were designed in-house and synthesised by Sigma Aldrich (see FIG. 17c for sequences).
2 The oligonucleotides were diluted to a stock concentration of 100 uM using sterile distilled water (ELGA VEOLIA).

Method

Ligation reaction on oligonucleotides was carried out using the procedure below:
1. A pipette (Gilson) was used to transfer 1 μl (5 pmols) of TAMRA or any fluorescently tagged phosphate hairpin oligo (SEQ ID NO: 46) into a 1.5 ml Eppendorf tube.
2. 15 μl (100 pmols) of inosine-containing hairpin construct (SEQ ID NO: 47) was then added into the same tube and gently mixed by resuspension with a pipette for 3 seconds.
3. 40 μl of Blunt/TA DNA Ligase NEB (180 units/μl) was added into the same tube.

4. Reaction mixture was then gently mixed by resuspension with a pipette, centrifuged at 13,000 rpm for 5 seconds and incubated at room temperature for 20 minutes.
5. Typically after incubation time had elapsed, the reaction was terminated with the addition of TBE-Urea sample buffer (Novex).
6. The reaction mixture was purified using the protocol outlined in purification steps 1-7 above.

Measurement of purified DNA concentration was determined using the protocol below:
1. NanoDrop One (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop One was blanked by adding 2 µl of Buffer EB QIAGEN (10 mM Tris.CL, pH 8.5). Then step 2 was repeated after blanking.
4. DNA concentration was measured by adding 2 µl of the sample onto the pedestal and selecting the measure icon on the touch screen.
5. Purified DNA was run on a polyacrylamide gel and visualized in accordance with the procedure in steps 5-8 as described above. No change in conditions or reagents was introduced.

Gel Electrophoresis and DNA Visualization.
1. 5 µl of DNA and TBE-Urea sample buffer (Novex) was added into a sterile 1.5 ml Eppendorf tube and heated to 95° C. for 2 minutes using a heat ThermoMixer (Eppendorf).
2. The DNA mixtures were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. Detection and visualization of DNA in the gel was carried out with ChemiDoc MP (BioRad) using Cy3 LEDS. Visualization and analysis was carried out on the Image lab 2.0 platform.

Results

Ligation of hairpin oligonucleotides with blunt/TA DNA ligase at room temperature (24° C.) in the presence of a helper strand resulted high yield of ligated product. Ligated hairpin oligonucleotide after 1 minute showed a high yield of ligated DNA product with a ratio of ~85%. The ligated hairpin oligonucleotide after 2 minutes showed a high yield of ligated DNA with a ratio of ~85%. The ligated hairpin oligonucleotide after 3 minutes showed a high yield of ligated DNA product with a ratio of ~85%. The ligated hairpin oligonucleotide after 4 minutes showed a high yield of ligated DNA product with a ratio of ~>85% (FIG. 17b).

Example 5. Version 2 Chemistry—Complete Cycle on Double Hairpin Model

This Example describes the synthesis of polynucleotides using 4 steps on a double hairpin model: incorporation of 3'-O-modified dNTPs from the nick site; cleavage, ligation and deprotection with the first step taking place opposite a naturally complementary nucleotide which is positioned in the support strand adjacent to a universal nucleotide, in this particular case inosine. One end of the hairpin serves as an attachment anchor.

The method starts by controlled addition of a 3'-O-protected single nucleotide to an oligonucleotide by enzymatic incorporation by DNA polymerase followed by inosine cleavage, ligation and deprotection (FIG. 18a).

Materials and Methods

Materials
1. 3'-O-modified dNTPs were synthesised in-house according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich (FIG. 18c). The stock solutions are prepared in concentration of 100 µM.
3. Therminator IX DNA polymerase was used that has been engineered by New England BioLabs with enhanced ability to incorporate 3-O-modified dNTPs.

3'-O-azidomethyl-dTTP was tested for incorporation:
3'-O-azidomethyl-dTTP:

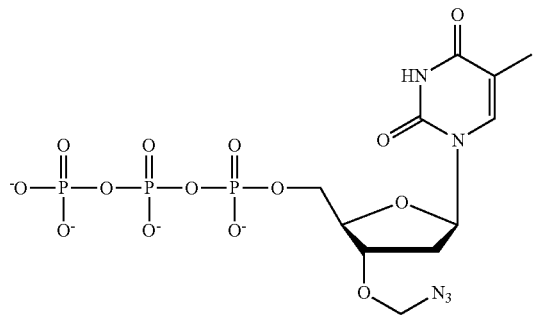 [SMILES: Cc1cn([C@H]2C[C@@H](OCN=[N+]=[N-])[C@@H](COP(=O)([O-])OP(=O)([O-])OP(=O)([O-])[O-])O2)c(=O)[nH]c1=O]

Method
1. 2 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.5 µl of sterile deionized water (ELGA VEOLIA) in 1.5 ml Eppendorf tube.
2. 2 µl of 10 µM double hairpin model oligonucleotide (20 pmol, 1 equiv) (SEQ ID NO: 48, FIG. 18c) were added to the reaction mixture.
3. 3'-O-modified-dTTP (2 µl of 100 µM) and $MnCl_2$ (1 µl of 40 mM) were added.
4. 1.5 µl of Therminator IX DNA polymerase (15 U, New England BioLabs) was then added.
5. The reaction was incubated for 10 minutes at 37° C.
6. The aliquot (5 µl) was taken out of the reaction mixture and 0.5 µl of natural dNTP mix was added and allowed to react for 10 minutes. The reaction was analysed by gel electrophoresis.
7. The reaction mixture was purified using the protocol outlined in purification steps 1-7.
8. The DNA sample was eluted by 20 µl of NEB reaction Buffer® (50 mM potassium acetate, 20 mM Tris-acetate, 10 mM magnesium acetate, 1 mM DTT, pH 7.9 @ 25° C.) into clean Eppendorf tube.

9. 1 µl of Human Endonuclease V (Endo V) NEB (30 units/µl) was added into the same tube.
10. Reaction mixture was then gently mixed by resuspension with a pipette, centrifuged at 13,000 rpm for 5 seconds and incubated at 37° C. for 1 hour.
11. After incubation time had elapsed, reaction was terminated by enzymatic heat inactivation (i.e. 65° C. for 20 minutes).
12. The aliquot (5 µl) was taken out of the reaction mixture and analysed on polyacrylamide gel (15%) using TBE buffer and visualized by ChemiDoc MP imaging system (BioRad).
13. Reaction mixture was purified using the protocol outlined in purification steps 1-7 above.
14. The DNA sample was eluted by 20 µl of NEB Reaction Buffer® (50 mM potassium acetate, 20 mM Tris-acetate, 10 mM magnesium acetate, 1 mM DTT, pH 7.9 @ 25° C.) into a clean Eppendorf tube.
15. 10 µl of 100 µM strand for ligation (1 nmol) (SEQ ID NO: 49, FIG. 18c) were added to the reaction mixture.
16. 40 µl of Blunt/TA DNA Ligase NEB (180 units/µl) was added into the purified DNA sample.
17. Reaction mixture was then gently mixed by resuspension with a pipette, centrifuged at 13,000 rpm for 5 seconds and incubated at room temperature for 20 minutes.
18. 40 µL of the 500 mM TCEP in 1M TRIS buffer pH 7.4 was added to the reaction mixture and allowed to react for 10 minutes at 37° C.
19. The reaction mixture was purified using QIAGEN nucleotide removal kit eluting by 20 µL of 1× Thermopol® buffer.

Gel Electrophoresis and DNA Visualization:

1. 5 µl of reaction mixture was added to 5 µl of TBE-Urea sample buffer (Novex) in a sterile 1.5 ml Eppendorf tube and heated to 95° C. for 5 minutes using a heat ThermoMixer (Eppendorf).
2. 5 µl of the sample were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 Amps for 40 minutes at room temperature.
4. The gel was visualized by ChemiDoc MP (BioRad) using Cy3 LEDS. Visualization and analysis was carried out on the Image lab 2.0 platform.

Measurement of purified DNA concentration was determined using the protocol below:

1. NanoDrop One (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop One was blanked by adding 2 µl of Buffer EB QIAGEN (10 mM Tris.CL, pH 8.5). Then step 2 was repeated after blanking.
4. DNA concentration was measured by adding 2 µl of the sample onto the pedestal and selecting the measure icon on the touch screen.
5. Purified DNA was run on a polyacrylamide gel and visualized in accordance with the procedure in section 2 steps 5-8. No change in conditions or reagents was introduced.

The sample mixture was purified after each step using the protocol outlined below:

1. 500 µl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 µl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.
6. For DNA elution, 20 µl of appropriate buffer for the reaction was added to the centre of the column membrane and left to stand for 1 min at room temperature.
7. The tube was then centrifuged at 13000 rpm for 1 minute. Eluted DNA concentration was measured and stored at −20° C. for subsequent use.

Results

DNA polymerase incorporates 3'-O-modified-dTTPs opposite its naturally complementary base in a double hairpin construct (FIG. 18b).

Example 6. Version 2 Chemistry—Complete Cycle on Single Hairpin Model Using Helper Strand This Example describes the synthesis of polynucleotides using 4 steps on single-hairpin model: incorporation of 3'-O-modified dNTPs from nick site; cleavage, ligation and deprotection with the first step taking place opposite a naturally complementary base. The DNA synthesis uses a helper strand in the process.

The method starts by controlled addition of a 3'-O-protected single nucleotide to an oligonucleotide by enzymatic incorporation by DNA polymerase followed by inosine cleavage, ligation and deprotection (FIG. 19a).

Materials and Methods

Materials 1. 3'-O-modified dNTPs were synthesised in-house according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma Aldrich (FIG. 19b). The stock solutions are prepared in concentration of 100 µM.

3. Terminator IX DNA polymerase was used that has been engineered by New England BioLabs with enhanced ability to incorporate 3-O-modified dNTPs. 3′-O-azidomethyl-dTTP was tested for incorporation:

3′-O-azidomethyl-dTTP:

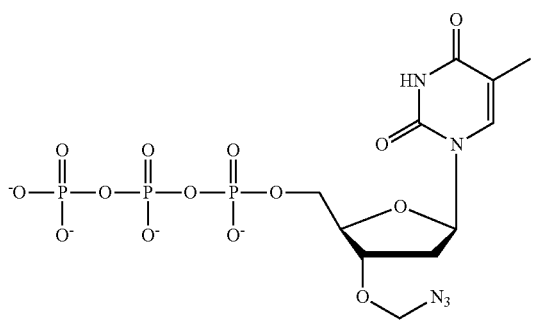

Method 1. 2 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.5 µl of sterile deionized water (ELGA VEOLIA) in 1.5 ml Eppendorf tube.
2. 2 µl of 10 µM Single hairpin model oligonucleotide (20 pmol, 1 equiv) (SEQ ID NO: 50, FIG. 19b) and Helper strand (30 pmol, 1.5 equiv) (SEQ ID NO: 51, FIG. 19b) were added to the reaction mixture.
3. 3′-O-modified-dTTP (2 µl of 100 µM) and $MnCl_2$ (1 µl of 40 mM) were added
4. 1.5 µl of Therminator IX DNA polymerase (15 U, New England BioLabs) was then added.
5. The reaction was incubated for 10 minutes at 37° C.
6. The aliquot (5 µl) was taken out of the reaction mixture and 0.5 µl of natural dNTP mix was added and allowed to react for 10 minutes. The reaction was analysed by gel electrophoresis.
7. The reaction mixture was purified using the protocol outlined in purification steps 1-7 above.
8. The DNA sample was eluted by 20 µl of NEB reaction Buffer® (50 mM potassium acetate, 20 mM Tris-acetate, 10 mM magnesium acetate, 1 mM DTT, pH 7.9 @ 25° C.) into a clean Eppendorf tube.
9. 1 µl of Human Endonuclease V (Endo V) NEB (30 units/µl) was added into the same tube.
10. Reaction mixture was then gently mixed by resuspension with a pipette, centrifuged at 13,000 rpm for 5 seconds and incubated at 37° C. for 1 hour.
11. After incubation time had elapsed, the reaction was terminated by enzymatic heat inactivation (i.e. 65° C. for 20 minutes).
12. The aliquot (5 µl) was taken out of the reaction mixture and analysed on polyacrylamide gel (15%) using TBE buffer and visualized by ChemiDoc MP imaging system (BioRad).
13. The reaction mixture was purified using the protocol outlined in purification steps 1-7 above.
14. The DNA sample was eluted by 20 µl of NEB reaction Buffer® (50 mM potassium acetate, 20 mM Tris-acetate, 10 mM magnesium acetate, 1 mM DTT, pH 7.9 @ 25° C.) into clean Eppendorf tube.
15. 10 µl of 100 µM strand for ligation (1 nmol) (SEQ ID NO: 52, FIG. 19b) and 10 µl of 100 µM helper strand for ligation (1 nmol) (SEQ ID NO: 53, FIG. 19b) were added to the reaction mixture.
16. 40 µl of Blunt/TA DNA Ligase NEB (180 units/µl) was added into the same tube.
17. Reaction mixture was then gently mixed by resuspension with a pipette, centrifuged at 13,000 rpm for 5 seconds and incubated at room temperature for 20 minutes.
18. 40 µL of the 500 mM TCEP in 1M TRIS buffer pH 7.4 was added to the reaction mixture and allowed to react for 10 minutes at 37° C.
19. The reaction mixture was purified using QIAGEN Nucleotide removal kit eluting by 20 µL of 1×NEB Thermopol® buffer.
20. Typically after incubation time had elapsed, reaction was terminated with the addition of TBE-Urea sample Buffer (Novex).

Gel Electrophoresis and DNA Visualization:

1. 5 µl of reaction mixture was added to 5 µl of TBE-Urea sample buffer (Novex) in a sterile 1.5 ml Eppendorf tube and heated to 95° C. for 5 minutes using a heat ThermoMixer (Eppendorf).
2. 5 µl of the sample were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 amps for 40 minutes at room temperature.
4. The gel was visualized by ChemiDoc MP (BioRad) using Cy3 LEDS. Visualization and analysis was carried out on the Image lab 2.0 platform.

Measurement of purified DNA concentration was determined using the protocol below:

1. NanoDrop One (Thermo Scientific) was equilibrated by adding 2 µl of sterile distilled water (ELGA VEOLIA) onto the pedestal.
2. After equilibration, the water was gently wiped off using a lint-free lens cleaning tissue (Whatman).
3. NanoDrop One was blanked by adding 2 µl of Buffer EB QIAGEN (10 mM Tris.CL, pH 8.5). Then step 2 was repeated after blanking.
4. DNA concentration was measured by adding 2 µl of the sample unto the pedestal and selecting the measure icon on the touch screen.
5. Purified DNA was run on a polyacrylamide gel and visualized in accordance with the procedure noted above in steps 5-8. No change in conditions or reagents was introduced.

The sample mixture was purified after each step using the protocol outlined below:

1. 500 µl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 µl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.

6. For DNA elution, 20 µl of appropriate buffer for the reaction was added to the centre of the column membrane and left to stand for 1 minute at room temperature.
7. The tube was then centrifuged at 13000 rpm for 1 minute. Eluted DNA concentration was measured and stored at −20° C. for subsequent use.

Example 7. Version 3 Chemistry—Complete Cycle on Double Hairpin Model

This Example describes the synthesis of polynucleotides using 4 steps on a double-hairpin construct model: incorporation of 3'-O-modified dNTPs from the nick site; cleavage, ligation and deprotection with the first step taking place opposite a universal nucleotide, in this particular case an inosine base.

The method starts by controlled addition of a 3'-O-protected single nucleotide to an oligonucleotide by enzymatic incorporation by DNA polymerase followed by inosine cleavage, ligation and deprotection (FIG. 20a).

Materials and Methods
Materials
1. 3'-O-modified dNTPs were synthesised in-housed according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich (FIG. 20b). The stock solutions are prepared in concentration of 100 µM.
3. Terminator IX DNA polymerase that has been engineered by New England BioLabs has enhanced ability to incorporate 3-O-modified dNTPs.

3'-O-azidomethyl-dTTP was tested for incorporation:

3'-O-azidomethyl-dTTP:

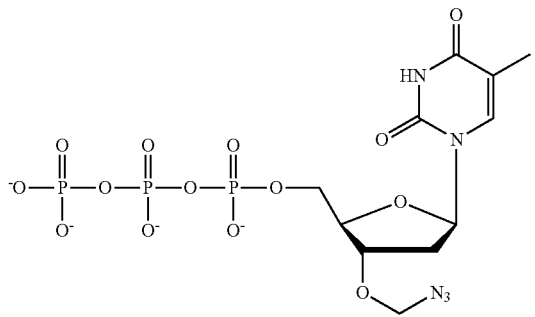

Method
1. 2 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.5 µl of sterile deionized water (ELGA VEOLIA) in 1.5 ml Eppendorf tube.
2. 2 µl of 10 µM double hairpin model oligonucleotide (20 pmol, 1 equiv) (SEQ ID NO: 54, FIG. 20b) were added to the reaction mixture.
3. 3'-O-modified-dTTP (2 µl of 100 µM) and $MnCl_2$ (1 µl of 40 mM) were added.
4. 1.5 µl of Terminator IX DNA polymerase (15 U, New England BioLabs) was then added.
5. The reaction was incubated for 10 minutes at 37° C.
6. The aliquot (5 µl) was taken out of the reaction mixture and 0.5 µl of natural dNTP mix was added and allowed to react for 10 minutes. The reaction was analysed by gel electrophoresis.
7. The reaction mixture was purified using the protocol outlined in purification steps 1-7.
8. The DNA sample was eluted by 20 µl of NEB Reaction Buffer® (50 mM potassium acetate, 20 mM Tris-acetate, 10 mM magnesium acetate, 1 mM DTT, pH 7.9 @ 25° C.) into clean Eppendorf tube.
9. 1 µl of Human Endonuclease V (Endo V) NEB (30 units/µl) was added into the same tube.
10. Reaction mixture was then gently mixed by resuspension with a pipette, centrifuged at 13,000 rpm for 5 seconds and incubated at 37° C. for 1 hour.
11. After the incubation time had elapsed, the reaction was terminated by enzymatic heat inactivation (i.e. 65° C. for 20 minutes).
12. The aliquot (5 µl) was taken out of the reaction mixture and analysed on polyacrylamide gel (15%) using TBE buffer and visualized by ChemiDoc MP imaging system (BioRad).
13. Reaction mixture was purified using the protocol outlined in purification steps 1-7 above.
14. The DNA sample was eluted by 20 µl of NEB Reaction Buffer® (50 mM potassium acetate, 20 mM Tris-acetate, 10 mM magnesium acetate, 1 mM DTT, pH 7.9 @ 25° C.) into a clean Eppendorf tube.
15. 10 µl of 100 µM strand for ligation (1 nmol) (SEQ ID NO: 55, FIG. 20b), were added to the reaction mixture.
16. 40 µl of Blunt/TA DNA Ligase NEB (180 units/µl) was added into the same tube.
17. Reaction mixture was then gently mixed by resuspension with a pipette, centrifuged at 13,000 rpm for 5 seconds and incubated at room temperature for 20 minutes.
18. 40 µL of the 500 mM TCEP in 1M TRIS buffer pH 7.4 was added to the reaction mixture and allowed to react for 10 minutes at 37° C.
19. The reaction mixture was purified using QIAGEN Nucleotide removal kit eluting by 20 µL of 1×NEB Thermopol® buffer.
20. Typically after incubation time had elapsed, reaction was terminated with the addition of TBE-Urea sample Buffer (Novex).

Gel Electrophoresis and DNA Visualization:
1. 5 µl of reaction mixture was added to 5 µl of TBE-Urea sample buffer (Novex) in a sterile 1.5 ml Eppendorf tube and heated to 95° C. for 5 minutes using a heat ThermoMixer (Eppendorf).
2. 5 µl of the sample were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and electrophoresis performed at the following conditions; 260V, 90 amps for 40 minutes at room temperature.
4. The gel was visualized by ChemiDoc MP (BioRad) using Cy3 LEDS. Visualization and analysis was carried out on the Image lab 2.0 platform.

Measurement of purified DNA concentration was determined using the protocol below:

1. NanoDrop One (Thermo Scientific) was equilibrated by adding 2 μl of sterile distilled water (ELGA VEOLIA) onto the pedestal.
2. After equilibration, the water was gently wiped off using a lint-free lens cleaning tissue (Whatman).
3. NanoDrop One was blanked by adding 2 μl of Buffer EB QIAGEN (10 mM Tris.CL, pH 8.5). Step 2 was then repeated after blanking.
4. DNA concentration was measured by adding 2 μl of the sample unto the pedestal and selecting the measure icon on the touch screen.
5. Purified DNA was run on a polyacrylamide gel and visualized in accordance with the procedure in section 2 steps 5-8. No change in conditions or reagents was introduced.

The sample mixture was purified after each step using the protocol outlined below:

1. 500 μl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 μl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.
6. For DNA elution, 20 μl of appropriate buffer for the reaction was added to the centre of the column membrane and left to stand for 1 min at room temperature.
7. The tube was then centrifuged at 13000 rpm for 1 minutes. Eluted DNA concentration was measured and stored at −20° C. for subsequent use.

Example 8. Version 2 Chemistry—Complete Two-Cycle Experiment on Double-Hairpin Model This example describes a complete two-cycle experiment for the synthesis of polynucleotides using 4 steps on a double-hairpin model: incorporation of 3'-O-modified dNTPs from the nick site; deprotection, cleavage, and ligation with the first step taking place opposite a complementary base.

The method starts by controlled addition of a 3'-O-protected single nucleotide to an oligonucleotide by enzymatic incorporation by DNA polymerase followed by deprotection, inosine cleavage and ligation, as depicted in the reaction schematic for the first cycle shown in FIG. 21a. FIG. 21b shows a reaction schematic for the second cycle.

Materials and Methods
Materials
1. 3'-O-modified dNTPs were synthesised in-house according to the protocol described in PhD thesis Jian Wu: Molecular Engineering of Novel Nucleotide Analogues for DNA Sequencing by Synthesis. Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Sigma-Aldrich (FIG. 21d). The stock solutions are prepared in concentration of 100 μM.
3. Therminator IX DNA polymerase that has been engineered by New England BioLabs has enhanced ability to incorporate 3'-O-modified dNTPs.

3'-O-azidomethyl-dTTP and 3'-O-azidomethyl-dCTP were used for incorporation:

3'-O-azidomethyl-dTTP:

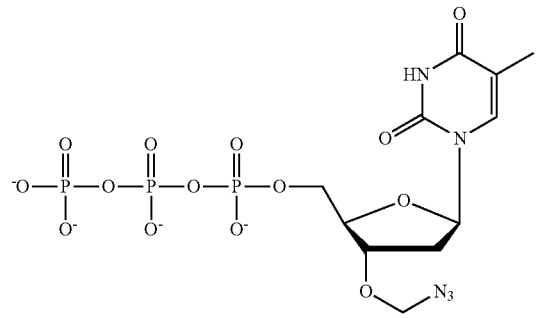

3'-O-azidomethyl-dCTP:

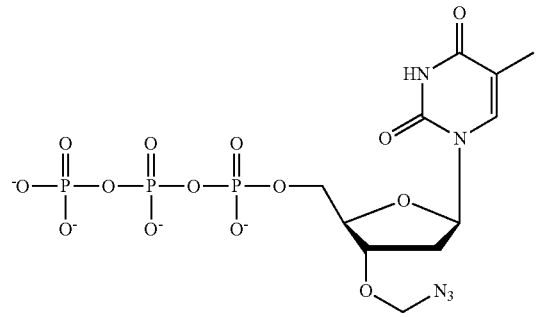 [SMILES: Cc1cn([C@H]2C[C@@H](OCN=[N+]=[N-])[C@@H](COP(=O)([O-])OP(=O)([O-])OP(=O)([O-])[O-])O2)c(=O)[nH]c1=O]

Method
1$^{st}$ Cycle:
1. 2 μl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) was mixed with 12.5 μl of sterile deionized water (ELGA VEOLIA) in 1.5 ml Eppendorf tube.
2. 2 μl of 10 μM double hairpin model oligonucleotide (20 pmol, 1 equiv) (SEQ ID NO: 56, FIG. 21d) were added to the reaction mixture.
3. 3'-O-modified-dTTP (2 μl of 100 μM) and $MnCl_2$ (1 μl of 40 mM) were added.
4. 1.5 μl of Therminator IX DNA polymerase (15 U, New England BioLabs) was then added.
5. The reaction was incubated for 10 minutes at 37° C.
6. The aliquot (5 μl) was taken out of the reaction mixture and 0.5 μl of natural dNTP mix was added and allowed to react for 10 min. The reaction was analysed by gel electrophoresis.
7. 40 μL of the 500 mM TCEP in 1M TRIS buffer pH=7.4 was added to the reaction mixture and allowed to react for 10 minutes at 37° C.
8. The reaction mixture was purified using the protocol outlined in purification steps 1-7.
9. The DNA sample was eluted by 20 μl of NEB Reaction Buffer® (50 mM potassium acetate, 20 mM Tris-acetate, 10 mM magnesium acetate, 1 mM DTT, pH 7.9 @ 25° C.) into a clean Eppendorf tube.

10. 1 μl of Human Endonuclease V (Endo V) NEB (30 units/μl) was added into the same tube.
11. Reaction mixture was then gently mixed by resuspension with a pipette, centrifuged at 13,000 rpm for 5 seconds and incubated at 37° C. for 1 hour.
12. After incubation time had elapsed, the reaction was terminated by enzymatic heat inactivation (i.e. 65° C. for 20 mins).
13. The aliquot (5 μl) was taken out of the reaction mixture and analysed on polyacrylamide gel (15%) using TBE buffer and visualized by ChemiDoc MP imaging system (BioRad).
14. Reaction mixture was purified by QIAGEN Nucleotide Removal kit using the protocol outlined in purification steps 1-7.
15. The DNA sample was eluted by 20 μl of NEB Reaction Buffer® (50 mM potassium acetate, 20 mM Tris-acetate, 10 mM magnesium acetate, 1 mM DTT, pH 7.9 @ 25° C.) into a clean Eppendorf tube.
16. 10 μl of 100 μM strand for ligation (1 nmol) (SEQ ID NO: 57, FIG. 21d), were added to the reaction mixture.
17. 40 μl of Blunt/TA DNA Ligase NEB (180 units/μl) was added into the same tube.
18. Reaction mixture was then gently mixed by resuspension with a pipette, centrifuged at 13,000 rpm for 5 seconds and incubated at room temperature for 20 mins.
19. Reaction mixture was purified by Streptavidin Magnetic Beads kit using the protocol outlined in purification steps 1-5.
20. Unligated oligonucleotide was digested by Lambda Exonuclease.
21. Reaction mixture was purified by QIAGEN Nucleotide Removal kit using the protocol outlined in purification steps 1-7.
22. The DNA sample was eluted by 20 μl of NEB Reaction Buffer® (50 mM potassium acetate, 20 mM Tris-acetate, 10 mM magnesium acetate, 1 mM DTT, pH 7.9 @ 25° C.) into a clean Eppendorf tube.

$2^{nd}$ Cycle:

23. 3'-O-modified-dCTP (2 μl of 100 μM) and $MnCl_2$ (1 μl of 40 mM) were added.
24. 1.5 μl of Therminator IX DNA polymerase (15 U, New England BioLabs) was then added.
25. The reaction was incubated for 10 minutes at 37° C.
26. The aliquot (5 μl) was taken out of the reaction mixture and 0.5 μl of natural dNTP mix was added and reacted for 10 min. The reaction was analysed by gel electrophoresis.
27. 40 μL of the 500 mM TCEP in 1M TRIS buffer pH=7.4 was added to the reaction mixture and reacted for 10 minutes at 37° C.
28. The reaction mixture was purified using the protocol outlined in purification steps 1-7.
29. The DNA sample was eluted by 20 μl of NEB Reaction Buffer® (50 mM potassium acetate, 20 mM Tris-acetate, 10 mM magnesium acetate, 1 mM DTT, pH 7.9 @ 25° C.) into a clean Eppendorf tube.
30. 1 μl of Human Endonuclease V (Endo V) NEB (30 units/μl) was added into the same tube.
31. The reaction mixture was then gently mixed by resuspension with a pipette, centrifuged at 13,000 rpm for 5 seconds and incubated at 37° C. for 1 hour.
32. After incubation time had elapsed, the reaction was terminated by enzymatic heat inactivation (i.e. 65° C. for 20 mins).
33. The aliquot (5 μl) was taken out of the reaction mixture and analysed on polyacrylamide gel (15%) using TBE buffer and visualized by ChemiDoc MP imaging system (BioRad).
34. The reaction mixture was purified using the protocol outlined in purification steps 1-7.
35. The DNA sample was eluted by 20 μl of NEB Reaction Buffer® (50 mM potassium acetate, 20 mM Tris-acetate, 10 mM magnesium acetate, 1 mM DTT, pH 7.9 @ 25° C.) into clean Eppendorf tube.
36. 10 μl of 100 μM strand for ligation (1 nmol) (SEQ ID NO: 58, FIG. 21d), were added to the reaction mixture.
37. 40 μl of Blunt/TA DNA Ligase NEB (180 units/μl) was added into the same tube.
38. Reaction mixture was then gently mixed by resuspension with a pipette, centrifuged at 13,000 rpm for 5 seconds and incubated at room temperature for 10 mins.
39. After incubation time had elapsed, the reaction was terminated with the addition of TBE-Urea sample Buffer (Novex).

Gel Electrophoresis and DNA Visualization:

1. 5 μl of reaction mixture was added to 5 μl of TBE-Urea sample buffer (Novex) in a sterile 1.5 ml Eppendorf tube and heated to 95° C. for 5 mins using a heat ThermoMixer (Eppendorf).
2. 5 μl of the sample were then loaded into the wells of a 15% TBE-Urea gel 1.0 mm×10 well (Invitrogen) which contained preheated 1×TBE buffer Thermo Scientific (89 mM Tris, 89 mM boric acid and 2 mM EDTA).
3. X-cell sure lock module (Novex) was fastened in place and subjected to electrophoresis by applying the following conditions; 260V, 90 amps for 40 mins at room temperature.
4. The gel was visualized by ChemiDoc MP (BioRad) using Cy3 LEDS. Visualization and analysis was carried out on the Image lab 2.0 platform.

Measurement of purified DNA concentration was determined using the protocol below:

1. NanoDrop One (Thermo Scientific) was equilibrated by adding 2 μl of sterile distilled water (ELGA VEOLIA) onto the pedestal.
2. After equilibration, the water was gently wiped off using a lint-free lens cleaning tissue (Whatman).
3. NanoDrop One was blanked by adding 2 μl of Buffer EB QIAGEN (10 mM Tris.CL, pH 8.5). Then step 2 was repeated after blanking.
4. DNA concentration was measured by adding 2 μl of the sample unto the pedestal and selecting the measure icon on the touch screen.

The sample mixture was purified by QIAGEN Nucleotide Removal kit using the protocol outlined below:

1. 500 μl of buffer PNI QIAGEN (5M guanidinium chloride) was added to the sample and mixed by gentle resuspension with a pipette.
2. The mixture was transferred into a QIAquick spin column (QIAGEN) and centrifuged for 1 min at 6000 rpm.
3. After centrifugation, flow-through was discarded and 750 μl of buffer PE QIAGEN (10 mM Tris-HCl pH 7.5 and 80% ethanol) was added into the spin column and centrifuged for 1 min at 6000 rpm.
4. The flow-through was discarded and the spin column was centrifuged for an additional 1 min at 13000 rpm to remove residual PE buffer.
5. The spin column was then placed in a sterile 1.5 ml Eppendorf tube.

6. For DNA elution, 20 µl of appropriate buffer for the reaction was added to the centre of the column membrane and left to stand for 1 min at room temperature.
7. The tube was then centrifuged at 13000 rpm for 1 min.

After the ligation step, the sample mixture was purified using Streptavidin Magnetic Beads via the protocol outlined below:

1. 100 µl of Streptavidin Magnetic Beads (New England BioLabs) were washed 3 times by 200 µl of binding buffer (20 mM TRIS, 500 mM NaCl, pH=7.4).
2. Reaction mixture after ligation step is mixed with 10 volumes of binding buffer (20 mM TRIS, 500 mM NaCl, pH=7.4) and incubated with Streptavidin Magnetic Beads for 15 minutes at 20° C.
3. Streptavidin Magnetic Beads were washed 3 times by 200 µl of binding buffer (20 mM TRIS, 500 mM NaCl, pH=7.4).
4. Streptavidin Magnetic Beads were washed 3 times by deionized water.
5. The oligonucleotides were eluted by 40 µl of deionized water by heating to 95° C. for 3 minutes.

The results shown in FIG. 21c demonstrate the performance two complete synthesis cycles using an exemplary method of the invention.

Example 9. Version 2 Chemistry—Complete Three-Cycle Experiment on Single-Hairpin Model This example describes a complete three-cycle experiment for the synthesis of polynucleotides using 5 steps on a double-hairpin model: incorporation of 3'-O-modified dNTPs from the nick site, deprotection, cleavage, ligation and denaturation step with the first step taking place opposite a complementary base.

Figure 26:
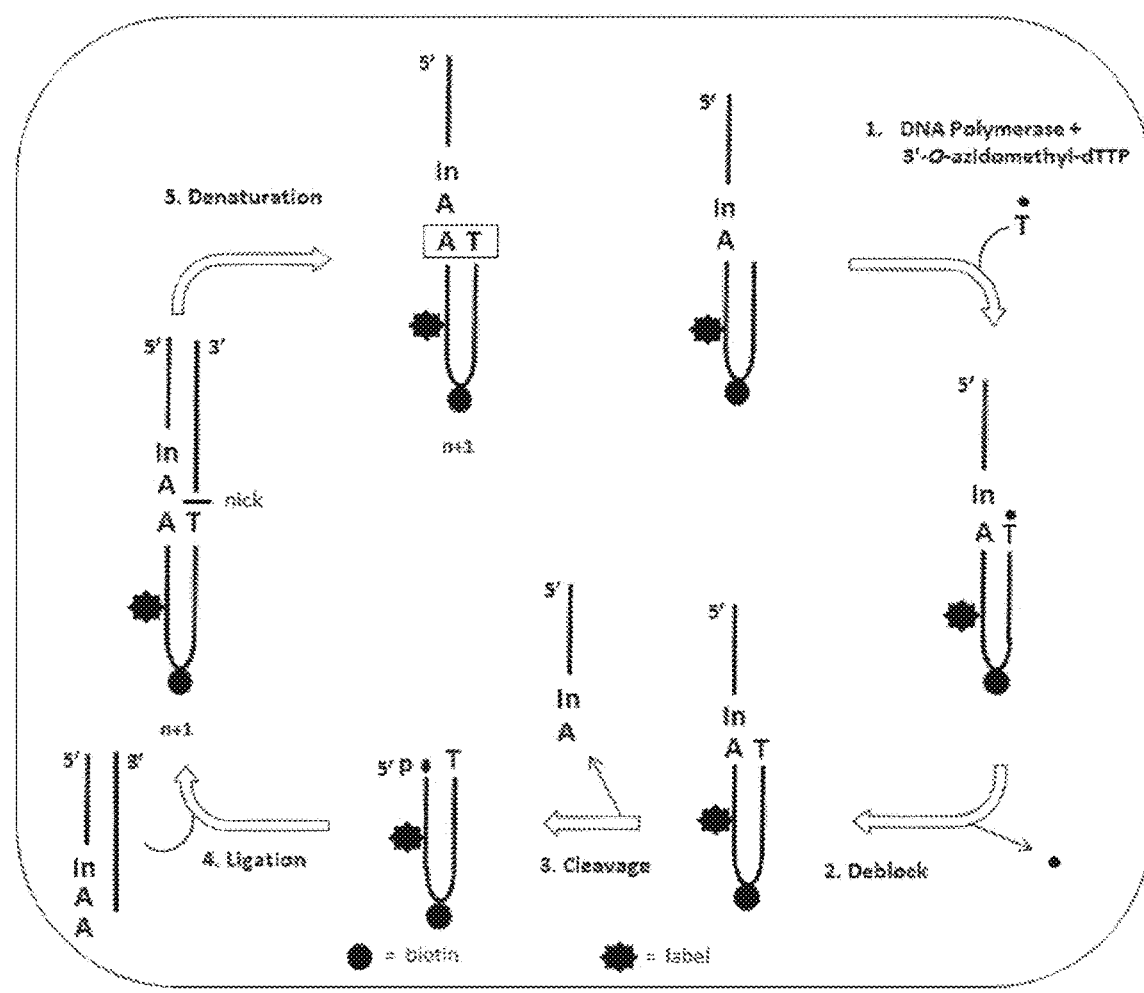
Figure 27:
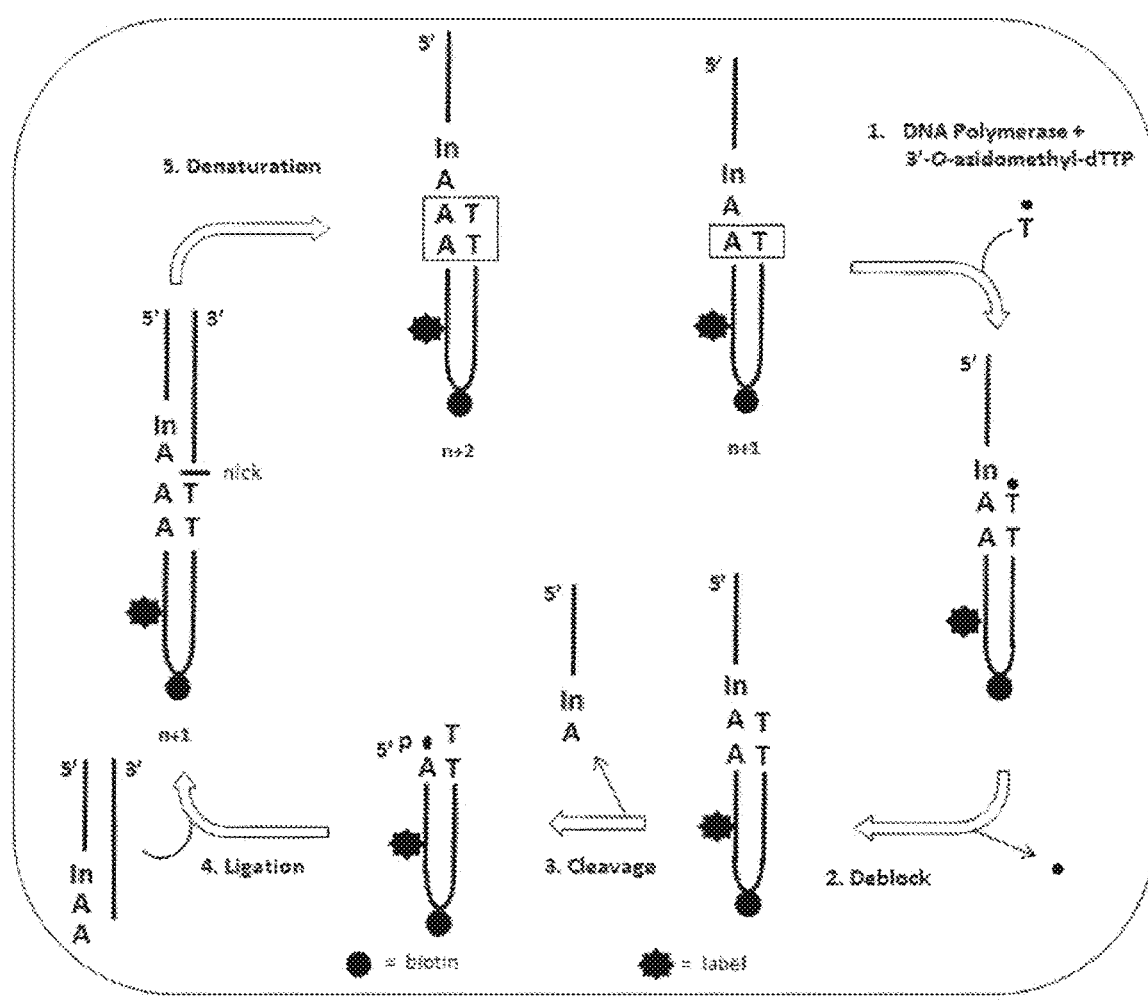
Figure 28:
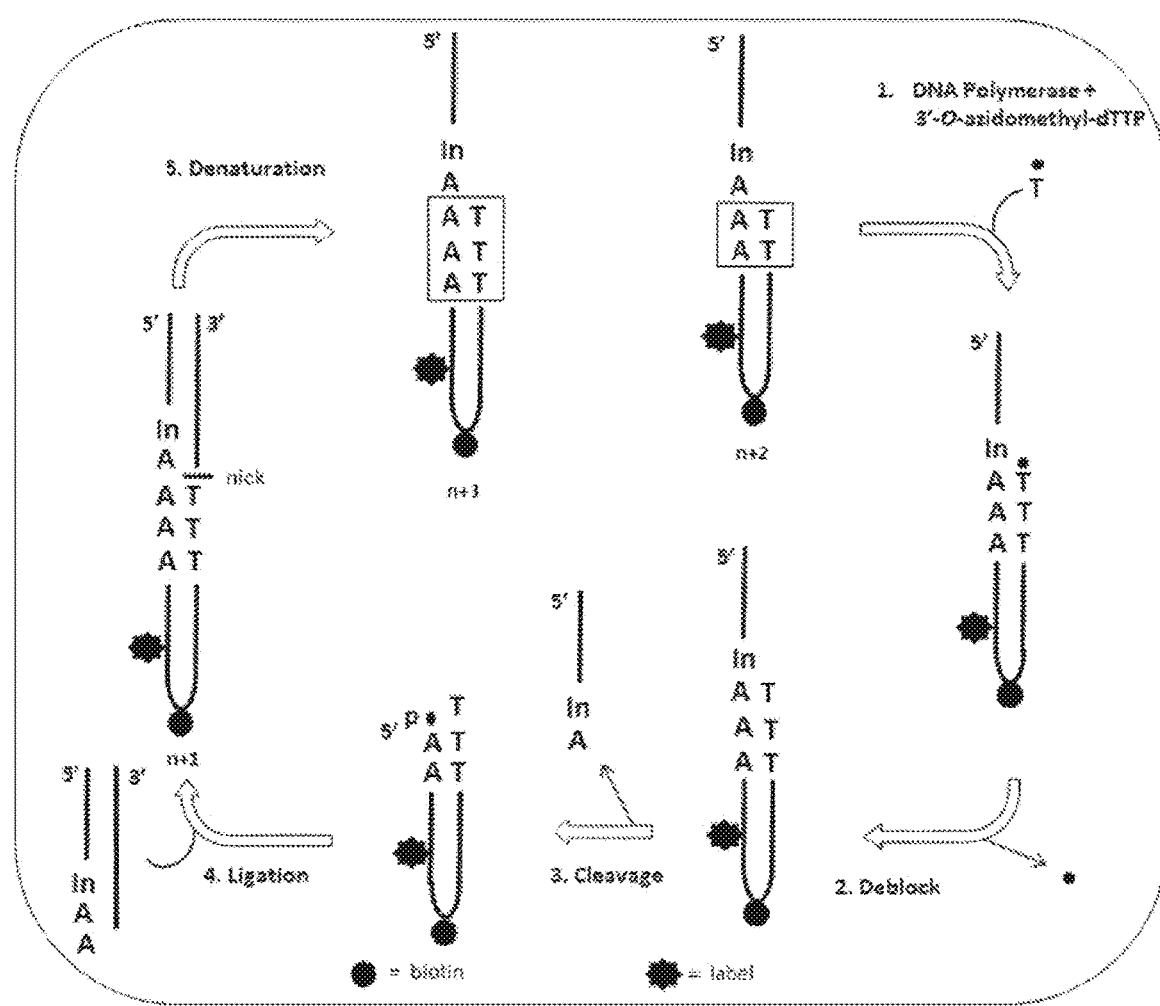

Exemplary schematic overviews of the method are shown in FIGS. 26, 27 and 28.

The method starts by the controlled addition of a 3'-O-protected single nucleotide to an oligonucleotide by enzymatic incorporation by DNA polymerase followed by deprotection, cleavage, ligation, and denaturation of the helper strand. FIG. 26 shows the 1st full cycle involving enzymatic incorporation, deprotection, cleavage, ligation and denaturation steps. In this example the oligonucleotide is extended by T nucleotide. FIG. 27 shows the 2nd full cycle following the 1st cycle involving enzymatic incorporation, deprotection, cleavage, ligation steps, and denaturation steps. In this example the oligonucleotide is extended by T nucleotide. FIG. 28 shows the 3rd full cycle following the 2nd cycle involving enzymatic incorporation, deprotection, cleavage, ligation, and denaturation steps. In this example the oligonucleotide is extended by T nucleotide.

Figures 29, 30:
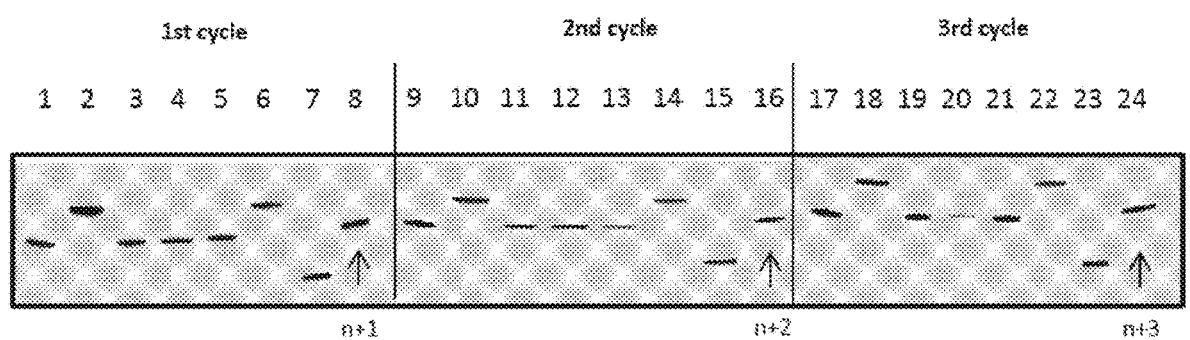

Materials and Methods
Materials
1. 3'-O-modified dNTPs were synthesised in-house according to the protocol described in PhD thesis Jian Wu: Molecular Engineering of Novel Nucleotide Analogues for DNA Sequencing by Synthesis, Columbia University, 2008. The protocol for synthesis is also described in the patent application publication: J. William Efcavitch, Juliesta E. Sylvester, Modified Template-Independent Enzymes for Polydeoxynucleotide Synthesis, Molecular Assemblies US2016/0108382A1.
2. Oligonucleotides were designed in house and obtained from Integrated DNA Technologies, Sigma-Aldrich (FIG. 29). The stock solutions are prepared in concentration of 100 µM.
3. Therminator X DNA polymerase was used that has been engineered by New England BioLabs with enhanced ability to incorporate 3-O-modified dNTPs. Any DNA polymerase or other enzyme that could incorporate modified dNTPs could alternatively be used.

3'-O-azidomethyl-dTTP was used for incorporation:

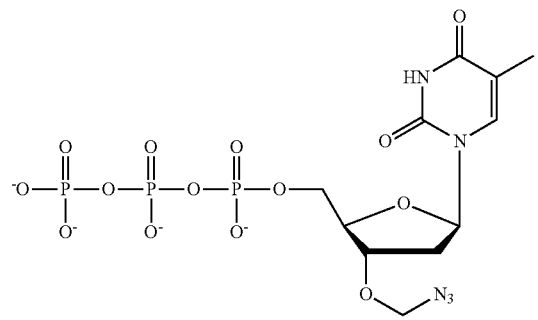

Method
1$^{st}$ Cycle:
1. 20 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs) and $MnCl_2$ solution (10 µl of 40 mM) were mixed with 139 µl of sterile deionized water (ELGA VEOLIA) in 1.5 ml Eppendorf tube.
2. 20 µl of 100 µM single hairpin model oligonucleotide (2 nmol, 1 equiv) (SEQ ID NO: 59, FIG. 29) was added to the reaction mixture.
3. The aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
4. 3'-O-modified-dTTP (10 µl of 2 mM) was added.
5. 5 µl of Therminator X DNA polymerase (50 U, New England BioLabs) was then added. However, any DNA polymerase or other enzyme that could incorporate modified dNTPs could be used.
6. The reaction was incubated for 30 minutes at 37° C.
7. The reaction mixture was purified using QIAGEN Nucleotide Removal kit outlined in purification steps 66-72.
8. The DNA sample was eluted by 200 µl of TE buffer into a clean Eppendorf tube.
9. The aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
10. 400 µL of the 500 mM TCEP was added to the reaction mixture and allowed to react for 10 minutes at 37° C.
11. The reaction mixture was purified using QIAGEN Nucleotide Removal kit outlined in purification steps 66-72.
12. The DNA sample was eluted by 150 µl of NEB Reaction Buffer® (50 mM potassium acetate, 20 mM Tris-acetate, 10 mM magnesium acetate, 1 mM DTT, pH 7.9 @ 25° C.) into clean Eppendorf tube.
13. The aliquot (4 µl) was taken out of the reaction mixture and 0.5 µl of natural dNTP mix (4 mM) and 0.5 µl of Bst DNA polymerase and 0.5 µl of *Sulfolobus*

DNA polymerase IV were added and allowed to react for 10 min. The reaction was analysed by gel electrophoresis.
14. 5 µl of Human Endonuclease V (Endo V) NEB (30 units/µl) was added to the eluate and incubated at 37° C. for 30 minutes. Any suitable alternative endonuclease could be used.
15. After incubation time had elapsed, the reaction was terminated by enzymatic heat inactivation at 65° C. for 20 mins.
16. An aliquot (5 µl) was taken out of the reaction mixture and analysed on a polyacrylamide gel.
17. The reaction mixture was purified by QIAGEN Nucleotide Removal kit using the protocol outlined in purification steps 66-72.
18. The DNA sample was eluted by 100 µl of T3 DNA ligase buffer (2× concentrate) into a clean Eppendorf tube.
19. 20 µl of 100 µM inosine strand for ligation (2 nmol) and 20 µl of 100 µM helper strand for ligation (2 nmol) (SEQ ID NO: 60, 51, FIG. 29), and 40 µl of water were added to the reaction mixture.
20. 20 µl of T3 DNA Ligase NEB (3000 units/µ1) was added into the same tube (this could include any DNA ligating enzyme) and incubated at room temperature for 30 mins.

The reaction mixture was purified using the protocol for Streptavidin Magnetic Beads kit including the denaturation step outlined in purification steps 73-78.

21. The reaction mixture was purified using the protocol for QIAGEN Nucleotide Removal kit outlined in purification steps 66-72.
22. The DNA sample was eluted by 100 µl of TE buffer into a clean Eppendorf tube.

$2^{nd}$ Cycle:

23. 15 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs), $MnCl_2$ solution (7.5 µl of 40 mM) and 19 µl of deionized water was added.
24. An aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
25. 3'-O-modified-dTTP (7.5 µl of 2 mM) was added.
26. 5 µl of Therminator X DNA polymerase (50 U, New England BioLabs) was then added. Any DNA polymerase that could incorporate modified dNTPs could be used.
27. The reaction was incubated for 30 minutes at 37° C.
28. The reaction mixture was purified using QIAGEN Nucleotide Removal kit outlined in purification steps 66-72.
29. The DNA sample was eluted by 100 µl of TE buffer into a clean Eppendorf tube.
30. An aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
31. 200 µL of the 500 mM TCEP was added to the reaction mixture and allowed to react for 10 minutes at 37° C.
32. The reaction mixture was purified using QIAGEN Nucleotide Removal kit outlined in purification steps 66-72.
33. The DNA sample was eluted by 100 µl of NEB Reaction Buffer® (50 mM potassium acetate, 20 mM Tris-acetate, 10 mM magnesium acetate, 1 mM DTT, pH 7.9 @ 25° C.) into a clean Eppendorf tube.
34. The aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
35. 5 µl of Human Endonuclease V (Endo V) NEB (30 units/µl) was added to the eluate. and incubated at 37° C. for 30 minutes. Any suitable alternative endonuclease could be used.
36. After incubation time had elapsed, the reaction was terminated by enzymatic heat inactivation at 65° C. for 20 mins.
37. The aliquot (5 µl) was taken out of the reaction mixture and analysed on a polyacrylamide gel.
38. The reaction mixture was purified by QIAGEN Nucleotide Removal kit using the protocol outlined in purification steps 66-72.
39. The DNA sample was eluted by 60 µl of T3 DNA ligase buffer (2× concentrate) into a clean Eppendorf tube.
40. 20 µl of 100 µM inosine strand for ligation (2 nmol) and 20 µl of 100 µM helper strand for ligation (2 nmol) (SEQ ID NO: 60, 51, FIG. 29), and 10 µl of deionized water were added to the reaction mixture.
41. 10 µl of T3 DNA Ligase NEB (3000 units/µ1) was added into the same tube and incubated at room temperature for 30 mins. Any suitable DNA ligase could be used.
42. The reaction mixture was purified using the protocol for Streptavidin Magnetic Beads kit including denaturation step outlined in purification steps 73-78.
43. The reaction mixture was purified using the protocol for QIAGEN Nucleotide Removal kit outlined in purification steps 66-72.
44. The DNA sample was eluted by 46 µl of TE buffer into a clean Eppendorf tube.

$3^{rd}$ Cycle:

45. 6 µl of 10× Thermopol® buffer (20 mM Tris-HCl, 10 mM $(NH_4)_2SO_4$, 10 mM KCl, 2 mM $MgSO_4$, 0.1% Triton® X-100, pH 8.8, New England BioLabs), $MnCl_2$ solution (3 µl of 40 mM) was added.
46. An aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
47. 3'-O-modified-dTTP (6 µl of 200 µM) was added.
48. 3 µl of Therminator X DNA polymerase (30 U, New England BioLabs) was then added. Any DNA polymerase or other suitable enzyme that could incorporate modified dNTPs could be used.
49. The reaction was incubated for 30 minutes at 37° C.
50. The reaction mixture was purified using QIAGEN Nucleotide Removal kit outlined in purification steps 66-72.
51. The DNA sample was eluted by 50 µl of TE buffer into a clean Eppendorf tube.
52. The aliquot (4 µl) was taken out of the reaction mixture and 0.5 µl of natural dNTP mix (4 mM) and 0.5 µl of Bst DNA polymerase and 0.5 µl of *Sulfolobus*

DNA polymerase IV were added and allowed to react for 10 min. The reaction was analysed by gel electrophoresis.

53. 100 µL of the 500 mM TCEP was added to the reaction mixture and allowed to react for 10 minutes at 37° C.
54. The reaction mixture was purified using QIAGEN Nucleotide Removal kit outlined in purification steps 66-72.
55. The DNA sample was eluted by 49 µl of NEB Reaction Buffer® (50 mM potassium acetate, 20 mM Tris-acetate, 10 mM magnesium acetate, 1 mM DTT, pH 7.9 @ 25° C.) into a clean Eppendorf tube.
56. An aliquot (4 µl) was taken out of the reaction mixture and 0.5 µl of natural dNTP mix (4 mM) and 0.5 µl of Bst DNA polymerase and 0.5 µl of *Sulfolobus* DNA polymerase IV were added and allowed to react for 10 min. The reaction was analysed by gel electrophoresis.
57. 5 µl of Human Endonuclease V (Endo V) NEB (30 units/µl) was added to the eluate and incubated at 37° C. for 30 minutes. Any suitable endonuclease could alternatively be used.
58. After incubation time had elapsed, the reaction was terminated by enzymatic heat inactivation at 65° C. for 20 mins.
59. The aliquot (5 µl) was taken out of the reaction mixture and analysed on a polyacrylamide gel.
60. The reaction mixture was purified by QIAGEN Nucleotide Removal kit using the protocol outlined in purification steps 66-72.
61. The DNA sample was eluted by 30 µl of T3 DNA ligase buffer (2× concentrate) into a clean Eppendorf tube.
62. 10 µl of 100 µM inosine strand for ligation (2 nmol), 10 µl of 100 µM helper strand for ligation (2 nmol) (SEQ ID NO: 60, 51, FIG. 29) and 5 µl of water were added to the reaction mixture.
63. 5 µl of T3 DNA Ligase NEB (3000 units/µl) was added into the same tube. (This could include any DNA ligating enzyme) and incubated at room temperature for 30 mins.
64. The reaction mixture was analysed by gel electrophoresis.

Purification of the reaction mixture by QIAGEN Nucleotide Removal kit after incorporation, deblock and cleavage steps using the protocol outlined below:
65. 10 volumes of buffer PNI QIAGEN (5M guanidinium chloride) was added to the sample and mixed by gentle resuspension with a pipette.
66. The mixture was transferred into a QIAquick spin column (QIAGEN) and centrifuged for 1 min at 6000 rpm.
67. After centrifugation, flow-through was discarded and 750 µl of buffer PE QIAGEN (10 mM Tris-HCl pH 7.5 and 80% ethanol) was added into the spin column and centrifuged for 1 min at 6000 rpm.
68. The flow-through was discarded and the spin column was centrifuged for an additional 1 min at 13000 rpm to remove residual PE buffer.
69. The spin column was then placed in a sterile 1.5 ml Eppendorf tube.
70. For DNA elution, 20-200 µl of appropriate buffer for the reaction was added to the centre of the column membrane and left to stand for 1 min at room temperature.
71. The tube was then centrifuged at 13000 rpm for 1 min.

Purification of the reaction after the ligation step using Streptavidin Magnetic Beads involving denaturation step was performed via the protocol outlined below:
72. 100 µl of Streptavidin Magnetic Beads (New England BioLabs) were washed 3 times by 200 µl of binding buffer (20 mM TRIS, 500 mM NaCl, pH=7.4).
73. Reaction mixture after ligation step is mixed with 10 volumes of binding buffer (20 mM TRIS, 500 mM NaCl, pH=7.4) and allowed to incubate with Streptavidin Magnetic Beads for 15 minutes at 20° C.
74. Streptavidin Magnetic Beads were washed 3 times by 200 µl of binding buffer (20 mM TRIS, 500 mM NaCl, pH=7.4).
75. To remove the helper strand, Streptavidin Magnetic Beads were heated to 80° C. in 200 µl of binding buffer (20 mM TRIS, 500 mM NaCl, pH=7.4), placed to magnet and supernatant was quickly discarded.
76. Streptavidin Magnetic Beads were washed 3 times with deionized water.
77. The oligonucleotides were eluted by 50-100 µl of deionized water by heating to 95° C. for 3 minutes.

Results and Conclusion

FIG. 30 depicts a gel showing reaction products corresponding to a full three-cycle experiment comprising: incorporation, deblock, cleavage and ligation steps. The results shown demonstrate the performance of three complete synthesis cycles using an exemplary method of the invention.

Example 10. Derivatization of a Polyacrylamide Surface and Subsequent Immobilisation of Molecules This example describes the presentation of bromoacetyl groups on a polyacrylamide surface using N-(5-bromoacetamidylpentyl) acrylamide (BRAPA) and the subsequent surface immobilisation of thiolated molecules by their covalent coupling to bromoacetyl groups.

Materials and Methods

Glass microscope slides and coverslips were cleaned by ultrasonication in acetone, ethanol and water sequentially for 10 mins each and dried with Argon. Clean glass coverslips were silanised with Trichloro(1H,1H,2H,2H-perfluorooctyl)silane in vapor phase in a polystyrene petri dish, sonicated twice in ethanol and dried with Ar ('fluorinated coverslips' hereafter). On glass microscope slides, 4% acrylamide/N,N'-Methylenebisacrylamide (19:1) solution was mixed with 100 µl of 10% (w/v) ammonium persulphate (APS), 10 µl of tetramethylethylenediamine (TEMED) spiked with N-(5-bromoacetamidylpentyl) acrylamide (BRAPA) at 0, 0.1, 0.2, and 0.3% (w/v) and quickly dispensed into a 4 mm diameter rubber gasket and subsequently sandwiched with a fluorinated coverslip with the fluorinated side facing towards the acrylamide solution and polymerised for 10 mins. After 10 mins, the surfaces were immersed in deionised water and left immersed for a total of 4 hrs, during which time the fluorinated coverslips were carefully removed. The polymerised polyacrylamide surfaces were dried with Argon.

The polyacrylamide surfaces were subsequently exposed to thiolated polyethylene glycol (1 kDa) fluorescein (FITC-PEG-SH), and carboxylated polyethylene glycol (1 kDa) fluorescein (FITC-PEG-COOH) as a negative control in sodium phosphate buffer (10 mM, pH 8) for 1 hr and subsequently washed sequentially with sodium phosphate buffer (10 mM, pH 7) and the same buffer containing 0.05% Tween20/0.5M NaCl to eliminate non-specifically adsorbed thiolated and carboxylated fluorophores. The surfaces were subsequently imaged by ChemiDoc (Bio-Rad) in the fluorescein channel.

Results and Conclusion

Figure 31:
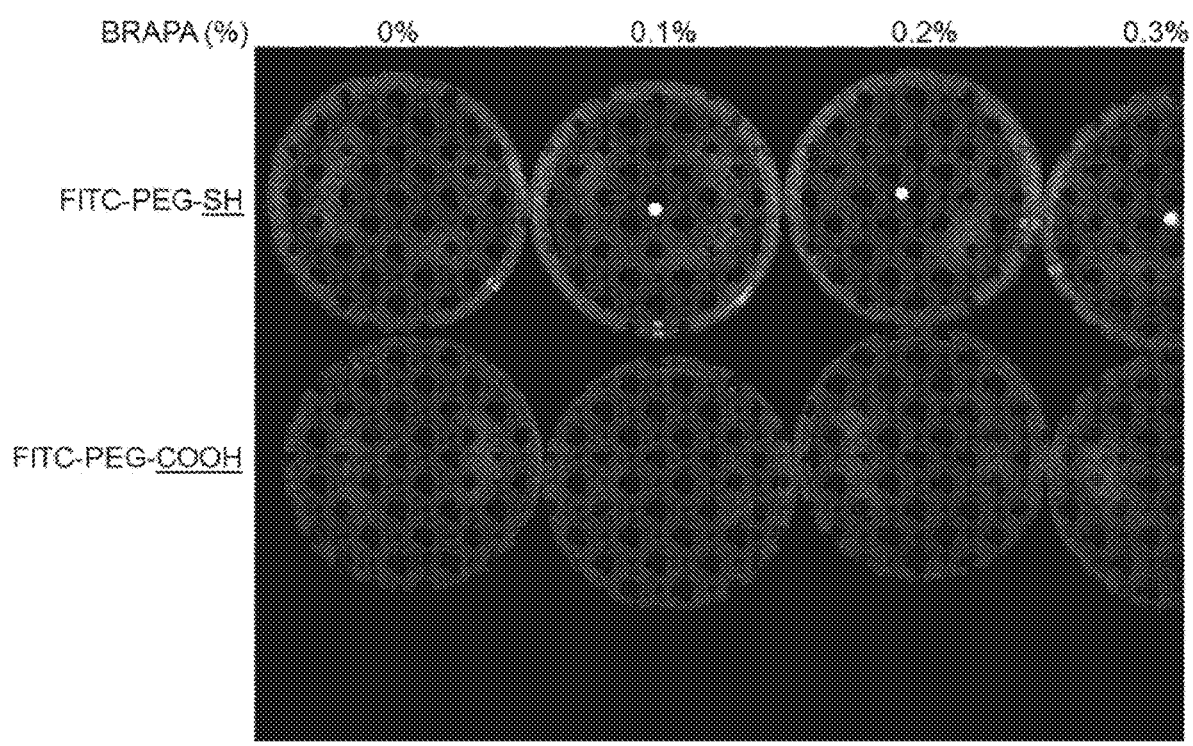
Figure 32:
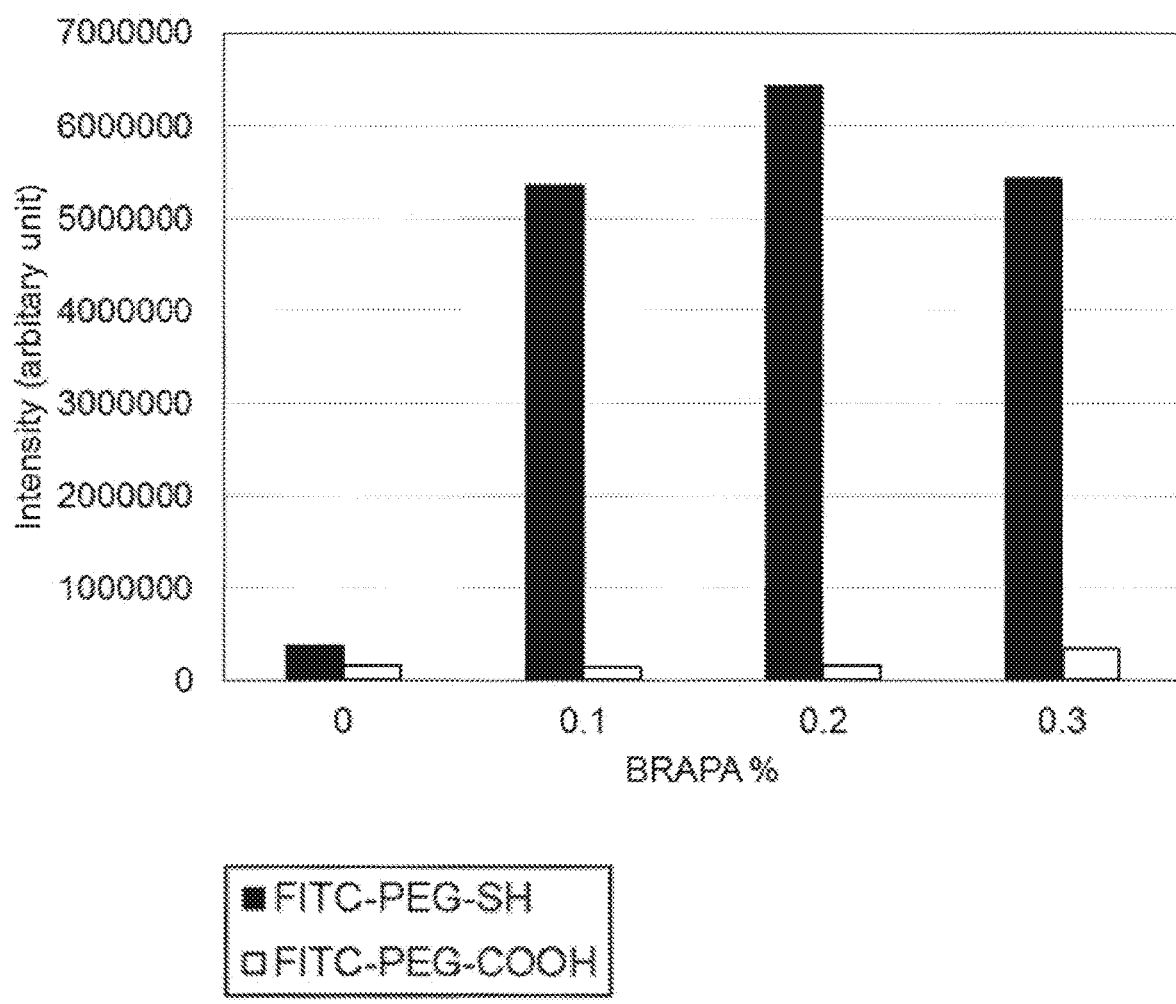

FIG. 31 shows fluorescence signals and FIG. 32 shown measured fluorescence from polyacrylamide gel surfaces spiked with different amount of BRAPA exposed to FITC-PEG-SH and FITC-PEG-COOH. Immobilisation of fluorescein was only successful with polyacrylamide surfaces that were spiked with BRAPA and solely with thiolated fluorescein, with close to zero non-specific adsorption of the carboxylated fluorescein.

Significantly high positive fluorescence signals were obtained from polyacrylamide surfaces containing BRAPA (BRAPA 0.1, 0.2 and 0.3%) and only from thiolated molecules (FITC-PEG-SH) compared to those polyacrylamide surfaces without BRAPA (BRAPA 0%) and those polyacrylamide surfaces containing BRAPA and carboxylated molecules (FITC-PEG-COOH). The results indicate that specific covalent coupling has occurred between the bromoacetyl moiety from the surface and the thiol moiety from the fluorescein tagged molecules.

The results demonstrate that molecules, such as a molecule comprising a support strand and a synthesis strand for use in the methods of the present invention, can readily be immobilised on a surface substrate compatible with the polynucleotide synthesis reactions described herein.

Example 11. Surface Immobilisation of Hairpin DNA Oligomers and Subsequent Incorporation of Fluorescently Labelled Deoxynucleoside Triphosphates This example describes:
(1) a method of presenting bromoacetyl groups on a thin polyacrylamide surface;
(2) the subsequent immobilisation of hairpin DNA via covalent coupling of thiophosphate functionalised hairpin DNA with or without a linker; and
(3) the incorporation of 2'-deoxynucleotide triphosphate (dNTP) into hairpin DNA.

The method is compatible with virtually any type of material surface (e.g. metals, polymers etc).

(1): Fabrication of a Bromoacetyl Functionalised Thin Polyacrylamide Surface

Materials and Methods

Glass microscope slides were first cleaned by ultrasonication in neat Decon 90 (30 mins), water (30 mins), 1M NaOH (15 mins), water (30 mins), 0.1M HCl (15 mins), water (30 mins) and finally dried with Argon.

2% (w/v) acrylamide monomer solution was first made by dissolving 1 g of acrylamide monomer in 50 ml of water. The acrylamide monomer solution was vortexed and degassed in argon for 15 mins. N-(5-bromoacetamidylpentyl) acrylamide (BRAPA, 82.5 mg) was dissolved in 825 µl of DMF and added to the acrylamide monomer solution and vortexed further. Finally, 1 ml of 5% (w/v) potassium persulphate (KPS) and 115 µl of neat tetramethylethylenediamine (TEMED) were added to the acrylamide solution, vortexed and the clean glass microscope slides were exposed to this acrylamide polymerisation mixture for 90 mins. After 90 mins, the surfaces were washed with deionised water and dried with argon. These surfaces will be referred to as 'BRAPA modified surfaces' in this example hereafter.

As a negative control, polyacrylamide surfaces without BRAPA was also made in a similar manner as described above by excluding the addition of BRAPA solution into the acrylamide monomer solution. These surfaces will be referred to as 'BRAPA control surface' in this example hereafter.

(2): Covalent Coupling of Thiophosphate Functionalised Hairpin DNA onto Polyacrylamide Surfaces Materials and Methods Rubber gaskets with a 4 mm diameter circular opening were placed and secured onto BRAPA modified and BRAPA control surfaces. The surfaces were first primed with sodium phosphate buffer (10 mM, pH 7) for 10 mins. The buffer was subsequently removed and the surfaces were exposed to 5'-fluorescently labelled (Alexa 647) hairpin DNA oligomers with and without a linker modified with six and single thiophosphates respectively at a 1 µM concentration and incubated for 1 hr in the dark. BRAPA modified surfaces were also incubated with DNA oligomers with and without linker but without thiophosphates as a control (referred to 'oligomer control surfaces' in this example hereafter). After incubation, the surfaces were rinsed in sodium phosphate (100 mM, pH 7) followed by Tris-EDTA buffer (10 mM Tris, 10 mM EDTA, pH 8) and finally with water. To remove any non-specifically adsorbed DNA oligomers, the surfaces were subsequently washed with water containing 1M sodium chloride and 0.05% (v/v) Tween20, washed with water and dried with argon. The surfaces were scanned on ChemiDoc imager in the Alexa 647 channel.

FIG. 33a shows the sequences of hairpin DNA without a linker immobilised on different samples. FIG. 33b shows the sequences of hairpin DNA with a linker immobilised on different samples.

Results

Figure 34:
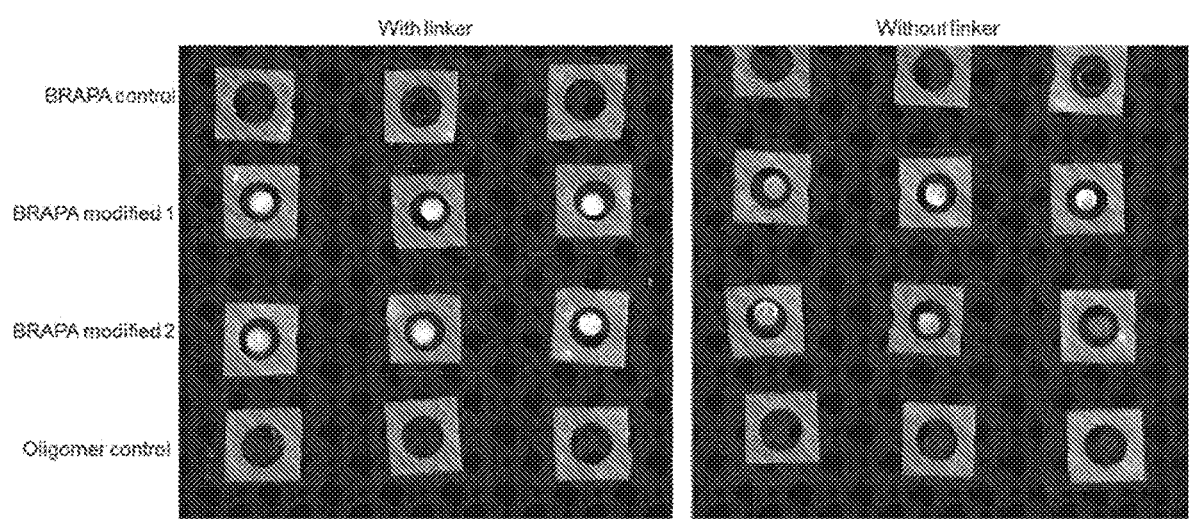
Figure 35:
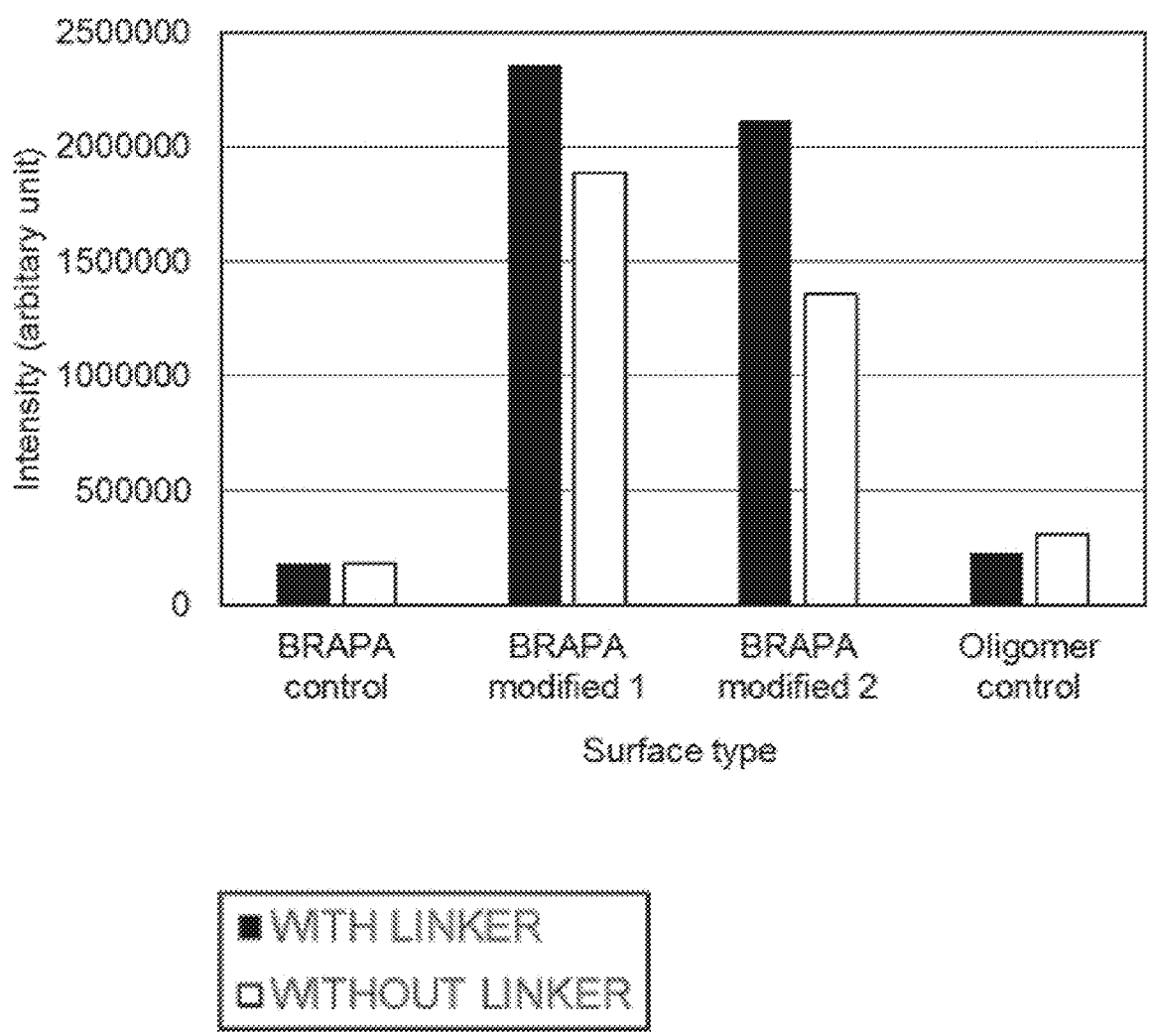

Results are shown in FIGS. 34 and 35. FIG. 34 shows fluorescence signals originating from hairpin DNA oligomers with and without a linker immobilised onto bromoacetyl functionalised polyacrylamide surfaces, but not from BRAPA or oligomer controls.

FIG. 35 shows measured fluorescence intensity following DNA immobilisation on polyacrylamide surface. The Figure shows the surface fluorescence signals obtained from various polyacrylamide surfaces and shows that significantly higher signals were obtained from hairpin DNA oligomers immobilised onto BRAPA modified surfaces compared to BRAPA and oligomer control surfaces (as described in (2)), due to successful covalent immobilisation of DNA onto bromoacetyl functionalised polyacrylamide surfaces.

Conclusion

Fluorescence signals from DNA were only prominently present from BRAPA modified surfaces that were spiked with BRAPA, indicative of successful covalent coupling of DNA onto the surface via the thiophosphate functionality. Homogenous and higher signals were obtained from DNA with the linker compared to DNA without the linker.

(3): Incorporation of Triphosphates into Hairpin DNA Oligomer with a Linker

Materials and Methods

Rubber gaskets with a 9 mm diameter circular opening were placed on the BRAPA modified surfaces immobilised with the DNA oligomer with the linker and primed with incorporation buffer (50 mM TRIS pH 8, 1 mM EDTA, 6 mM $MgSO_4$, 0.05% tween20 and 2 mM $MnCl_2$) for 10 mins. The surfaces were subsequently exposed to incorporation buffer containing DNA polymerase (0.5 U/µl Therminator X DNA polymerase) and triphosphates (20 µM Alexa 488 labelled dUTP) and incubated for 1 hr (referred to as 'polymerase surface' in this example hereafter). Additional set of surfaces were also exposed to incorporation buffer without Therminator X DNA polymerase for 1 hr as a negative control (referred to as 'negative surface' in this example hereafter). After 1 hr, both types of sample were washed in water, subsequently exposed to water containing 1M sodium chloride and 0.05% (v/v) Tween20, and washed again with water. Fluorescence signals from the surfaces were measured using ChemiDoc in the Alexa 647 and Alexa 488 channels to monitor both the presence of hairpin DNA (Alexa 647) and incorporation of dUTP (Alexa 488).

Results

Figure 36:
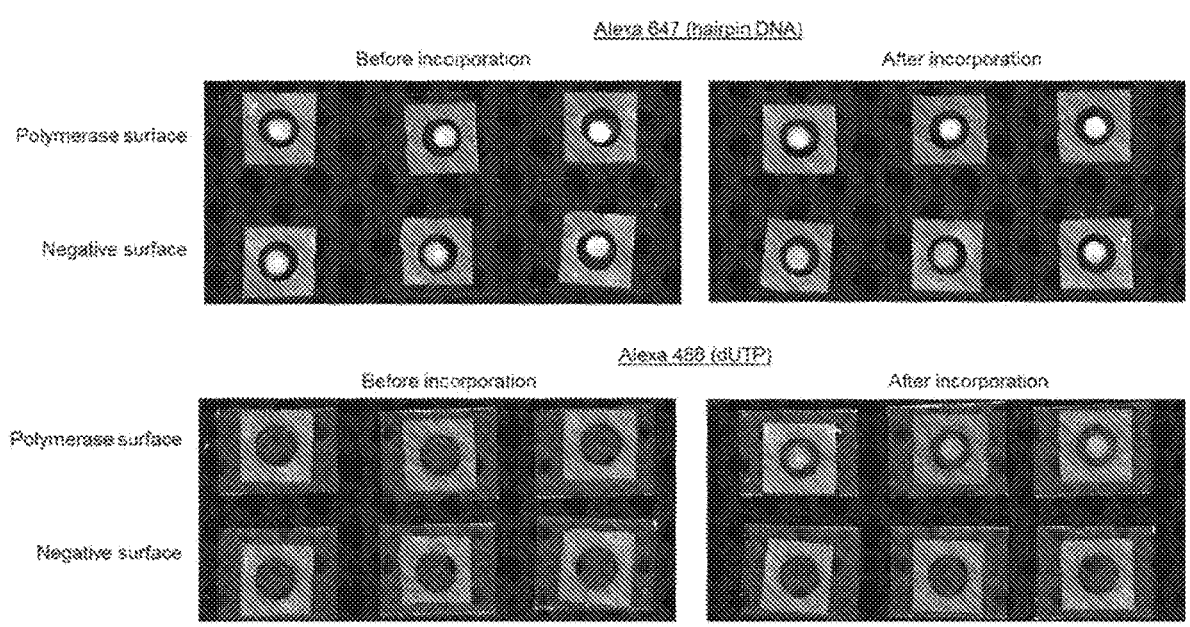

FIG. 36 shows fluorescence signals detected from Alexa 647 and Alexa 488 channels before and after incorporation of Alexa 488-labelled dUTP. Unchanged positive signals from Alexa 647 before and after incorporation indicates that the surface immobilised hairpin DNA is stable during the incorporation reaction, while positive signals from Alexa 488 were only observed from the polymerase surfaces after incorporation reaction showing the successful incorporation of dUTPs only with the presence of polymerase.

FIG. 37 shows measured fluorescence signals in the Alexa 647 (hairpin DNA) and Alexa 488 (dUTP) channels obtained from 'polymerase surfaces' and 'negative surfaces' before and after incorporation of Alexa 488-labelled dUTP as described in (3). A significant increase in the Alexa 488 fluorescence signals was obtained after the incorporation reaction from the polymerase surface as a result of the successful incorporation, while the signals from negative surfaces remained the same after the incorporation reaction due to the absence of polymerase. Fluorescence signals in the Alexa 647 channel remained virtually unchanged after the incorporation reaction, indicating the presence of hairpin DNA on the surface. The slight reduction in the fluorescence signal maybe attributed to the effect of photo-bleaching due to the second round of light exposure.

Conclusion

The results demonstrate that a molecule comprising a support strand and a synthesis strand for use in the methods of the present invention, can readily be immobilised on a surface substrate compatible with the polynucleotide synthesis reactions described herein. The results further demonstrate that such a molecule can accept the incorporation of a new dNTP so as to extend the synthesis strand, whilst at the same time the molecule remains stable and attached to the substrate.

Example 12. Cleavage and Ligation of Hairpin DNA Oligomers Immobilised to Derivatized Surfaces Via a Linker and Thiophosphate Covalent Linkage This example describes the covalent coupling to derivatized surfaces of thiophosphate functionalised hairpin DNA with a linker, followed by cleavage and ligation reactions. The substrate preparation and coupling of hairpin DNA was carried out as described in Example 11.

(1): Cleavage of Immobilised Hairpin DNA Oligomers with a Linker

Materials and Methods

Hairpin DNA was immobilised on surface BRAPA modified surfaces as described in Example 11. Four sets of triplicate surfaces including all the experimental controls for cleavage and ligation reactions were prepared. The experimental conditions are described in FIG. 38a. FIG. 38b shows the sequences of hairpin DNA immobilised on different samples.

After the DNA immobilisation step, rubber gaskets with a 9 mm diameter circular opening were placed on all surfaces that were immobilised with DNA labelled with Alexa 647 at the 5' end and primed with 1× NEBuffer 4 (50 mM Potassium Acetate, 20 mM Tris-acetate, 10 mM Magnesium Acetate, 1 mM DTT, pH 7.9) for 10 mins. Note that for sample D, the immobilised hairpin DNA does not contain inosine and inosine is replaced by guanine. All the samples were subsequently exposed to either NEBuffer 4 containing 1.5 U/µl Endonuclease V (sample A, B and D) or NEBuffer 4 without Endonuclease V (sample C) for 1 hr. All the samples were subsequently washed with 1× T3 DNA Ligase buffer (66 mM Tris-HCl, 10 mM MgCl$_2$, 1 mM ATP, 7.5% PEG6000, 1 mM DTT, pH 7.6), 1× T3 DNA Ligase buffer containing 1M sodium chloride and 0.05% (v/v) Tween20, washed again with 1× T3 DNA Ligase buffer and scanned on ChemiDoc Imager in the Alexa 647 channel.

Results

Figure 39:
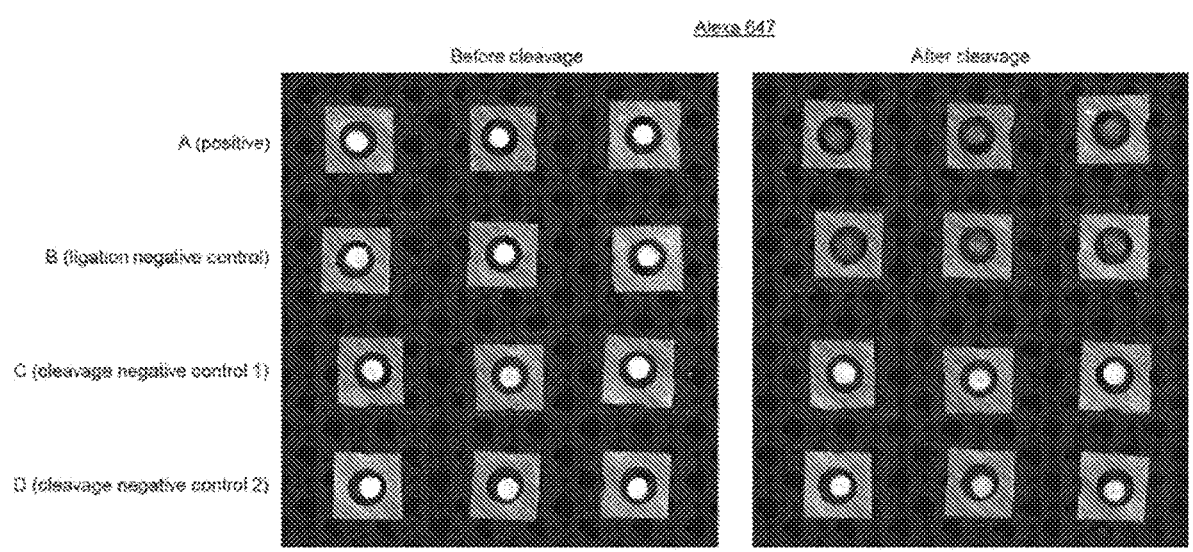

FIG. 39 shows fluorescence signals from hairpin DNA oligomers before and after cleavage reactions.

Figures 40, 41:
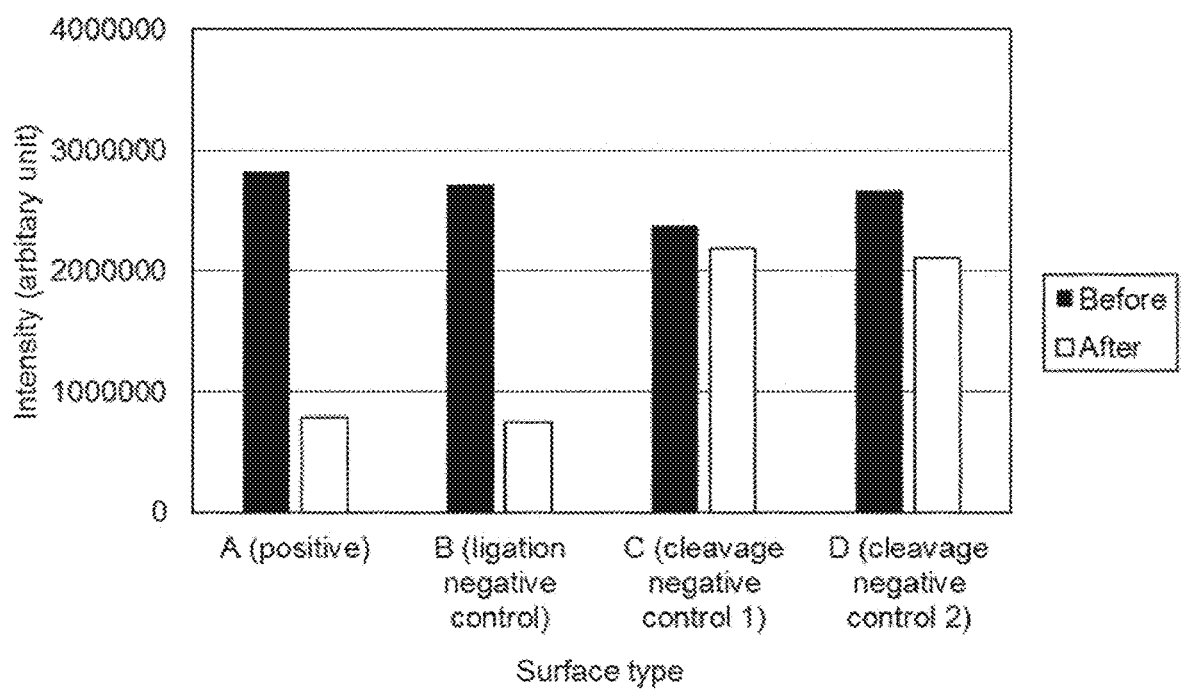

FIG. 40 shows measured fluorescence signals before and after cleavage reactions obtained from DNA immobilised surfaces as described above. Successful cleavage reactions were only observed from samples A and B, while fluorescence signal intensities remained almost the same for samples C and D due to absence of either Endonuclease V (sample C) or inosine in the sequence (sample D).

Significant reductions in the fluorescence signals were observed from samples A and B as a result of successful cleavage reactions at the inosine site within the DNA strand with the presence of Endonuclease V. For samples C and D, absence of Endonuclease V and lack of inosine in the DNA respectively resulted in the fluorescence signals to remain almost the same level as the initial signals obtained after DNA immobilisation.

(2): Ligation Reactions

Materials and Methods

After the cleavage reaction as described in (1), samples A and B (as described in FIG. 38a) were exposed to 1× T3 DNA Ligase buffer containing MnCl$_2$ (2 mM), inosine strands labelled with Alexa 647 at the 5' end (16 µM) and complimentary 'helper' strands (16 µM) (the sequences are shown in FIG. 41 below) with T3 DNA ligase (250 U/µl) for sample A, and without T3 DNA Ligase as a negative control for sample B. Samples were incubated in the respective solutions for 1 hr. After 1 hr, the surfaces were washed in water, subsequently exposed to water containing 1M sodium chloride and 0.05% (v/v) Tween20, and washed again with water. Fluorescence signals from the surfaces were measured using ChemiDoc in the Alexa 647 channels. FIG. 41 shows the sequences for the inosine-containing strand and the complimentary 'helper' strand for ligation reactions.

Results

Figure 42:
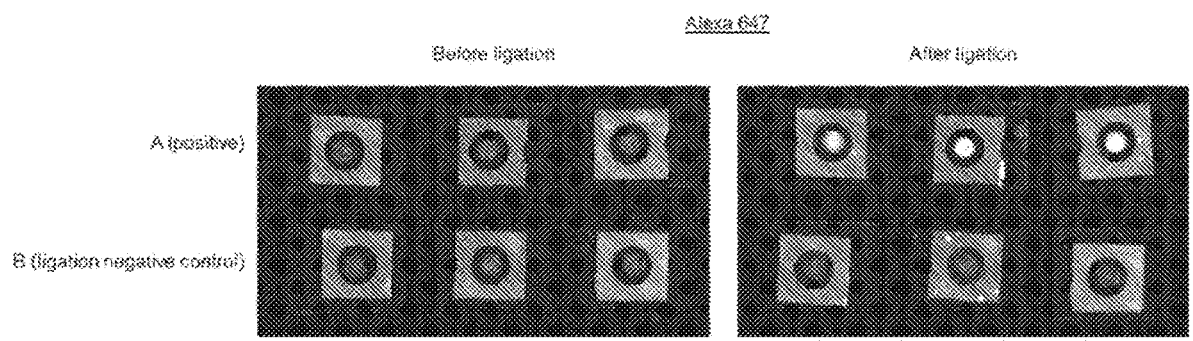

FIG. 42 shows results relating to the monitoring of ligation reactions. Fluorescence signals detected from Alexa 647 channel before and after ligation reactions. An increase in fluorescence signals in the Alexa 647 channels after ligation were only obtained from sample A with T3 DNA ligase, while fluorescence signals remained at the same level after ligation reaction for sample B due to the absence of T3 DNA ligase.

Figure 43:
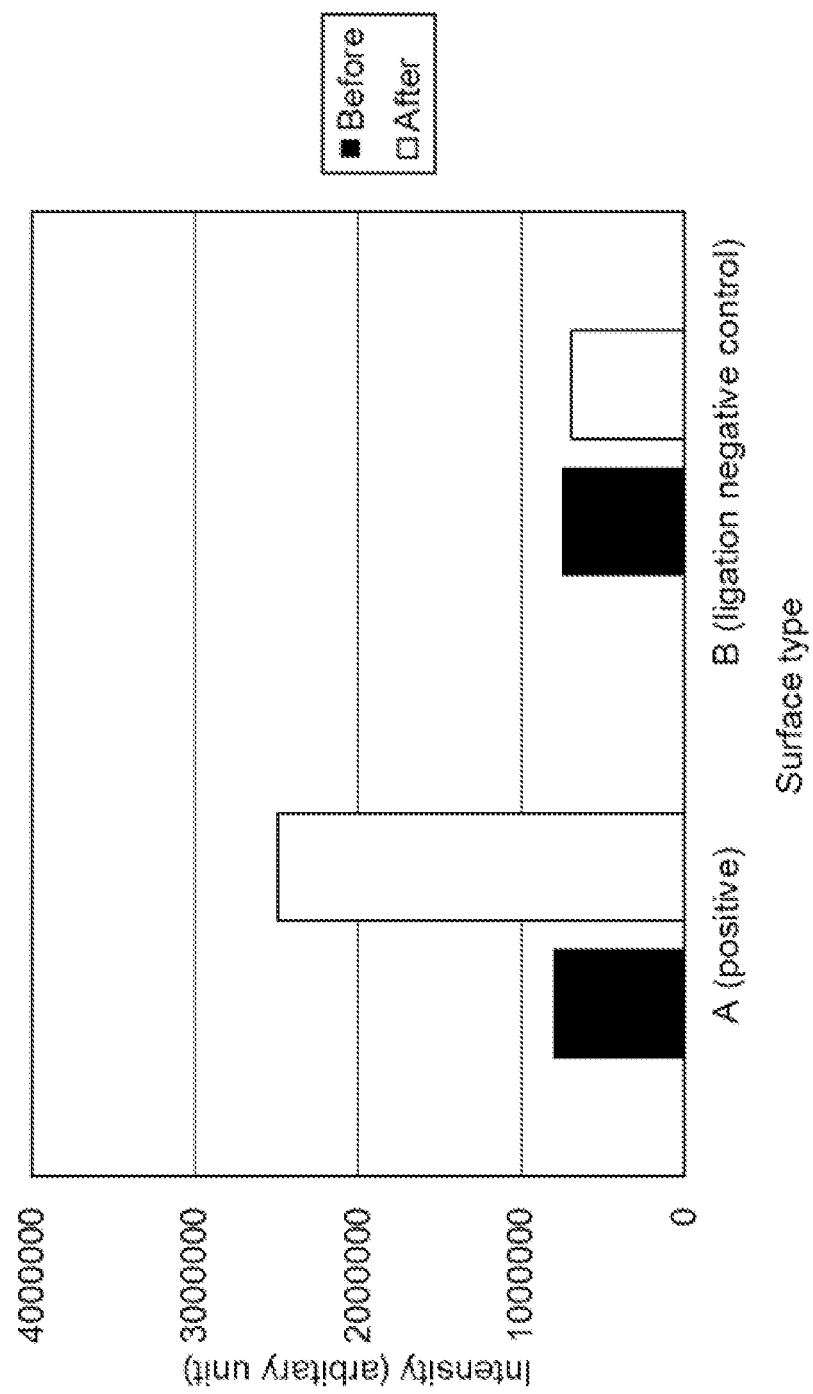

FIG. 43 shows that a significant increase in the Alexa 647 fluorescence signal was obtained after ligation reaction from sample A as a result of the successful ligation, where the signal level recovers to the initial signal level after DNA immobilisation and prior to cleavage reaction as shown in FIG. 40. The fluorescence signals from the sample B remained the same after the ligation reaction due to the absence of T3 DNA ligase.

Conclusion

The results in this Example demonstrate that a molecule comprising a support strand and a synthesis strand for use in the methods of the present invention, can readily be immobilised on a surface substrate compatible with the polynucleotide synthesis reactions described herein and can be subjected to cleavage and ligation reactions whilst at the same time remaining stable and attached to the substrate.

In the above Examples, all oligonucleotides presented in SEQ ID NOS 1-67 have a hydroxyl group at the 3' terminus. All oligonucleotides presented in SEQ ID NOS 1-67 lack a phosphate group at the 5' terminus except for SEQ ID NO 7, SEQ ID NO 18 and SEQ ID NO 35.

It is to be understood that different applications of the disclosed methods and products may be tailored to the specific needs in the art. It is also to be understood that the terminology used herein is for the purpose of describing particular embodiments of the invention only, and is not intended to be limiting.

As used in this specification and the appended claims, the singular forms "a", "an", and "the" include plural referents unless the content clearly dictates otherwise. Thus, for example, reference to "a ligation polynucleotide" includes two or more such polynucleotides, reference to "a scaffold polynucleotide" includes two or more such scaffold polynucleotides, and the like.

All publications, patents and patent applications cited herein are hereby incorporated by reference in their entirety.

The invention claimed is:

1. A method of assembling a polynucleotide having a predefined sequence, the method comprising synthesizing a first double-stranded polynucleotide having a predefined sequence and one or more additional double-stranded polynucleotides having a predefined sequence, cleaving the first double-stranded polynucleotide and the one or more additional double-stranded polynucleotides to create compatible termini, and joining together the first and one or more additional double-stranded polynucleotides by ligation;

wherein the first double-stranded polynucleotide and the one or more additional double-stranded polynucleotides are synthesized by an in vitro method comprising performing cycles of synthesis wherein in each cycle, a first strand is extended by incorporation of a nucleotide of the predefined sequence and the second strand which is hybridized to the first strand is extended by incorporation of a nucleotide thereby forming a nucleotide pair with the incorporated nucleotide of the first strand;

wherein each cycle comprises extending the first strand by incorporating the nucleotide of the predefined sequence together with an attached reversible terminator group followed by extending the second strand;

further wherein in each cycle the nucleotides are incorporated into a scaffold polynucleotide and wherein each cycle comprises:

(1) providing a scaffold polynucleotide;
(2) incorporating into the scaffold polynucleotide by action of a polymerase a nucleotide of the predefined sequence, the nucleotide comprising a reversible terminator group which prevents further extension by the polymerase;
(3) cleaving the scaffold polynucleotide at a cleavage site;
(4) ligating a ligation polynucleotide to the cleaved scaffold polynucleotide, the ligation polynucleotide comprising a partner nucleotide for the nucleotide of the predefined sequence, wherein upon ligation, the nucleotide of the predefined sequence pairs with the partner nucleotide; and
(5) removing the reversible terminator group from the nucleotide of the predefined sequence after step (4) or removing the reversible terminator group from the nucleotide of predefined sequence after step (2) and before step (3), or after step (3) and before step (4).

2. The method according to claim 1, wherein step (1) comprises providing a scaffold polynucleotide comprising a synthesis strand and a support strand hybridized thereto, wherein the synthesis strand comprises a primer strand portion, and the support strand comprises a universal nucleotide, wherein step (3) comprises cleaving the scaffold polynucleotide at a cleavage site, the site defined by a sequence comprising the universal nucleotide in the support strand, wherein cleavage comprises cleaving the support strand and removing the universal nucleotide; and wherein in step (4) the ligation polynucleotide comprises a support strand comprising a universal nucleotide which defines a cleavage site for use in the next cycle, and wherein the ligation polynucleotide is ligated to the support strand of the cleaved scaffold polynucleotide.

3. The method according to claim 2, the method comprising:

(1) providing a scaffold polynucleotide comprising a synthesis strand and a support strand hybridized thereto, wherein the synthesis strand comprises a primer strand portion and a helper strand portion separated by a single-strand break, and the support strand comprises a universal nucleotide;
(2) incorporating a first nucleotide of the predefined sequence into the synthesis strand by the action of the polymerase, the first nucleotide comprising a reversible terminator group which prevents further extension by the polymerase;
(3) cleaving the scaffold polynucleotide at a cleavage site, the site defined by a sequence comprising the universal nucleotide in the support strand, wherein cleavage comprises cleaving the support strand and removing the universal nucleotide to provide in the synthesis strand an overhanging end comprising the first nucleotide;
(4) ligating a double-stranded ligation polynucleotide to the cleaved scaffold polynucleotide, the ligation polynucleotide comprising a support strand, a helper strand and a complementary ligation end, the ligation end comprising in the support strand a universal nucleotide and a partner nucleotide for the first nucleotide which overhangs the helper strand, and in the helper strand a terminal nucleotide lacking a phosphate group, wherein upon ligation of the support strands the first nucleotide pairs with the partner nucleotide,
(5) removing the reversible terminator group from the first nucleotide after step (4) and before step (6), or after step (2) and before step (3), or after step (3) and before step (4);
(6) incorporating the next nucleotide of the predefined nucleotide sequence into the synthesis strand of the scaffold polynucleotide by the action of the polymerase, the next nucleotide comprising a reversible terminator group which prevents further extension by the polymerase;
(7) cleaving the scaffold polynucleotide at a cleavage site, the site defined by a sequence comprising a universal nucleotide in the support strand, wherein cleavage comprises cleaving the support strand and removing the universal nucleotide to provide in the synthesis strand an overhanging end comprising the next nucleotide;
(8) ligating a double-stranded ligation polynucleotide to the cleaved scaffold polynucleotide, the ligation polynucleotide comprising a support strand, a helper strand and a complementary ligation end, the ligation end comprising in the support strand a universal nucleotide and a partner nucleotide for the next nucleotide which overhangs the helper strand, and in the helper strand a terminal nucleotide lacking a phosphate group, wherein upon ligation of the support strands the next nucleotide pairs with the partner nucleotide;

(9) removing the reversible terminator group from the next nucleotide after step (8) and before step (10), or after step (6) and before step (7), or after step (7) and before step (8); and

(10) repeating steps £6 to M multiple times to provide the double-stranded polynucleotide having a predefined nucleotide sequence.

4. The method according to claim 3, wherein in a given synthesis cycle the universal nucleotide occupies position n in:

(a) the support strand of the scaffold polynucleotide in steps (1) and (6), wherein position n is the nucleotide position in the support strand which is opposite the position in the synthesis strand which will be occupied by the nucleotide of the predefined sequence upon its incorporation in that cycle, and (b) the support strand of the ligation polynucleotide in steps (4) and (8), wherein position n is the nucleotide position in the support strand which is opposite the position in the synthesis strand which will be occupied by the next nucleotide of the predefined sequence upon its incorporation in the next synthesis cycle, wherein position n−1 is the next nucleotide position in the support strand relative to the position occupied by the universal nucleotide in the direction distal to the helper strand and proximal to the primer strand; and wherein the support strand of the scaffold polynucleotide is cleaved between positions n and n−1 in steps (3) and (7).

5. The method according to claim 3, wherein in a given synthesis cycle the universal nucleotide occupies position n+1 in:

(a) the support strand of the scaffold polynucleotide in steps (1) and (6), wherein position n is the nucleotide position in the support strand which is opposite the position in the synthesis strand which will be occupied by the nucleotide of the predefined sequence upon its incorporation in that cycle, and (b) the support strand of the ligation polynucleotide in steps (4) and (8) wherein position n is the nucleotide position in the support strand which is opposite the position in the synthesis strand which will be occupied by the next nucleotide of the predefined sequence upon its incorporation in the next synthesis cycle, wherein position n−1 is the next nucleotide position in the support strand relative to position n in the direction distal to the helper strand and proximal to the primer strand, and wherein position n+1 is the next nucleotide position in the support strand relative to position n in the direction proximal to the helper strand and distal to the primer strand; and wherein the support strand of the scaffold polynucleotide is cleaved between positions n and n−1 in steps (3) and (7).

6. The method according to claim 3, wherein in a given synthesis cycle the universal nucleotide occupies position n in:

(a) the support strand of the scaffold polynucleotide in steps (1) and (6), wherein position n is the nucleotide position in the support strand which is opposite the position in the synthesis strand which will be occupied by the nucleotide of the predefined sequence upon its incorporation in that cycle, and (b) the support strand of the ligation polynucleotide in steps (4) and (8) wherein position n is the nucleotide position in the support strand which is opposite the position in the synthesis strand which will be occupied by the next nucleotide of the predefined sequence upon its incorporation in the next synthesis cycle, wherein position n−1 is the next nucleotide position in the support strand relative to the position occupied by the universal nucleotide in the direction distal to the helper strand and proximal to the primer strand, and wherein position n−2 is the next nucleotide position in the support strand relative to position n−1 in the direction distal to the helper strand and proximal to the primer strand; and wherein the support strand of the scaffold polynucleotide is cleaved between positions n−1 and n−2 in steps (3) and (7).

7. The method according to claim 3, wherein:

a) in steps (1) and (6) the universal nucleotide in the support strand is positioned opposite the terminal nucleotide of the helper strand adjacent the single-strand break and is paired therewith (position n);

b) in step (2) the first nucleotide is incorporated into the synthesis strand at a position opposite the universal nucleotide in the support strand (position n), whereupon the first nucleotide pairs with the universal nucleotide and in step (6) the next nucleotide is incorporated into the synthesis strand at a position opposite the universal nucleotide in the support strand (position n), whereupon the next nucleotide pairs with the universal nucleotide;

c) in step (3) the support strand is cleaved at a position between the universal nucleotide position (position n) and the nucleotide next to the universal nucleotide position in the support strand (position n−1, in the direction distal to the helper strand and proximal to the primer strand), wherein cleavage generates a single-nucleotide overhang in the scaffold polynucleotide comprising the first nucleotide overhanging the support strand and in step (7) the support strand is cleaved at a position between the universal nucleotide position (position n) and the nucleotide next to the universal nucleotide position in the support strand (position n−1, in the direction distal to the helper strand and proximal to the primer strand), wherein cleavage generates a single-nucleotide overhang in the scaffold polynucleotide comprising the next nucleotide overhanging the support strand; and d) in steps (4) and (8), the ligation end of the ligation polynucleotide comprises a single-nucleotide overhang and wherein:

i. the universal nucleotide in the support strand is positioned (position n) opposite the terminal nucleotide of the helper strand and is paired therewith;

ii. the universal nucleotide is positioned next to the terminal nucleotide of the support strand; and iii. the terminal nucleotide of the support strand (position n−1) overhangs the terminal nucleotide of the helper strand, is the partner nucleotide for the first nucleotide of step (2) and is the partner nucleotide for the next nucleotide of step (6).

8. The method according to claim 3, wherein:

a) in step (1) the scaffold polynucleotide is provided in the support strand with a nucleotide (position n) which is the partner nucleotide for the first nucleotide of step (2), and the universal nucleotide in the support strand is positioned next to the partner nucleotide (position n+1, in the direction proximal to the helper strand and distal to the primer strand);

b) in step (2) the first nucleotide is incorporated into the synthesis strand at the position opposite the partner nucleotide in the support strand (position n), whereupon the first nucleotide pairs with the partner nucleotide and in step (6) the next nucleotide is incorporated into the synthesis strand at the position opposite the partner nucleotide in the support strand (position n), whereupon the next nucleotide pairs with the partner nucleotide;

c) in step (3) the support strand is cleaved at a position between the first nucleotide (position n) and the second nucleotide (position n−1) from the universal nucleotide in the support strand in the direction distal to the helper strand and proximal to the primer strand, wherein cleavage removes the universal nucleotide and creates a single-nucleotide overhang in the scaffold polynucleotide comprising the first nucleotide overhanging the support strand and in step (7) the support strand is cleaved at a position between the first nucleotide (position n) and the second nucleotide (position n−1) from the universal nucleotide in the support strand in the direction distal to the helper strand and proximal to the primer strand, wherein cleavage removes the universal nucleotide and creates a single-nucleotide overhang in the scaffold polynucleotide comprising the next nucleotide overhanging the support strand; and d) in step (4) and (8), the complementary ligation end of the ligation polynucleotide comprises a single-nucleotide overhang and wherein:
  i. the universal nucleotide in the support strand is positioned opposite the penultimate nucleotide of the helper strand (position n+1) and is paired therewith;
  ii. the universal nucleotide is positioned next to the penultimate nucleotide of the support strand (position n);
  iii. the penultimate nucleotide of the support strand (position n) is paired with the terminal nucleotide of the helper strand and is a partner nucleotide for the next nucleotide in step (6) of the next synthesis cycle; and
  iv. the terminal nucleotide of the support strand (position n−1) overhangs the terminal nucleotide of the helper strand and is a partner nucleotide for the first nucleotide of step (2) or is a partner nucleotide for the newly-incorporated nucleotide of step (6) of the current synthesis cycle.

9. The method according to claim 3, wherein:
a) in steps (1) and (6) the universal nucleotide in the support strand of the scaffold polynucleotide is positioned opposite the terminal nucleotide of the helper strand adjacent the single-strand break and is paired therewith (position n);
b) in step (2), the first nucleotide is incorporated into the synthesis strand at a position opposite the universal nucleotide in the support strand, whereupon the first nucleotide pairs with the universal nucleotide and in step (6), the next nucleotide is incorporated into the synthesis strand at a position opposite the universal nucleotide in the support strand, whereupon the next nucleotide pairs with the universal nucleotide;
c) in step (3) the support strand is cleaved at a position between the first nucleotide (position n−1) and the second nucleotide (position n−2) from the universal nucleotide in the support strand in the direction distal to the helper strand and proximal to the primer strand, wherein cleavage removes the universal nucleotide and creates a double-nucleotide overhang in the scaffold polynucleotide comprising the first nucleotide overhanging the support strand and in step (7) the support strand is cleaved at a position between the first nucleotide (position n−1) and the second nucleotide (position n−2) from the universal nucleotide in the support strand in the direction distal to the helper strand and proximal to the primer strand, wherein cleavage removes the universal nucleotide and creates a double-nucleotide overhang in the scaffold polynucleotide comprising the next nucleotide overhanging the support strand; and d) in steps (4) and (8) the complementary ligation end of the ligation polynucleotide comprises a double-nucleotide overhang and wherein:
  i. the universal nucleotide in the support strand is positioned (position n) opposite the terminal nucleotide of the helper strand and is paired therewith;
  ii. the universal nucleotide is positioned next to the penultimate nucleotide of the support strand; and
  iii. the penultimate nucleotide of the support strand (position n−1) overhangs the terminal nucleotide of the helper strand, is the partner nucleotide for the first nucleotide in step (2) and is the partner nucleotide for the next nucleotide in step (6).

10. The method according to claim 3, wherein in any one or more cycles of synthesis, or in all cycles of synthesis, after the step of ligating the double-stranded ligation polynucleotide to the cleaved scaffold polynucleotide and before the step of incorporating the next nucleotide of the predefined nucleotide sequence into the synthesis strand of the scaffold polynucleotide, the helper strand portion of the synthesis strand is removed from the scaffold polynucleotide.

11. The method according to claim 3, wherein in step (1) and/or
  (6): (a) the helper strand and the portion of the support strand hybridized thereto are connected by a hairpin loop; and
  (b) the synthesis strand comprising the primer strand portion and the portion of the support strand hybridized thereto are connected by a hairpin loop;
  optionally wherein at least one of the ligation polynucleotides is provided as a single molecule comprising a hairpin loop connecting the support strand and the helper strand at the end opposite the overhanging end; optionally wherein the ligation polynucleotides of each synthesis cycle are provided as single molecules each comprising a hairpin loop connecting the support strand and the helper strand at the end opposite the overhanging end.

12. The method according to claim 1, wherein the step of removing the reversible terminator group from a nucleotide of the predefined sequence is performed before the cleavage step, or before the ligation step.

13. The method according to claim 1, wherein the first polynucleotide and the one or more additional polynucleotides are cleaved by a restriction enzyme at a cleavage site.

14. The method according to claim 1, wherein the assembly steps and/or synthesis steps are performed in droplets within a microfluidic system.

15. The method according to claim 14 wherein the assembly steps comprise providing a first droplet comprising a first synthesised double-stranded polynucleotide having a predefined sequence and a second droplet comprising an additional one or more synthesised double-stranded polynucleotides having a predefined sequence, wherein the droplets are brought in contact with each other and wherein the synthesised double-stranded polynucleotides are joined together thereby assembling a polynucleotide comprising the first and additional one or more double-stranded polynucleotides.

16. The method according to claim 15 wherein the synthesis steps are performed by providing a plurality of droplets each droplet comprising reaction reagents corresponding to a step of the synthesis cycle, and sequentially delivering the droplets to the scaffold polynucleotide in accordance with the steps of the synthesis cycles.

17. The method according to claim 16, wherein following delivery of a droplet and prior to the delivery of a next droplet, a washing step is carried out to remove excess reaction reagents.

18. The method according to claim 16, wherein the microfluidic system is an electrowetting system.

19. The method according to claim 18, wherein the microfluidic system is an electrowetting-on-dielectric system (EWOD).

20. The method according to claim 16, wherein synthesis and assembly steps are performed within the same system.

* * * * *

UNITED STATES PATENT AND TRADEMARK OFFICE
CERTIFICATE OF CORRECTION

PATENT NO. : 11,884,950 B2
APPLICATION NO. : 17/143318
DATED : January 30, 2024
INVENTOR(S) : John Milton et al.

It is certified that error appears in the above-identified patent and that said Letters Patent is hereby corrected as shown below:

In the Claims

At Claim 3, Column 151, Line 7:
"steps £6 to M"
Should read:
--steps (6) to (9)--

Signed and Sealed this
Tenth Day of September, 2024

*Katherine Kelly Vidal*
Katherine Kelly Vidal
*Director of the United States Patent and Trademark Office*

SEQUENCE LISTING

<160> NUMBER OF SEQ ID NOS: 67

<210> SEQ ID NO 1
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 1
gcgacaggtg actgcagc                                                    18

<210> SEQ ID NO 2
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 2
cacatcacgt cgtagtcngc tgcagtcacc tgtcgc                                36

<210> SEQ ID NO 3
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 3
cacatcacgt cgtagtcngc tgcagtcacc tgtcgc                                36

<210> SEQ ID NO 4
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 4
gcgacaggtg actgcagct                                                   19

<210> SEQ ID NO 5

```
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 5
gcgacaggtg actgcagctg actacgacgt gatgtg                                 36

<210> SEQ ID NO 6
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (17)..(17)
<223> OTHER INFORMATION: 2'-deoxyinosine

<400> SEQUENCE: 6
cacatcacgt cgtagtnagc tgcagtcacc tgtcgc                                 36

<210> SEQ ID NO 7
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 7
gctgcagtca cctgtcgc                                                     18

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
gcgacaggtg actgcagct                                                    19

<210> SEQ ID NO 9
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (17)..(17)
<223> OTHER INFORMATION: 2'-deoxyinosine

<400> SEQUENCE: 9
cacatcacgt cgtagtna                                                     18

<210> SEQ ID NO 10
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 10
gcgacaggtg actgcagc                                                     18
```

```
<210> SEQ ID NO 11
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 11
cacatcacgt cgtagtcngc tgcagtcacc tgtcgc                              36

<210> SEQ ID NO 12
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 12
cgactacgac gtgatgtg                                                  18

<210> SEQ ID NO 13
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: Deoxyinosine

<400> SEQUENCE: 13
cacatcacgt cgtagtcngc tgcagtcacc tgtcgc                              36

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
gcgacaggtg actgcagct                                                 19

<210> SEQ ID NO 15
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 15
gcgacaggtg actgcagctg actacgacgt gatgtg                              36

<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 16
tgactacgac gtgatgtg                                                  18
```

```
<210> SEQ ID NO 17
<211> LENGTH: 36
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (17)..(17)
<223> OTHER INFORMATION: 2'-deoxyinosine

<400> SEQUENCE: 17
cacatcacgt cgtagtnagc tgcagtcacc tgtcgc                            36

<210> SEQ ID NO 18
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 18
gctgcagtca cctgtcgc                                                18

<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19
gcgacaggtg actgcagct                                               19

<210> SEQ ID NO 20
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (17)..(17)
<223> OTHER INFORMATION: 2'-deoxyinosine

<400> SEQUENCE: 20
cacatcacgt cgtagtna                                                18

<210> SEQ ID NO 21
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 21
cactacgacg tgatgtg                                                 17

<210> SEQ ID NO 22
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 22
gcgacaggtg actgcagc                                                18
```

```
<210> SEQ ID NO 23
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 23
cacatcacgt cgtagtcnag ctgcagtcac ctgtcgc                              37

<210> SEQ ID NO 24
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 24
cacatcacgt cgtagtcngg ctgcagtcac ctgtcgc                              37

<210> SEQ ID NO 25
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 25
cacatcacgt cgtagtcnag ctgcagtcac ctgtcgc                              37

<210> SEQ ID NO 26
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2'-deoxyinosine

<400> SEQUENCE: 26
cacatcacgt cgtagtcnag ctgcagtcac ctgtcgc                              37

<210> SEQ ID NO 27
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 27
tcgactacga cgtgatgtg                                                  19

<210> SEQ ID NO 28
```

```
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 28
ccgactacga cgtgatgtg                                              19

<210> SEQ ID NO 29
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 29
acgactacga cgtgatgtg                                              19

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
gcgactacga cgtgatgtg                                              19

<210> SEQ ID NO 31
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: Deoxyinosine

<400> SEQUENCE: 31
cacatcacgt cgtagtcnag ctgcagtcac ctgtcgc                          37

<210> SEQ ID NO 32
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 32
gcgacaggtg actgcagct                                              19

<210> SEQ ID NO 33
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 33
gcgacaggtg actgcagctg actacgacgt gatgtg                           36

<210> SEQ ID NO 34
<211> LENGTH: 19
<212> TYPE: DNA
<213> ORGANISM: Artificial Sequence
```

```
<220> FEATURE:
<223> OTHER INFORMATION: Synthetic Polynucleotide

<400> SEQUENCE: 34
tcgactacga cgtgatgtg                                                    19

<210> SEQ ID NO 35
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 35
gctgcagtca cctgtcgc                                                     18

<210> SEQ ID NO 36
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 36
gcgacaggtg actgcagct                                                    19

<210> SEQ ID NO 37
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (17)..(17)
<223> OTHER INFORMATION: 2'-deoxyinosine

<400> SEQUENCE: 37
cacatcacgt cgtagtnga                                                    19

<210> SEQ ID NO 38
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 38
ccactacgac gtgatgtg                                                     18

<210> SEQ ID NO 39
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 39
gcgacaggtg actgcagc                                                     18

<210> SEQ ID NO 40
<211> LENGTH: 36
<212> TYPE: DNA
<213> ORGANISM: Artificial Sequence
<220> FEATURE:
<223> OTHER INFORMATION: Synthetic Polynucleotide
```

```
<400> SEQUENCE: 40
cacatcacgt cgtagtcagc tgcagtcacc tgtcgc                              36

<210> SEQ ID NO 41
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 41
cacatcacgt cgtagtcggc tgcagtcacc tgtcgc                              36

<210> SEQ ID NO 42
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 42
cacatcacgt cgtagtctgc tgcagtcacc tgtcgc                              36

<210> SEQ ID NO 43
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 43
cacatcacgt cgtagtccgc tgcagtcacc tgtcgc                              36

<210> SEQ ID NO 44
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (36)..(36)
<223> OTHER INFORMATION: 2'-deoxyinosine
<220> FEATURE:
<221> NAME/KEY: misc_feature
<222> LOCATION: (58)..(58)
<223> OTHER INFORMATION: Tamra-dT

<400> SEQUENCE: 44
tcgactacga cgtgactttt agtcacgtcg tagtcnagct gcagtcacct gctgcttntt    60
gcagcaggtg actgcagc                                                  78

<210> SEQ ID NO 45
<211> LENGTH: 79
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (36)..(36)
<223> OTHER INFORMATION: 2'-deoxyinosine
<220> FEATURE:
<221> NAME/KEY: misc_feature
<222> LOCATION: (58)..(58)
<223> OTHER INFORMATION: Tamra-dT

<400> SEQUENCE: 45
```
tcgactacga cgtgactttt agtcacgtcg tagtcnagct gcagtcacct gctgcttntt     60
gcagcaggtg actgcagct                                                  79

<210> SEQ ID NO 46
<211> LENGTH: 42
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(21)
<223> OTHER INFORMATION: Tamra-dT phosphate

<400> SEQUENCE: 46
gctgcagtca cctgctgctt nttgcagcag gtgactgcag ct                        42

<210> SEQ ID NO 47
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (36)..(36)
<223> OTHER INFORMATION: 2'-deoxyinosine

<400> SEQUENCE: 47
ccgactacga cgtgactttt agtcacgtcg tagtcnga                             38

<210> SEQ ID NO 48
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (36)..(36)
<223> OTHER INFORMATION: 2'-deoxyinosine
<220> FEATURE:
<221> NAME/KEY: misc_feature
<222> LOCATION: (58)..(58)
<223> OTHER INFORMATION: Tamra-dT

<400> SEQUENCE: 48
tcgactacga cgtgactttt agtcacgtcg tagtcnagct gcagtcacct gctgcttntt     60
gcagcaggtg actgcagc                                                   78

<210> SEQ ID NO 49
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (36)..(36)
<223> OTHER INFORMATION: 2'-deoxyinosine

<400> SEQUENCE: 49
ccgactacga cgtgactttt agtcacgtcg tagtcnga                             38

<210> SEQ ID NO 50
<211> LENGTH: 58
<212> TYPE: DNA

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine
<220> FEATURE:
<221> NAME/KEY: misc_feature
<222> LOCATION: (38)..(38)
<223> OTHER INFORMATION: Tamra-dT

<400> SEQUENCE: 50
agtcacgtcg tagtcnagct gcagtcacct gctgcttntt gcagcaggtg actgcagc      58

<210> SEQ ID NO 51
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 51
tcgactacga cgtgact                                                    17

<210> SEQ ID NO 52
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine

<400> SEQUENCE: 52
agtcacgtcg tagtcnga                                                   18

<210> SEQ ID NO 53
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 53
ccgactacga cgtgact                                                    17

<210> SEQ ID NO 54
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (35)..(35)
<223> OTHER INFORMATION: 2'-deoxyinosine
<220> FEATURE:
<221> NAME/KEY: misc_feature
<222> LOCATION: (57)..(57)
<223> OTHER INFORMATION: Tamra-dT

<400> SEQUENCE: 54
cgactacgac gtgactttta gtcacgtcgt agtcnagctg cagtcacctg ctgcttnttg     60
cagcaggtga ctgcagct                                                   78
```

```
<210> SEQ ID NO 55
<211> LENGTH: 37
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (35)..(35)
<223> OTHER INFORMATION: 2'-deoxyinosine

<400> SEQUENCE: 55
cgactacgac gtgactttta gtcacgtcgt agtcnaa                              37

<210> SEQ ID NO 56
<211> LENGTH: 78
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (35)..(35)
<223> OTHER INFORMATION: 2'-deoxyinosine
<220> FEATURE:
<221> NAME/KEY: misc_feature
<222> LOCATION: (52)..(52)
<223> OTHER INFORMATION: Tamra-dT
<220> FEATURE:
<221> NAME/KEY: misc_feature
<222> LOCATION: (57)..(57)
<223> OTHER INFORMATION: Biotin-dT

<400> SEQUENCE: 56
cgactacgac gtgactttta gtcacgtcgt agtcnagctg cagtcacctg cngcttnttg    60
cagcaggtga ctgcagct                                                  78

<210> SEQ ID NO 57
<211> LENGTH: 38
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (36)..(36)
<223> OTHER INFORMATION: 2'-deoxyinosine

<400> SEQUENCE: 57
ccgactacga cgtgactttt agtcacgtcg tagtcnga                            38

<210> SEQ ID NO 58
<211> LENGTH: 62
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (60)..(60)
<223> OTHER INFORMATION: 2'-deoxyinosine

<400> SEQUENCE: 58
acgagtgacc tggtttttt ttttttttt ttttttttt tttttttacc aggtcactcn       60
tg                                                                   62

<210> SEQ ID NO 59
<211> LENGTH: 58
<212> TYPE: DNA
```

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine
<220> FEATURE:
<221> NAME/KEY: misc_feature
<222> LOCATION: (33)..(33)
<223> OTHER INFORMATION: Tamra-dT
<220> FEATURE:
<221> NAME/KEY: misc_feature
<222> LOCATION: (38)..(38)
<223> OTHER INFORMATION: Biotin-dT

<400> SEQUENCE: 59
agtcacgtcg tagtcnagct gcagtcacct gcngcttntt gcagcaggtg actgcagc      58

<210> SEQ ID NO 60
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine

<400> SEQUENCE: 60
agtcacgtcg tagtcnaa                                                   18

<210> SEQ ID NO 61
<211> LENGTH: 67
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine

<400> SEQUENCE: 61
agtcacgtcg tagtcnagct gcagtcacct gctgcttttt ttttttttg cagcaggtga      60 ctgcagc                                                               67

<210> SEQ ID NO 62
<211> LENGTH: 67
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine

<400> SEQUENCE: 62
agtcacgtcg tagtcnagct gcagtcacct gctgcttttt ttttttttg cagcaggtga      60 ctgcagc                                                               67

<210> SEQ ID NO 63
<211> LENGTH: 58
<212> TYPE: DNA
<213> ORGANISM: Artificial Sequence
<220> FEATURE:
<223> OTHER INFORMATION: Synthetic Polynucleotide
```

```
<220> FEATURE:
<221> NAME/KEY: misc_feature
<222> LOCATION: (16)..(16)
<223> OTHER INFORMATION: 2'-deoxyinosine
<220> FEATURE:
<221> NAME/KEY: misc_feature
<222> LOCATION: (38)..(38)
<223> OTHER INFORMATION: 5''-thiophosphate-Sp9-Sp9-Sp9-5-methylC

<400> SEQUENCE: 63
agtcacgtcg tagtcnagct gcagtcacct gctgcttctt gcagcaggtg actgcagc      58

<210> SEQ ID NO 64
<211> LENGTH: 58
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine
<220> FEATURE:
<221> NAME/KEY: misc_feature
<222> LOCATION: (38)..(38)
<223> OTHER INFORMATION: 5''-phosphate-Sp9-Sp9-Sp9-5-methylC

<400> SEQUENCE: 64
agtcacgtcg tagtcnagct gcagtcacct gctgcttctt gcagcaggtg actgcagc      58

<210> SEQ ID NO 65
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2'-deoxyinosine
<220> FEATURE:
<221> NAME/KEY: misc_feature
<222> LOCATION: (38)..(38)
<223> OTHER INFORMATION: 5''-thiophosphate-Sp9-Sp9-Sp9-5-methylC

<400> SEQUENCE: 65
agtcacgtcg tagtcnagct gcagtcacct gctgcttctt gcagcaggtg actgcagct     59

<210> SEQ ID NO 66
<211> LENGTH: 59
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (38)..(38)
<223> OTHER INFORMATION: 5''-thiophosphate-Sp9-Sp9-Sp9-5-methylC

<400> SEQUENCE: 66
agtcacgtcg tagtcgagct gcagtcacct gctgcttctt gcagcaggtg actgcagct     59

<210> SEQ ID NO 67
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
```

-continued

<223> OTHER INFORMATION: 2'-deoxyinosine

<400> SEQUENCE: 67
agtcacgtcg tagtcnaa                                           18